US009408901B2

(12) United States Patent
Livengood et al.

(10) Patent No.: US 9,408,901 B2
(45) Date of Patent: Aug. 9, 2016

(54) COMPOSITIONS, METHODS AND USES FOR DENGUE VIRUS SEROTYPE-4 CONSTRUCTS

(71) Applicants: Inviragen, Inc., Fort Collins, CO (US); The United States of America as Represented by the Secretary of Health and Human Services, Washington, DC (US)

(72) Inventors: Jill A. Livengood, Fort Collins, CO (US); Claire Y. Huang, Fort Collins, CO (US); Timothy D. Powell, Fort Collins, CO (US); Dan T. Stinchcomb, Fort Collins, CO (US); Jorge Osorio, Mount Horeb, WI (US)

(73) Assignees: TAKEDA VACCINES, INC, Deerfield, IL (US); THE UNITED STATES OF AMERICA AS REPRESENTED BY THE SECRETARY OF HEALTH & HUMAN SERVICES, Washington, DC (US)

(*) Notice: Subject to any disclaimer, the term of this patent is extended or adjusted under 35 U.S.C. 154(b) by 115 days.

(21) Appl. No.: 14/076,034

(22) Filed: Nov. 8, 2013

(65) Prior Publication Data

US 2014/0134205 A1    May 15, 2014

Related U.S. Application Data

(60) Provisional application No. 61/724,190, filed on Nov. 8, 2012, provisional application No. 61/788,536, filed on Mar. 15, 2013.

(51) Int. Cl.
*A61K 39/00* (2006.01)
*A61K 39/12* (2006.01)

(52) U.S. Cl.
CPC .......... *A61K 39/12* (2013.01); *A61K 2039/5254* (2013.01); *A61K 2039/5256* (2013.01); *A61K 2039/53* (2013.01); *A61K 2039/70* (2013.01); *C12N 2770/24121* (2013.01); *C12N 2770/24122* (2013.01); *C12N 2770/24134* (2013.01)

(58) Field of Classification Search
None
See application file for complete search history.

(56) References Cited

FOREIGN PATENT DOCUMENTS

| WO | 0160847 A2 | 8/2001 |
|---|---|---|
| WO | 2008157136 A1 | 12/2008 |
| WO | 2010085358 A2 | 7/2010 |
| WO | 2012065105 A2 | 5/2012 |

OTHER PUBLICATIONS

International Search Report and Written Opinion issued in PCT/US2013/069287 mailed Jan. 7, 2014, 14 pages.
Kelly et al. Evolution of Attenuating Mutations in Dengue-2 Strain S16803 PDK50 Vaccine and Comparison of Growth Kinetics With Parent Virus; Virus Genes (2011) 43: 18-26, DOI 10.1007/s11262-011-0602-z.

*Primary Examiner* — Stacy B Chen
(74) *Attorney, Agent, or Firm* — Faegre Baker Daniels LLP

(57) ABSTRACT

Embodiments herein report compositions, methods and uses for dengue-4 (DENV-4) virus constructs. Some embodiments concern a composition that includes, but is not limited to, DENV-4 virus constructs alone or in combination with other constructs, can be used in a vaccine composition to induce an immune response in a subject. In certain embodiments, compositions can include constructs of more than one serotypes of dengue virus, such as dengue-1 virus, dengue-2 virus, or dengue-3 virus in combination with DENV-4 virus constructs disclosed herein. In other embodiments, DENV-4 constructs disclosed herein can be combined in a composition with other flavivirus constructs to generate a vaccine against more than one flavivirus. Other embodiments provide methods and uses for DENV-4 virus constructs in vaccine compositions that when administered to a subject induce an immune response in the subject against DENV-4 that is improved by modified constructs compared to other vaccine compositions.

27 Claims, 23 Drawing Sheets

Fig. 2

| Group | Schedule | Formulation |
|---|---|---|
| Group 1 | Prime 2 doses (0,0) | 1) High Dose DENVax [2e4, 5e4, 1e5, 3e5] |
| Group 2 | Prime 2 doses (0,0) | 2) High Dose w/2nd Gen. DEN-r (4b-P10) [2e4, 5e4, 1e5, 3e5] |

Fig. 5

| | DENVa x-4 | DENVa x-4b | DENVa x-4e | DENVa x-4f | DENVa x-4g | DENVa x-4h | DENVa x-4i | DENVa x-4j | DENVa x-4k |
|---|---|---|---|---|---|---|---|---|---|
| P1 | yes | yes | yes | yes | yes | yes | yes | yes | no |
| Pheno-type | | | lytic | | | lytic | lytic | | |
| IFU Size | 2 mm | | 3 mm | | | 3 mm | 1 mm | 2 mm | |
| Peak Titer in Vero Cells | 10E7 | | TBD | nacent | nacent | nacent | nacent | nacent | |
| Growth in C6/36 | no | no | nacent | nacent | nacent | nacent | nacent | nacent | |

Figure 10:
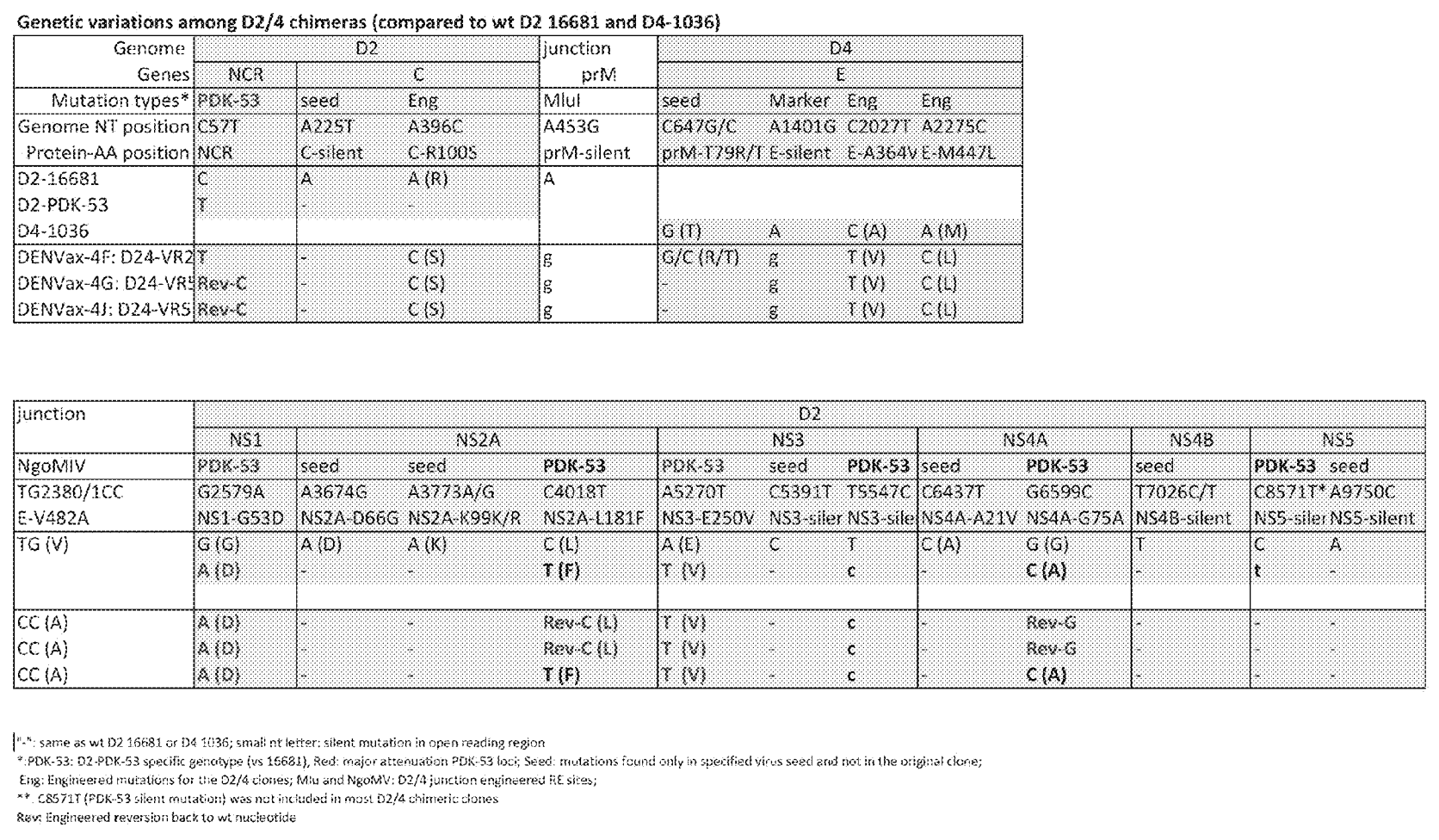

Genetic variations among D2/4 chimeras (compared to wt D2 16681 and D4-1036)

| Genome | NCR | | D2 C | | junction prM | | | D4 E | | | |
|---|---|---|---|---|---|---|---|---|---|---|---|
| Genes | | | | | | | | | | | |
| Mutation types* | PDK-53 seed | | PDK-53 seed | Eng | Mlul

Fig. 11

Genetic variations among D2/4 chimeras (compared to wt D2 16681 and D4-1036)

| Genome | D2 | | | junction | D4 | | | |
|---|---|---|---|---|---|---|---|---|
| Genes | NCR | C | | prM | E | | | |
| Mutation types* | PDK-53 | seed | Eng | MluI | seed | Marker | Eng | Eng |
| Genome NT position | C57T | A225T | A396C | A453G | C647G/C | A1401G | C2027T | A2275C |
| Protein-AA position | NCR | C-silent | C-R100S | prM-silent | prM-T79R/T | E-silent | E-A364V | E-M447L |
| D2-16681 | C | A | A (R) | A | | | | |
| D2-PDK-53 | T | - | - | | | | | |
| D4-1036 | | | | | G (T) | A | C (A) | A (M) |
| Cloned D2/4-V1 (pD2 | T | - | C (S) | g | - | g | T (V) | C (L) |
| DENVax-4 (MVS) | T | t | C (S) | g | - | g | T (V) | C (L) |

See Below

*Continued*

| junction | D2 | | | | | | | | | | | |
|---|---|---|---|---|---|---|---|---|---|---|---|---|
| | NS1 | NS2A | | | NS3 | | | NS4A | | NS4B | NS5 | |
| NgoMIV | PDK-53 | seed | seed | PDK-53 | PDK-53 | seed | PDK-53 | seed | PDK-53 | seed | PDK-53 | seed |
| TG2380/1CC | G2579A | A3674G | A3773A/G | C4018T | A5270T | C5391T | T5547C | C6437T | G6599C | T7026C/T | C8571T** | A9750C |
| E-V482A | NS1-G53 | NS2A-D66G | NS2A-K99K/R | NS2A-L181F | NS3-E250V | NS3-silent | NS3-silent | NS4A-A21V | NS4A-G75A | NS4B-silen | NS5-silent | NS5-silent |
| TG (V) | G (G) | A (D) | A (K) | C (L) | A (E) | C | T | C (A) | G (G) | T | C | A |
| | A (D) | - | - | T (F) | T (V) | - | c | - | C (A) | - | t | - |
| CC (A) | A (D) | - | - | T (F) | T (V) | - | c | - | C (A) | - | - | - |
| CC (A) | A (D) | G (G) | A/G (K/R) | T (F) | T (V) | t | c | T (V) | C (A) | c/t | - | c |

"-": same as wt D2 16681 or D4 1036; small nt letter: silent mutation in open reading region
*:PDK-53: D2-PDK-53 specific genotype (vs 16681), Red: major attenuation PDK-53 loci; Seed: mutations found only in specified virus seed and not in the original clone:
Eng: Engineered mutations for the D2/4 clones; Mlu and NgoMV: D2/4 junction engineered RE sites;
**: C8571T (PDK-53 silent mutation) was not included in most D2/4 chimeric clones
MVS/ master virus seed

Fig. 12

- DEN-2 PDK53
- 9 attenuating mutations
  - 3 silent
  - 6 amino acid changes
    - 5 in PDK-53 backbone

- 5' NC C to T
- NS1-53 Gly-to-Asp
- NS3-250 Glu-to-Val

- *NS2A-181 Leu-to-Phe*
- *NS4A-75 Gly-to-Ala*

Fig. 13  Cloning of DENVax-4e, DENVax-4h, and DENVax-4i

Fig. 14

Mosquito growth in vitro (C6/36)

Immunogenicity in AG129 Mice: Results

Fig. 17

Change in stem of envelope protein could increase efficiency of endosome membrane fusion (DENVax-4h)

… erating a novel construct in order to enhance in vitro growth, or in vivo the immune response to DENV-4 in a subject upon administration.

In some embodiments, a current dengue chimeric construct denoted as DENVax-4 strain (SEQ ID NO:21) was modified to contain a capsid/PrM junction of the DEN-2 backbone to be more genetically similar to that of DENV-4 instead of DEN-2 in order to improve replication efficiency of the virus both in vitro for production and in vivo as a construct of use for inducing an immune response to DENV-4. The current strain of DEN-4, DENVax-4, has a capsid/PrM sequence that is identical to DEN-2 instead of DEN-4, possibly creating an inefficient transcription and translation from the genomic RNA, which is different than that of wild type DENV-4.

In some embodiments, structural protein genes can include prM and E genes of DENV-4 on another dengue virus backbone (e.g. dengue-2, DEN-2 PDK-53), making a dengue-dengue chimera. For example, a DEN-4 construct, in certain embodiments can include those construct termed DENVax-4e (Capsid 107 Cysteine to Tyrosine; DenVax-4b backbone, modifications at Capsid/prM junction), DENVax-4f (where the PDK-53 backbone NS2A and NS4A mutations are reverted to that of 16681) or DENVax-4h (Envelope 417 Glu to Lys) (see for example FIG. 4) where for certain constructs the DEN-2 PDK-53 backbone has one or more reversions to wild-type DEN-2 (e.g. in the non-coding region (NCR) or a non-structural region (NS2 etc.)) and one or more mutations in the DENV-4 structural region (e.g. prM or E), while encoding one or more structural proteins of DENV-4 (e.g. strain 1036). A modified DENV-4 construct disclosed herein can include a modified attenuated DEN-2 PDK-53 backbone, having one or more modified structural proteins of DENV-4 strain 1036. In some embodiments, one or more mutations present in live, attenuated DEN-2 PDK-53 virus can be reverted back to a wildtype nucleic acid (which may be a silent mutation) or another nucleic acid to produce constructs herein that generate a modified DEN-2/DENV-4 construct having increased replication ability and immunogenicity without affecting its attenuation or safety but may affect growth and/or replication of the DEN-4 virus. In certain embodiment, the reversions may lead to increased growth and/or replication.

In other embodiments, a modified DENV-4 construct can incorporate mutations introduced to one or more structural regions and/or non-structural regions of DENV-4 in order to generate constructs inducing an improved immunological response while maintaining safety and viral attenuation. For example, a modified or mutated dengue-dengue chimera of DEN-2/DENV-4 may contain mutations at one or more non-structural regions of a DEN-2 PDK-53 backbone, such as NS2A, and NS4A, and/or mutations at 5' non-coding region (5'NCR). In another embodiment, a modified DENV-4 chimera construct can include NS2A and NS4A of DEN-2 16681 by reverting mutations at NS2A and NS4A of PDK-53 (e.g. an M-L substitution at NS4A). Some embodiments include a modified DENV-4 chimera construct having 5'NCR, NS2A and NS4A of DEN-2 16681 by reverting corresponding mutations in the DEN-2 PDK-53 backbone of a target construct. Other embodiments can include a modified DENV-4 chimera construct having 5'NCR of DEN-2 16681 by reverting corresponding mutations in the DEN-2 PDK-53 backbone. A modified DEN-4 chimera construct can also include DEN-2 PDK-53 backbone, and encode one or more structural proteins of DEN-4 strain H241. It is contemplated that, to induce an immune response, any DEN-4 structural protein can be substituted for structural regions of a chimeric virus containing a dengue-2 serotype backbone (e.g. PDK-53 or modified PDK-53). In some embodiments, a modified DEN-4 construct contains live attenuated DEN-2 PDK-53 as a backbone, and DEN-4 structural proteins where mutations can be introduced to modify structural regions of a DEN-4 (e.g. strain 1036).

In other embodiments, mutations can be introduced to capsid/prM junction amino acid sequences of a DENV virus in order to increase immunogenicity of a construct containing such a mutation. For example, a mutation in DEN-4 can be a Cys-Tyr mutation at capsid position 107 of the DEN-4. In other embodiments, it is contemplated that the cysteine in position 107 can be mutated to any other aromatic amino acid with a hydrophobic side chain (see for example DEN-4e). Other DEN-2 PDK-53 reversion of a chimeric construct can be found in NS2A or NS4A. Yet other embodiments include a DEN-4 construct where a DEN-2 backbone comprises PDK-53 (MVS, SEQ ID NO:21) where amino acid positions 102-107 of the capsid region of PDK-53 are converted to a homologous DEN-4 counterpart amino acid to generate DENV-4b (see for example, FIG. 4). These backbone constructs can then further comprise a cysteine in the capsid region to aromatic amino acid in position (e.g. tyrosine, tryptophan etc). In certain embodiments, this construct is represented by SEQ ID NO:22 or SEQ ID NO:23.

Other DENV-4 constructs disclosed herein can include an amino acid substitution at Envelope position 417. For example, DEN-4 strain 1036 strain sequence or equivalent strain position thereof where a PDK-53 (MVS DEN2/4, SEQ ID NO:21) backbone of Dengue-2 with DEN-4 structural proteins is provided. Embodiments include further mutating Envelope position 417 from a negative to a positively charged side-chain amino acid (e.g. lysine). It is contemplated that any charged side chain will provide increased immunogenicity of the DEN-4 construct without affecting its safety or attenuation. In certain embodiments, this construct is represented by SEQ ID NO:24 or SEQ ID NO:25.

In certain embodiments, DEN-2 PDK-53 reversions of a chimeric DENV construct have the 5' NC, NS1 and NS3 mutations found in DEN-2 PDK-53 MVS while having other reversions or mutations. It has been demonstrated that these three mutations can be important for attenuation (e.g. small plaque size, reduced growth rate, lower titer, increased temperature sensitivity and decreased neurovirulence compared to a control).

In other embodiments, DEN-2 PDK-53 genome backbones can be used to generate chimeric constructs of DEN-1 and DEN-3, where one or more structural protein genes of DEN-2 PDK-53 genome can be replaced by one or more structural protein genes of DEN-1 and DEN-3. These constructs can include a combination of both DEN-1 and DEN-3 in a single chimera having a DEN-2 PDK-53 backbone. In some embodiments, a structural protein can be the C, prM or E protein of DEN-1 and/or DEN-3. In certain embodiments, structural protein genes include the prM and E genes of DEN-1 or DEN-3. These hybrid/chimeric viruses express the surface antigens of DEN-1, DEN-3 or DENV-4 while retaining the attenuation phenotypes of the parent DEN-2. In certain embodiments, these constructs can be represented by SEQ ID NO:15, DEN-2/DEN-1 and SEQ ID NO: 19, DEN-2/DEN-3 where these constructs can be used in di-, tri or tetravalent compositions disclosed herein.

In some embodiment, constructs disclosed herein can include chimeric constructs of DENV-4, DEN-2, DEN-1, and DEN-3 expressing surface antigens of DEN-1, DEN-3 and DENV-4 using attenuated DEN-2 PDK-53 virus as a backbone.

Some embodiments disclose methods for making modified or mutated DENV-4 constructs of use in any vaccine composition including, but not limited to, a single vaccine composition having only DENV-4 constructs, a mixture single vaccine composition capable of inducing an immune response against two or more dengue virus serotypes, a mixture single vaccine composition having chimeric (and non-chimeric) constructs disclosed herein in combination with other flavivirus constructs capable in inducing an immune response to a flavivirus as well as one or more dengue virus serotypes that include DENV-4.

BRIEF DESCRIPTION OF THE DRAWINGS

The following drawings form part of the present specification and are included to further demonstrate certain embodiments. Some embodiments may be better understood by reference to one or more of these drawings alone or in combination with the detailed description of specific embodiments presented.

FIG. 2 is a table that illustrates an exemplary experimental design for analyzing certain vaccines including DENV-4 chimeric constructs of some embodiments disclosed herein in non-human primates.

FIG. 5 is a table illustrating some exemplary data of analysis of plaque phenotypes, Vero cell titers and mosquito growth of some DENV-4 virus constructs of certain embodiments disclosed herein.

FIG. 7 is a graphic representation of viral titers over time of various DENV-4 chimeric constructs after growth in mammalian cells, illustrated as "Days Post Infection."

FIG. 10 illustrates an alignment of various DENV-4 chimeric constructs, illustrating common sequences and exemplary mutations and/or reversions.

FIG. 11 illustrates an alignment of various DENV-4 chimeric constructs, illustrating common sequences and exemplary mutations and/or reversions.

FIG. 12 illustrates a schematic representation of a live, attenuated virus construct of DEN-2 virus.

Figure 14:
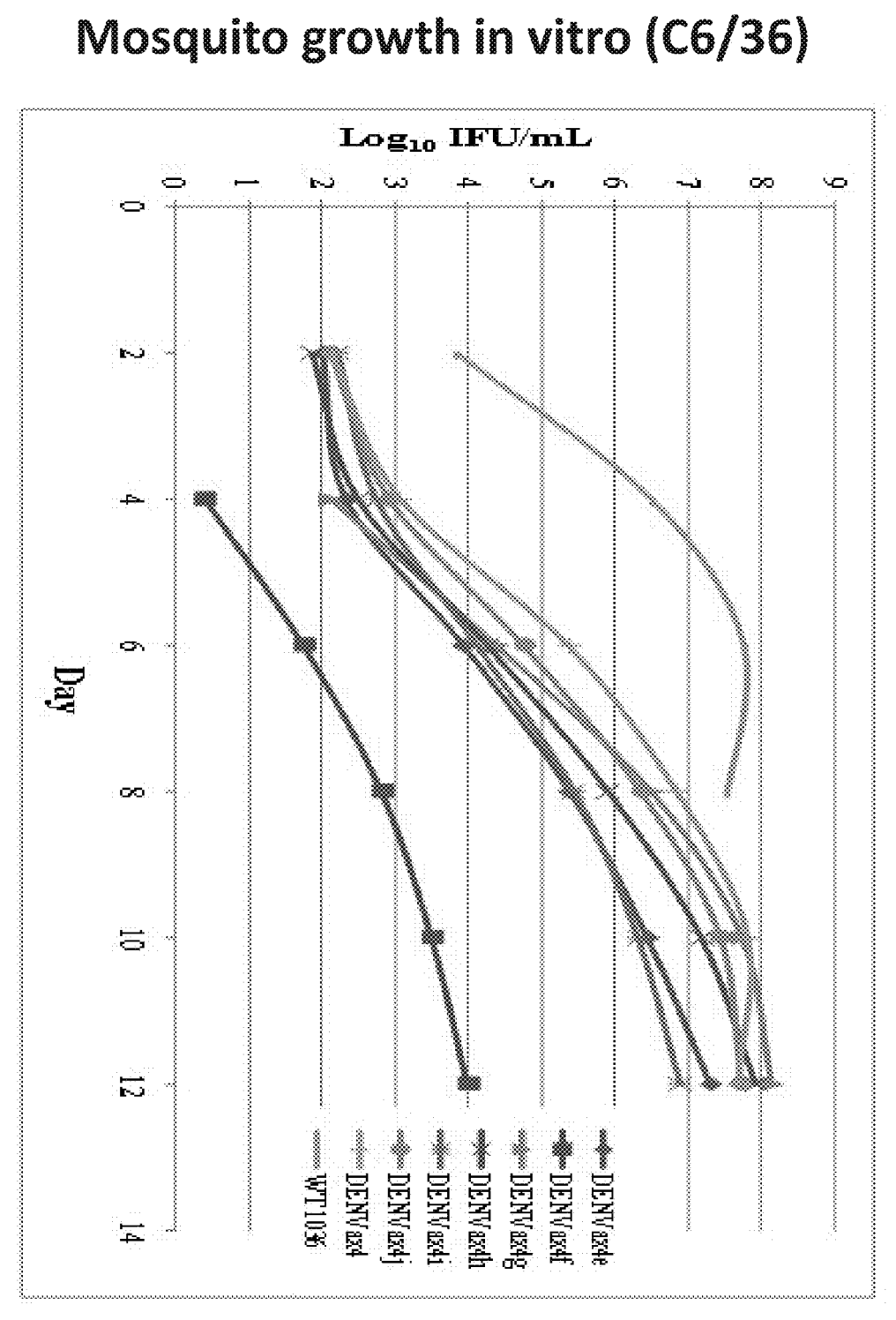

FIG. 14 represents a graph comparing various DENV-4 constructs growth in mosquito cells.

FIG. 17 represents an alignment of the flavivirus envelope protein.

DEFINITIONS

Figures 1A, 1B:
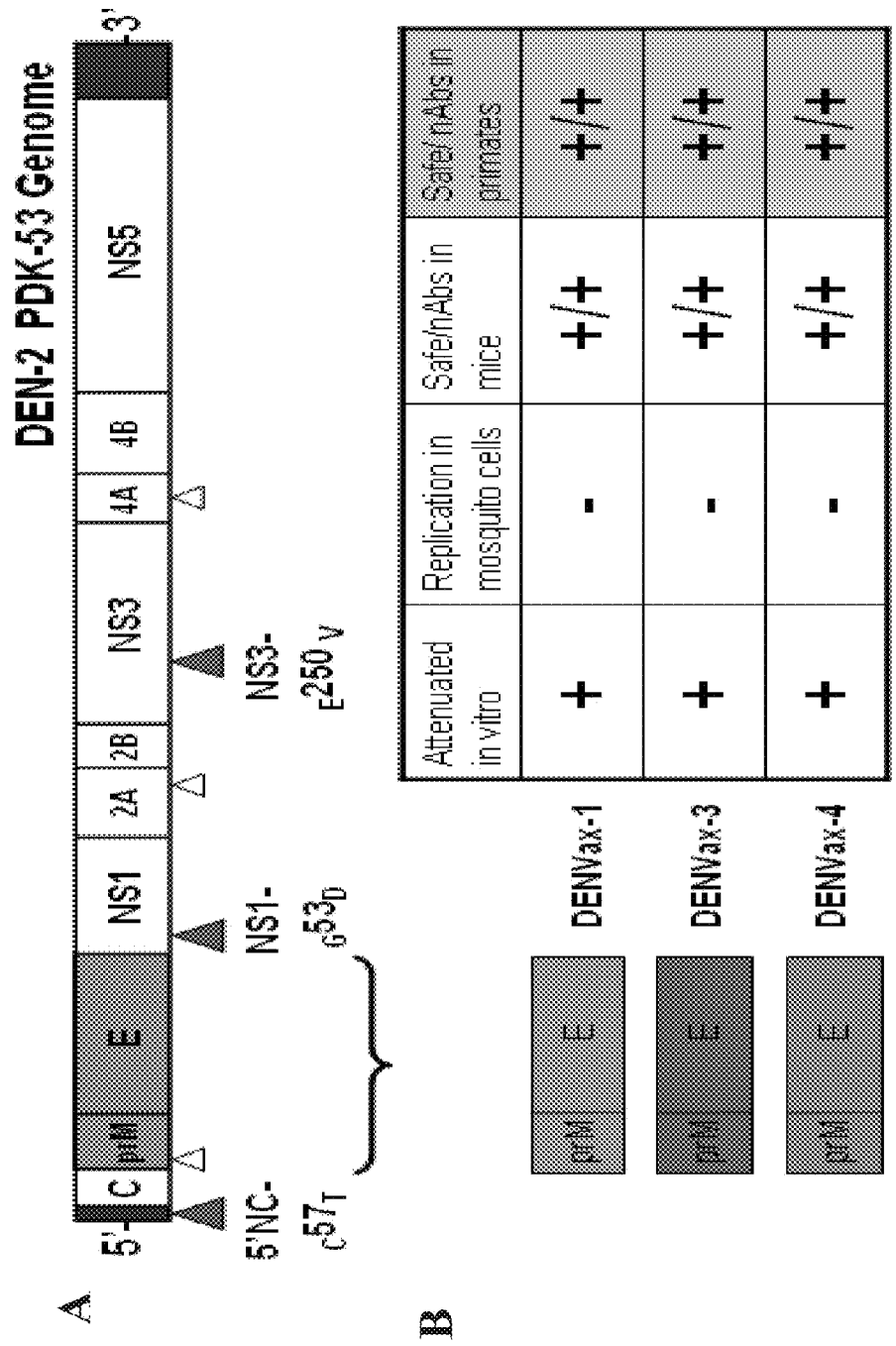
FIGS. 1A-1B illustrates (A) a representative schematic diagram of structural and non-structural genes of DEN-2 PDK-53, and (B) exemplary results of certain chimeric dengue virus constructs of some embodiments disclosed herein expressing structural proteins of different dengue virus serotypes respectively in the DEN-2 PDK-53 backbone.

As used herein, "a" or "an" may mean one or more than one of an item.

As used herein the specification, "subject" or "subjects" may include, but are not limited to, mammals such as humans (e.g. adults and juveniles) or mammals, domesticated or wild, for example dogs, cats, other household pets (e.g. hamster, guinea pig, mouse, rat), ferrets, rabbits, pigs, horses, cattle, prairie dogs, wild rodents, or zoo animals.

As used herein, the terms "chimeric construct," "virus chimera," "chimeric virus," "flavivirus chimera" and "chimeric flavivirus" can mean a construct comprising a portion of the nucleotide sequence of a dengue-2 virus and further nucleotide sequence that is not from dengue-2 virus or is from a different dengue virus serotype or a different flavivirus. A "dengue chimera" comprises at least two different dengue virus serotypes. Examples of other dengue viruses or flaviviruses include, but are not limited to, sequences from dengue-1 virus, dengue-3 virus, dengue-4 virus, West Nile virus, Japanese encephalitis virus, St. Louis encephalitis virus, tick-borne encephalitis virus, yellow fever virus and any combination thereof.

As used herein, "nucleic acid chimera" can mean a construct disclosed herein including nucleic acid sequences comprising a portion of the nucleotide sequence of a dengue-2 virus and further one or more nucleotide sequences are not of the same origin as the nucleotide sequence of the dengue-2 virus. Correspondingly, any chimeric flavivirus, any dengue chimera or flavivirus chimera disclosed herein can be recognized as an example of a nucleic acid chimera.

DESCRIPTION

In the following sections, various exemplary compositions and methods are described in order to detail various embodiments. It will be obvious to one skilled in the art that practicing the various embodiments does not require the employment of all or even some of the specific details outlined herein, but rather that concentrations, times and other specific details may be modified through routine experimentation. In some cases, well-known methods or components have not been included in the description.

In accordance with embodiments of the present invention, there may be employed conventional molecular biology, protein chemistry, microbiology, and recombinant DNA techniques within the skill of the art. Such techniques are explained fully in the literature. See, e.g., Sambrook, Fritsch & Maniatis, Molecular Cloning: A Laboratory Manual, Second Edition 1989, Cold Spring Harbor Laboratory Press, Cold Spring Harbor, N.Y.; Animal Cell Culture, R. I. Freshney, ed., 1986).

Embodiments herein concern compositions, methods and uses for inducing improved immune responses against DEN-4 alone or in combination with one or more agents for inducing immune responses against other dengue virus serotypes or flaviviruses in a subject. In accordance with these embodiments, live, attenuated dengue viruses and nucleic acid chimeras of DEN-4 are generated and used in immunogenic compositions disclosed herein. Some embodiments concern modified or mutated DEN-4 constructs. Some embodiments concern introducing mutations and/or reversions into DEN-4 chimeric constructs to modify the amino acid sequence of the chimeric construct. Some embodiments concern introducing mutations and/or reversions into the DEN-2 PDK-53 backbone constructs to modify the amino acid sequence or RNA sequence of the chimeric construct. In certain embodiments, mutations and/or reversions into DEN-4 chimeric constructs to modify the amino acid sequence of the chimeric construct can include mutations upstream of the C/prM cleavage site of a known chimeric construct referred to as DENVax-4 (SEQ ID NO: 21) by techniques including, but not limited to mutagenesis.

Embodiments herein concern compositions, methods and uses of DENV-4 virus chimera constructs. In some embodiments, a composition can include DENV-4 virus chimera constructs alone or in combination with other dengue virus serotype constructs or live, attenuated dengue viruses of the same or other serotypes or other flavivirus constructs capable of inducing an immune response to a target virus (e.g. dengue virus or other flavivirus). Other embodiments can include a composition of a live, attenuated virus construct against DENV-4 and optionally, one or more live, attenuated viral constructs against DEN-1, DEN-2 and DEN-3. In yet other embodiments, an immunogenic composition is provided that includes a DENV-4 live, attenuated chimeric virus constructs with increased immunogenicity compared to other known constructs when introduced to a subject. In accordance with these embodiments, these live, attenuated viral chimera constructs can be used alone or in combination with one or more other DEN-1, DEN-2 and DEN-3 constructs (e.g. live, attenuated viruses or chimeras), and a pharmaceutically acceptable excipient to generate a vaccine formulation against one or more dengue virus serotypes. In certain embodiments, monovalent, bivalent, trivalent or tetravalent pharmaceutically effective formulations against one or more dengue viruses are generated. In certain embodiments, an immunogenic composition can include one or more of DEN-1, DEN-2, DEN-3 dengue-dengue chimeric constructs or live, attenuated dengue virus in combination with a chimeric DENV-4 construct disclosed herein.

In certain embodiments, an immunogenic composition including a DENV-4 construct of the present invention in combination with one or more of DEN-1, DEN-2 and DEN-3 can be used to confer simultaneous protection against two or more dengue virus serotypes in a single vaccine administration. In other embodiments, an immunogenic composition including DEN-1, DEN-2, DEN-3 and modified or mutated DENV-4 constructs of embodiments disclosed herein can be administered to a subject to induce improved immunogenic responses against each dengue virus serotype and where immune response interference to DENV-4 is reduced.

In certain embodiments, DENV constructs can include a dengue-dengue chimeric construct having adaptive mutations in the structural or non-structural regions of the backbone (PDK-53) or structural regions of DEN-4. In other embodiments, DENV-4 constructs can include a backbone of another dengue virus serotype, DEN-1, DEN-2 or DEN-3. In yet other embodiments, a chimeric construct can include a DEN-2 backbone where DENV-4 structural or non-structural regions of DENV-4 are substituted for DEN-2 structural and/or non-structural regions. In accordance with these embodiments, a DEN-2 backbone can include any live, attenuated DEN-2 virus having safety and efficacy while inducing an immune response to DEN-2. In other embodiments, a DEN-2 backbone can include live, attenuated DEN-2 PDK-53 (53 passages in primary dog kidney cells (PDK)) or derived from DEN-16681 strain virus as a backbone where the live, attenuated DEN-2 PDK-53 virus further includes structural proteins of one or more of prM (premembrane) and E (envelope) structural proteins of DENV-4. In addition, a DEN-2 PDK-53 backbone can include additional mutations or reversions of mutations of DEN-2 PDK-53 in order to enhance the immune response to DENV-4 in a subject upon administration (see for example FIG. 4).

In some embodiments, structural protein genes can include prM and E genes of DENV-4 on another dengue virus backbone, making a dengue-dengue chimera. For example, a DENV-4 construct, in certain embodiments can include those construct termed DENVax-4e, DENVax-4f, or DENVax-4h (see for example FIG. 4) where the DEN-2 PDK-53 backbone has one or more reversions to wild-type DEN-2 amino acids (e.g. in the non-coding region (NCR) or a non-structural region (NS1 etc.)) and one or more mutations in the DENV-4 structural region (e.g. prM or E), while encoding one or more structural proteins of DENV-4 (e.g. strain 1036). A modified DENV-4 construct disclosed herein can include a modified attenuated DEN-2 PDK-53 backbone, having one or more modified structural regions of DENV-4 strain 1036. In some embodiments, one or more mutations present in live, attenuated DEN-2 PDK-53 virus can be reverted back to a control amino acid or another amino acid to produce constructs herein that generate a modified DEN-2/DENV-4 chimeric construct (when compared to MVS sequence SEQ ID. NO: 21) having increased immunogenicity without affecting its safety or attenuation but may affect in vitro growth and/or replication of the DEN-4 virus. In certain embodiment, the reversions may lead to increased growth and/or replication.

In other embodiments, a modified DENV-4 construct can incorporate mutations introduced to one or more structural regions and/or non-structural regions of DENV-4 in order to generate constructs inducing an improved immunological response while maintaining safety and viral attenuation. For example, a modified or mutated dengue-dengue chimera of DEN-2/DENV-4 may contain mutations at one or more non-structural regions of a DEN-2 PDK-53 backbone, such as NS2A, and NS4A, and/or mutations at 5' non-coding region (5'NCR). In another embodiment, a modified DENV-4 chimera construct can include NS2A and NS4A of DEN-2 16681 by reverting mutations at NS2A and NS4A of PDK-53 (e.g. an M-L substitution at NS4A). Some embodiments include a modified DENV-4 chimera construct having 5'NCR, NS2A and NS4A of DEN-2 16681 by reverting corresponding mutations in the DEN-2 PDK-53 backbone of a target construct. Other embodiments can include a modified DENV-4 chimera construct having 5'NCR of DEN-2 16681 by reverting corresponding mutations in the DEN-2 PDK-53 backbone. A modified DENV-4 chimera construct can also include DEN-2 PDK-53 backbone, and encode one or more structural proteins of DENV-4 strain H241.

It is contemplated that DENV-4 structural proteins can substitute for structural or non-structural regions of a dengue-2 serotype backbone (e.g. PDK-53 or modified PDK-53 identified herein) In some embodiments, a modified DENV-4 construct contains live attenuated modified DEN-2 PDK-53 as a backbone, and DENV-4 structural proteins where mutations can be introduced to modify structural regions of a DENV-4 (e.g. strain 1036). In some embodiments, mutations can be introduced to capsid/prM junction amino acid sequences of DENV-4 in order to increase replication and/or immunogenicity of a construct containing such a mutation. For example, a mutation in DENV-4 can be a C-Y mutation at capsid position 107 of the DENV-4 (see for example, DEN-Vax-4e). In accordance with these embodiments, a cysteine can be mutated to an aromatic amino acid (e.g. tyrosine or other) on a modified PDK-53 backbone (DENV-4b). Other mutations can include an amino acid substitution at Envelope position 417 (glutamic acid, E) in a DENV-4 1036 strain sequence (see for example, DENVax-4h) or equivalent position thereof in another DENV-4, where a negative amino acid is replaced by a positive amino acid with a charged side chain (e.g. lysine, arginine, histidine etc.). Other DEN-2 PDK-53 reversion of a chimeric construct can be found in the NS2A or NS4A regions.

In other embodiments, DEN-2 PDK-53 genome backbones can be used to generate chimeric dengue virus constructs of DEN-1 and DEN-3, where one or more structural or non-structural protein genes of DEN-2 PDK-53 genome can be replaced by one or more structural protein or non-structural genes of DEN-1 and DEN-3. These constructs can include a combination of both DEN-1 and DEN-3 structural or non-structural genes in a single chimera having a DEN-2 PDK-53 backbone. In some embodiments, a structural protein can be the C, prM or E protein of DEN-1 and/or DEN-3. In certain embodiments, structural protein genes include the prM and E genes of DEN-1 or DEN-3 or a combination thereof. These hybrid/chimeric viruses can express surface antigens of DEN-1, DEN-3 or DENV-4 while retaining the attenuation phenotypes of the parent DEN-2.

In some embodiment, constructs disclosed herein can include chimeric constructs of DENV-4, DEN-2, DEN-1, and DEN-3 expressing surface antigens of DEN-1, DEN-3 and DENV-4 using attenuated DEN-2 PDK-53 or live, attenuated DEN-2 16681 virus (or a dengue-2 virus with one or more reversion of any of the mutations found in dengue-2 serotype PDK-53 back to its wildtype 16681 virus) as a backbone. In addition, constructs that are part of a pharmaceutical composition can include other agents such as other live, attenuated viruses (e.g. DEN-2, other flaviviruses). Further, other agents of use in these compositions can include other pharmaceutically acceptable anti-viral agents, adjuvants or stabilizing agents to reduce degradation of the live, attenuated viruses.

Some embodiments herein disclose methods for making modified or mutated DENV-4 constructs of use in any vaccine composition against DENV-4 including, but not limited to, a single vaccine composition having only DENV-4 constructs, a mixture of dengue virus constructs of a single vaccine composition capable of inducing an immune response against two or more dengue virus serotypes, a mixture in a single vaccine composition having chimeric (and non-chimeric) constructs disclosed herein in combination with other flavivirus constructs capable in inducing an immune response to a different flavivirus (e.g. yellow fever, West Nile, Japanese encephalitis etc.) as well as one or more dengue virus serotypes that include DENV-4.

In other embodiments, other combinations are contemplated of use with DENV-4 constructs disclosed herein. For example, a dengue virus serotype 1 wild-type virus passaged in PDK cells 13 times is designated as DEN-1 PDK-13 virus. Other vaccine candidates are DEN-2 PDK-53, DEN-3 PGMK-30/FRhL-3 (e.g. thirty passages in primary green monkey kidney cells, followed by three passages in fetal rhesus lung cells) and DENV-4 PDK-48. These four candidate vaccine viruses were derived by tissue culture passage of wild-type parental DEN-1 16007, DEN-2 16681, DEN-3 16562 and DENV-4 1036 viruses, respectively. Any of these existing live, attenuated dengue viruses are contemplated of use in combination with the DENV-4 chimeric virus constructs disclosed herein.

Previous human clinical trials with these attenuated viruses have indicated that DEN-2 PDK-53 has the lowest infectious dose (50% minimal infectious dose of 5 plaque forming units or PFU) in humans, is strongly immunogenic, and produces no apparent safety concerns. The DEN-1 PDK-13, DEN-3 PGMK-30/FRhL-3 and DENV-4 PDK-48 vaccine virus candidates have higher 50% minimal infectious doses of 10,000, 3500, and 150 PFU, respectively, in humans.

DEN-2 PDK-53 virus vaccine candidate, henceforth abbreviated PDK-53, has several measurable biological markers associated with attenuation, including temperature sensitivity, small plaque size, decreased replication in mosquito C6136 cell culture, decreased replication in intact mosquitoes, loss of neurovirulence for suckling mice and decreased incidence of viremia in monkeys. Clinical trials of the candidate PDK-53 vaccine have demonstrated its safety and immunogenicity in humans. Furthermore, the PDK-53 vaccine induces dengue virus-specific T-cell memory responses in human vaccine recipients.

In certain embodiments, a nucleic acid molecule can include a chimeric flavivirus construct having a nucleic acid sequences encoding nonstructural proteins and at least one or more structural proteins from a live, attenuated dengue-2 virus and at least encoding one or more structural proteins from a second flavivirus, wherein the chimeric construct further comprises one or more mutations comprising a mutation in the envelope (E) protein at a position synonymous to amino acid 417, a mutation in the capsid protein at a position synonymous to position 107, and a mutation in NS4A at a position synonymous to amino acid position 17. In other embodiments, a nucleic acid can further include a mutation in the envelope (E) protein at a position synonymous to amino acid 417 that changes the wild type glutamic acid to a lysine. Yet other nucleic acid molecules disclosed herein can further include a mutation in the capsid (C) protein at a position synonymous to amino acid 107 that changes a cysteine to a tyrosine. In other nucleic acid molecules, the mutation in the NS4A protein at a position synonymous to amino acid 17 changes methionine (e.g. wild type sequence) to a leucine. It is contemplated that the second flavivirus can be a DENV-1, DENV-3 or DENV-4. In certain embodiments, the nucleic acid molecule can include a second flavivirus that is DENV-4. In other embodiments, the nucleic acid molecules having a live attenuated dengue-2 backbone contains a mutation at position 57 in the 5'NCR, at position 53 of ns1 and position 250 of ns3. According to these embodiments, a live, attenuated dengue-2 virus contains a mutation at position 53 of ns1 and position 250 of ns1 plus a dengue-1, 3 or 4 substitution of one or more structural proteins. In certain embodiments, a nucleic acid construct can be DENV-4e (SEQ ID NO:22), DENV-4h (SEQ ID NO:24) or DENV-4i (SEQ ID NO:9) capable of inducing an immune response to dengue-4 virus in a subject. It is contemplated herein that the structural sequences of dengue virus serotype 4 can be substituted using dengue-virus 1 or 3 and further contain the above referenced mutations for increasing an immune response to the construct.

Some embodiments concern a nucleic acid molecule having a chimeric flavivirus construct including a nucleic acid sequences encoding nonstructural proteins and at least one or more structural proteins from a live, attenuated dengue-2 virus and at least encoding one or more structural proteins from a second flavivirus, wherein the attenuated dengue-2 contains a mutation at position 53 of ns1 and position 250 of ns3 but does not contain mutations in NS2A or NS4A. In certain embodiments, a nucleic acid construct can be DENV-4f (SEQ ID NO:30). In other embodiments, nucleotide position 674 can be mutated to C from its wild-type nucleotide of G of DENV-4f. In yet other embodiments, a mixture of DENV-2/DENV-4 constructs of the instant application can be combined in a pharmaceutically acceptable composition of use as an immunogenic agent against dengue virus infection.

In certain embodiments, an attenuated dengue-2 virus backbone of DENV-2/DENV-4 constructs can further include one or more mutations/substitutions at positions 102-107 to a wild-type dengue 4 sequence (e.g. 1086) in a DENV-2/DENV-4 construct. For example, one or more of TITLLC at respective positions 102-107 from dengue-4 can replace wild type dengue-2 virus one or more of AGMIIM, at synonymous positions 102-107, respectively. In accordance with these embodiments, a DEN-2/DEN-4 construct having a substitution in this region can further include a mutation of cysteine to an aromatic amino acid (e.g. tyrosine, tryptophan etc.).

In other embodiments, a DENV-2/DENV-4 construct of any immunogenic compositions disclosed herein can be DENV-4g (SEQ ID NO:28) or DENV-4j (SEQ ID NO:32).

Immunogenic flavivirus chimeras having a dengue-2 virus backbone and at least one structural protein of dengue-4 virus can be used for preparing the dengue virus chimeras and methods for producing the dengue virus or flavivirus chimeras are described. The immunogenic flavivirus chimeras are provided, alone or in combination, in a pharmaceutically acceptable carrier as immunogenic compositions to minimize, inhibit, or immunize individuals against infection by one or more dengue virus or flaviviral strains, such as dengue virus serotypes DENV-4, alone or in combination with DEN-2, DEN-3 and DEN-1. When combined, the immunogenic flavivirus chimeras may be used as multivalent vaccines to confer simultaneous protection against infection by more than one species or strain of flavivirus. In certain embodiments, the flavivirus chimeras are combined in an immunogenic composition useful as a bivalent, trivalent or tetravalent vaccine against the known dengue virus serotypes or confer immunity to other pathogenic flaviviruses by including nucleic acids encoding one or more proteins from a different flavivirus. The nucleic acid sequence for each of the DEN-1, DEN-2, DEN-3 and DENV-4 viruses can be used to generate a probe for use in detecting dengue virus in a biological sample in order, for example, to assess efficacy of the vaccine and/or level of a dengue virus infection.

In some embodiments, avirulent, immunogenic flavivirus chimeras provided herein contain the nonstructural protein genes of the attenuated dengue-2 virus (e.g. PDK-53), or the equivalent thereof, and one or more of the structural protein genes or immunogenic portions thereof of the flavivirus against which immunogenicity is to be induced in a subject. For example, some embodiments concern a chimera having attenuated dengue-2 virus PDK-53 genome as the viral backbone, and one or more structural protein genes encoding capsid, premembrane/membrane, or envelope of the PDK-53 genome, or combinations thereof, replaced with one or more corresponding structural protein genes from DENV-4 virus or other flavivirus to be protected against, such as a different flavivirus or a different dengue virus serotype. In accordance with these embodiments, the PDK-53 backbone is further mutated or reverted to increase immunogenicity of the construct. Further, a nucleic acid chimera disclosed herein can have functional properties of the attenuated dengue-2 virus and is avirulent, but expresses antigenic epitopes of the structural gene products of DENV-4 in addition to other flaviviruses and is immunogenic (e.g. induces an immune response to the gene products in a subject). The mutations and/or reversions do not affect the attenuation and/or safety of the chimeric construct.

In another embodiment, a nucleic acid chimera can be a nucleic acid chimera having, but not limited to, a first nucleotide sequence encoding nonstructural proteins from an attenuated dengue-2 virus, and a second nucleotide sequence encoding a structural protein from dengue-4 virus alone or in combination with another flavivirus. In other embodiments, the attenuated dengue-2 virus can be vaccine strain PDK-53 or 16681. Some embodiments include structural proteins of one or more of C, prM or E protein of a dengue or other flavivirus. Examples of flaviviruses from which the structural protein may be selected include, but are not limited to, DEN-1, DEN-2, DEN-3, West Nile virus, Japanese encephalitis virus, St. Louis encephalitis virus, yellow fever virus and tick-borne encephalitis virus in combination with the DENV-4 constructs disclosed herein. In other embodiments, the structural protein may be selected from non-flavivirus species that are closely related to the flaviviruses, such as hepatitis C virus.

Other aspects disclosed herein include that chimeric viruses can include nucleotide and amino acid substitutions, deletions or insertions for example, in the DEN-2 PDK-53; these changes can reduce interference with immunogenicity responses to DENV-4 virus. These modifications can be made in structural and nonstructural proteins alone or in combination with the example modifications disclosed herein.

Embodiments herein include structural and nonstructural proteins of a flavivirus that can be any protein including or any gene encoding the sequence of the complete protein, an epitope of the protein, or any fragment comprising, for example, five or more amino acid residues thereof.

Certain embodiments disclosed herein provide for method for making the chimeric viruses of this invention using recombinant techniques, by inserting the required substitutions into the appropriate backbone genome.

Flavivirus Chimeras

Dengue virus types 1-4 (DEN-1 to DENV-4) are mosquito-borne flavivirus pathogens. The flavivirus genome contains a 5'-noncoding region (5'-NC), followed by a capsid protein (C) encoding region, followed by a premembrane/membrane protein (prM) encoding region, followed by an envelope protein (E) encoding region, followed by the region encoding the nonstructural proteins (NS1-NS2A-NS2B-NS3-NS4A-NS4B-NS5) and finally a 3' noncoding region (3'NC) (See for example FIG. 1A). The viral structural proteins are C, prM and E, and the nonstructural proteins are NS1-NS5. The structural and nonstructural proteins are translated as a single polyprotein and processed by cellular and viral proteases.

Structure of Dengue Virus Genome

5'- C prM E NS1 2A 2B NS3 4A 4B NS5 -3'

Flavivirus chimeras can be constructs formed by fusing non-structural protein genes from one type, or serotype, of dengue virus or virus species of the flaviviridae, with protein genes, for example, structural protein genes, from a different type, or serotype, of dengue virus or virus species of the flaviviridae. Alternatively, a flavivirus chimera disclosed herein is a construct formed by fusing non-structural protein genes from one type, or serotype, of dengue virus or virus species of the flaviviridae, with further nucleotide sequences that direct the synthesis of polypeptides or proteins selected from other dengue virus serotypes or other viruses of the flaviviridae.

In other embodiments, avirulent, immunogenic flavivirus chimeras provided herein contain the nonstructural protein genes of the attenuated dengue-2 virus, or the equivalent thereof, and one or more of the structural protein genes, or antigenic portions thereof, of the flavivirus against which immunogenicity is to be conferred.

Other suitable flaviviruses for use in constructing the flavivirus chimeras can be wild-type, virulent DEN-1 16007, DEN-2 16681, DEN-3 16562 and DENV-4 1036 and attenuated, vaccine-strain DEN-1 PDK-13, DEN-2 PDK-53, DEN-3 PMK-30/FRhL-3 and DENV-4 PDK-48. Genetic differences between the DEN-1, DEN-2, DEN-3 and DENV-4 wild type/attenuated virus pairs are contemplated along with changes in the amino acid sequences encoded by the viral genomes. Any DENV-4 strain of use herein would contain synonymous mutations to the constructs contemplated and/or disclosed herein.

Sequence listings for DEN-2 PDK-53 correspond to the DEN-2 PDK-53-V variant, wherein genome nucleotide position 5270 is mutated from an A to a T and amino acid position 1725 of the polyprotein or amino acid position 250 of the NS3 protein contains a valine residue. The DEN-2 PDK-53 variant without this nucleotide mutation, DEN-2 PDK-53-E, differs from PDK-53-V only in this one position. DEN-2 PDK-53-E has an A at nucleotide position 5270 and a glutamate at polyprotein amino acid position 1725, NS3 protein amino acid position 250. It is understood that embodiments herein can include modified DEN-2 PDK-53 that include one or more reversions/mutations of these positions to the native derived sequence.

Sequence listings for DEN-3 16562 correspond to the variant wherein genome nucleotide position 1521 is a T and amino acid position 476 of the polyprotein or amino acid position 196 of the E protein contain a leucine. A second variant, present in DEN-3 16562 cultures has a T at nucleotide position 1521 and amino acid position 476 of the polyprotein or amino acid position 196 of the E protein contain a serine.

Sequence listings for DENV-4 PDK-48 correspond to the variant wherein genome nucleotide positions: 6957 is a T and amino acid position 2286 of the polyprotein and amino acid position 44 of NS4B protein is a phenylalanine, 7546 is a T and amino acid position 2366 of the polyprotein and amino acid position 240 of NS4B protein is a valine, and 7623 is a T and amino acid position 2508 of the polyprotein and amino acid position 21 of NS5 protein is a tyrosine.

In certain embodiments, designations of the chimeras are based on the DEN-2 virus-specific infectious clone backbones and the structural genes (prM-E or C-prM-E) insert of other flaviviruses. DEN-2 for the dengue-2 backbone, followed by the strain from which the structural genes are inserted. The particular backbone variant is reflected in next. The particular DEN-2 backbone variant from which the chimera was constructed is indicated by the following letter placed after a hyphen, parent 16681 (P), PDK-53-E (E), or PDK-53-V (V); the last letter indicates the C-prM-E structural genes from the parental (P) strain or its vaccine derivative (V) or the prM-E structural genes from the parental (P) or its vaccine derivative (V1). For example; DEN-2/1-VP denotes the chimera comprising the attenuated DEN-2 PDK-53V backbone comprising a valine at NS3-250 and the C-prM-E genes from wild-type DEN-1 16007; DEN-2/1-VV denotes the DEN-2 PDK-53V backbone with the vaccine strain of dengue-1, DEN-1 PDK-13; DEN-2/1-VP1 denotes the DEN-2 PDK-53V backbone and the prM-E genes from wild-type DEN-1 16007; DEN-2/3-VP1 denotes the DEN-2 PDK-53V backbone and the prM-E genes from wild-type DEN-3 16562; DEN-2/4VP1 denotes the DEN-2 PDK-53V backbone and the prM-E genes from wild-type DENV-4 1036; and DEN-2/WN-PP1 denotes the DEN-2 16681 backbone and the prM-E genes from West Nile NY99. Other chimeras disclosed herein are indicated by the same manner.

In one embodiment, chimeras disclosed herein contain attenuated DEN-2 virus PDK-53 genome as the viral backbone, in which the structural protein genes encoding C, prM and E proteins of the PDK-53 genome, or combinations thereof, are replaced with the corresponding structural protein genes from DENV-4 virus and optionally, another flavivirus to be protected against, such as a different flavivirus or a different dengue virus strain. Newly discovered flaviviruses or flavivirus pathogens can also be incorporated into the DEN-2 backbone.

In the nonstructural protein regions, a Gly-to-Asp (wild type-to-PDK-53) mutation was discovered at nonstructural protein NS1-53 (genome nucleotide position 2579); a Leu-to-Phe (wild type-to-PDK-53) mutation was discovered at nonstructural protein NS2A-181 (genome nucleotide position 4018); a Glu-to-Val (wild type-to-PDK-53) mutation was discovered at nonstructural protein NS3-250 (genome nucleotide position 5270); and a Gly-to-Ala mutation (wild type-to-PDK-53) was discovered at nonstructural protein NS4A-75 (genome nucleotide position 6599).

Attenuated PDK-53 virus strain has a mixed genotype at genome nt 5270. A significant portion (approximately 29%) of the virus population encodes the non-mutated NS3-250-Glu that is present in the wild type DEN-2 16681 virus rather than the NS3-250-Val mutation. As both genetic variants are avirulent, this mutation may not be necessary in an avirulent chimera.

Previously, it was discovered that avirulence of the attenuated PDK-53 virus strain can be attributed to mutations in the nucleotide sequence encoding nonstructural proteins and in the 5' noncoding region. For example, a single mutation at NS1-53, a double mutation at NS1-53 and at 5'NC-57, a double mutation at NS1-53 and at NS3-250 and a triple mutation at NS1-53, at 5'NC-57 and at NS3-250, result in attenuation of the DEN-2 virus. Therefore, the genome of any dengue-2 virus containing such non-conservative amino acid substitutions or nucleotide substitutions at these loci can be used as a base sequence for deriving the modified PDK-53 viruses disclosed herein. Another mutation in the stem of the stem/loop structure in the 5' noncoding region will provide additional avirulent phenotype stability, if desired. Mutations to this region disrupt potential secondary structures important for viral replication. A single mutation in this short (only 6 nucleotide residues in length) stem structure in both DEN and Venezuelan equine encephalitis viruses disrupts the formation of the hairpin structure. Further mutations in this stem structure decrease the possibility of reversion at this locus, while maintaining virus viability.

Mutations disclosed herein can be achieved by any method known in the art including, but not limited to, site-directed mutagenesis, direct synthesis, deletion, or other method using techniques known to those skilled in the art. It is understood by those skilled in the art that the virulence screening assays, as described herein and as are well known in the art, can be used to distinguish between virulent and avirulent backbone structures.

Construction of Flavivirus Chimeras

Flavivirus chimeras described herein can be produced by splicing one or more of the structural protein genes of the flavivirus against which immunity is desired into a PDK-53 dengue virus genome backbone, or other methods known in the art, using recombinant engineering to remove the corresponding PDK-53 gene and replace it with a dengue-4 virus gene or other gene known in the art.

Alternatively, nucleic acid sequences of any construct disclosed herein, nucleic acid molecules encoding the flavivirus proteins, may be synthesized using any known nucleic acid synthesis techniques and inserted into an appropriate vector. Avirulent, immunogenic viruses of embodiments herein can therefore be produced using recombinant engineering techniques known to those skilled in the art.

A target gene can be inserted into the backbone that encodes a flavivirus structural protein of interest for DENV-4, alone or in combination with another flavivirus. A flavivirus (e.g. dengue virus) gene to be inserted can be a gene encoding a C protein, a PrM protein and/or an E protein. For example, a sequence inserted into the dengue-2 backbone can encode both PrM and E structural proteins, or just a single structural protein. A sequence inserted into the dengue-2 backbone can encode all or one of C, prM and E structural proteins.

Suitable chimeric viruses or nucleic acid chimeras containing nucleotide sequences encoding structural proteins of other flaviviruses or dengue virus serotypes can be evaluated for usefulness as vaccines by screening them for phenotypic markers of attenuation that indicate avirulence and by screening them for immunogenicity. Antigenicity and immunogenicity can be evaluated using in vitro and/or in vivo reactivity with flavivirus antibodies or immunoreactive serum using routine screening procedures known to those skilled in the art.

Dengue Virus Vaccines

In certain embodiments, chimeric viruses and nucleic acid chimeras can provide live, attenuated viruses useful as immunogens or vaccines. Some embodiments include chimeras that exhibit high immunogenicity to dengue-4 virus while producing no dangerous pathogenic or lethal effects.

To reduce occurrence of DHF/DSS in subjects vaccinated against only one serotype of dengue virus, a di-, tri or tetravalent vaccine is needed to provide simultaneous immunity for two to all four serotypes of the virus. A tetravalent vaccine can be produced by combining live, attenuated dengue-2 (e.g. dengue-2 PDK-53) with dengue-2/1, dengue-2/3, and dengue-2/4 novel chimeras described herein in a suitable pharmaceutical carrier for administration as a multivalent vaccine against all four dengue virus serotypes. Other formulations can include divalent or trivalent formulations of the above where the formulation includes one or more novel DENV-4 chimeric construct.

Chimeric viruses or nucleic acid chimeras disclosed in certain embodiments herein can include structural genes of either wild-type or attenuated viruses in a virulent or an attenuated DEN-2 virus backbone. For example, the chimera may express the structural protein genes of wild-type DENV-4 1036 virus, and its candidate vaccine derivative in either DEN-2 PDK-53 backgrounds. In certain embodiments, pharmaceutical or experimental compositions disclosed herein can include one or more constructs having the designation of DENVax-4e, DENVax-4g, and/or DENVax-4h alone, or in combination with other flavivirus constructs. In certain examples, these constructs can be used in combination with one or more master virus seed (MVS) constructs disclosed herein (e.g. DEN-1/DEN-2). Other embodiments can include DENV-4 constructs disclosed herein in combination with other flavivirus chimeras such as those made on a Yellow Fever backbone or West Nile backbone or other flavivirus backbone where these flavivirus chimeras are capable of forming a chimeric construct with a dengue virus serotype that when introduced to a subject induces an immune response to the virus in the subject.

Viruses used in the chimeras described herein can be grown using techniques known in the art. Virus plaque titrations are then performed and plaques counted in order to assess the viability and phenotypic characteristics of the growing cultures. Wild type viruses are passaged through cultured cell lines to derive attenuated candidate starting materials.

Chimeric infectious clones can be constructed from the various dengue serotype clones available. The cloning of virus-specific cDNA fragments can also be accomplished, if desired. The cDNA fragments containing the structural protein or nonstructural protein genes can be amplified by reverse transcriptase-polymerase chain reaction (RT-PCR) from dengue virus RNA with various primers. Amplified fragments can be cloned into the cleavage sites of other intermediate clones. Intermediate, chimeric dengue virus clones can then be sequenced to verify the accuracy of the inserted dengue virus-specific cDNA.

In certain embodiments, full genome-length chimeric plasmids constructed by inserting the structural protein or non-structural protein gene region of dengue serotype viruses into vectors are obtainable using recombinant techniques well known to those skilled in the art.

Nucleotide and Amino Acid Analysis

In certain embodiments, PDK-53, contains no amino acid mutations in the E protein relative to wild type dengue-2 virus; DEN-1, DEN-3 and DENV-4 attenuated viruses can have amino acid mutations in the E protein. Wild-type DEN-3 16562 has been demonstrated to comprise traces of a variant comprising a T at nucleotide position 1521 which directs incorporation of a leucine at polyprotein position 476, amino acid residue position 476 of the E protein. Each of the latter three viruses can possess a Glu-to-Lys (parent-to-vaccine) mutation in the E protein, although the mutation is located at a different amino acid residue in the E protein. This substitution causes a shift from a negatively charged amino acid to a positively charged one. The Glu-to-Lys substitution in the E protein of DENV-4 vaccine virus was the only mutation present in the E protein, while the E proteins of DEN-1 and DEN-3 vaccine viruses had five and three amino acid mutations, respectively.

In certain embodiments, an NS1-53 mutation occurs in the DEN-2 PDK-53 virus and is significant for the attenuated phenotype of this virus, because the NS1-53-Gly of the DEN-2 16681 virus is conserved in nearly all flaviviruses, including the tick-borne viruses, sequenced to date. DENV-4 virus constructs disclosed herein can contain an amino acid mutation in the NS1 protein at position 253. This locus, which is a Gln-to-His mutation in DENV-4 PDK-48 virus is Gln in all four wild serotypes of dengue virus. This Gln residue is unique to the dengue viruses within the flavivirus genus. The NS1 protein is a glycoprotein that is secreted from flavivirus-infected cells. It is present on the surface of the infected cell and NS1-specific antibodies are present in the serum of virus-infected individuals. Protection of animals immunized with NS1 protein or passively with NS1-specific antibody has been reported.

Certain mutations are found in NS2A, NS2B, NS4A, and NS4B proteins of the DEN-1, -2, -3 and -4 attenuated strains that are conservative in nature. The NS4A-75 and NS4A-95 mutations of DEN-2 and DENV-4 vaccine viruses, respectively, occurred at sites of amino acid conservation among dengue viruses, but not among flaviviruses in general.

Flaviviral NS3 protein possesses at least two recognized functions: the viral proteinase and RNA helicase/NTPase. The 698-aa long (DEN-2 virus) NS3 protein contains an amino-terminal serine protease domain (NS3-51-His, -75-Asp, -135-Ser catalytic triad) that is followed by sequence motifs for RNA helicase/NTPase functions (NS3-196-GAGKT), -284-DEAH, -459-GRIGR (SEQ ID NO:26), previously presented). None of the mutations in the NS3 proteins of DEN-1, DEN-2, or DEN-3 virus occur within a recognized motif. NS3-510 Tyr-to-Phe mutation in DEN-1 PDK-13 virus is a conservative mutation. Since the wild-type DEN-2, -3 and -4 viruses contain Phe at this position, it is unlikely that the Tyr-to-Phe mutation plays a role in the attenuation of DEN-1 virus. The NS3-182 Glu-to-Lys mutation in DEN-1 PDK-13 virus occurred at a position that is conserved as Asp or Glu in most mosquito-borne flaviviruses and it may play some role in attenuation. This mutation was located 15 amino acid residues upstream of the GAGKT (SEQ ID NO:27) helicase motif. In certain dengue-2 viruses, the NS3-250-Glu in DEN-2 16681 virus is conserved in all mosquito-borne flaviviruses except for yellow fever virus.

Nucleic acid probes of use in certain embodiments herein selectively hybridize with nucleic acid molecules encoding the DEN-1, DEN-3 and DENV-4 viruses or complementary sequences thereof. By "selective" or "selectively" is meant a sequence which does not hybridize with other nucleic acids to prevent adequate detection of the dengue virus. Therefore, in the design of hybridizing nucleic acids, selectivity will depend upon the other components present in a sample. Hybridizing nucleic acids should have at least 70% complementarity with the segment of the nucleic acid to which it hybridizes. As used herein to describe nucleic acids, the term "selectively hybridizes" excludes the occasional randomly hybridizing nucleic acids, and thus, has the same meaning as "specifically hybridizing." The selectively hybridizing nucleic acids disclosed herein can have at least 70%, 80%, 85%, 90%, 95%, 97%, 98%, and 99% complementarity with the segment of the sequence to which it hybridizes, preferably 85% or more.

Sequences, probes and primers which selectively hybridize to the encoding nucleic acid or the complementary, or opposite, strand of the nucleic acid are contemplated. Specific hybridization with nucleic acid can occur with minor modifications or substitutions in the nucleic acid, so long as functional species-specific hybridization capability is maintained.

By "probe" is meant nucleic acid sequences that can be used as probes or primers for selective hybridization with complementary nucleic acid sequences for their detection or amplification, which probes can vary in length from about 5 to 100 nucleotides, or preferably from about 10 to 50 nucleotides, or most preferably about 18-24 nucleotides.

If used as primers, the composition preferably includes at least two nucleic acid molecules which hybridize to different regions of the target molecule so as to amplify a desired region. Depending on the length of the probe or primer, the target region can range between 70% complementary bases and full complementarity and still hybridize under stringent conditions. For example, for the purpose of detecting the presence of the dengue virus, the degree of complementarity between the hybridizing nucleic acid (probe or primer) and the sequence to which it hybridizes is at least enough to distinguish hybridization with a nucleic acid from other organisms.

Nucleic acid sequences encoding the DENV-4, DEN-3 or DEN-1 virus can be inserted into a vector, such as a plasmid, and recombinantly expressed in a living organism to produce recombinant dengue virus peptides and/or polypeptides.

Nucleic Acid Detection Methods

A rapid genetic test that is diagnostic for each of the vaccine viruses described herein is provided by the current invention. This embodiment of the invention enhances analyses of viruses isolated from the serum of vaccinated humans who developed a viremia, as well as enhancing characterization of viremia in nonhuman primates immunized with the candidate vaccine viruses.

These sequences include a diagnostic TaqMan probe that serves to report the detection of the cDNA amplicon amplified from the viral genomic RNA template by using a reverse-transcriptase/polymerase chain reaction (RT/PCR), as well as the forward and reverse amplimers that are designed to amplify the cDNA amplicon, as described below. In certain instances, one of the amplimers has been designed to contain a vaccine virus-specific mutation at the 3'-terminal end of the amplimer, which effectively makes the test even more specific for the vaccine strain because extension of the primer at the target site, and consequently amplification, will occur only if the viral RNA template contains that specific mutation.

Automated PCR-based nucleic acid sequence detection system can be used, which is becoming widely used in diagnostic laboratories. The TaqMan assay is a highly specific and sensitive assay that permits automated, real time visualization and quantitation of PCR-generated amplicons from a sample nucleic acid template. TaqMan can determine the presence or absence of a specific sequence. In this assay, a forward and a reverse primer are designed to anneal upstream and downstream of the target mutation site, respectively. A specific detector probe, which is designed to have a melting temperature of about 10° C., higher than either of the amplimers and containing the vaccine virus-specific nucleotide mutation or its complement (depending on the strand of RT/PCR amplicon that is being detected), constitutes the third primer component of this assay. A probe designed to specifically detect a mutated locus in one of the chimeric constructs can contain a specific nucleotide change for detecting any mutation.

One strategy for diagnostic genetic testing makes use of molecular beacons. The molecular beacon strategy also utilizes primers for RT/PCR amplification of amplicons, and detection of a specific sequence within the amplicon by a probe containing reporter and quencher dyes at the probe termini. In this assay, the probe forms a stem-loop structure. The 5'- and 3'-terminal reporter dye and quencher dye, respectively, are located at the termini of the short stem structure, which brings the quencher dye in close juxtaposition with the reporter dye. The stem-structure is melted during the denaturation step of the RT/PCR assay. If the target viral RNA contains the target sequence and is amplified by the forward and reverse amplimers, the opened loop of the probed hybridizes to the target sequence during the annealing step of the cycle. When the probe is annealed to either strand of the amplicon template, the quencher and reporter dyes are separated, and the fluorescence of the reporter dye is detected. This is a real-time identification and quantitation assay that is very similar to the TaqMan assay. The molecular beacons assay employs quencher and reporter dyes that differ from those used in the TaqMan assay.

Pharmaceutical Formulations

Any pharmaceutical formulation known in the art for a vaccine is contemplated herein. In certain embodiments, a formulation can contain, DENV-4 constructs alone or one or more additional DEN serotype (or other flavivirus compositions) in various ratios in combination with DENV-4 constructs disclosed herein, depending on predetermined exposure to or existence of dengue virus subtype prevalence in a region. It is contemplated that formulations can contain other agents of use in vaccination of a subject including, but not limited to other active or inactive ingredients or compositions known to one skilled in the art. In certain embodiments, an adjuvant may be included in a formulation disclosed herein.

Other aspects of the present invention can include modulating an immune response to a vaccine against dengue virus to a subject. Vaccines against dengue virus may include a composition comprising ratios of serotypes of dengue virus, live attenuated dengue virus, or fragments thereof such as proteins or nucleic acids derived or obtained from dengue virus serotypes. Ratios of various serotypes may be equal or certain serotypes may be represented more than others depending on need or exposure or potential exposure to the virus. In accordance with these embodiments, a ratio may be a 1:2, 1:3, 1:4, 1:10, 1:20; 1:1:1, 1:2:2, 1:2:1, 1:1:1:1, 1:2:1:2; 1:3:1:3, 2:3:3:3, 5:4:5:5, 4:4:4:5, 1:2:2, 4:4:5:5, 4:4:5:6 or any ratio for any of serotypes 1, 2, 3 in combination with the DENV-4 constructs disclosed herein, depending on for example, number of serotypes represented in the formulation, predetermined response and effect desired. The last number represents the amount of DENV-4 construct in a formulation. Each number represents the power of ten ($6=10^6$ PFU). It is contemplated that any dengue virus serotype formulation may be used to generate a vaccine (e.g. attenuated virus etc.) of use in administration to a subject in need thereof.

Embodiments herein provide for administration of compositions to subjects in a biologically compatible form suitable for pharmaceutical administration in vivo. By "biologically compatible form suitable for administration in vivo" is meant a form of the active agent (e.g. pharmaceutical protein, peptide, or gene etc. of the embodiments) to be administered in which any toxic effects are outweighed by the therapeutic effects of the active agent. Administration of a therapeutically active amount of the therapeutic compositions is defined as an amount effective, at dosages and for periods of time necessary to achieve the desired result. For example, a therapeutically active amount of a compound may vary according to factors such as the disease state, age, sex, and weight of the individual, and the ability of antibody to elicit a desired response in the individual. Dosage regima may be adjusted to provide the optimum therapeutic response.

In one embodiment, the compound (e.g. pharmaceutical protein, peptide etc. of the embodiments) may be administered in a convenient manner such as subcutaneous, intravenous, intradermal, by oral administration, inhalation, transdermal application, intradermal, intravaginal application, topical application, intranasal or rectal administration. Depending on the route of administration, the active compound may be coated in a material to protect the compound from degradation by enzymes, acids and other natural conditions that may inactivate the compound. In one embodiment, the compound may be administered intranasally, such as inhalation.

A compound may be administered to a subject in an appropriate carrier or diluent, co-administered with enzyme inhibitors or in an appropriate carrier such as liposomes. The term "pharmaceutically acceptable carrier" as used herein is intended to include diluents such as saline and aqueous buffer solutions. It may be necessary to coat the compound with, or co-administer the compound with, a material to prevent its inactivation. The active agent may also be administered parenterally or intraperitoneally. Dispersions can also be prepared in glycerol, liquid polyethylene glycols, and mixtures thereof and in oils. Under ordinary conditions of storage and use, these preparations may contain a preservative to prevent the growth of microorganisms.

Pharmaceutical compositions suitable for injectable use may be administered by means known in the art. For example, sterile aqueous solutions (where water soluble) or dispersions and sterile powders for the extemporaneous preparation of sterile injectable solutions or dispersion may be used. In all cases, the composition can be sterile and can be fluid to the extent that easy syringability exists. It might be stable under the conditions of manufacture and storage and may be preserved against the contaminating action of microorganisms such as bacteria and fungi. The pharmaceutically acceptable carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of microorganisms can be achieved by heating, exposing the agent to detergent, irradiation or adding various antibacterial or antifungal agents.

Sterile injectable solutions can be prepared by incorporating active compound in the required amount with one or a combination of ingredients enumerated above, as required.

Aqueous compositions can include an effective amount of a therapeutic compound, peptide, epitopic core region, stimulator, inhibitor, and the like, dissolved or dispersed in a pharmaceutically acceptable carrier or aqueous medium. Compounds and biological materials disclosed herein can be purified by means known in the art.

Upon formulation, solutions will be administered in a manner compatible with the dosage formulation and in such amount as is therapeutically effective. The formulations are easily administered in a variety of dosage forms, such as the type of injectable solutions described above. It is contemplated that slow release capsules, timed-release microparticles, and the like can also be employed. These particular aqueous solutions are especially suitable for intravenous, intramuscular, subcutaneous and intraperitoneal administration.

The active therapeutic agents may be formulated within a mixture to comprise about $10^2$ to about $5 \times 10^6$ PFU of each construct contemplated herein. Single dose or multiple doses can also be administered on an appropriate schedule for a predetermined condition. In certain embodiments, a dual dose on day 0 may be administered in single anatomical or multiple anatomical locations in order to induce an immune response with reduced interference or different lymph nodes. In certain embodiments, a mono-, bi-, tri- or tetravalent formulation of dengue virus constructs may be administered to a subject. Any of these formulations can be provided to a subject as a single or in multiple doses. In certain embodiments, one dose can be administered then a boost some time later may be provided.

In another embodiment, nasal solutions or sprays, aerosols or inhalants may be used to deliver the compound of interest. Additional formulations that are suitable for other modes of administration include suppositories and pessaries. A rectal pessary or suppository may also be used. In general, for suppositories, traditional binders and carriers may include, for example, polyalkylene glycols or triglycerides; such suppositories may be formed from mixtures containing the active ingredient in the range of 0.5% to 10%, preferably 1% 2%.

The pharmaceutical compositions containing the α1-antitrypsin, analog thereof, or inhibitor of serine protease activity or a functional derivative thereof may be administered to individuals, particularly humans, for example by subcutaneously, intramuscularly, intranasally, orally, topically, transdermally, parenterally, gastrointestinally, transbronchially and transalveolarly.

In certain embodiments of the methods of the present invention, the subject may be a mammal such as a human or a veterinary and/or a domesticated animal.

In one embodiment of the present invention, methods provide for vaccinating a subject preparing to travel to a country with dengue virus. In other embodiments, a subject may be a resident in an endemic area. It is contemplated that a subject may be administered a single injection or dual injections on day 0, optionally followed by a boost less than 30 days, 2 months, 3 months, 6 months or as much as one year later.

Kits

Other embodiments concern kits of use with the methods (e.g. methods of application or administration of a vaccine) and compositions described herein. Some embodiments concern kits having vaccine compositions of use to prevent or treat subjects having, exposed or suspected of being exposed to one or more dengue viruses. In certain embodiments, a kit may contain one or more than one formulation of dengue virus serotype(s) (e.g. attenuated vaccines) at predetermined ratios. Kits can be portable, for example, able to be transported and used in remote areas such as military installations or remote villages. Other kits may be of use in a health facility to treat a subject having been exposed to one or more dengue viruses or suspected of being at risk of exposure to dengue virus.

Kits can also include a suitable container, for example, vials, tubes, mini- or microfuge tubes, test tube, flask, bottle, syringe or other container. Where an additional component or agent is provided, the kit can contain one or more additional containers into which this agent or component may be placed. Kits herein will also typically include a means for containing the agent, composition and any other reagent containers in close confinement for commercial sale. Such containers may include injection or blow-molded plastic containers into which the desired vials are retained. Optionally, one or more additional agents such as immunogenic agents or other antiviral agents, anti-fungal or antibacterial agents may be needed for compositions described, for example, for compositions of use as a vaccine against one or more additional microorganisms.

Embodiments of the present invention are further illustrated by the following non-limiting examples, which are not to be construed in any way as imposing limitations upon the scope thereof. It should be appreciated by those of skill in the art that the techniques disclosed in the Examples which follow represent techniques discovered to function well in the practices disclosed herein, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope herein.

EXAMPLES

Example 1

In certain exemplary methods, DENV-4 chimera constructs are generated of use in pharmaceutically acceptable compositions.

FIG. 1A illustrates an exemplary viral backbone of some embodiments disclosed herein referred to as DEN-2 PDK-53 genome (previously disclosed in PCT/US01/05142, U.S. application Ser. No. 10/204,252, each incorporated herein by reference in their entirety for all purposes) which can be used to generate modified DENV-4 constructs (also indicated as a second generation). As shown in FIG. 1A, specific amino acid substitution mutations in the nonstructural regions, such as NS1-G53D, NS3-E250V and a nucleotide substitution mutation in the 5' non-coding region, C57T in the DEN-2 PDK-53 genome have been identified. Original DENV-1, 3, and 4 constructs (also indicated as first generation) were generated by replacing the coding sequence of prM and E in the DENV-2 backbone with structural coding sequences of respective serotypes (FIG. 1B). To generate modified DEN-Vax-4 constructs that can boost replication efficiency in vitro and in vivo, and improve immunogenicity in the host, point mutations were introduced to the non-coding region, structural protein coding sequences and/or non-structural regions of the original DENVax-4 construct. For example, modifications can be made to the amino acid sequence upstream of the current DENVax-4 C/prM cleavage site to mimic wild-type dengue-4 as opposed to dengue-2 (which DENVax-4 currently contains).

Some additional modifications in certain exemplary DENV-4 constructs are provided in Table 1. Illustrated below are sequences included in certain modified DENVax-4 constructs (DENVax-4b, DENVax-4c, and DENVax-4d) aligned to the wild type sequence of DENV-2, DENV-1 and original DENVax-4. The selected changes in these sequences are in bold and underlined:

|  | C-100 Capsid --- prM |  |
|---|---|---|
| DENV-2: | NILNRRRRSAGMIIMLIPTVMA | FHLTTRN SEQ ID NO: 1 |
| DENV-4 WT: | NILNGRKRSTITLLCLIPTVMA | FHLSTRD SEQ ID NO: 2 |
| DENVax-4ori: | NILNRRRSSAGMIIMLIPTVMA | FHLTTRD SEQ ID NO: 3 |

```
                                -continued
DENVax-4b:    NILNRRRSSTITLLCLIPTVMA        FHLSTRD  SEQ ID NO: 4

DENVax-4c:    NILNGRKRSTITLLCLIPTVMA        FHLSTRD  SEQ ID NO: 5

DENVax-4d:    *ILNGRKRSTITLLCLIPTVMA        FHLSTRD  SEQ ID NO: 6
```

Figure 4:
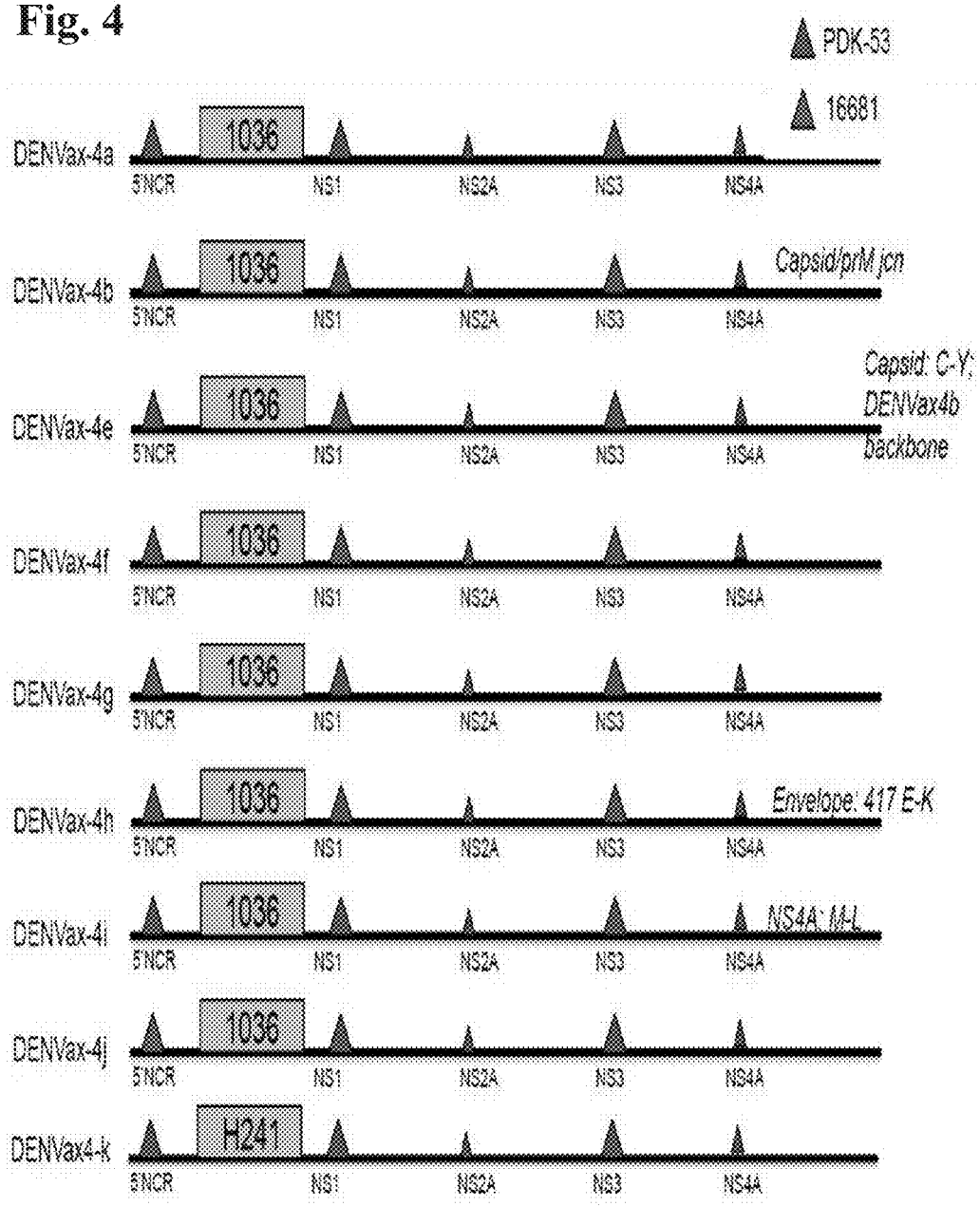
FIG. 4 represents a schematic of certain DENV-4 chimera constructs disclosed in some embodiments herein and used in vaccine formulations alone or in combination with other live, attenuated virus constructs.

FIG. 4 presents a schematic map of the original and modified DENV-4 constructs. DENVax-4e is generated using DENVax-4b sequence as a backbone, and further incorporates a C to Y mutation at amino acid 107 of Capsid protein. DENVax4f, DENVax4g and DENVax4j were built on the DENVax-4a backbone, but contain wild type reversions of the attenuating mutations of the PDK-53 sequence as indicated in FIG. 4: DENVax-4f contains wild type (DEN-2 16681) NS2A and NS4A; DENVax-4g contains wild type 5'NCR, NS2A and NS4A; and DENVax-4j contains wild type 5'NCR. DENVax4h has an E to K substitution at Envelope 417 in the DENV4 1036 sequence. DENVax4i has a methionine to leucine amino acid substitution at NS4A position 17 (synonymous position 6424 A to T of the genomic nucleic acid or amino acid position 2110 of the construct). DENVax4k has the PrM/E genes from DENV-4 H241 strain instead of 1036 strain (Table 1). Mutations constructed in DENVax4e, h, and i were based on sequence data from DENVax4 and DENVax-4b serial passages in Vero cells.

DENVax-4b contains 7 total amino acid changes, DENVax-4c contains 9 total amino acid changes, and DENVax-4d contains an amino acid deletion resulting in a frame shift of the sequence. RNA was transcribed and electroporated into Vero cells for amplification and virus rescue. DENVax-4b and DENVax-4c were tested for growth efficiency in Vero and C6/36 cells in a growth kinetics experiment, with DENVax4-P2, DENVax4-P8 and DENVax2-P2 used as controls. DENVax-4-P2 and DENVax-2-P2 are virus samples that have not been genotypically selected by viral plaque purification, a process in which individual viral plaques are picked from a DENVax-infected Vero cell monolayer, and then over-layed with agarose gel containing neutral red to visualize single plaques. DENVax-4-P8 had been selected by plaque purification to obtain a virus stock with a clonal DENVax-4 genotype. This procedure is done to generate a master seed virus (MVS) with no reverted attenuating mutations. DENVax-4c did not reach an adequate peak titer after growth in Vero cells, and had a slower initial growth rate than either DENVax-4 or DENVax-4b. There was no significant difference between the peak titers of DENVax-4 and DENVax-4b in the Vero growth curve, and both had similar initial growth rates. In the analysis C6/36 mosquito cells, growth of DENVax-4b and DENVax-4c both reached peak titers that were significantly less than wild type DENV-4, confirming their attenuation.

TABLE 1

Exemplary DENV-4 chimeric constructs: Differences in the constructs compared to DENV-4/DEN-2 PDK-53 previously disclosed

| Exemplary DENV-4 Constructs | Modifications |
| --- | --- |
| DENVax-4e | Capsid 107 C to Y mutation at position 416 with G mutated to A of DENVax-4b backbone |
| DENVax-4f | Attenuating mutations in NS2 and NS4 reverted to corresponding sequences of Dengue virus strain 16681 |
| DENVax-4g | Attenuating mutations in 5' NCR, NS2 and NS4 reverted to corresponding sequences of Dengue virus serotype 2 strain 16681 |

TABLE 1-continued

Exemplary DENV-4 chimeric constructs: Differences in the constructs compared to DENV-4/DEN-2 PDK-53 previously disclosed

| Exemplary DENV-4 Constructs | Modifications |
| --- | --- |
| DENVax-4h | Envelope 417 E to K mutation at position 2185 with G mutated to A of DENVax-4b backbone |
| DENVax-4i | NS4A 17 M to L mutation at position 6424 with A mutated to T of DENVax-4b backbone |
| DENVax-4j | Attenuating mutations in 5' NCR reverted to corresponding sequences of Dengue virus serotype 2 strain 16681 |
| DENVax-4k | Coding sequence of prM and E of DENV-2 backbone replaced with structural coding sequences of Dengue virus serotype 4 strain H241 |

Example 2

Generation of Full-Length Infectious cDNA Clones

To generate full-length infectious cDNA clones containing modified DENVax-4 construct sequences, a multi-step digestion/ligation scheme can be used. It can have the following steps: 1) insert the AgeI/MluI synthetic fragment including a modified nucleic acid sequence or a modified structural protein coding sequence (for example, b, c or d, or any of the above constructs) into pD2/3-PP1-5' to generate pD2/4i-b, c or d; 2) digest the pDENVax-4 full length cDNA clone to extract the MluI/NgoMIV fragment and insert it into the corresponding position of pD2/4i-b, c or d to obtain pD2/4i-b, c or d; 3) digest the pDENVax-4 full length cDNA clone to extract NgoMIV/XbaI fragment and insert it into the corresponding position of pD2/4i-b, c or d to generate the full length infectious clones containing modified sequences. The sequences of the final full-length infectious clones were confirmed by sequence analysis.

Virus Generation

The cDNA clones for each of the modified construct was transcribed into genomic viral RNA. The RNA was transformed into Vero cells by electroporation. The viruses were grown for 12 days while monitoring CPE, and harvested. This first harvest after electroporation was termed P1 (Passage 1). The subsequent amplifications and passages were called P2, P3, etc. There was limited CPE for the original DENVax-4, and DENVax-4b, and c, whereas DENVax-4d did not generate any noticeable CPE. Unlike other viruses when grown in vitro, the dengue viruses do not produce much CPE when/grown in Vero cells. Although the DENVax-4d virus did not generate any CPE in vitro, it was amplified in parallel with the other strains. Amplified P1 viruses (for example, DENVax-4b, c, d P1) produced high enough titers to perform sequence analysis and growth curve experiments. DENVax-4d had no titer and therefore, no virus was made after electroporation.

The DENVax-4b and -4c viruses were fully sequenced. The DENVax-4b-P2 virus had two mutations. Nucleotide 416 was at the position of a modification engineered in the capsid (near the C/prM junction) of the DENVax-4b virus. Since this was a mixed population, the nt 416 was reverting back to the "A" nucleotide instead of the engineered "G" nucleotide, causing the expected amino acid arginine to instead be a lysine. The second mutation found in the DENVax-4b-P2 virus was at nucleotide 8769. This caused a change in the amino acid from the expected glutamine to a proline. This mutation was in the NS5 gene region of the infectious clone. The DENVax-4c-P2 virus had four mutations. They were all complete conversions, unlike the DENVax-4b virus that had mixed populations. The mutation at nucleotide 400 in the capsid region of the genome affected an engineered modification at the C/prM junction. This caused the expected amino acid at that position to be a proline instead of threonine. The other three mutations were in the nonstructural genes, two of which caused amino acid changes, and one that was a silent mutation.

Phenotypic and Genetic Characterization of the Viruses

Figures 6A, 6B, 6C, 6D, 6E, 6F:
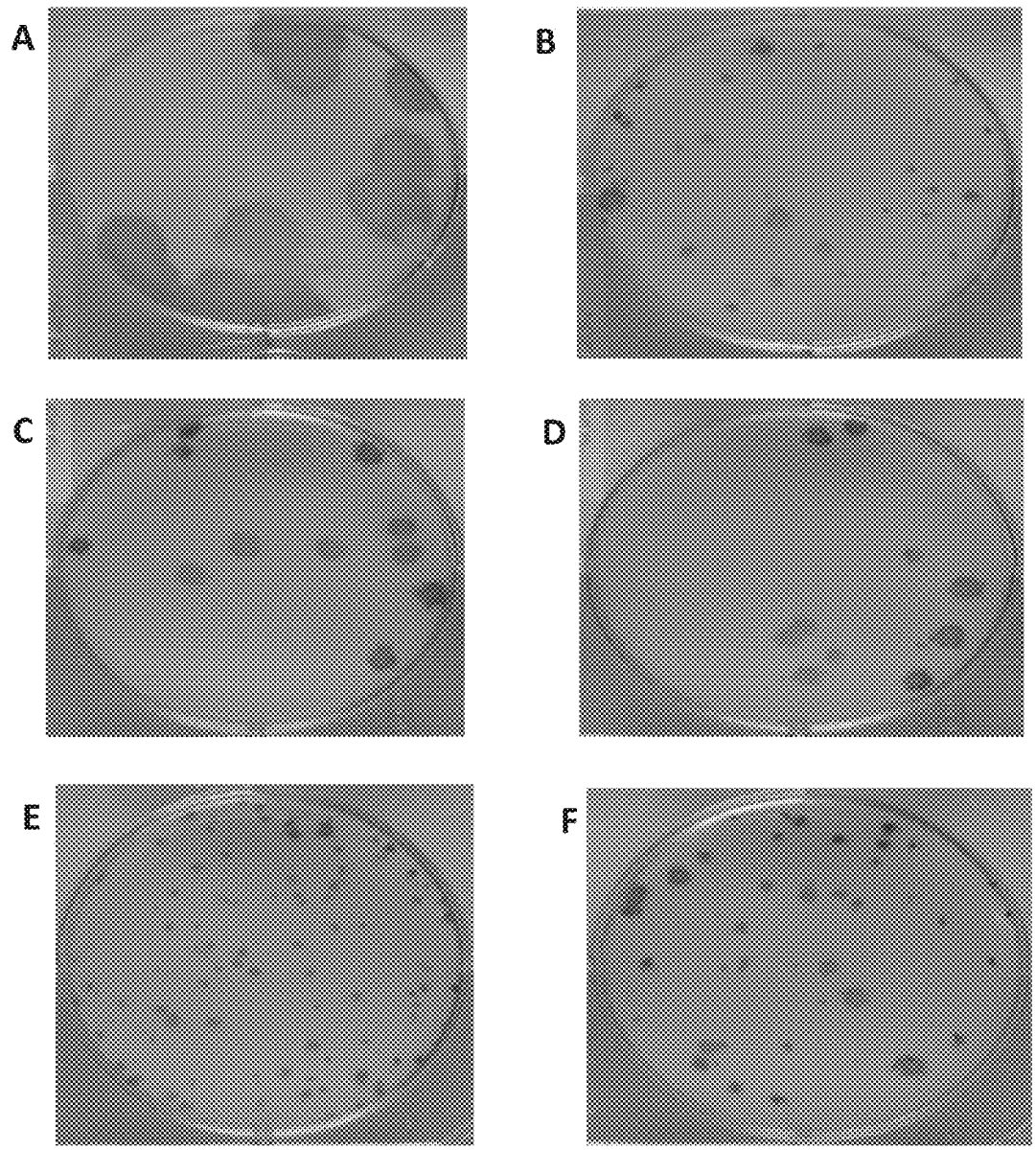
FIGS. 6A-6F are photographs providing exemplary phenotypes of ImmunoFoci (plaques) results of an exemplary experiment using certain DENV-4 chimera constructs including DENV-4 wild type (A), DENVax-4 (B), DENVax-4e (C), DENVax-4h (D), DENVax-4i (E), and DENVax-4j (F).

Phenotypic characterization of the viruses was performed in Vero cells and C6/36 (*Aedes albopictus*) cells. FIGS. 5-6 represent exemplary phenotypic character of the virus variants generated from the modified DENVax-4 constructs. Plaque size is an important attenuation marker, and was analyzed for each of the virus variants. As shown in FIG. 5, the plaque size of the DENVax-4b viruses was roughly 0.3 cm in diameter. The plaque size of the DENVax-4c viruses was about 0.1 cm in diameter. The plaque size of the DENVax-4h viruses was about 0.3 cm in diameter. The plaque size of the DENVax-4i viruses was about 0.1 cm in diameter. The plaque size of the DENVax-4c viruses was about 0.2 cm in diameter. Each of the sizes represents an average of 5-10 plaques. The plaques in the b and c candidate viruses, especially DENVax-4c were not homogenous. There was a mixed population of viruses with some small and some large plaques. The sequence variability of these small and large plaques can be characterized for possible nucleotide changes which would contribute to attenuation and fitness in vitro. If needed, these mutations could be engineered into further DENVax-4 variants. FIGS. 6A-6F present exemplary results of ImmunoFoci of the wild type DENV-4 virus (A) and each of the DENVax-4b-f virus variants (B-F).

In some exemplary methods, growth curves of DENV-4 constructs generated viruses were determined. Monolayers of Vero cells were infected at a MOI of 0.001 with various DENV-4 construct compositions (for example, DENVax-4b-j, and DENVax-4P1). In some exemplary experiments, samples were taken every other day through day 13, and aliquots were titrated. The DENVax-2-P2 virus reached peak titers more rapidly. The DENVax-4b virus was similar in peak titer and growth rate to the DENVax-4-P2 and P8 viruses. The DENVax-4c virus initially had a slower growth rate, but it finally reached a similar peak titer. The efficiency and peak titers of the DENVax-4b and DENVax-4c viruses were comparable to the original DENVax-4. In other exemplary experiments, samples were obtained every other day from day 2 through day 12. Harvested media was retained and stabilized at days 7, 9 and 11 for further study. Samples from day 2 to 12 were titered by IFA. The DENVax-4e-4h viruses showed similar peak titer to control DENVax-4 (FIG. 7).

To demonstrate attenuation, the replication efficiency of each vaccine virus should be decreased in C6/36 mosquito cells as compared to the wild-type virus. This phenotype is an essential safety feature of DENVax vaccine viruses, to ensure that there is no potential for transmission of the attenuated chimeric viruses in nature. In some exemplary methods, growth in C6/36 mosquito cells was conducted to compare the growth characteristics of the DENVax4b and DENVax-4c viruses to the wild-type dengue 4 virus (strain 1036). In other exemplary experiments, comparison was done between DENVax4e-4j and original DENVax4. Duplicate flasks of C6/36 cells were infected at a MOI of 0.001 with each of the P2 viruses (-b, -c, and wild-type) and grown for 14 days. The dengue 4 wild-type virus (WT D4 1036) replicated most efficiently and to the highest titer. The DENVax-4b virus replicated reasonably well in the C6/36 cells, reaching a peak titer of $2.7 \times 10^6$ pfu/mL by day 14. DENVax4c virus was very slow growing until after day 6 when growth was accelerated until day 14, and reaching a peak titer of $2.2 \times 10^4$ pfu/mL. At day 6, both DENVax-4b and DENVax4c were similarly attenuated for growth as compared to the wild-type in C6/36 cells, and had similar titers to the original DENVax-4. In other exemplary experiments, chimeric dengue viruses of certain embodiments herein were grown in C6/36 mosquito cells. Growth in the mosquito cells DENVax4e-4j was compared to a control DENVax4. Duplicate flasks of C6/36 cells were infected at a MOI of 0.001 with each of the P2 viruses and grown for 12 days. Samples were harvested on day 2 through day 12. Growth in the mosquito cells were compared to growth in Vero cell. Culture media was obtained and stabilized at days 7, 9 and 11. Samples from day 2 to 12 were titered by IFA and analyzed for virus production. Virus titer and growth of the constructs were compared to control DENVax4 (see FIG. 8).

Figure 7:
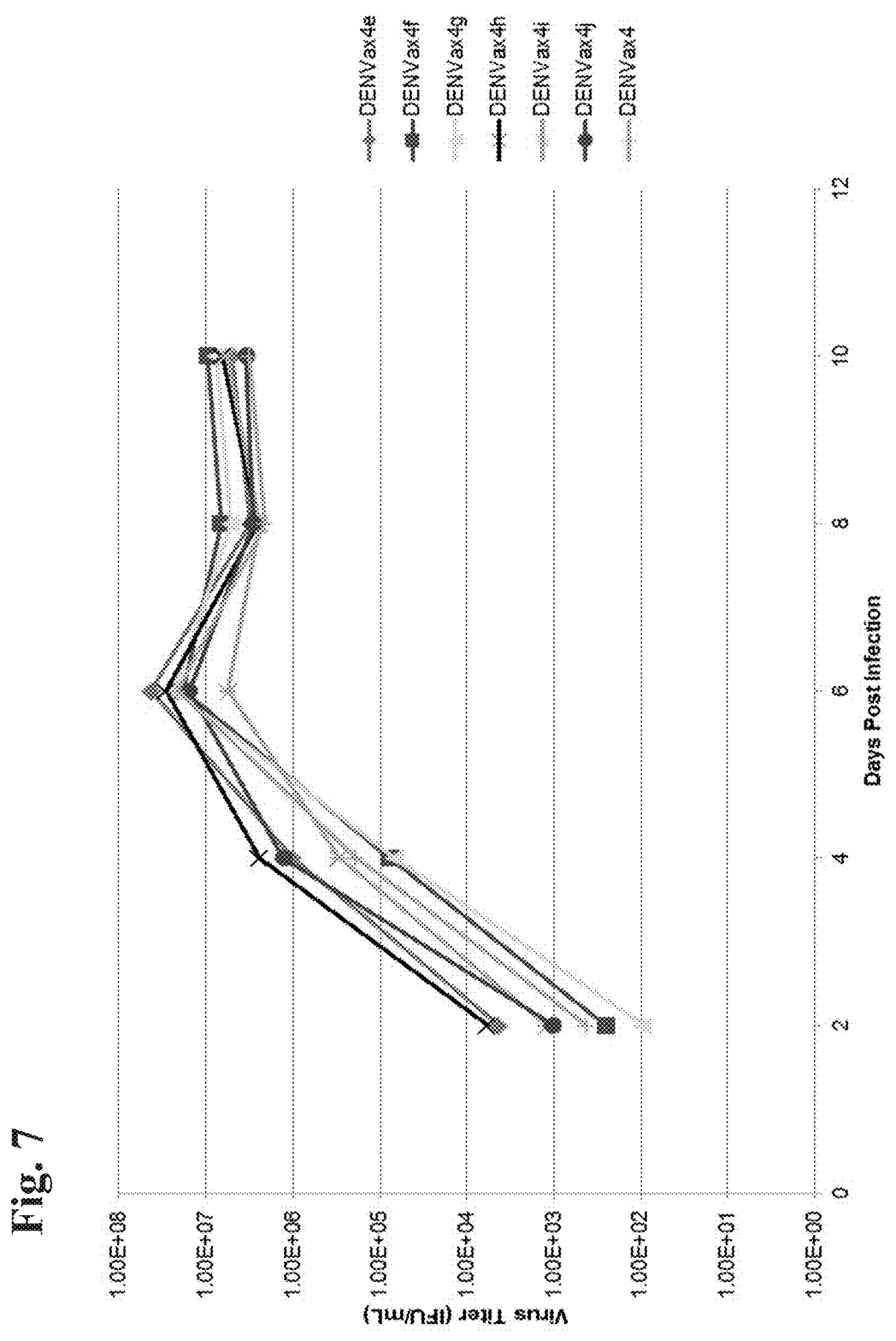
Figure 8:
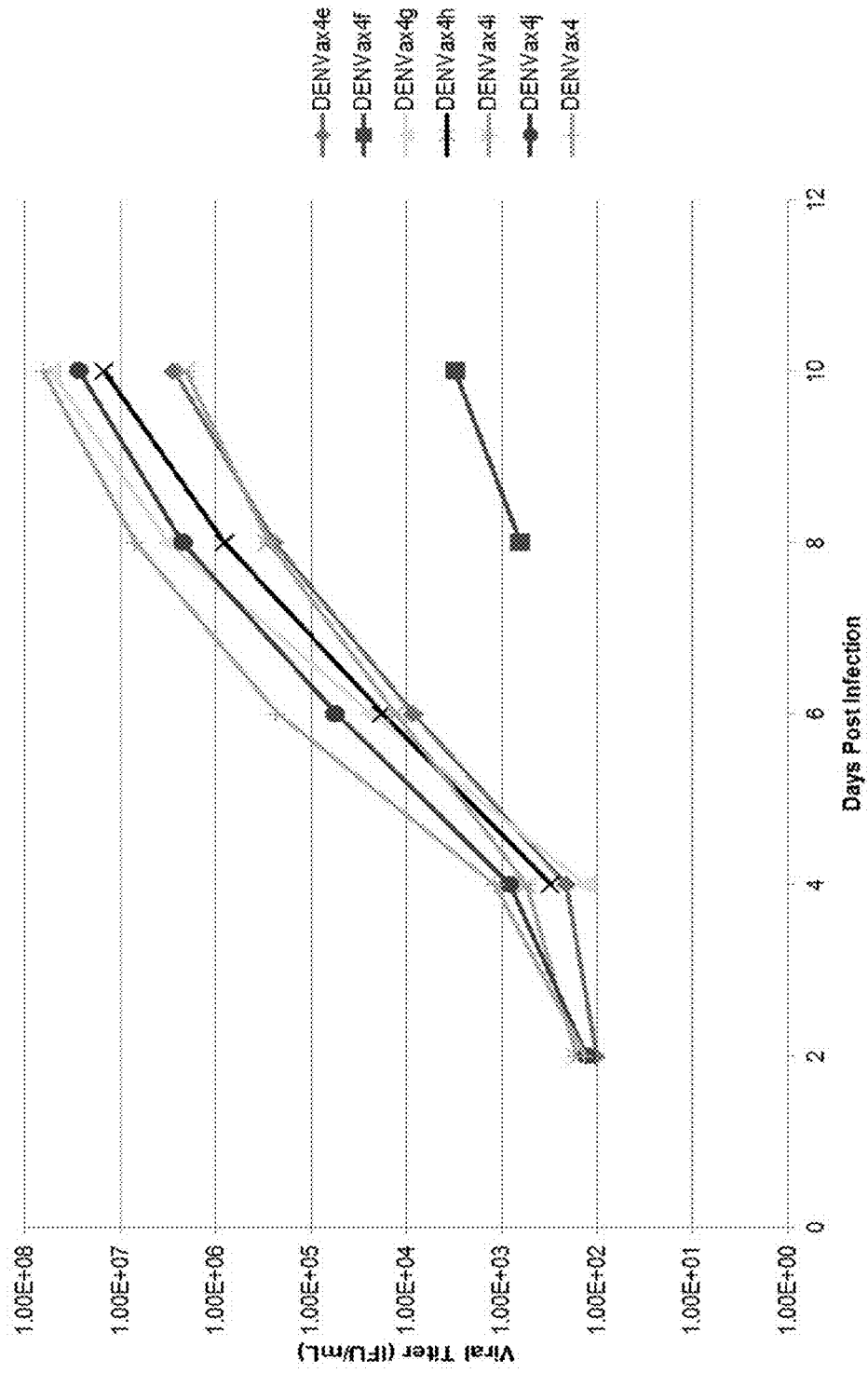
FIG. 8 is a graphic representation of viral titers over time of various DENV-4 chimeric constructs after growth in mosquito cells illustrated as "Days Post Infection."

FIGS. 7-8 represent exemplary graphs illustrating growth curves of viruses of various DENV4 constructs in Vero cells (FIG. 7) and in C6/36 mosquito cells (FIG. 8). Several novel DENVax4 constructs of certain embodiments herein produced higher titers in Vero cells (FIG. 7) than the control DENVax4 and lower titers in mosquito cells (FIG. 8) than control DENVax4, as desired for further assessment in animal models (see Table 2 below).

Safety and Efficacy of the Virus Variants in Mice

Studies were performed to analyze the immunogenicity of DENVax-4b, c or other variant viruses. Table 2 presents an exemplary study design. Groups of 10 AG129 mice were vaccinated intradermally (in the footpad) with $10^4$ PFU each of the original DENVax-4, and the separate variants. A control group was injected with excipient solution only. These mice received a booster dose after 42 days. Serum samples for serology were taken on days 42 and 56 post primary inoculation, and seroconversion was analyzed by PRNT. There was no significant improvement in the immunogenicity of DENVax-4 when using the second generation DENVax-4b and c variants as immunogens.

TABLE 2

Summary of Mouse Study Design

| | Group | Dose | Number of immunizations | Number of animals |
|---|---|---|---|---|
| 1 | DENVax-4 | $10^4$ PFU | 2 | 10 |
| 2 | DENVax-4b | $10^4$ PFU | 2 | 10 |
| 3 | DENVax-4c | $10^4$ PFU | 2 | 10 |
| 4 | TFA | NA | 2 | 10 |

To further modify and amplify the immunogenicity of DENVax-4b, this virus was adapted in vitro to Vero cell growth. This was performed by 10 blind passages in Vero cells, with the hypothesis that adaptation in mammalian cell culture would boost the replicative capacity of the virus and thus its immunogenicity. This "new" second generation DENVax-4 was termed DENVax-4b-P10 (Passage-10).

Another study was performed to evaluate different tetravalent formulations of dengue virus vaccine including three separate DEN4 viruses; first generation, second generation (4b construct) and the homologous wildtype DEN4 1036. Groups of 6 mice were injected intradermally with a tetravalent vaccine formulation containing $10^4$ PFU DENVax-1, $10^3$ PFU DENVax-2, $10^4$ PFU DENVax-3 and $10^5$ PFU DENVax 4 (4:3:4:5) in a 50 µL volume. Control mice were injected by the same route with $10^5$ PFU of $1^{st}$ generation, $2^{nd}$ generation or wildtype 1036 monovalent DENV4. A group of mice injected with diluent only was included as a control. All mice received a booster injection on day 42 with the corresponding vaccine formulation, and mice were bled on days 0, 21, 41 and 56 post primary inoculation to assess the presence of neutralizing antibodies against all four DENV serotypes. On day 56, mice from groups 4, 5 and 6 were challenged with DENV-2 (NGC strain) to assess for survival (there is currently no mouse-adapted lethal DENV4 strain to use for efficacy analysis). As illustrated in Table 3, the first and second generation DENVax-4 vaccines have comparable immunogenic profile when administered alone. However, when they are given in the context of tetravalent dengue virus vaccine, immune responses to DENV-4 are diminished due to interference affecting only the second generation DENVax-4. Wild type DENV4 was highly immunogenic and in the context of tetravalent dengue virus vaccine it interferes and suppresses the neutralizing antibody responses elicited by the other three dengue virus vaccines. Wild type DENV4, the first generation and the second generation DENVax-4 provided partial protection against heterologous DENV-2 challenge.

Safety and Efficacy of Second Generation DENVax in NHP

TABLE 3

Mouse study #2 study design and PRNT results

| Group | Dose | DENV1 | DENV2 | DENV3 | DENV4 |
|---|---|---|---|---|---|
| 1 DENVax ($1^{ST}$ generation DENVax-4) | 4:3:4:5 | 1280 (320) | 640 (320) | >1280 (320) | 640 (160) |
| 2 DENVax (DENVax-4 was replaced with wild type DENV-4) | 4:3:4:5 | 160 (320) | 160 (160) | 320 (160) | 640 (640) |
| 3 DENVax (DENVax-4 was replaced with $2^{nd}$ generation DENVax-4) | 4:3:4:5 | >1280 (640) | 640 (320) | >1280 (640) | 80 (80) |
| 4 DENVax-4 ($2^{nd}$ generation) | $10^5$ | X | X | X | 320 (80) |

TABLE 3-continued

Mouse study #2 study design and PRNT results

| Group | Dose | DENV1 | DENV2 | DENV3 | DENV4 |
|---|---|---|---|---|---|
| 5 Wild type DENV-4 | $10^5$ | X | X | X | 640 (320) |
| 6 DENVax-4 ($1^{st}$ generation) | $10^5$ | X | X | X | 320 (80) |

Figure 3:
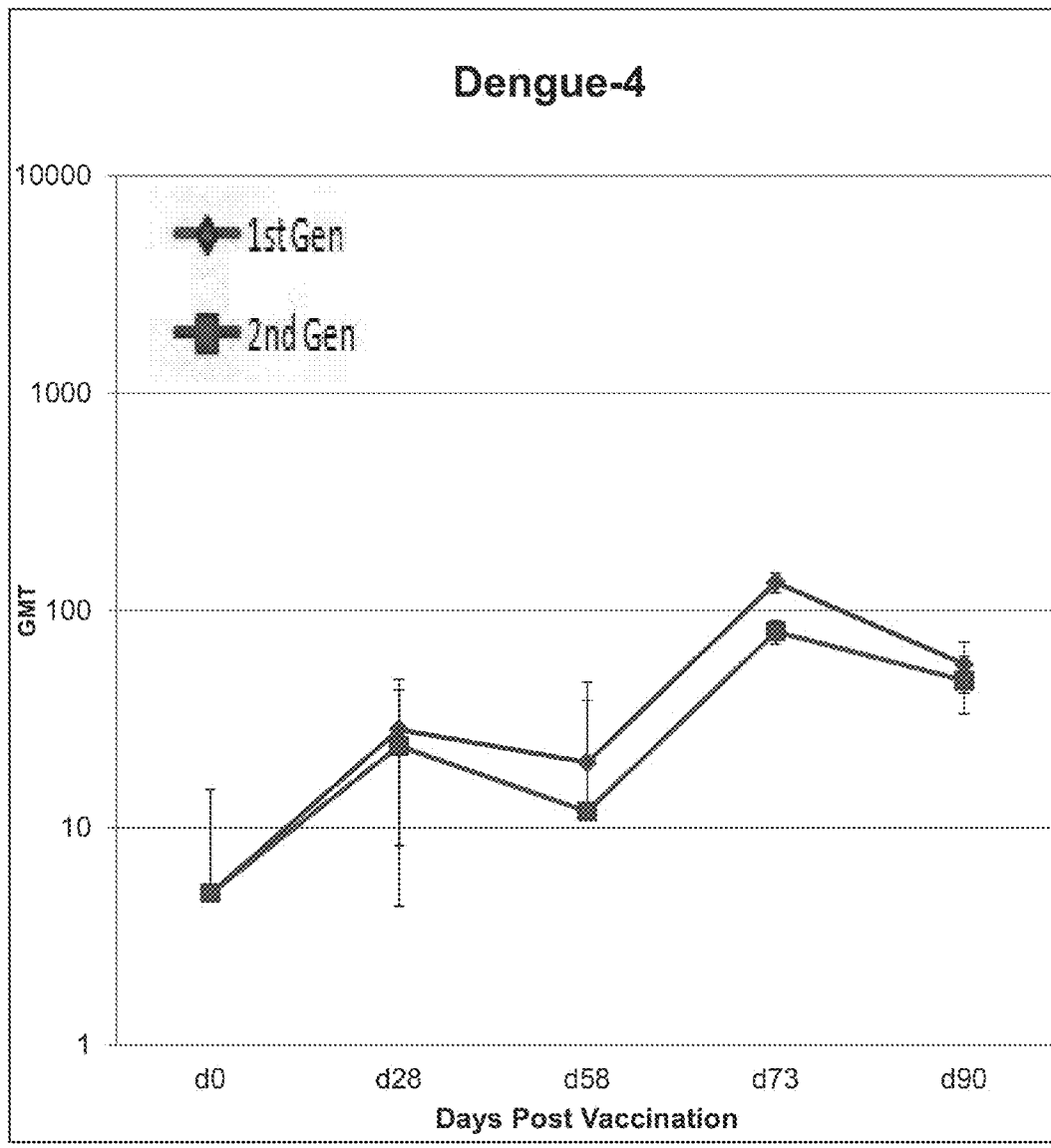
FIG. 3 represents an exemplary graph of an experiment related to production of DENV-4 neutralizing antibody titers produced by an animal model immunized with a vaccine composition having DENV-4 chimeric viral constructs of certain embodiments disclosed herein.

The immunogenicity of DENVax in groups of four Cynomologus macaques was evaluated after subcutaneous injection of each tetravalent DENVax formulation (Table 4 and FIG. 2) in 0.5 mL injection volume. The goal of this study was to evaluate the lead second generation DENVax-4 construct, as compared with the first generation DENVax-4. Additionally, different methods were explored to improve the neutralizing antibody responses to DENV-4 elicited by DENVax. These included testing a formulation which contained 10× the dose of DENVax-4 as used previously (termed "new formulation"), and also lowering the DENVax-2 component of the tetravalent mixture, as this vaccine is the most immunogenic of the four vaccine virus strains. Different dosing days were tested, and priming and boosting on the same day were compared (Day 0) to priming on Day 0 and boosting on Day 60. Samples for serology were taken on days 0, 28, 58, 73, and 90. The kinetics of neutralizing antibody titers against DENV-4 variant virus and the original was shown in FIG. 3 as an example, where comparable levels were observed.

TABLE 4

NHP Study Design:

| Groups | Vaccine Source | Formulation | Treatment |
|---|---|---|---|
| 1 | DENVax Formulation (Clinical Stock) | 2e4, 5e4, 1e5, 3e5 | 2 dose (day 0) |
| 2 | DENVax Formulation (4b-P10) | 2e4, 5e4, 1e5, 3e5(4b) | 2 dose (day 0) |
| 3 | DENVax Formulation (Clinical Stock) w/10x DENVax-4 | 2e4, 5e4, 1e5, 3e6 | 2 dose (day 0) |
| 4 | DENVax Formulation (Clinical Stock) w/10x DENVax-4 | 2e4, 5e4, 1e5, 3e6 | 2 dose (0, 60) |
| 5 | DENVax New formulation | 2e4, 1e4, 1e5, 3e6 | 2 dose (0, 60) |

Vaccine formulations for the NHP studies were prepared in bulk. Group 1 received vaccine which was cGMP manufactured and is identical to the vaccine which is currently being tested in human clinical trials. Vaccines were given to the NHPs and subsequently back-titrated to determine the actual dose. These results are presented in Table 5 below.

TABLE 5

Vaccine Stocks-back titration results:

| DENVax | iFFU/dose GP1 | desired dose GP2 | back titration | desired dose GP3 and 4 | back titration | desired dose GP5 | back titration |
|---|---|---|---|---|---|---|---|
| D1 | 2.00E+04 | 2.00E+04 | 1.90E+04 | 2.00E+04 | 1.80E+04 | 2.00E+04 | 1.80E+04 |
| D2 | 5.00E+04 | 5.00E+04 | 2.60E+04 | 5.00E+04 | 2.40E+04 | 1.00E+04 | 3.60E+03 |
| D3 | 1.00E+05 | 1.00E+05 | 1.80E+05 | 1.00E+05 | 1.40E+05 | 1.00E+05 | 1.70E+05 |
| D4 | 3.00E+05 | 300000 (4b) | 2.10E+05 | 3.00E+06 | 2.90E+06 | 3.00E+06 | 3.00E+06 |

Samples for viremia were taken after the primary dose on days −11 (baseline), 3, 5, 7, 9, 11, 13, 15, 17, 21, 28, 58, 62 and 66. RNA was extracted from the serum sample and virus titer was determined by tetraplex qRT-PCR assay. The only virus which gave any detectable viremia was DENVax-2, and this resolved by day 21 after primary vaccination. No virus was detected after the booster dose of vaccine was administered.

Serology was evaluated using a high throughput PRNT assay in a 96 well plate. Comparison of the first and second generation DENVax-4 (Group 1 compared to group 2) showed no significant difference in immunogenicity of these two viruses (Table 6).

TABLE 6

Geometric Mean Titers of NHP study.

| Group | DEN | d0 | d28 | d58 | d73 | d90 | d128 | d149 | d181 | d210 |
|---|---|---|---|---|---|---|---|---|---|---|
| 1 | 1 | 5 | 226.3 | 134.5 | 160.0 | 95.1 | 67.3 | 95.1 | 226.3 | 226.3 |
| 5455a | 2 | 5 | 1810.2 | 1280.0 | 905.1 | 905.1 | 761.1 | 761.1 | 761.1 | 380.5 |
| 0.0 | 3 | 5 | 226.3 | 190.3 | 320.0 | 226.3 | 95.1 | 134.5 | 226.3 | 160.0 |
|  | 4 | 5 | 28.3 | 20.0 | 134.5 | 56.6 | 23.8 | 33.6 | 113.1 | 67.3 |
| 2 | 1 | 5 | 33.6 | 16.8 | 47.6 | 40.0 | 23.8 | 23.8 | 20.0 | 67.3 |
| 5455b | 2 | 5 | 1076.3 | 1280.0 | 905.1 | 1076.3 | 1076.3 | 1280.0 | 640.0 | 640.0 |
| 0.0 | 3 | 5 | 67.3 | 33.6 | 226.3 | 80.0 | 23.8 | 28.3 | 28.3 | 33.6 |
|  | 4 | 5 | 23.8 | 11.9 | 80.0 | 47.6 | 23.8 | 33.6 | 23.8 | 20.0 |
| 3 | 1 | 5 | 80.0 | 47.6 | 56.6 | 67.3 | 40.0 | 33.6 | 134.5 | 134.5 |
| 5456 | 2 | 5 | 380.5 | 320.0 | 538.2 | 538.2 | 190.3 | 508.0 | 269.1 | 269.1 |
| 0.0 | 3 | 5 | 95.1 | 80.0 | 134.5 | 95.1 | 40.0 | 40.0 | 160.0 | 113.1 |
|  | 4 | 5 | 95.1 | 134.5 | 160.0 | 160.0 | 134.5 | 134.5 | 320.0 | 226.3 |
| 4 | 1 | 5 | 16.8 | 16.8 | 80.0 | 56.6 | 23.8 | 23.8 | 16.8 | 20.0 |
| 5456 | 2 | 5 | 134.5 | 134.5 | 269.1 | 320.0 | 134.5 | 134.5 | 95.1 | 80.0 |
| 0.60 | 3 | 5 | 23.8 | 23.8 | 134.5 | 95.1 | 23.8 | 20.0 | 28.3 | 28.3 |
|  | 4 | 5 | 23.8 | 20.0 | 134.5 | 113.1 | 56.6 | 80.0 | 28.3 | 28.3 |
| 5 | 1 | 5 | 20.0 | 11.9 | 134.5 | 134.5 | 33.6 | 20.0 | 28.3 | 14.1 |
| 5356 | 2 | 5 | 28.3 | 8.4 | 95.1 | 80.0 | 10.0 | 5.9 | 5.0 | 5.0 |
| 0.60 | 3 | 5 | 23.8 | 11.9 | 190.3 | 190.3 | 23.8 | 28.3 | 33.6 | 28.3 |
|  | 4 | 5 | 33.6 | 33.6 | 269.1 | 134.5 | 113.1 | 56.6 | 80.0 | 67.3 |

Evaluating a higher dose of DENVax-4 (Group 3) revealed that a significant difference in the kinetics of DENV-4 neutralizing antibody responses could be obtained. The peak titers remained roughly equivalent (within a 2-fold dilution range) when comparing the two different vaccine formulations, but the rate in which the peak titer to DENV-4 was obtained was much earlier when the immunization was performed with a greater amount of DENVax-4. Further, when the amount of DENVax-2 was lowered in the formulation (Group 5), this had no marked difference in the kinetics or peak titer of DENV-4 in serum responses in this tetravalent DENVax vaccine.

Figure 9:
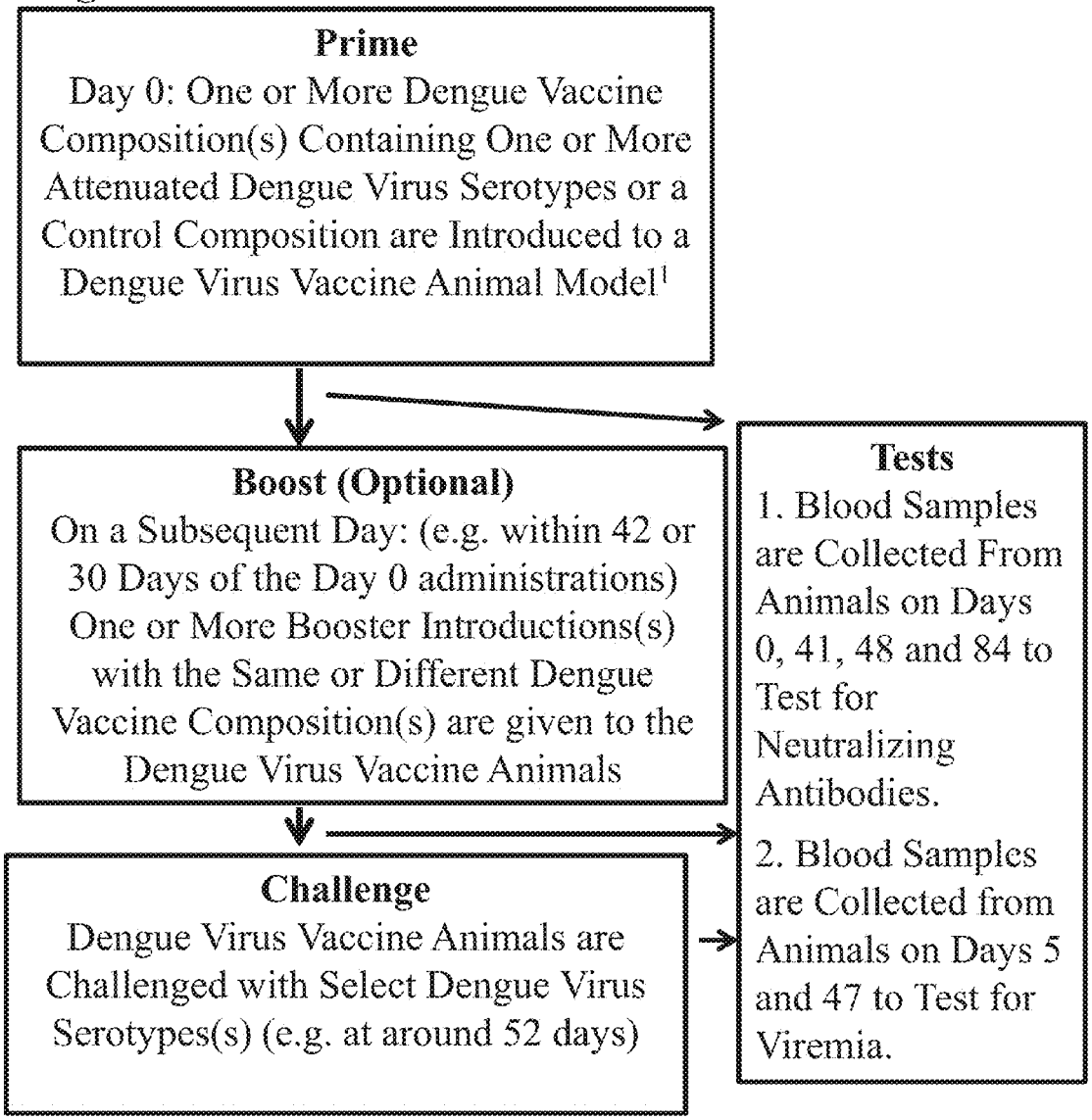
FIG. 9 is a flow chart representing an acceptable animal model used to test various DENV-4 chimeric constructs to induce an immune response to DENV-4 in the animal model.
Figure 13:
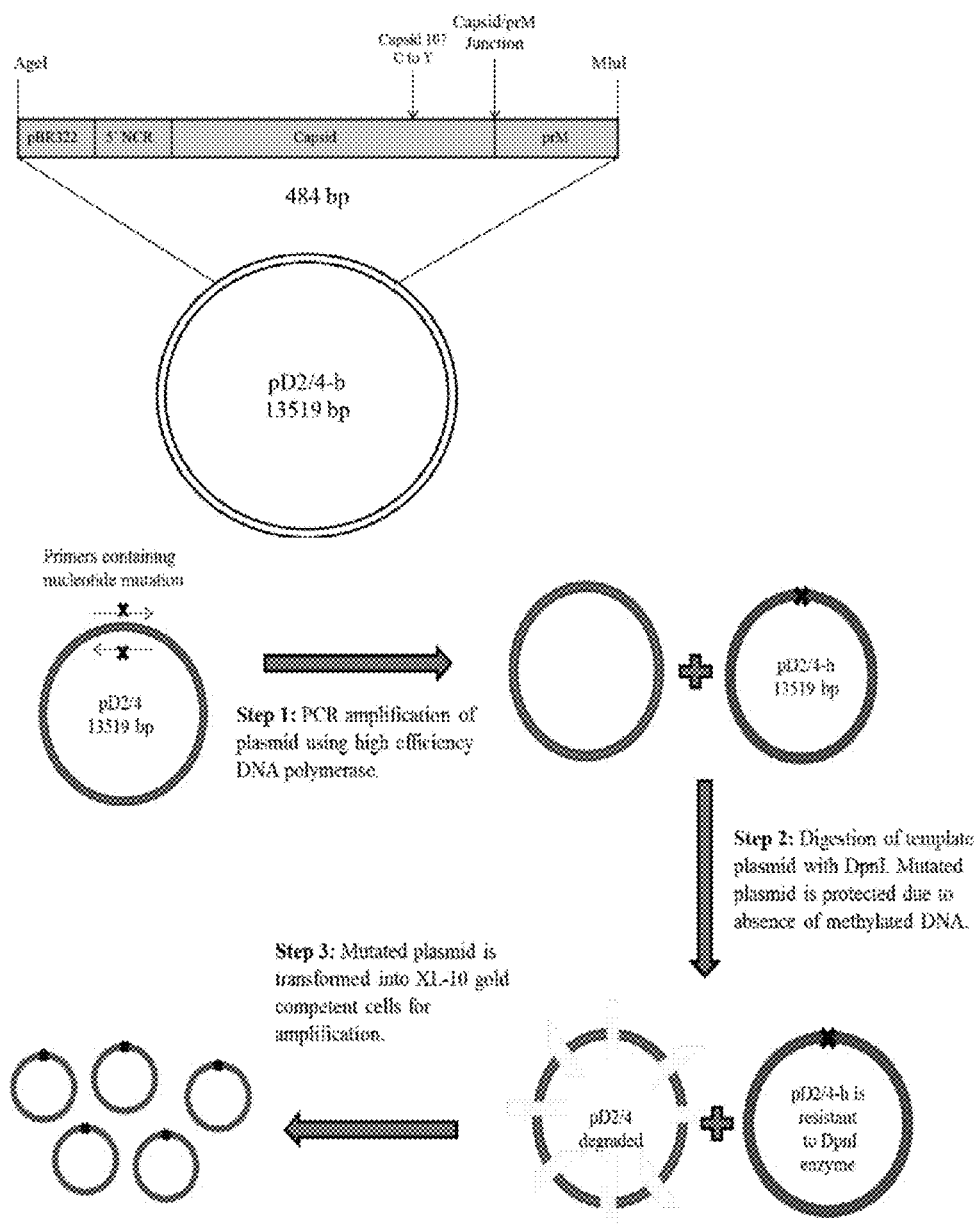
FIG. 13 illustrates an exemplary schematic of cloning of various DENV-4 constructs disclosed herein.
Figure 15:
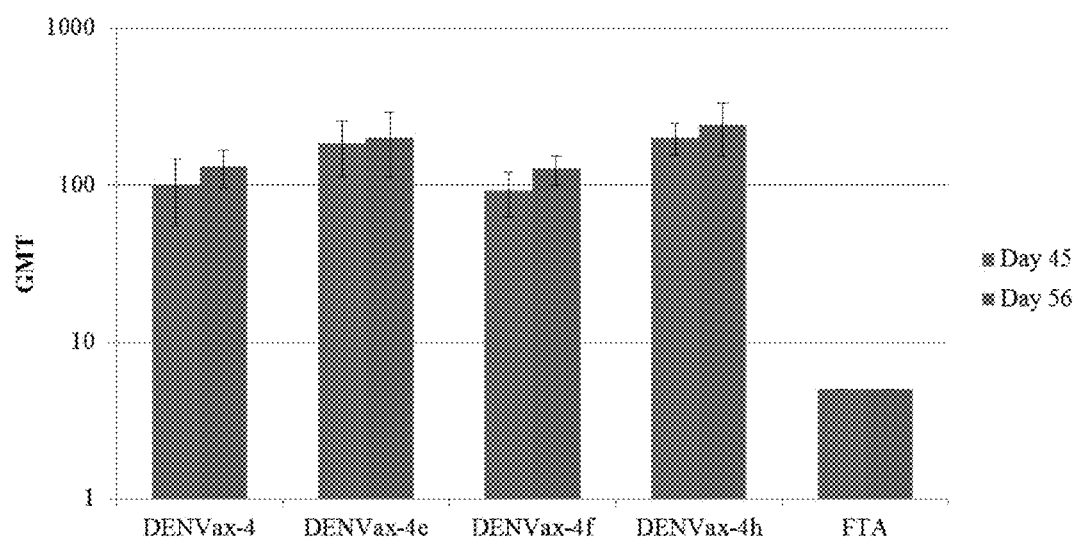
FIG. 15 represents an exemplary histogram plot comparing immunogenicity in mice of various DENV-4 constructs disclosed herein.
Figure 16:
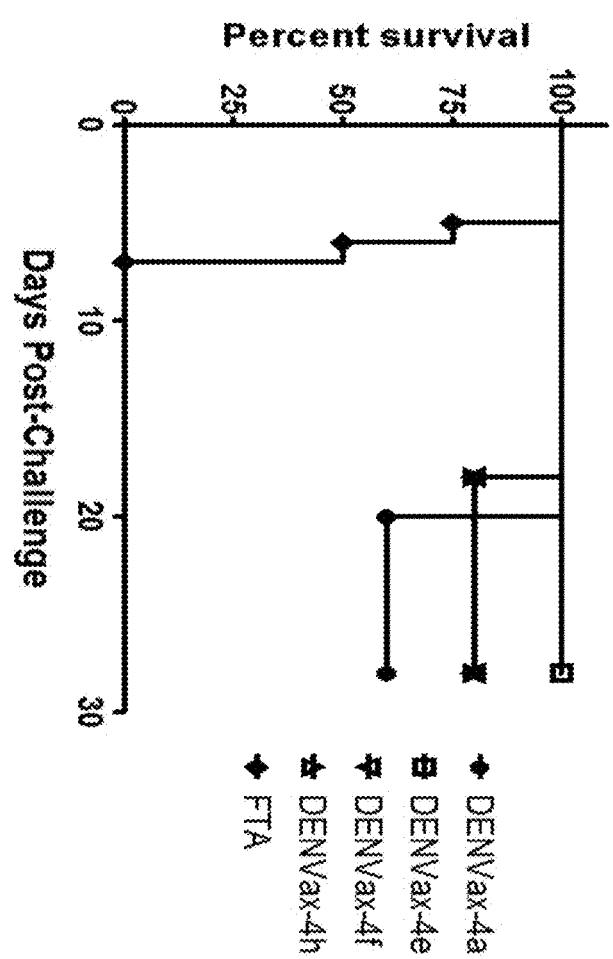
FIG. 16 represents an exemplary graph illustrating efficacy using various DEN-4 constructs in mice to protect immunized mice against challenge by wt-DENV, represented as survival.
Figure 18:
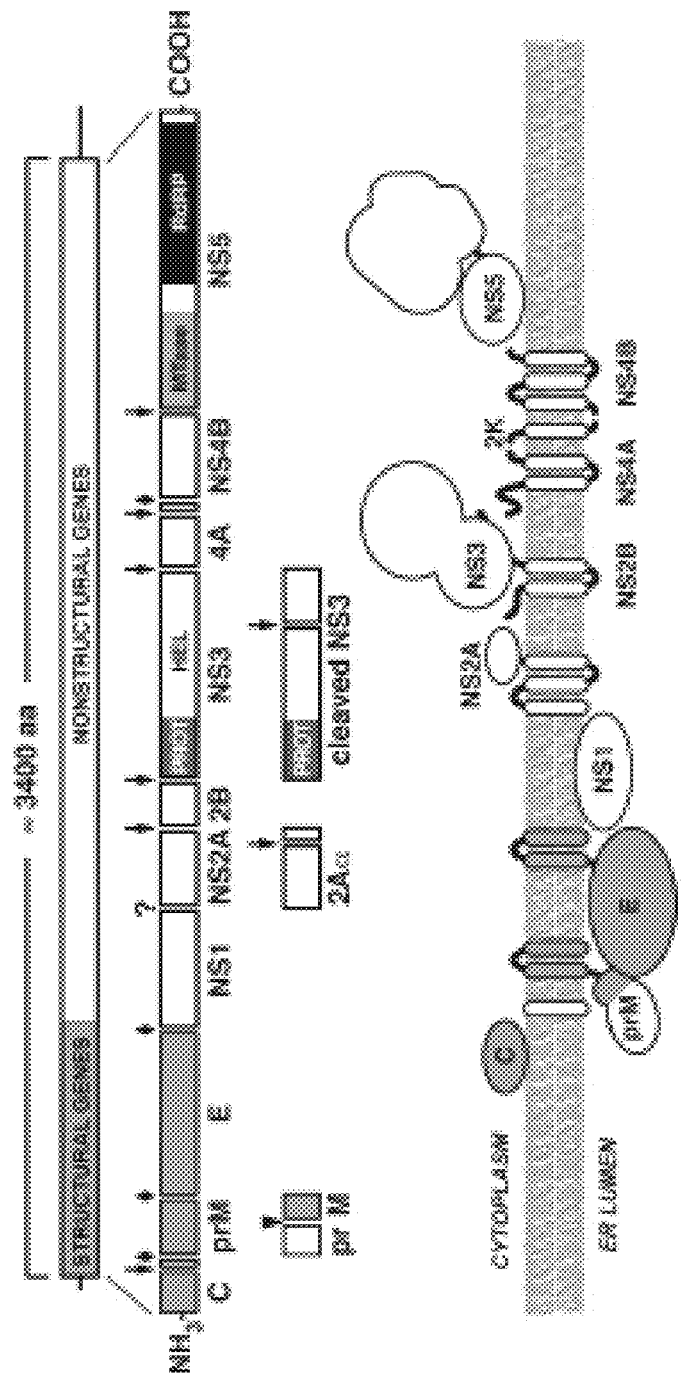
FIG. 18 represents a schematic of a DENV virus including open reading frames for proteins of DENV.

FIG. 9 represents a flow chart of one exemplary procedure for testing safety and efficacy of the virus construct disclosed herein in an animal model. For example, composition(s) that include one or more chimeric Dengue viruses of use as a vaccine, such as compositions of DENVax4e, DENVax4f or DENVax4h, or other chimeric constructs or a control composition can be tested in animal models, e.g. AG129. Animals can be primed on day 0, and subsequently boosted with the same or different Dengue virus vaccine compositions on or before day 30 or day 42 or other appropriate time. Then, the animals can be challenged with exposure to one or more Dengue virus serotypes to assess induction of an immune response to the challenge. Blood samples can be collected, for example, on days 0, 30, 41, 48, 52 or 84 or other appropriate day to test for neutralizing antibodies, and on other days such as 5 and 47 to test for viremia (or as deemed appropriate for the composition and administration protocol chosen).

Virus Cloning and Rescue to P1

Plasmid mutagenesis was used to create the new DENV-4 chimeric clones of use in vaccine compositions disclosed herein. Primers coding for point mutations were synthesized and used to amplify an entire new infectious clone. The template was digested by DpnI and the subsequent plasmid was sequenced. RNA was transcribed and electroporated into Vero cells to create a virus at passage level 0 (P0) and then amplified by a single passage in Vero cells (P1).

Modifications at the Capsid/PrM junction in the DENVax-4b clone did not appear to cause an increase in DENV-4 immunogenicity in NHP studies. Using the sequencing data from the blind serial passages of DENV-4 and DENVax-4b, 3 point mutations that may increase Vero cell adaptation were identified. In addition some attenuating mutations were reverted back to the wild-type sequence to increase immunogenicity in mice. As presented in FIG. 6, the larger IFU size and lytic phenotypes of DENVax-4e and DENVax-4h illustrates the potential that either of these clones may show an increase in immunogenicity in mice. Experiments to analyze the growth kinetics of each of the new DENVax-4 clones were conducted to determine whether the inserted modifications increase Vero cell adaptation. Test in A129 mice to analyze immunogenicity are also conducted.

Growth Kinetics

Serial passaging of Dengue vaccine strains in Vero cells is a classic method for selecting strains which are better fit to grow in vitro. In these exemplary growth experiments, DENVax-2 (FIG. 1) was included as a control and displayed the highest initial titer at day 2, followed by DENVax-4b-P10, DENVax-4, and DENVax-4b-P1. At the end of the growth period (day 12) DENVax-2 had the highest peak titer, followed by DENVax-4b-P10, DENVax-4b-P1, and DENVax-4.

Amino Acid Changes in Sequences

DENVax4-P10 genomic sequencing demonstrated mutations which corresponded to amino acids E-417 E-K (Glu-Lys) and NS4A-17 M-L. DENVax4b-P10 sequencing showed a mutation which corresponded to amino acid C-107 C-Y. The E-417 E-K mutation changes the amino acid residue so that an amine group (NH2) is substituted for a carbonyl hydroxyl group. However, the R group is still charged and remains hydrophilic. The NS4A-17 M-L mutation results in removal of a sulfate from the R group, but maintains nonpolarity resulting in a hydrophobic amino acid. The C-107 C-Y mutation results in drastic change in the R group. Cysteine has an SH group that is capable of forming disulfide bonds, while tyrosine has a carbon benzene ring with a hydroxyl group. This causes the amino acid residue to become hydrophilic instead of hydrophobic, affecting its interaction with the other amino acid R groups.

Figure 19:
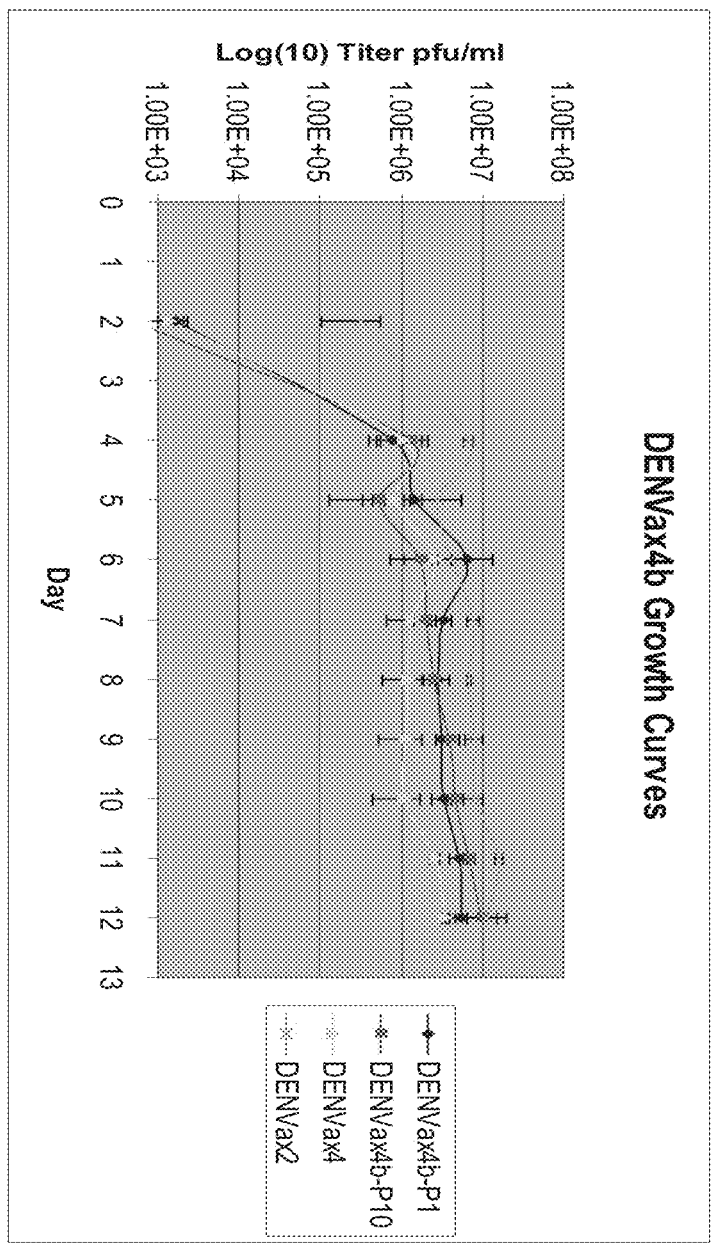
FIG. 19 represents a graphic illustration of titer achieved after growth of various DEN-4 constructs in a mammalian cell line contemplated of use herein.

FIG. 19 is a graphic representation of titers of DENVax-4 constructs during growth kinetics experiment. The day each sample was taken is plotted on the x-axis and the titer is plotted on the y-axis.

Neutralizing Antibodies in NHP Vaccinated with DENVax

Figure 20:
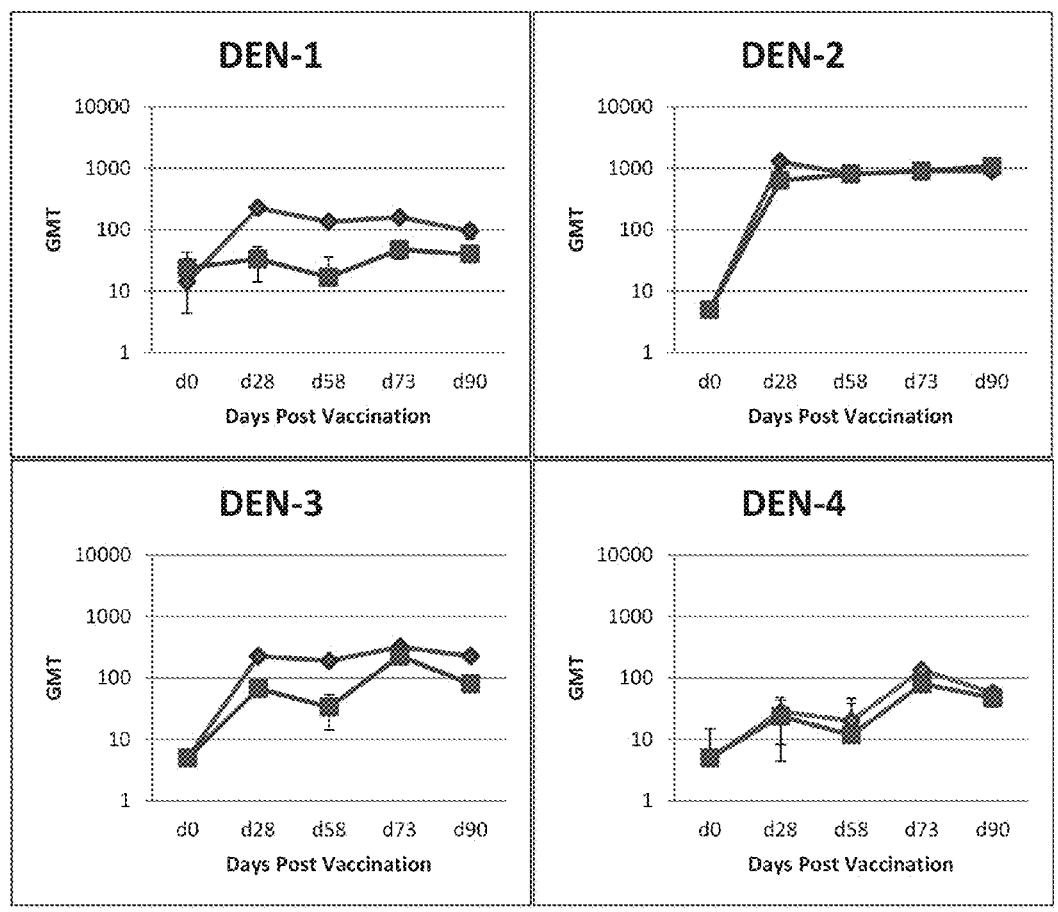
FIG. 20 represents various levels of neutralizing antibodies after vaccination with various dengue constructs in non-human primates post vaccination, represented as days post vaccination.

In certain methods, evaluation of the DENV-4 chimeric construct viruses took place with a larger study testing immunization regimens. The immunogenicity of DENVax-4b compared to that of DENVax-4a was tested. Groups 1 and 2 were vaccinated on Day 0 with 2 doses and given no booster vaccination. Equivalent titers of either DENVax-4 (diamonds) or DENVax-4b (squares) were used in all doses. No significant differences in geometric mean titers (GMT) of neutralizing antibodies were found between any of the serotypes including DENV-4. This suggests that using DENVax-4b in tetravalent DENVax does affect or increase the neutralizing antibody response against DENV-4. FIG. 20: GMT values comparing Groups 1 (DENVax-4, diamonds) and 2 (DENVax-4b, squares). GMT values are measurements of neutralizing antibody values from Plaque Reduction Neutralization Technique.

Figure 21:
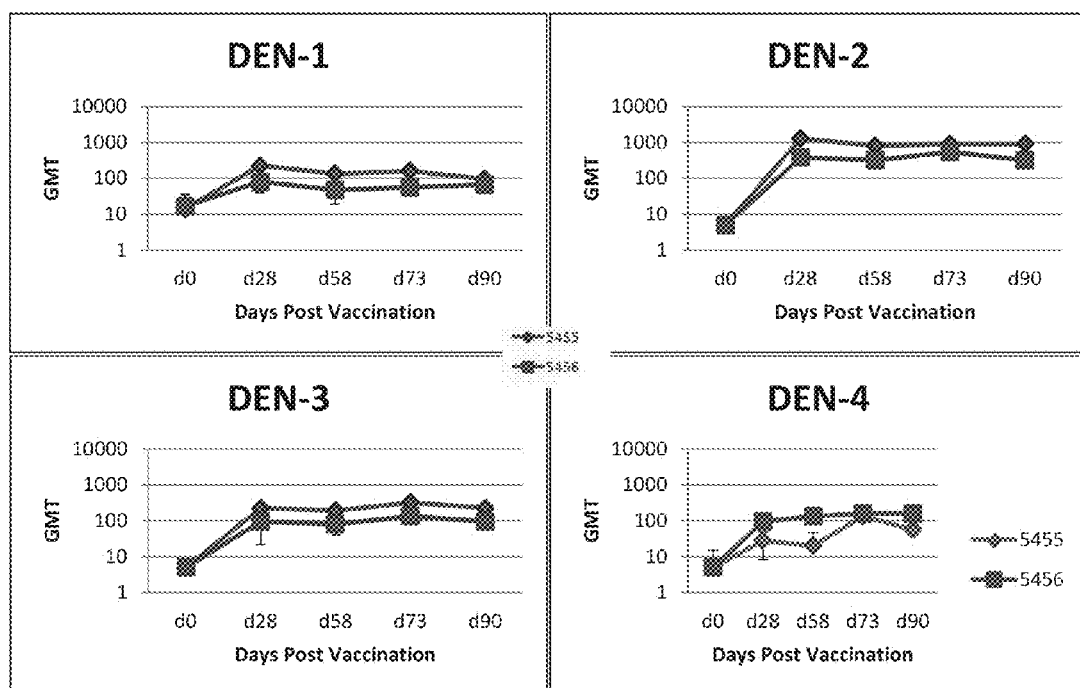
FIG. 21 represents various levels of neutralizing antibodies after vaccination with various dengue constructs in non-human primates post vaccination, represented as days post vaccination.

Neutralizing antibody responses in Groups 1 and 3 were compared to determine whether increasing the dose of DENVax-4 in tetravalent DENVax increased immunogenicity against DENV-4. Results demonstrated that primates immunized with a higher dose of DENVax-4 showed an increased in GMT of primary neutralizing antibodies detected in the first 60 days compared to those immunized with traditional tetravalent DENVax. There was no significant difference in GMT between the other DENV serotypes (FIG. 21). This suggests that a higher dose of DENVax-4 improves the neutralizing antibody response against DENV-4.

Figure 22:
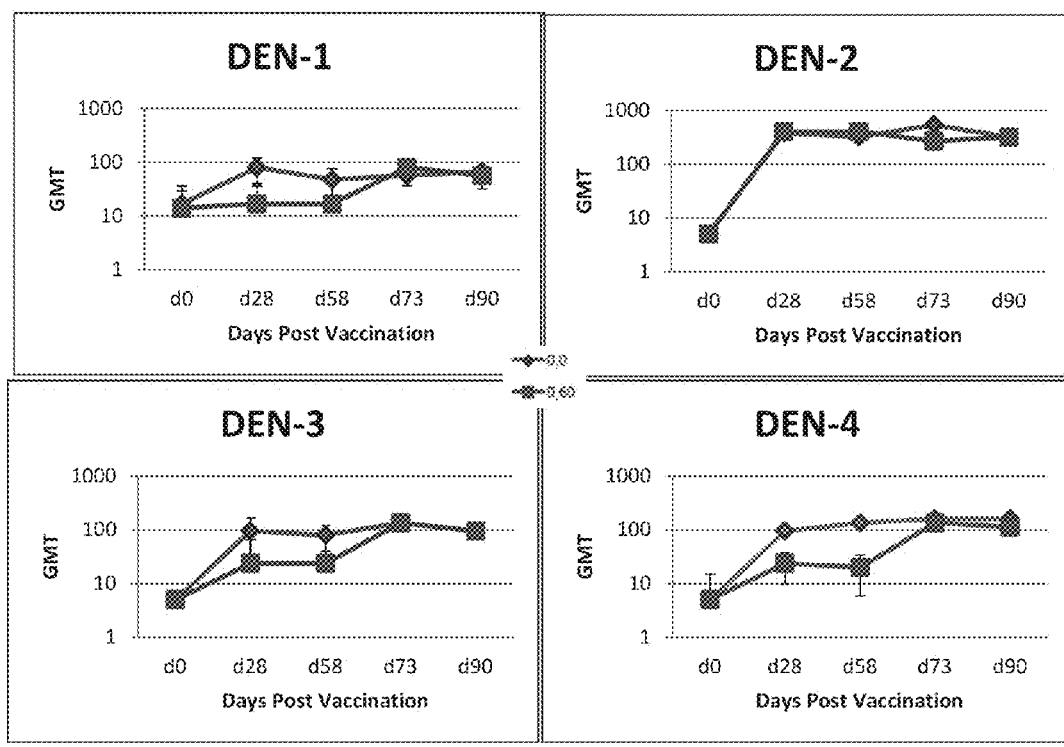
FIG. 22 represents various levels of dengue constructs in a mouse post vaccination, represented as days post vaccination.
Figure 23:
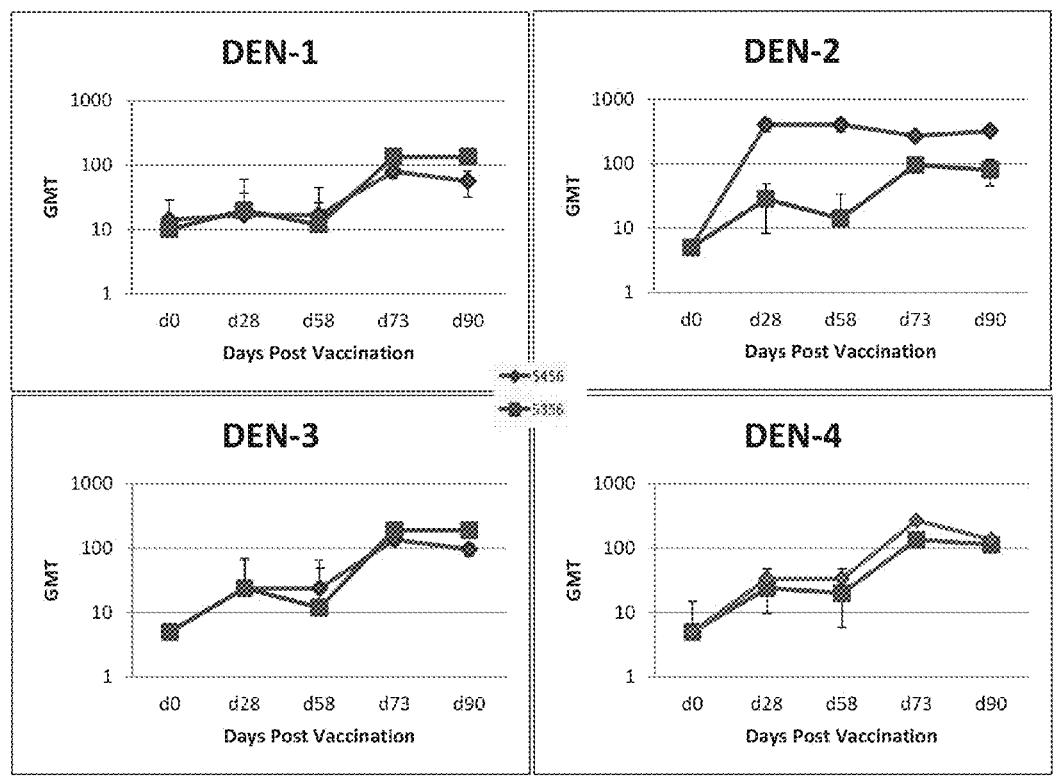
FIG. 23 represents various levels of dengue constructs in a mouse post vaccination, represented as days post vaccination.

Neutralizing antibody responses were compared in Groups 1 (diamonds) and 4 (squares) to test the effect of the immunization schedule on immunogenicity (FIG. 22). FIG. 22 illustrates GMT values demonstrating effect of vaccine schedule on neutralizing antibody response. This indicates that 2 doses on Day 0 and no boost has no adverse effects compared to 1 dose on Day 0 and 1 dose on Day 60. Finally, data from Groups 4 (diamonds) and 5 (squares) were compared to see if decreasing the dose of DENVax-2 had an effect on immunogenicity of DENVax-4. Results show no significant difference in GMT against DENV-4, but GMT against DENV-2 is significantly reduced in Group 5. This indicates that the antibody response elicited by the DENVax-2 dose does not have an adverse effect on the antibody response elicited by DENVax-4 (FIG. 23). FIG. 23 represents GMT values for Groups 4 (diamonds) and 5 (squares) for all DENV serotypes. Results were determined using Plaque Reduction Neutralization Technique.

The results of these experiments support that constructs disclosed herein improve DENV-4 neutralizing antibody responses. Increased DENVax-4 in the dose formulation does show a significant increase in neutralizing antibody production. The DENVax-2 dose also does not appear to have an impact on neutralizing antibody responses of DENVax-4. There may be little to no difference in antibody production between the prime 2 doses vaccination method and prime and boost vaccination method. Sufficient neutralizing antibody titers were produced against DENV-4 1036, the strain that is currently used in DENVax-4. A successful DENV-4 vaccine should be able to adequately neutralize multiple strains of wild type DENV-4 including newly evolved strains with genome modifications, different genotypes and different phenotypes.

During sequencing there were three point mutations identified between passage 1 and passage 10 in both constructs. These mutations were located in the capsid region of DENVax-4b and in the prM and envelope genes of DENVax-4 as previously discussed. Incorporating these mutations into the constructs may provide increased growth in Vero cells by decreasing the attenuation of the virus, which could improve immunogenicity. As disclosed herein DENVax-4h had a 2-fold increase in neutralizing antibody titers while DENVax-4e had a 1.5-fold increase in neutralizing antibody titers. In other methods, increased DENV-4 immunogenicity is tested and compared to other bivalent, trivalent and tetravalent construct compositions.

Materials and Methods
Cell Culture

Vero cells are mammalian cells derived from African Green Monkey kidney. The Vero cell line used in the in vitro experiments. Vero cells were grown at 37° C. in Dulbecco's Modification of Eagle's Medium (DMEM, Mediatech Inc., Manassas Va.) supplemented with 10% Fetal Bovine serum (FBS, Hyclone, Logan Utah), 2% L-glutamine (Hyclone), and 1% Penicillin-Streptomycin (Pen-Strep, Hyclone). To passage the cells Tryple Express solution (Life Technologies, Grand Island N.Y.) was used to remove the cells from the flask surface.

Viral Infection of Vero Monolayers

Vero cells were seeded on T-75 $cm^2$ flasks approximately 48 hours before infection. DMEM supplemented with 10% FBS, 2% L-glutamine, and 1% Penicillin-Streptomycin was used as cell growth medium. Upon cell confluency, 1 flask was trypsinized using 4 mL of a 0.25% trypsin solution diluted 1:5 in PBS. Cells were counted to establish an MOI. Two of the remaining flasks were infected at a predetermined MO1 in 1 mL of either DENVax-4-P2 ($1^{st}$ generation DENVax-4) or DENVax-4b-P3 or other construct and diluted in BA-1 diluent (Bovine serum albumin, 1×M199, 0.05M Tris-HCL, 1× L-glutamine, 7.5% Sodium bicarbonate, 1× Pen-strep, 1× Fungizone). Viruses were adsorbed onto Vero cells for 90 minutes with rocking every 10 minutes to prevent drying of cell monolayers. After adsorption 20 mL DMEM supplemented with 5% FBS was added to each flask. Flasks were incubated for 7 days at 37° C.

Viral Harvests and Subsequent Infections: Blind Passage

After a pre-determined period, the CPE was observed on each flask and viral supernatant was harvested and stabilized in 20% FBS for storage at −80° C. Previously seeded confluent T-75 $cm^2$ Vero flasks were infected with 1 mL of the viral supernatant from the preceding flask. Virus was adsorbed for 90 minutes with rocking every 10 minutes. After viral adsorption, 20 mL DMEM 5% FBS was added to each flask. New non-infected control flasks were plated every 7 days. This process was repeated every 7 days for 10 subsequent weeks, yielding 10 passages per virus denoted either DENVax-4-P2-P1 through P10 or DENVax-4b-P3-P1 through P10 or other indicated denotations for the various constructs.

Plaque Titration of Viruses

Samples from DENVax-4-P2 and DENVax-4b-P3 and other chimeric constructs were taken weeks 1, 5 and 10 were plaque titrated to measure titer. Virus samples were serially diluted $1×10^{-1}$ to $1×10^{-6}$ in BA-1 diluent. Samples were plaque titrated in triplicate, and 100 uL of each dilution was adsorbed to a pre-seeded 6-well plate of Vero cells for 90 minutes with rocking every 8 minutes. After adsorption, wells were overlayed with 4 mL of BSS/Agar (NaCl, KCl, $NaH_2PO_4$—$H_2O$, glucose, $CaCl_2$-$2H_2O$, $MgSO_4$-$7H_2O$) solution and incubated for 4 days at 37° C. On day 4 wells were overlayed with 2 mL BSS/Agar/Neutral Red solution and incubated overnight at 37° C. Plaques were counted on Days 5, 6 and 7.

Growth Curve Analysis

Growth kinetics of the adapted strains were analyzed by performing a growth curve on Vero cells. Vero flasks were seeded as previously described. On day 0 a confluent flask of Vero cells was counted to calculate the virus PFU needed to infect the flasks at an MOI of 0.001. Flasks were infected with 1 mL of DENVax-4, DENVax-4b-P1, DENVax-4b-P10, or DENVax-2 or other chimeric construct (e.g. DENVax-4e, 4h etc.). Viruses were adsorbed to the monolayers for 90 minutes with rocking every 8 minutes. After adsorption, 10 mL cDMEM without FBS supplemented with 1% F-127 was added to each flask and the samples were incubated at 37° C. with 5% $CO_2$. Samples were collected from the supernatant from each flask on Day 2 and Days 4-12. Vaccines were harvested by collecting the entire amount of the supernatant in the flask, and the growth media was replaced with fresh cDMEM-F127 on Day 4 and Days 6-12. Flasks were washed 3 times with PBS during media changes. Samples were stabilized in 1×FTA (FTA:15% trehalose, 1% F-127, 0.1% human serum albumin, PBS) and plaque titrated as previously described to determine titer.

After DENVax-4 and DENVax-4b were both blindly passaged 10 times in Vero cells, each passage was sequenced to identify mutations between P1 and P10. Sequencing reactions were done on DENVax-4-P2-P1 and P10 and DENVax-4b-P3-P1 and P10 at the CDC. Viral RNA was isolated from virus stocks using a QIAmp viral RNA kit. Reverse transcriptase PCR (RT-PCR) was used to transcribe the RNA into DNA, using primers previously designed by the CDC. The primers are designed from the sequences of DENV-2 16681 and DENV-4 1036. Approximately 7-9 PCR fragments per construct were amplified by RT-PCR. The DNA fragments were then sequenced by Beckman Coulter using an automated sequencing reaction, and aligned for comparison.

Sequencing

After the various constructs are passaged 10 or more times in Vero cells, each passage was sequenced to identify mutations. Sequencing reactions were performed on each sample. Viral RNA was isolated from virus stocks using a QIAmp viral RNA kit. Reverse transcriptase PCR (RT-PCR) was used to transcribe the RNA into DNA, using primers previously designed by the CDC. The primers are designed from the sequences of DENV-2 16681 and DENV-4 1036. Approximately 7-9 PCR fragments per construct were amplified by RT-PCR. The DNA fragments were then sequenced by Beckman Coulter using an automated sequencing reaction, and aligned for comparison.

Non-Human Primate Study

Cynomolgus macaques are place in different study groups and vaccinated with doses of tetravalent DENVax having various DENV-4 constructs. One formulation per group can be tested. Formulation 1 can contained a high dose of DENVax with DENVax-4 $1^{st}$ generation, and primates in Group 1 are primed with 2 doses on Day 0 and given no boost. Formulation 2 contained a high dose of DENVax with a DENV-4 construct included and primates in Group 2 can be primed with 2 doses on Day 0 and given no boost. A vaccine can be administered sub-cutaneous or ID or by other method using a needle or needleless system and syringe. Samples to test for serology can be taken on days 0, 28, 58, 73, 90, 128 or other appropriate timing. Neutralizing antibody responses in sera are measured by plaque reduction neutralization technique.

Plaque Reduction Neutralization Technique

To test for neutralizing antibody production in sera samples, a plaque reduction neutralization assay can be used. Vero 6-well plates are seeded 2 days before inoculation to ensure monolayer confluency. Sera samples were diluted serially two-fold in BA-1 diluent in a 96-well plate and incubated with dengue virus for approximately 20 hours at 4° C. After incubation Vero wells are inoculated with prepared virus/sera dilutions. Samples are adsorbed for 90 minutes with rocking every 8 minutes to prevent drying of the monolayers. After adsorption wells are over-layed with 1:1 solution of BSS and agarose, and incubated at 37° C. for 4 days. On Day 4 cells can be over-layed with a 1:1 ratio of BSS supplemented with neutral red solution and agarose. Plaques visible on wells are counted on for example, Days 5, 6, and 7. A GMT value refers to the average dilution of sera that can neutralize 50% of the virus. This is measured by determining the number of plaques formed in the absence of sera, dividing that value by 2 (to account for dilution), and noting which dilution of sera caused plaque formation equal to or less than that amount.

The higher immunogenicity of DENVax-4h (envelope mutation) compared to DENVax-4e (capsid mutation) suggest that the DENVax-4 envelope protein could be optimized. The envelope protein provides epitopes for the generation of neutralizing antibodies, and modifying the sequence to optimize epitope sites for eliciting a strong antibody response may increase antibody titer. The envelope mutation in DENVax-4h at position 417 is in the conserved portion in the stem region. DENV-4 has a different amino acid in this position compared to other flaviviruses. The stem region is in domain III of the E protein where the strongest neutralizing epitope sites exist. Antibodies that bind and neutralize this site prevent the stem region from fusing with the endosomal membrane after endocytosis. In fact, position 417 is conserved among the flavivirus family including DENV-1, -2, -3, and WNV. A reversion from E to K may change the secondary structure to favor a more robust immune response. A further mutation would be to revert back to the conserved charged Aspartic Acid (D) as seen in the other flaviviruses.

The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed:

1. A nucleic acid molecule comprising a chimeric flavivirus construct comprising nucleic acid sequences encoding nonstructural proteins and one or more structural proteins from a live, attenuated dengue-2 virus and at least encoding one or more structural proteins from a second dengue virus, the second flavivirus is selected from the group dengue-1, dengue-3 or dengue-4 virus wherein the chimeric construct further comprises one or more mutations comprising, a mutation in an envelope (E) protein at an amino acid position synonymous of dengue 4 to amino acid 417 when the E protein is from the second flavivirus wherein the mutation in the envelope (E) protein at the position synonymous to amino acid 417 changes glutamic acid to a positively charged residue; a mutation in the capsid protein at an amino acid position synonymous to amino acid 107 in the attenuated dengue-2 wherein the mutation in the capsid (C) protein at the position synonymous to amino acid 107 changes cysteine to an aromatic amino acid residue in the attenuated dengue-2, and a mutation in NS4A at an amino acid position synonymous to amino acid position 17 in the attenuated dengue-2.

2. The nucleic acid molecule according to claim 1, wherein the second flavivirus is dengue-4.

3. The nucleic acid molecule according to claim 1, wherein the position synonymous to 417 is a lysine instead of the glutamic acid in the at least second flavivirus.

4. The nucleic acid molecule according to claim 1, wherein the nucleic acid molecule comprises the mutation in the capsid (C) protein at a position synonymous to amino acid 107 changes cysteine to an aromatic amino acid residue; a mutation in the envelope (E) protein at the position synonymous to amino acid 417 changes glutamic acid to a positively charged residue; and a mutation in NS4A at an amino acid position synonymous to amino acid position 17 in the attenuated dengue-2.

5. The nucleic acid molecule according to claim 1, wherein the aromatic amino acid at the position synonymous to amino acid 107 is a tyrosine.

6. The nucleic acid molecule according to claim 1, wherein the mutation in the NS4A protein at the position synonymous to amino acid 17 changes methionine to a basic amino acid.

7. The nucleic acid molecule according to claim 1, wherein the mutation in the NS4A protein at a position synonymous to amino acid 17 changes methionine to a leucine.

8. The nucleic acid molecule according to claim 1, wherein the live, attenuated dengue-2 contains a mutation at position 57 in the 5'NCR, a mutation at position 53 of NS1 and a mutation at position 250 of NS3.

9. The nucleic acid molecule according to claim 1, wherein the live, attenuated dengue-2 contains a mutation at position 53 of NS1 and a mutation at position 250 of NS3.

10. The nucleic acid molecule according to claim 2, wherein amino acid positions 102-106 of attenuated dengue-2 are substituted with synonymous amino acids of a dengue-4 virus in these positions.

11. The nucleic acid molecule according to claim 1, further comprising a structural protein from a third different flavivirus.

12. The nucleic acid molecule according to claim 11, wherein the third different flavivirus is selected from the group consisting of West Nile virus, Japanese encephalitis virus, St. Louis encephalitis virus, tickborne encephalitis virus, and yellow fever virus.

13. A composition comprising one or more nucleic acid molecules according to claim 1, and a pharmaceutically acceptable carrier.

14. The composition according to claim 13, wherein the composition further comprises additional dengue-dengue chimeric constructs.

15. The composition according to claim 13, wherein the composition is part of a divalent, trivalent or tetravalent dengue virus composition.

16. The composition according to claim 13, wherein the composition further comprises other live, attenuated flaviviruses.

17. A method of inducing an immune response to dengue virus in a subject comprising administering the composition of claim 13 to the subject.

18. The method according to claim 17, wherein an immune response to at least one of dengue-1, dengue-2, dengue-3 and dengue-4 is induced in the subject.

19. A kit comprising one or more compositions according to claim 13 and a container.

20. A live, attenuated virus comprising the nucleic acid molecule according to claim 1.

21. A live, attenuated dengue-4 chimera comprising DENVax4e, DENVax4i or DENVax4h.

22. The chimera according to claim 21, wherein the chimera comprises SEQ ID NO: 22, SEQ ID NO:9, or SEQ ID NO: 24.

23. A composition comprising one or more nucleic acid chimeras according to claim 21, and a pharmaceutically acceptable carrier.

24. A method of inducing an immune response to dengue virus in a subject comprising administering the composition of claim 23 to the subject.

25. The nucleic acid molecule according to claim 2, wherein dengue-4 is from strain 1036.

26. The nucleic acid molecule according to claim 1, wherein the live, attenuated dengue-2 virus comprises a mutated PDK-53 backbone.

27. The live, attenuated virus of claim 20, wherein the live, attenuated virus is part of an immunogenic composition against two or more dengue virus serotypes.

* * * * *

SEQUENCE LISTING

<160> NUMBER OF SEQ ID NOS: 27

<210> SEQ ID NO 1
<211> LENGTH: 29
<212> TYPE: PRT
<213> ORGANISM: Artificial
<220> FEATURE:
<223> OTHER INFORMATION: Derived from Dengue virus serotype 2 (DENV-2)

<400> SEQUENCE: 1

Asn Ile Leu Asn Arg Arg Arg Ser Ala Gly Met Ile Ile Met Leu
1               5                   10                  15

Ile Pro Thr Val Met Ala Phe His Leu Thr Thr Arg Asn
            20                  25

<210> SEQ ID NO 2
<211> LENGTH: 29
<212> TYPE: PRT
<213> ORGANISM: Artificial
<220> FEATURE:
<223> OTHER INFORMATION: Derived from Dengue virus serotype 4
      (DENV-4 WT)

<400> SEQUENCE: 2

Asn Ile Leu Asn Gly Arg Lys Arg Ser Thr Ile Thr Leu Leu Cys Leu
1               5                   10                  15

Ile Pro Thr Val Met Ala Phe His Leu Ser Thr Arg Asp
            20                  25

<210> SEQ ID NO 3
<211> LENGTH: 29
<212> TYPE: PRT
<213> ORGANISM: Artificial
<220> FEATURE:
<223> OTHER INFORMATION: Derived from Dengue virus seroptype 4
      (DENVax-4ori)

<400> SEQUENCE: 3

Asn Ile Leu Asn Arg Arg Arg Ser Ser Ala Gly Met Ile Ile Met Leu
1               5                   10                  15

Ile Pro Thr Val Met Ala Phe His Leu Thr Thr Arg Asp
            20                  25

<210> SEQ ID NO 4
<211> LENGTH: 29
<212> TYPE: PRT
<213> ORGANISM: Artificial
<220> FEATURE:
<223> OTHER INFORMATION: Derived from Dengue virus serotype 4
      (DENVax-4b)

<400> SEQUENCE: 4

Asn Ile Leu Asn Arg Arg Arg Ser Ser Thr Ile Thr Leu Leu Cys Leu
1               5                   10                  15

Ile Pro Thr Val Met Ala Phe His Leu Ser Thr Arg Asp
            20                  25

<210> SEQ ID NO 5
<211> LENGTH: 29
<212> TYPE: PRT
<213> ORGANISM: Artificial
<220> FEATURE:
<223> OTHER INFORMATION: Derived from Dengue virus serotype 4
      (DENVax-4c)

<400> SEQUENCE: 5

-continued

Asn Ile Leu Asn Gly Arg Lys Arg Ser Thr Ile Thr Leu Leu Cys Leu
1               5                   10                  15

Ile Pro Thr Val Met Ala Phe His Leu Ser Thr Arg Asp
            20                  25

<210> SEQ ID NO 6
<211> LENGTH: 28
<212> TYPE: PRT
<213> ORGANISM: Artificial
<220> FEATURE:
<223> OTHER INFORMATION: Derived from Dengue virus serotype 4
      (DENVax-4d)

<400> SEQUENCE: 6

Ile Leu Asn Gly Arg Lys Arg Ser Thr Ile Thr Leu Leu Cys Leu Ile
1               5                   10                  15

Pro Thr Val Met Ala Phe His Leu Ser Thr Arg Asp
            20                  25

<210> SEQ ID NO 7
<211> LENGTH: 10722
<212> TYPE: DNA
<213> ORGANISM: Artificial
<220> FEATURE:
<223> OTHER INFORMATION: Dengue virus chimeric construct DENVax-4e

<400> SEQUENCE: 7
agttgttagt ctacgtggac cgacaaagac agattctttg agggagctaa gctcaatgta      60
gttctaacag ttttttaatt agagagcaga tctctgatga ataaccaacg aaaaaggcg      120 aaaaacacgc ctttcaatat gctgaaacgc gagagaaacc gcgtgtcgac tgtgcaacag    180
ctgacaaaga gattctcact tggaatgctg cagggacgag gaccattaaa actgttcatg    240
gccctggtgg cgttccttcg tttcctaaca atcccaccaa cagcagggat attgaagaga    300
tggggaacaa ttaaaaaatc aaaagctatt aatgttttga gagggttcag aaagagaatt    360
ggaaggatgc tgaacatctt gaataggaga cgcagctcaa cgataacatt gctgtacttg    420
attcccaccg taatggcgtt tcacttgtca acgcgtgatg cgaacccct catgatagtg     480 gcaaaacatg aaagggggag acctctcttg tttaagacaa cagagggat caacaaatgc    540 actctcattg ccatggactt gggtgaaatg tgtgaggaca ctgtcacgta taatgcccc    600 ttactggtca ataccgaacc tgaagacatt gattgctggt gcaatctcac gtctacctgg    660
gtcatgtatg gacatgcac ccagagcgga gaacggagac gagagaagcg ctcagtagct    720
ttaacaccac attcaggaat gggattggaa acaagagctg acatggat gtcatcggaa    780 ggggcttgga agcatgctca gagagtagag agctggatac tcagaaaccc aggattcgcg    840
ctcttggcag gatttatggc ttatatgatt gggcaaacag gaatccagcg aactgtcttc    900
tttgtcctaa tgatgctggt cgccccatcc tacggaatgc gatgcgtagg agtaggaaac    960 agagacttg tggaaggagt ctcaggtgga gcatgggtcg atctggtgct agaacatgga   1020
ggatgcgtca aaccatggc ccagggaaaa ccaaccttgg attttgaact gactaagaca   1080
acagccaagg aagtggctct gttaagaacc tattgcattg aagcctcaat atcaaacata   1140
accacggcaa caagatgtcc aacgcaagga gagccttatc taaaagagga caagaccaa   1200 cagtacattt gccggagaga tgtggtagac agagggtggg gcaatggctg tggcttgttt   1260
ggaaaaggag gagttgtgac atgtgcgaag ttttcatgtt cggggaagat aacaggcaat   1320
ttggtccaaa ttgagaacct tgaatacaca gtggttgtaa cagtccacaa tggagacacc   1380

```
catgcagtag gaaatgacac gtccaatcat ggagttacag ccacgataac tcccaggtca   1440
ccatcggtgg aagtcaaatt gccggactat ggagaactaa cactcgattg tgaacccagg   1500
tctggaattg actttaatga gatgattctg atgaaaatga aaagaaaac atggcttgtg    1560 cataagcaat ggttttgga tctacctcta ccatggacag caggagcaga cacatcagag    1620
gttcactgga attacaaaga gagaatggtg acatttaagg ttcctcatgc caagagacag   1680
gatgtgacag tgctgggatc tcaggaagga gccatgcatt ctgccctcgc tggagccaca   1740
gaagtggact ccgtgatgg aaatcacatg tttgcaggac atctcaagtg caaagtccgt    1800
atggagaaat tgaagaatcaa gggaatgtca tacacgatgt gttcaggaaa gttctcaatt   1860
gacaaagaga tggcagaaac acagcatggg acaacagtgg tgaaagtcaa gtatgaaggt   1920
gctggagctc cgtgtaaagt ccccatagag ataagagatg tgaacaagga aaagtggtt    1980 gggcgtatca tctcatccac ccctttggct gagaatacca acagtgtaac caacatagag   2040
ttagaacccc cctttgggga cagctacata gtgataggtg ttggaaacag tgcattaaca   2100
ctccattggt tcaggaaagg gagttccatt ggcaagatgt ttgagtccac atacagaggt   2160
gcaaaacgaa tggccattct aggtgaaaca gcttgggatt ttggttccgt tggtggactg   2220
ttcacatcat tgggaaaggc tgtgcaccag ttttttggaa gtgtgtatac aaccctgttt   2280
ggaggagtct catggatgat tagaatccta attgggttcc tagtgttgtg gattggcacg   2340
aactcaagga acacttcaat ggctatgacg tgcatagctg ccggcattgt gacactgtat   2400
ttgggagtca tggtgcaggc cgatagtggt tgcgttgtga gctggaaaaa caaagaactg   2460
aaatgtggca gtgggatttt catcacagac aacgtgcaca catggacaga acaatacaag   2520
ttccaaccag aatccccttc aaaactagct tcagctatcc agaaagccca tgaagaggac   2580
atttgtggaa tccgctcagt aacaagactg gagaatctga tgtggaaaca aataacacca   2640
gaattgaatc acattctatc agaaaatgag gtgaagttaa ctattatgac aggagacatc   2700
aaaggaatca tgcaggcagg aaaacgatct ctgcggcctc agcccactga gctgaagtat   2760
tcatggaaaa catggggcaa agcaaaaatg ctctctacag agtctcataa ccagacettt   2820 ctcattgatg gccccgaaac agcagaatgc cccaacacaa atagagcttg gaattcgttg   2880
gaagttgaag actatggctt tggagtattc accaccaata tatggctaaa attgaaagaa   2940
aaacaggatg tattctgcga ctcaaaactc atgtcagcgg ccataaaaga caacagagcc   3000
gtccatgccg atatgggtta ttggatagaa agtgcactca tgacacatg gaagatagag    3060 aaagcctctt tcattgaagt taaaaactgc cactggccaa atcacacac cctctggagc    3120 aatggagtgc tagaaagtga gatgataatt ccaagaatc tcgctggacc agtgtctcaa    3180
cacaactata gaccaggcta ccatacacaa ataacaggac catggcatct aggtaagctt    3240
gagatggact ttgatttctg tgatggaaca acagtggtag tgactgagga ctgcggaaat    3300
agaggaccct ctttgagaac aaccactgcc tctggaaaac tcataacaga atggtgctgc    3360
cgatcttgca cattaccacc gctaagatac agaggtgagg atgggtgctg gtacgggatg    3420
gaaatcagac cattgaagga gaaagaagag aatttggtca actccttggt cacagctgga    3480
catgggcagg tcgacaactt ttcactagga gtcttggaa tggcattgtt cctggaggaa     3540
atgcttagga cccgagtagg aacgaaacat gcaatactac tagttgcagt ttctttttgtg    3600 acattgatca cagggaacat gtccttagga gacctgggaa gagtgatggt tatggtaggc    3660
gccactatga cggatgacat aggtatgggc gtgacttatc ttgccctact agcagccttc    3720
```

-continued

```
aaagtcagac caacttttgc agctggacta ctcttgagaa agctgacctc caaggaattg    3780
atgatgacta ctataggaat tgtactcctc tcccagagca ccataccaga gaccattctt    3840
gagttgactg atgcgttagc cttaggcatg atggtcctca aaatggtgag aaatatggaa    3900
aagtatcaat tggcagtgac tatcatggct atcttgtgcg tcccaaacgc agtgatatta    3960
caaaacgcat ggaaagtgag ttgcacaata ttggcagtgg tgtccgtttc cccactgttc    4020
ttaacatcct cacagcaaaa aacagattgg ataccattag cattgacgat caaaggtctc    4080
aatccaacag ctatttttct aacaaccctc tcaagaacca gcaagaaaag gagctggcca    4140
ttaaatgagg ctatcatggc agtcgggatg gtgagcattt tagccagttc tctcctaaaa    4200
aatgatattc ccatgacagg accattagtg gctggagggc tcctcactgt gtgctacgtg    4260
ctcactggac gatcggccga tttgaactg gagagagcag ccgatgtcaa atggaagac    4320
caggcagaga tatcaggaag cagtccaatc ctgtcaataa caatatcaga agatggtagc    4380
atgtcgataa aaaatgaaga ggaagaacaa acactgacca tactcattag aacaggattg    4440
ctggtgatct caggactttt tcctgtatca ataccaatca cggcagcagc atggtacctg    4500
tgggaagtga agaaacaacg ggccggagta ttgtgggatg ttccttcacc cccacccatg    4560
ggaaaggctg aactggaaga tggagcctat agaattaagc aaaaagggat tcttggatat    4620
tcccagatcg gagccggagt ttacaaagaa ggaacattcc atacaatgtg gcatgtcaca    4680
cgtggcgctg ttctaatgca taaggaaag aggattgaac catcatgggc ggacgtcaag    4740
aaagacctaa tatcatatgg aggaggctgg aagttagaag gagaatggaa ggaaggagaa    4800
gaagtccagg tattggcact ggagcctgga aaaaatccaa gagccgtcca aacgaaacct    4860
ggtcttttca aaccaacgc cggaacaata ggtgctgtat ctctggactt ttctcctgga    4920
acgtcaggat ctccaattat cgacaaaaaa ggaaagttg tgggtcttta tggtaatggt    4980
gttgttacaa ggagtggagc atatgtgagt gctatagccc agactgaaaa aagcattgaa    5040
gacaacccag agatcgaaga tgacatttttc cgaaagagaa gactgaccat catgacctc    5100
caccaggag cgggaaagac gaagagatac cttccggcca tagtcagaga agctataaaa    5160
cggggtttga gaacattaat cttggccccc actagagttg tggcagctga atgaggaa    5220
gcccttagag gacttccaat aagataccag accccagcca tcagagctgt gcacaccggg    5280
cgggagattg tggacctaat gtgtcatgcc acatttacca tgaggctgct atcaccagtt    5340
agagtgccaa actacaacct gattatcatg gacgaagccc atttcacaga cccagcaagt    5400
atagcagcta gaggatacat ctcaactcga gtggagatgg gtgaggcagc tgggattttt    5460
atgacagcca ctcccccggg aagcagagac ccatttcctc agagcaatgc accaatcata    5520
gatgaagaaa gagaaatccc tgaacgctcg tggaattccg gacatgaatg ggtcacggat    5580
tttaaaggga agactgtttg gttcgttcca agtataaaag caggaaatga tatagcagct    5640
tgcctgagga aaaatggaaa gaaagtgata caactcagta ggaagacctt tgattctgag    5700
tatgtcaaga ctagaaccaa tgattgggac ttcgtggtta caactgacat ttcagaaatg    5760
ggtgccaatt tcaaggctga gggttata ccccagac gctgcatgaa accagtcata    5820
ctaacagatg tgaagagcg ggtgattctg gcaggaccta tgccagtgac ccactctagt    5880
gcagcacaaa gaagagggag aataggaaga aatccaaaaa atgagaatga ccagtacata    5940
tacatgggg aacctctgga aaatgatgaa gactgtgcac actggaaaga agctaaaatg    6000
ctcctagata acatcaacac gccagaagga atcattccta gcatgttcga accagagcgt    6060
gaaaaggtgg atgccattga tggcgaatac cgcttgagag gagaagcaag gaaaaccttt    6120
```

```
gtagacttaa tgagaagagg agacctacca gtctggttgg cctacagagt ggcagctgaa    6180
ggcatcaact acgcagacag aaggtggtgt tttgatggag tcaagaacaa ccaaatccta    6240
gaagaaaacg tggaagttga atctggaca aaagaagggg aaaggaagaa attgaaaccc     6300
agatggttgg atgctaggat ctattctgac ccactggcgc taaaagaatt taaggaattt    6360
gcagccggaa gaaagtctct gaccctgaac ctaatcacag aaatgggtag gctcccaacc    6420
ttcatgactc agaaggcaag agacgcactg gacaacttag cagtgctgca cacggctgag    6480
gcaggtggaa gggcgtacaa ccatgctctc agtgaactgc cggagaccct ggagacattg    6540
cttttactga cacttctggc tacagtcacg ggagggatct ttttattctt gatgagcgca    6600
aggggcatag ggaagatgac cctgggaatg tgctgcataa tcacggctag catcctccta    6660
tggtacgcac aaatacagcc acactggata gcagcttcaa taatactgga gttttttctc    6720
atagttttgc ttattccaga acctgaaaaa cagagaacac cccaagacaa ccaactgacc    6780
tacgttgtca tagccatcct cacagtggtg gccgcaacca tggcaaacga gatgggtttc    6840
ctagaaaaaa cgaagaaaga tctcggattg ggaagcattg caacccagca acccgagagc    6900
aacatcctgg acatagatct acgtcctgca tcagcatgga cgctgtatgc cgtggccaca    6960
acatttgtta caccaatgtt gagacatagc attgaaaatt cctcagtgaa tgtgtccta     7020 acagctatag ccaaccaagc cacagtgtta atgggtctcg ggaaaggatg gccattgtca    7080
aagatggaca tcggagttcc ccttctcgcc attggatgct actcacaagt caaccccata    7140
actctcacag cagctctttt cttattggta gcacattatg ccatcatagg gccaggactc    7200
caagcaaaag caaccagaga agctcagaaa agagcagcgg cgggcatcat gaaaaaccca    7260
actgtcgatg gaataacagt gattgaccta gatccaatac cttatgatcc aaagtttgaa    7320
aagcagttgg gacaagtaat gctcctagtc ctctgcgtga ctcaagtatt gatgatgagg    7380
actacatggg ctctgtgtga ggctttaacc ttagctaccg ggcccatctc cacattgtgg    7440
gaaggaaatc cagggaggtt ttggaacact accattgcgg tgtcaatggc taacattttt    7500
agagggagtt acttggccgg agctggactt ctcttttcta ttatgaagaa cacaaccaac    7560
acaagaaggg gaactggcaa cataggagag acgcttggag agaaatggaa aagccgattg    7620
aacgcattgg gaaaaagtga attccagatc tacaagaaaa gtggaatcca ggaagtggat    7680
agaaccttag caaagaaggg cattaaaaga ggagaaacgg accatcacgc tgtgtcgcga    7740
ggctcagcaa aactgagatg gttcgttgag agaaacatgg tcacaccaga agggaaagta    7800
gtggacctcg gttgtggcag aggaggctgg tcatactatt gtggaggact aaagaatgta    7860
agagaagtca aaggcctaac aaaaggagga ccaggacacg aagaacccat ccccatgtca    7920
acatatgggt ggaatctagt gcgtcttcaa agtggagttg acgttttctt catcccgcca    7980
gaaaagtgtg acacattatt gtgtgacata ggggagtcat caccaaatcc cacagtggaa    8040
gcaggacgaa cactcagagt ccttaactta gtagaaaatt ggttgaacaa caacactcaa    8100
ttttgcataa aggttctcaa cccatatatg ccctcagtca tagaaaaaat ggaagcacta    8160
caaaggaaat atggaggagc cttagtgagg aatccactct cacgaaactc cacacatgag    8220
atgtactggg tatccaatgc ttccgggaac atagtgtcat cagtgaacat gatttcaagg    8280
atgttgatca acagatttac aatgagatac aagaaagcca cttacgagcc ggatgttgac    8340
ctcggaagcg gaacccgtaa catcgggatt gaaagtgaga taccaaacct agatataatt    8400
gggaaaagaa tagaaaaaat aaagcaagag catgaaacat catggcacta tgaccaagac    8460
```

```
cacccataca aaacgtgggc ataccatggt agctatgaaa caaaacagac tggatcagca    8520
tcatccatgg tcaacggagt ggtcaggctg ctgacaaaac cttggacgt cgtccccatg     8580
gtgacacaga tggcaatgac agacacgact ccatttggac aacagcgcgt ttttaaagag    8640
aaagtggaca cgagaaccca agaaccgaaa gaaggcacga agaaactaat gaaaataaca    8700
gcagagtggc tttggaaaga attagggaag aaaaagacac ccaggatgtg caccagagaa    8760
gaattcacaa gaaaggtgag aagcaatgca gccttggggg ccatattcac tgatgagaac    8820
aagtggaagt cggcacgtga ggctgttgaa gatagtaggt tttgggagct ggttgacaag    8880
gaaaggaatc tccatcttga aggaaagtgt gaaacatgtg tgtacaacat gatgggaaaa    8940
agagagaaga agctagggga attcggcaag gcaaaaggca gcagagccat atggtacatg    9000
tggcttggag cacgcttctt agagtttgaa gccctaggat tcttaaatga agatcactgg    9060
ttctccagag agaactccct gagtggagtg aaggagaag ggctgcacaa gctaggttac    9120
attctaagag acgtgagcaa gaaagaggga ggagcaatgt atgccgatga caccgcagga    9180
tgggatacaa gaatcacact agaagaccta aaaaatgaag aaatggtaac aaaccacatg    9240
gaaggagaac acaagaaact agccgaggcc attttcaaac taacgtacca aaacaaggtg    9300
gtgcgtgtgc aaagaccaac accaagaggc acagtaatgg acatcatatc gagaagagac    9360
caaagaggta gtggacaagt tggcacctat ggactcaata ctttcaccaa tatggaagcc    9420
caactaatca gacagatgga gggagaagga gtctttaaaa gcattcagca cctaacaatc    9480
acagaagaaa tcgctgtgca aaactggtta gcaagagtgg ggcgcgaaag gttatcaaga    9540
atggccatca gtgagatga ttgtgttgtg aaacctttag atgacaggtt cgcaagcgct    9600
ttaacagctc taaatgacat gggaaagatt aggaaagaca tacaacaatg gaaccttca    9660
agaggatgga atgattggac acaagtgccc ttctgttcac accatttcca tgagttaatc    9720
atgaaagacg gtcgcgtact cgttgttcca tgtagaaacc aagatgaact gattggcaga    9780
gcccgaatct cccaaggagc agggtggtct ttgcgggaga cggcctgttt ggggaagtct    9840
tacgcccaaa tgtggagctt gatgtacttc cacagacgcg acctcaggct ggcggcaaat    9900
gctatttgct cggcagtacc atcacattgg gttccaacaa gtcgaacaac ctggtccata    9960
catgctaaac atgaatggat gacaacggaa gacatgctga cagtctggaa cagggtgtgg   10020
attcaagaaa acccatggat ggaagacaaa actccagtgg aatcatggga ggaaatccca   10080
tacttgggga aagagaaga ccaatggtgc ggctcattga ttgggttaac aagcagggcc    10140
acctgggcaa gaacatcca gcagcaata aatcaagtta gatcccttat aggcaatgaa    10200
gaatacacag attacatgcc atccatgaaa agattcagaa gagaagagga agaagcagga    10260
gttctgtggt agaaagcaaa actaacatga aacaaggcta gaagtcaggt cggattaagc    10320
catagtacgg aaaaaactat gctacctgtg agccccgtcc aaggacgtta aaagaagtca    10380
ggccatcata aatgccatag cttgagtaaa ctatgcagcc tgtagctcca cctgagaagg    10440
tgtaaaaaat ccgggaggcc acaaaccatg gaagctgtac gcatggcgta gtggactagc    10500
ggttagagga gaccccctccc ttacaaatcg cagcaacaat gggggcccaa ggcgagatga   10560
agctgtagtc tcgctggaag gactagaggt tagaggagac cccccgaaa caaaaaacag    10620
catattgacg ctgggaaaga ccagagatcc tgctgtctcc tcagcatcat tccaggcaca   10680
gaacgccaga aaatggaatg gtgctgttga atcaacaggt tc                      10722
```

<210> SEQ ID NO 8
<211> LENGTH: 10722

<212> TYPE: DNA
<213> ORGANISM: Artificial
<220> FEATURE:
<223> OTHER INFORMATION: Dengue virus chimeric construct DENVax-4h

<400> SEQUENCE: 8

| | | | | | |
|---|---|---|---|---|---|
| agttgttagt | ctacgtggac | cgacaaagac | agattctttg | agggagctaa | gctcaatgta | 60 |
| gttctaacag | ttttttaatt | agagagcaga | tctctgatga | ataaccaacg | gaaaaaggcg | 120 |
| aaaaacacgc | ctttcaatat | gctgaaacgc | gagagaaacc | gcgtgtcgac | tgtgcaacag | 180 |
| ctgacaaaga | gattctcact | tggaatgctg | cagggacgag | gaccattaaa | actgttcatg | 240 |
| gccctggtgg | cgttccttcg | tttcctaaca | atcccaccaa | cagcagggat | attgaagaga | 300 |
| tggggaacaa | ttaaaaaatc | aaaagctatt | aatgttttga | gagggttcag | gaaagagatt | 360 |
| ggaaggatgc | tgaacatctt | gaataggaga | cgcagctctg | caggcatgat | cattatgctg | 420 |
| attccaacag | tgatggcgtt | ccatttaacc | acgcgtgatg | gcgaacccct | catgatagtg | 480 |
| gcaaaacatg | aaaggggag | acctctcttg | tttaagacaa | cagaggggat | caacaaatgc | 540 |
| actctcattg | ccatggactt | gggtgaaatg | tgtgaggaca | ctgtcacgta | taaatgcccc | 600 |
| ttactggtca | ataccgaacc | tgaagacatt | gattgctggt | gcaatctcac | gtctacctgg | 660 |
| gtcatgtatg | ggacatgcac | ccagagcgga | gaacggagac | gagagaagcg | ctcagtagct | 720 |
| ttaacaccac | attcaggaat | gggattggaa | acaagagctg | agacatggat | gtcatcggaa | 780 |
| ggggcttgga | agcatgctca | gagagtagag | agctggatac | tcagaaaccc | aggattcgcg | 840 |
| ctcttggcag | gatttatggc | ttatatgatt | gggcaaacag | gaatccagcg | aactgtcttc | 900 |
| tttgtcctaa | tgatgctggt | cgccccatcc | tacggaatgc | gatgcgtagg | agtaggaaac | 960 |
| agagactttg | tggaaggagt | ctcaggtgga | gcatgggtcg | atctggtgct | agaacatgga | 1020 |
| ggatgcgtca | caaccatggc | ccagggaaaa | ccaaccttgg | attttgaact | gactaagaca | 1080 |
| acagccaagg | aagtggctct | gttaagaacc | tattgcattg | aagcctcaat | atcaaacata | 1140 |
| accacggcaa | caagatgtcc | aacgcaagga | gagccttatc | taaaagagga | acaagaccaa | 1200 |
| cagtacattt | gccggagaga | tgtggtagac | agagggtggg | gcaatggctg | tggcttgttt | 1260 |
| ggaaaaggag | gagttgtgac | atgtgcgaag | ttttcatgtt | cggggaagat | aacaggcaat | 1320 |
| ttggtccaaa | ttgagaacct | tgaatacaca | gtggttgtaa | cagtccacaa | tggagacacc | 1380 |
| catgcagtag | gaaatgacac | gtccaatcat | ggagttacag | ccacgataac | tcccaggtca | 1440 |
| ccatcggtgg | aagtcaaatt | gccggactat | ggagaactaa | cactcgattg | tgaacccagg | 1500 |
| tctgaattg | actttaatga | gatgattctg | atgaaaatga | aaaagaaaac | atggcttgtg | 1560 |
| cataagcaat | ggttttttga | tctacctcta | ccatggacag | caggagcaga | cacatcagag | 1620 |
| gttcactgga | attacaaaga | gagaatggtg | acatttaagg | ttcctcatgc | caagagacag | 1680 |
| gatgtgacag | tgctgggatc | tcaggaagga | gccatgcatt | ctgccctcgc | tggagccaca | 1740 |
| gaagtggact | ccggtgatgg | aaatcacatg | tttgcaggac | atctcaagtg | caaagtccgt | 1800 |
| atggagaaat | tgagaatcaa | gggaatgtca | tacacgatgt | gttcaggaaa | gttctcaatt | 1860 |
| gacaaagaga | tggcagaaac | acagcatggg | acaacagtgg | tgaaagtcaa | gtatgaaggt | 1920 |
| gctggagctc | cgtgtaaagt | ccccatagag | ataagagatg | tgaacaagga | aaaagtggtt | 1980 |
| gggcgtatca | tctcatccac | ccctttggct | gagaatacca | acagtgtaac | caacatagag | 2040 |
| ttagaacccc | cctttgggga | cagctacata | gtgataggtt | tggaaacag | tgcattaaca | 2100 |
| ctccattggt | tcaggaaagg | gagttccatt | ggcaagatgt | ttgagtccac | atacagaggt | 2160 |

```
gcaaaacgaa tggccattct aggtaaaaca gcttgggatt ttggttccgt tggtggactg    2220
ttcacatcat tgggaaaggc tgtgcaccag gttttttggaa gtgtgtatac aaccctgttt    2280
ggaggagtct catggatgat tagaatccta attgggttcc tagtgttgtg gattggcacg    2340
aactcaagga acacttcaat ggctatgacg tgcatagctg ccggcattgt gacactgtat    2400
ttgggagtca tggtgcaggc cgatagtggt tgcgttgtga gctggaaaaa caagaactg     2460 aaatgtggca gtgggatttt catcacagac aacgtgcaca catggacaga acaatacaag    2520
ttccaaccag aatcccttc aaaactagct tcagctatcc agaaagccca tgaagaggac     2580
atttgtggaa tccgctcagt aacaagactg gagaatctga tgtggaaaca ataacacca    2640 gaattgaatc acattctatc agaaaatgag gtgaagttaa ctattatgac aggagacatc    2700
aaaggaatca tgcaggcagg aaaacgatct ctgcggcctc agcccactga gctgaagtat    2760
tcatggaaaa catggggcaa agcaaaaatg ctctctacag agtctcataa ccagaccttt    2820
ctcattgatg gccccgaaac agcagaatgc cccaacacaa atagagcttg gaattcgttg    2880
gaagttgaag actatggctt tggagtattc accaccaata tatggctaaa attgaaagaa    2940
aaacaggatg tattctgcga ctcaaaactc atgtcagcgg ccataaaaga caacagagcc    3000
gtccatgccg atatgggtta ttggatagaa agtgcactca atgacacatg gaagatagag    3060
aaagcctctt tcattgaagt taaaaactgc cactggccaa aatcacacac cctctggagc    3120 aatgagtgc tagaaagtga gatgataatt ccaaagaatc tcgctggacc agtgtctcaa    3180
cacaactata gaccaggcta ccatacacaa ataacaggac catggcatct aggtaagctt    3240
gagatggact ttgatttctg tgatggaaca acagtggtag tgactgagga ctgcggaaat    3300
agaggaccct cttttgagaac aaccactgcc tctggaaaaac tcataacaga atggtgctgc    3360
cgatcttgca cattaccacc gctaagatac agaggtgagg atgggtgctg gtacgggatg    3420
gaaatcagac cattgaagga gaaagaagag aatttggtca actccttggt cacagctgga    3480
catgggcagg tcgacaactt ttcactagga gtcttgggaa tggcattgtt cctggaggaa    3540
atgcttagga cccgagtagg aacgaaacat gcaatactac tagttgcagt ttcttttgtg    3600
acattgatca cagggaacat gtcctttaga gacctgggaa gagtgatggt tatggtaggc    3660
gccactatga cggatgacat aggtatgggc gtgacttatc ttgccctact agcagccttc    3720
aaagtcagac caacttttgc agctggacta ctcttgagaa agctgacctc caaggaattg    3780
atgatgacta ctataggaat tgtactcctc tcccagagca ccataccaga gaccattctt    3840
gagttgactg atgcgttagc cttaggcatg atggtcctca aaatggtgag aaatatggaa    3900
aagtatcaat tggcagtgac tatcatggct atcttgtgcg tcccaaacgc agtgatatta    3960
caaaacgcat ggaaagtgag ttgcacaata ttggcagtgg tgtccgtttc cccactgttc    4020
ttaacatcct cacagcaaaa aacagattgg ataccattag cattgacgat caaaggtctc    4080
aatccaacag ctattttct aacaacccctc tcaagaacca gcaagaaaag gagctggcca    4140
ttaaatgagg ctatcatggc agtcgggatg gtgagcattt tagccagttc tctcctaaaa    4200
aatgatattc ccatgacagg accattagtg gctggagggc tcctcactgt gtgctacgtg    4260
ctcactggac gatcggccga tttgaactg gagagagcag ccgatgtcaa atgggaagac    4320
caggcagaga tatcaggaag cagtccaatc ctgtcaataa caatatcaga agatggtagc    4380
atgtcgataa aaaatgaaga ggaagaacaa acactgacca tactcattag aacaggattg    4440
ctggtgatct caggactttt tcctgtatca ataccaatca cggcagcagc atggtacctg    4500
tgggaagtga agaaacaacg ggccggagta ttgtgggatg ttccttcacc cccacccatg    4560
```

```
ggaaaggctg aactggaaga tggagcctat agaattaagc aaaaagggat tcttggatat    4620
tcccagatcg gagccggagt ttacaaagaa ggaacattcc atacaatgtg gcatgtcaca    4680
cgtggcgctg ttctaatgca taaaggaaag aggattgaac catcatgggc ggacgtcaag    4740
aaagacctaa tatcatatgg aggaggctgg aagttagaag gagaatggaa ggaaggagaa    4800
gaagtccagg tattggcact ggagcctgga aaaaatccaa gagccgtcca acgaaaacct    4860
ggtcttttca aaaccaacgc cggaacaata ggtgctgtat ctctggactt ttctcctgga    4920
acgtcaggat ctccaattat cgacaaaaaa ggaaaagttg tgggtcttta tggtaatggt    4980
gttgttacaa ggagtggagc atatgtgagt gctatagccc agactgaaaa aagcattgaa    5040
gacaacccag agatcgaaga tgacattttc cgaaagagaa gactgaccat catggacctc    5100
cacccaggag cgggaaagac gaagagatac cttccggcca tagtcagaga gctataaaa    5160 cggggtttga gaacattaat cttggccccc actagagttg tggcagctga aatggaggaa    5220
gcccttagag gacttccaat aagataccag accccagcca tcagctgtgt gcacaccggg    5280
cgggagattg tggacctaat gtgtcatgcc acatttacca tgaggctgct atcaccagtt    5340
agagtgccaa actacaacct gattatcatg gacgaagccc atttcacaga cccagcaagt    5400
atagcagcta gaggatacat ctcaactcga gtggagatgg gtgaggcagc tgggattttt    5460
atgacagcca ctcccccggg aagcagagac ccatttcctc agagcaatgc accaatcata    5520
gatgaagaaa gagaaatccc tgaacgctcg tggaattccg gacatgaatg ggtcacggat    5580
tttaagggaa gactgttttg gttcgttcca agtataaaag caggaaatga tatagcagct    5640
tgcctgagga aaaatggaaa gaaagtgata caactcagta ggaagacctt tgattctgag    5700
tatgtcaaga ctagaaccaa tgattgggac ttcgtggtta caactgacat ttcagaaatg    5760
ggtgccaatt tcaaggctga gagggttata gaccccagac gctgcatgaa accagtcata    5820
ctaacagatg gtgaagagcg ggtgattctg gcaggaccta tgccagtgac ccactctagt    5880
gcagcacaaa gaagagggag aataggaaga aatccaaaaa atgagaatga ccagtacata    5940
tacatggggg aacctctgga aaatgatgaa gactgtgcac actggaaaga agctaaaatg    6000
ctcctagata acatcaacac gccagaagga atcattccta gcatgttcga accagagcgt    6060
gaaaaggtgg atgccattga tggcgaatac cgcttgagag gagaagcaag gaaaaccttt    6120
gtagacttaa tgagaagagg agacctacca gtctggttgg cctacagagt ggcagctgaa    6180
ggcatcaact acgcagacag aaggtggtgt tttgatggag tcaagaacaa ccaaatccta    6240
gaagaaaacg tggaagttga aatctggaca aaagaagggg aaaggaagaa attgaaaccc    6300
agatggttgg atgctaggat ctattctgac ccactggcgc taaaagaatt taaggaattt    6360
gcagccggaa gaaagtctct gacccctgaac ctaatcacag aaatgggtag gctcccaacc    6420
ttcatgactc agaaggcaag agacgcactg gacaacttag cagtgctgca cacggctgag    6480
gcaggtggaa gggcgtacaa ccatgctctc agtgaactgc cggagaccct ggagacattg    6540
cttttactga cacttctggc tacagtcacg ggagggatct ttttattctt gatgagcgca    6600
aggggcatag ggaagatgac cctgggaatg tgctgcataa tcacggctag catcctccta    6660
tggtacgcac aaatacagcc acactggata gcagcttcaa taatactgga gttttttctc    6720
atagttttgc ttattccaga acctgaaaaa cagagaacac cccaagacaa ccaactgacc    6780
tacgttgtca tagccatcct cacagtggtg gccgcaacca tggcaaacga gatgggtttc    6840
ctagaaaaaa cgaagaaaga tctcggattg ggaagcattg caacccagca acccgagagc    6900
```

| | | | | |
|---|---|---|---|---|
| aacatcctgg | acatagatct | acgtcctgca | tcagcatgga | cgctgtatgc cgtggccaca | 6960 |
| acatttgtta | caccaatgtt | gagacatagc | attgaaaatt | cctcagtgaa tgtgtcccta | 7020 |
| acagctatag | ccaaccaagc | cacagtgtta | atgggtctcg | ggaaaggatg gccattgtca | 7080 |
| aagatggaca | tcggagttcc | ccttctcgcc | attggatgct | actcacaagt caaccccata | 7140 |
| actctcacag | cagctctttt | cttattggta | gcacattatg | ccatcatagg gccaggactc | 7200 |
| caagcaaaag | caaccagaga | agctcagaaa | agagcagcgg | cgggcatcat gaaaaaccca | 7260 |
| actgtcgatg | gaataacagt | gattgaccta | gatccaatac | cttatgatcc aaagtttgaa | 7320 |
| aagcagttgg | gacaagtaat | gctcctagtc | ctctgcgtga | ctcaagtatt gatgatgagg | 7380 |
| actacatggg | ctctgtgtga | ggctttaacc | ttagctaccg | ggcccatctc cacattgtgg | 7440 |
| gaaggaaatc | cagggaggtt | ttggaacact | accattgcgg | tgtcaatggc taacattttt | 7500 |
| agagggagtt | acttggccgg | agctggactt | ctcttttcta | ttatgaagaa cacaaccaac | 7560 |
| acaagaaggg | gaactggcaa | cataggagag | acgcttggag | agaaatggaa aagccgattg | 7620 |
| aacgcattgg | gaaaagtga | attccagatc | tacaagaaaa | gtggaatcca ggaagtggat | 7680 |
| agaaccttag | caaagaagg | cattaaaaga | ggagaaacgg | accatcacgc tgtgtcgcga | 7740 |
| ggctcagcaa | aactgagatg | gttcgttgag | agaaacatgg | tcacaccaga agggaaagta | 7800 |
| gtggacctcg | gttgtggcag | aggaggctgg | tcatactatt | gtggaggact aaagaatgta | 7860 |
| agagaagtca | aaggcctaac | aaaaggagga | ccaggacacg | aagaacccat ccccatgtca | 7920 |
| acatatgggt | ggaatctagt | gcgtcttcaa | agtggagttg | acgttttctt catcccgcca | 7980 |
| gaaaagtgtg | acacattatt | gtgtgacata | ggggagtcat | caccaaatcc cacagtggaa | 8040 |
| gcaggacgaa | cactcagagt | ccttaactta | gtagaaaatt | ggttgaacaa caacactcaa | 8100 |
| ttttgcataa | aggttctcaa | cccatatatg | ccctcagtca | tagaaaaaat ggaagcacta | 8160 |
| caaaggaaat | atggaggagc | cttagtgagg | aatccactct | cacgaaactc cacacatgag | 8220 |
| atgtactggg | tatccaatgc | ttccgggaac | atagtgtcat | cagtgaacat gatttcaagg | 8280 |
| atgttgatca | acagatttac | aatgagatac | aagaaagcca | cttacgagcc ggatgttgac | 8340 |
| ctcggaagcg | gaacccgtaa | catcgggatt | gaaagtgaga | taccaaacct agatataatt | 8400 |
| gggaaaagaa | tagaaaaaat | aaagcaagag | catgaaacat | catggcacta tgaccaagac | 8460 |
| cacccataca | aaacgtgggc | ataccatggt | agctatgaaa | caaaacagac tggatcagca | 8520 |
| tcatccatgg | tcaacggagt | ggtcaggctg | ctgacaaaac | cttgggacgt cgtccccatg | 8580 |
| gtgacacaga | tggcaatgac | agacacgact | ccatttggac | aacagcgcgt ttttaaagag | 8640 |
| aaagtggaca | cgagaaccca | agaaccgaaa | gaaggcacga | agaaactaat gaaaataaca | 8700 |
| gcagagtggc | tttggaaaga | attagggaag | aaaaagacac | caggatgtg caccagagaa | 8760 |
| gaattcacaa | gaaaggtgag | aagcaatgca | gccttggggg | ccatattcac tgatgagaac | 8820 |
| aagtggaagt | cggcacgtga | ggctgttgaa | gatagtaggt | tttgggagct ggttgacaag | 8880 |
| gaaaggaatc | tccatcttga | aggaaagtgt | gaaacatgtg | tgtacaacat gatgggaaaa | 8940 |
| agagagaaga | agctagggga | attcggcaag | gcaaaggca | gcagagccat atggtacatg | 9000 |
| tggcttggag | cacgcttctt | agagtttgaa | gccctaggat | tcttaaatga agatcactgg | 9060 |
| ttctccagag | agaactccct | gagtggagtg | aaggagaag | ggctgcacaa gctaggttac | 9120 |
| attctaagag | acgtgagcaa | gaaagaggga | ggagcaatgt | atgccgatga caccgcagga | 9180 |
| tgggatacaa | gaatcacact | agaagaccta | aaaaatgaag | aaatggtaac aaaccacatg | 9240 |
| gaaggagaac | acaagaaact | agccgaggcc | attttcaaac | taacgtacca aaacaaggtg | 9300 |

```
gtgcgtgtgc aaagaccaac accaagaggc acagtaatgg acatcatatc gagaagagac    9360
caaagaggta gtggacaagt tggcacctat ggactcaata ctttcaccaa tatggaagcc    9420
caactaatca gacagatgga gggagaagga gtctttaaaa gcattcagca cctaacaatc    9480
acagaagaaa tcgctgtgca aaactggtta gcaagagtgg ggcgcgaaag gttatcaaga    9540
atggccatca gtggagatga ttgtgttgtg aaacctttag atgacaggtt cgcaagcgct    9600
ttaacagctc taaatgacat gggaaagatt aggaaagaca tacaacaatg gaaccttca    9660
agaggatgga atgattggac acaagtgccc ttctgttcac accatttcca tgagttaatc    9720
atgaaagacg gtcgcgtact cgttgttcca tgtagaaacc aagatgaact gattggcaga    9780
gcccgaatct cccaaggagc agggtggtct ttgcgggaga cggcctgttt ggggaagtct    9840
tacgcccaaa tgtggagctt gatgtacttc cacagacgcg acctcaggct ggcggcaaat    9900
gctatttgct cggcagtacc atcacattgg gttccaacaa gtcgaacaac ctggtccata    9960
catgctaaac atgaatggat gacaacggaa gacatgctga cagtctggaa cagggtgtgg   10020
attcaagaaa acccatggat ggaagacaaa actccagtgg aatcatggga ggaaatccca   10080
tacttgggga aaagaagaa ccaatggtgc ggctcattga ttgggttaac aagcagggcc   10140
acctgggcaa agaacatcca agcagcaata aatcaagtta tcccttat aggcaatgaa   10200
gaatacacag attacatgcc atccatgaaa agattcagaa gagaagagga agaagcagga   10260
gttctgtggt agaaagcaaa actaacatga acaaggcta gaagtcaggt cggattaagc   10320
catagtacgg aaaaactat gctacctgtg agccccgtcc aaggacgtta aagaagtca   10380
ggccatcata aatgccatag cttgagtaaa ctatgcagcc tgtagctcca cctgagaagg   10440
tgtaaaaaat ccgggaggcc acaaaccatg gaagctgtac gcatggcgta gtggactagc   10500
ggttagagga gacccctccc ttacaaatcg cagcaacaat ggggccca ggcgagatga   10560
agctgtagtc tcgctggaag gactagaggt tagaggagac cccccgaaa caaaaaacag   10620
catattgacg ctgggaaaga ccagagatcc tgctgtctcc tcagcatcat ccaggcaca   10680
gaacgccaga aaatggaatg gtgctgttga atcaacaggt tc                     10722
```

<210> SEQ ID NO 9
<211> LENGTH: 10722
<212> TYPE: DNA
<213> ORGANISM: Artificial
<220> FEATURE:
<223> OTHER INFORMATION: Dengue virus chimeric construct DENVax-4i

<400> SEQUENCE: 9

```
agttgttagt ctacgtggac cgacaaagac agattctttg agggagctaa gctcaatgta     60
gttctaacag tttttaatt agagagcaga tctctgatga ataaccaacg gaaaaaggcg    120
aaaaacacgc ctttcaatat gctgaaacgc gagagaaacc gcgtgtcgac tgtgcaacag    180
ctgacaaaga gattctcact tggaatgctg caggacgag gaccattaaa actgttcatg    240
gccctggtgg cgttccttcg tttcctaaca atcccaccaa cagcagggat attgaagaga    300
tggggaacaa ttaaaaaatc aaaagctatt aatgttttga gggggttcag gaaagagatt    360
ggaaggatgc tgaacatctt gaataggaga cgcagctctg caggcatgat cattatgctg    420
attccaacag tgatggcgtt ccatttaacc acgcgtgatg gcgaacccct catgatagtg    480
gcaaaacatg aaaggggga acctctcttg tttaagacaa cagagggat caacaaatgc    540
actctcattg ccatggactt gggtgaaatg tgtgaggaca ctgtcacgta taatgccccc    600
```

```
ttactggtca ataccgaacc tgaagacatt gattgctggt gcaatctcac gtctacctgg    660
gtcatgtatg ggacatgcac ccagagcgga aacggagac gagagaagcg ctcagtagct     720
ttaacaccac attcaggaat gggattggaa acaagagctg agacatggat gtcatcggaa    780
ggggcttgga agcatgctca gagagtagag agctggatac tcagaaaccc aggattcgcg    840
ctcttggcag gatttatggc ttatatgatt gggcaaacag gaatccagcg aactgtcttc    900
tttgtcctaa tgatgctggt cgccccatcc tacggaatgc gatgcgtagg agtaggaaac    960
agagactttg tggaaggagt ctcaggtgga gcatgggtcg atctggtgct agaacatgga   1020
ggatgcgtca caaccatggc ccagggaaaa ccaaccttgg attttgaact gactaagaca   1080
acagccaagg aagtggctct gttaagaacc tattgcattg aagcctcaat atcaaacata   1140
accacggcaa caagatgtcc aacgcaagga gagccttatc taaaagagga caagaccaa    1200 cagtacattt gccggagaga tgtggtagac agagggtggg gcaatggctg tggcttgttt   1260
ggaaaaggag gagttgtgac atgtgcgaag ttttcatgtt cggggaagat aacaggcaat   1320
ttggtccaaa ttgagaacct tgaatacaca gtggttgtaa cagtccacaa tggagacacc   1380
catgcagtag gaaatgacac gtccaatcat ggagttacag ccacgataac tcccaggtca   1440
ccatcggtgg aagtcaaatt gccggactat ggagaactaa cactcgattg tgaacccagg   1500
tctggaattg acttaatga gatgattctg atgaaaatga aaagaaaac atggcttgtg    1560 cataagcaat ggtttttgga tctacctcta ccatggacag caggagcaga cacatcagag   1620
gttcactgga attacaaaga gagaatggtg acatttaagg ttcctcatgc caagagacag   1680
gatgtgacag tgctgggatc tcaggaagga gccatgcatt ctgccctcgc tggagccaca   1740
gaagtggact ccgtgatgg aaatcacatg tttgcaggac atctcaagtg caaagtccgt    1800
atggagaaat tgagaatcaa gggaatgtca tacacgatgt gttcaggaaa gttctcaatt    1860
gacaaagaga tggcagaaac acagcatggg acaacagtgg tgaaagtcaa gtatgaaggt   1920
gctggagctc cgtgtaaagt ccccatagag ataagagatg tgaacaagga aaaagtggtt   1980
gggcgtatca tctcatccac ccctttggct gagaatacca acagtgtaac caacatagag   2040
ttagaacccc cctttgggga cagctacata gtgataggtt tggaaacag tgcattaaca   2100 ctccattggt tcaggaaagg gagttccatt ggcaagatgt ttgagtccac atacagaggt   2160
gcaaaacgaa tggccattct aggtgaaaca gcttgggatt ttggttccgt tggtggactg    2220
ttcacatcat tgggaaaggc tgtgcaccag ttttttggaa gtgtgtatac aaccctgttt    2280
ggaggagtct catggatgat tagaatccta attgggttcc tagtgttgtg gattggcacg   2340
aactcaagga acacttcaat ggctatgacg tgcatagctg ccggcattgt gacactgtat    2400
ttgggagtca tggtgcaggc cgatagtggt tgcgttgtga gctggaaaaa caaagaactg   2460
aaatgtggca gtgggatttt catcacagac aacgtgcaca catggacaga acaatacaag   2520
ttccaaccag aatccccttc aaaactagct tcagctatcc agaaagccca tgaagaggac    2580
atttgtggaa tccgctcagt aacaagactg gagaatctga tgtggaaaca ataaccaca   2640 gaattgaatc acattctatc agaaaatgag gtgaagttaa ctattatgac aggagacatc    2700
aaaggaatca tgcaggcagg aaaacgatct ctgcggcctc agcccactga gctgaagtat    2760
tcatggaaaa catggggcaa agcaaaaatg ctctctacag agtctcataa ccagacctt     2820 ctcattgatg gccccgaaac agcagaatgc cccaacacaa atagagcttg gaattcgttg    2880
gaagttgaag actatggctt tggagtattc accaccaata tatggctaaa attgaaagaa   2940
aaacaggatg tattctgcga ctcaaaactc atgtcagcgg ccataaaaga caacagagcc   3000
```

```
gtccatgccg atatgggtta ttggatagaa agtgcactca atgacacatg aagatagag   3060
aaagcctctt tcattgaagt taaaaactgc cactggccaa atcacacac cctctggagc    3120
aatggagtgc tagaaagtga gatgataatt ccaaagaatc tcgctggacc agtgtctcaa   3180
cacaactata gaccaggcta ccatacacaa ataacaggac catggcatct aggtaagctt   3240
gagatggact ttgatttctg tgatggaaca acagtggtag tgactgagga ctgcggaaat   3300
agaggaccct ctttgagaac aaccactgcc tctggaaaac tcataacaga atggtgctgc   3360
cgatcttgca cattaccacc gctaagatac agaggtgagg atgggtgctg gtacgggatg   3420
gaaatcagac cattgaagga gaaagaagag aatttggtca actccttggt cacagctgga   3480
catgggcagg tcgacaactt ttcactagga gtcttgggaa tggcattgtt cctggaggaa   3540
atgcttagga cccgagtagg aacgaaacat gcaatactac tagttgcagt ttcttttgtg   3600
acattgatca cagggaacat gtcctttaga gacctgggaa gagtgatggt tatggtaggc   3660
gccactatga cggatgacat aggtatgggc gtgacttatc ttgccctact agcagccttc   3720
aaagtcagac caacttttgc agctggacta ctcttgagaa agctgaccct caaggaattg   3780
atgatgacta ctataggaat tgtactcctc tcccagagca ccataccaga gaccattctt   3840
gagttgactg atgcgttagc cttaggcatg atggtcctca aaatggtgag aaatatggaa   3900
aagtatcaat tggcagtgac tatcatggct atcttgtgcg tcccaaacgc agtgatatta   3960
caaaacgcat ggaaagtgag ttgcacaata ttggcagtgg tgtccgtttc cccactgttc   4020
ttaacatcct cacagcaaaa aacagattgg ataccattag cattgacgat caaaggtctc   4080
aatccaacag ctattttct aacaacccctc tcaagaacca gcaagaaaag gagctggcca   4140
ttaaatgagg ctatcatggc agtcgggatg gtgagcattt tagccagttc tctcctaaaa   4200
aatgatattc ccatgacagg accattagtg gctggagggc tcctcactgt gtgctacgtg   4260
ctcactggac gatcggccga tttggaactg gagagagcag ccgatgtcaa atgggaagac   4320
caggcagaga tatcaggaag cagtccaatc ctgtcaataa caatatcaga gatggtagc    4380
atgtcgataa aaaatgaaga ggaagaacaa acactgacca tactcattag aacaggattg   4440
ctggtgatct caggactttt tcctgtatca ataccaatca cggcagcagc atggtacctg   4500
tgggaagtga agaaacaacg ggccggagta ttgtgggatg ttccttcacc cccacccatg   4560
ggaaaggctg aactggaaga tggagcctat agaattaagc aaaaagggat tcttggatat   4620
tcccagatcg gagccggagt ttacaaagaa ggaacattcc atacaatgtg gcatgtcaca   4680
cgtggcgctg ttcctaatgca taaaggaaag aggattgaac catcatgggc ggacgtcaag   4740
aaagacctaa tatcatatgg aggaggctgg aagttagaag gagaatggaa ggaaggagaa   4800
gaagtccagg tattggcact ggagcctgga aaaaatccaa gagccgtcca aacgaaacct   4860
ggtcttttca aaccaacgc cggaacaata ggtgctgtat ctctggactt ttctcctgga   4920
acgtcaggat ctccaattat cgacaaaaaa ggaaaagttg tgggtctttta tggtaatggt   4980
gttgttacaa ggagtggagc atatgtgagt gctatagccc agactgaaaa aagcattgaa   5040
gacaacccag atcgaagat gacattttc cgaaagagaa gactgaccat catggacctc   5100
cacccaggag cggaaagac gaagagatac cttccggcca tagtcagaga agctataaaa   5160
cggggtttga gaacattaat cttggccccc actagagttg tggcagctga atggaggaa    5220
gccttagag gacttccaat aagataccag accccagcca tcagagctgt gcacaccggg   5280
cgggagattg tggacctaat gtgtcatgcc acatttacca tgaggctgct atcaccagtt   5340
```

```
agagtgccaa actacaacct gattatcatg gacgaagccc atttcacaga cccagcaagt    5400
atagcagcta gaggatacat ctcaactcga gtggagatgg gtgaggcagc tgggattttt    5460
atgacagcca ctcccccggg aagcagagac ccatttcctc agagcaatgc accaatcata    5520
gatgaagaaa gagaaatccc tgaacgctcg tggaattccg gacatgaatg ggtcacggat    5580
tttaaggga agactgtttg gttcgttcca agtataaaag caggaaatga tatagcagct    5640
tgcctgagga aaaatggaaa gaaagtgata caactcagta ggaagacctt tgattctgag    5700
tatgtcaaga ctagaaccaa tgattgggac ttcgtggtta caactgacat tcagaaatg    5760
ggtgccaatt tcaaggctga gagggttata gaccccagac gctgcatgaa accagtcata    5820
ctaacagatg gtgaagagcg ggtgattctg gcaggaccta tgccagtgac ccactctagt    5880
gcagcacaaa aagagggag aataggaaga aatccaaaaa atgagaatga ccagtacata    5940
tacatggggg aacctctgga aaatgatgaa gactgtgcac actggaaaga agctaaaatg    6000
ctcctagata acatcaacac gccagaagga atcattccta gcatgttcga accagagcgt    6060
gaaaaggtgg atgccattga tggcgaatac cgcttgagag agaagcaag gaaaaccttt    6120
gtagacttaa tgaagaagag agacctacca gtctggttgg cctacagagt ggcagctgaa    6180
ggcatcaact acgcagacag aaggtggtgt tttgatggag tcaagaacaa ccaaatccta    6240
gaagaaaacg tggaagttga atctggaca aaagaagggg aaaggaagaa attgaaaccc    6300
agatggttgg atgctaggat ctattctgac ccactggcgc taaaagaatt taaggaattt    6360
gcagccggaa gaaagtctct gaccctgaac ctaatcacag aaatgggtag gctcccaacc    6420
ttcttgactc agaaggcaag agacgcactg gacaacttag cagtgctgca cacggctgag    6480
gcaggtggaa gggcgtacaa ccatgctctc agtgaactgc cggagaccct ggagacattg    6540
cttttactga cacttctggc tacagtcacg ggagggatct ttttattctt gatgagcgca    6600
aggggcatag gaagatgac cctgggaatg tgctgcataa tcacggctag catcctccta    6660
tggtacgcac aaatacagcc acactggata gcagcttcaa taatactgga gttttttctc    6720
atagttttgc ttattccaga acctgaaaaa cagagaacac cccaagacaa ccaactgacc    6780
tacgttgtca tagccatcct cacagtggtg gccgcaacca tggcaaacga gatgggtttc    6840
ctagaaaaaa cgaagaaaga tctcggattg ggaagcattg caacccagca acccgagagc    6900
aacatcctgg acatagatct acgtcctgca tcagcatgga cgctgtatgc cgtggccaca    6960
acatttgtta caccaatgtt gagacatagc attgaaaatt cctcagtgaa tgtgtcccta    7020
acagctatag ccaaccaagc cacagtgtta atgggtctcg ggaaaggatg gccattgtca    7080
aagatggaca tcggagttcc ccttctcgcc attggatgct actcacaagt caaccccata    7140
actctcacag cagctctttt cttattggta gcacattatg ccatcatagg gccaggactc    7200
caagcaaaag caaccagaga agctcagaaa agagcagcgg cgggcatcat gaaaaaccca    7260
actgtcgatg gaataacagt gattgaccta gatccaatac cttatgatcc aaagtttgaa    7320
aagcagttgg acaagtaat gctcctagtc ctctgcgtga ctcaagtatt gatgatgagg    7380
actacatggg ctctgtgtga ggctttaacc ttagctaccg ggcccatctc cacattgtgg    7440
gaaggaaatc cagggaggtt ttggaacact accattgcgg tgtcaatggc taacattttt    7500
agagggagtt acttggccgg agctggactt ctctttttcta ttatgaagaa cacaaccaac    7560
acaagaaggg gaactggcaa cataggagag acgcttggag agaaatgaa agccgattg    7620
aacgcattgg gaaaaagtga attccagatc tacaagaaaa gtggaatcca ggaagtggat    7680
agaaccttag caaaagaagg cattaaaaga ggagaaacgg accatcacgc tgtgtcgcga    7740
```

```
ggctcagcaa aactgagatg gttcgttgag agaaacatgg tcacaccaga agggaaagta   7800
gtggacctcg gttgtggcag aggaggctgg tcatactatt gtggaggact aaagaatgta   7860
agagaagtca aaggcctaac aaaaggagga ccaggacacg aagaacccat ccccatgtca   7920
acatatgggt ggaatctagt gcgtcttcaa agtggagttg acgttttctt catcccgcca   7980
gaaaagtgtg acacattatt gtgtgacata ggggagtcat caccaaatcc cacagtggaa   8040
gcaggacgaa cactcagagt ccttaactta gtagaaaatt ggttgaacaa caacactcaa   8100
ttttgcataa aggttctcaa cccatatatg ccctcagtca tagaaaaaat ggaagcacta   8160
caaaggaaat atggaggagc cttagtgagg aatccactct cacgaaactc cacacatgag   8220
atgtactggg tatccaatgc ttccgggaac atagtgtcat cagtgaacat gatttcaagg   8280
atgttgatca acagatttac aatgagatac aagaaagcca cttacgagcc ggatgttgac   8340
ctcggaagcg aacccgtaa catcgggatt gaaagtgaga taccaaacct agatataatt   8400
gggaaaagaa tagaaaaaat aaagcaagag catgaaacat catggcacta tgaccaagac   8460 caccccataca aaacgtgggc ataccatggt agctatgaaa caaaacagac tggatcagca   8520
tcatccatgg tcaacggagt ggtcaggctg ctgacaaaac cttgggacgt cgtccccatg   8580
gtgacacaga tggcaatgac agacacgact ccatttggac aacagcgcgt ttttaaagag   8640
aaagtggaca cgagaaccca agaaccgaaa gaaggcacga agaaactaat gaaaataaca   8700
gcagagtggc tttggaaaga attagggaag aaaaagacac ccaggatgtg caccagagaa   8760
gaattcacaa gaaaggtgag aagcaatgca gccttggggg ccatattcac tgatgagaac   8820
aagtggaagt cggcacgtga ggctgttgaa gatagtaggt tttgggagct ggttgacaag   8880
gaaaggaatc tccatcttga aggaaagtgt gaaacatgtg tgtacaacat gatgggaaaa   8940
agagagaaga agctaggga attcggcaag gcaaaaggca gcagagccat atggtacatg   9000
tggcttggag cacgcttctt agagtttgaa gccctaggat tcttaaatga agatcactgg   9060
ttctccagag agaactccct gagtggagtg gaaggagaag ggctgcacaa gctaggttac   9120
attctaagag acgtgagcaa gaaagaggga ggagcaatgt atgccgatga caccgcagga   9180
tgggatacaa gaatcacact agaagaccta aaaaatgaag aaatggtaac aaaccacatg   9240
gaaggagaac acaagaaact agccgaggcc atttttcaaac taacgtacca aaacaaggtg   9300
gtgcgtgtgc aaagaccaac accaagaggc acagtaatgg acatcatatc gagaagagac   9360
caaagaggta gtggacaagt tggcacctat ggactcaata ctttcaccaa tatggaagcc   9420
caactaatca gacagatgga gggagaagga gtctttaaaa gcattcagca cctaacaatc   9480
acagaagaaa tcgctgtgca aaactggtta gcaagagtgg ggcgcgaaag gttatcaaga   9540
atggccatca gtgagatga ttgtgttgtg aaacctttag atgacaggtt cgcaagcgct   9600
ttaacagctc taatgacat gggaaagatt aggaaagaca tacaacaatg gaaaccttca   9660
agaggatgga atgattggac acaagtgccc ttctgttcac accatttcca tgagttaatc   9720
atgaaagacg gtcgcgtact cgttgttcca tgtagaaacc aagatgaact gattggcaga   9780
gcccgaatct cccaaggagc agggtggtct ttgcgggaga cggcctgttt ggggaagtct   9840
tacgcccaaa tgtggagctt gatgtacttc cacagacgcg acctcaggct ggcggcaaat   9900
gctatttgct cggcagtacc atcacattgg gttccaacaa gtcgaacaac ctggtccata   9960
catgctaaac atgaatggat gacaacgaa gacatgctga cagtctggaa cagggtgtgg  10020
attcaagaaa acccatggat ggaagacaaa actccagtgg aatcatggga ggaaatccca  10080
```

```
tacttgggga aaagagaaga ccaatggtgc ggctcattga ttgggttaac aagcagggcc   10140
acctgggcaa agaacatcca agcagcaata aatcaagtta gatcccttat aggcaatgaa   10200
gaatacacag attacatgcc atccatgaaa agattcagaa gagaagagga agaagcagga   10260
gttctgtggt agaaagcaaa actaacatga acaaggcta aagtcaggt cggattaagc     10320 catagtacgg aaaaaactat gctacctgtg agccccgtcc aaggacgtta aaagaagtca   10380
ggccatcata aatgccatag cttgagtaaa ctatgcagcc tgtagctcca cctgagaagg   10440
tgtaaaaaat ccgggaggcc acaaaccatg gaagctgtac gcatggcgta gtggactagc   10500
ggttagagga gacccctccc ttacaaatcg cagcaacaat gggggcccaa ggcgagatga   10560
agctgtagtc tcgctggaag gactagaggt tagaggagac cccccgaaa caaaaaacag     10620 catattgacg ctgggaaaga ccagagatcc tgctgtctcc tcagcatcat tccaggcaca   10680
gaacgccaga aaatggaatg gtgctgttga atcaacaggt tc                       10722

<210> SEQ ID NO 10
<211> LENGTH: 10699
<212> TYPE: DNA
<213> ORGANISM: Artificial
<220> FEATURE:
<223> OTHER INFORMATION: Synthetic construct

<400> SEQUENCE: 10
agttgttagt ctacgtggac cgacaagaac agtttcgact cggaagcttg cttaacgtag     60
tgctgacagt ttttattag agagcagatc tctgatgaac aaccaacgga aaaagacggg      120
aaaaccgtct atcaatatgc tgaaacgcgt gagaaaccgt gtgtcaactg atcacagtt     180 ggcgaagaga ttctcaagag gattgctgaa cggccaagga ccaatgaaat tggttatggc    240
atttatagct ttcctcagat ttctagccat tccaccgaca gcaggagtct tggctagatg    300
gggtaccttt aagaagtcgg gggctattaa ggtcttaaaa ggcttcaaga aggagatctc    360
aaacatgctg agcattatca acaaacggaa aaagacatcg ctctgtctca tgatgatgtt    420
accagcaaca cttgctttcc acttaacttc acgagatgga gagccgcgca tgattgtggg    480
gaagaatgaa agaggaaaat ccctactttt caagacagcc tctggaatca acatgtgcac    540
actcatagcc atggatctgg agagatgtg tgatgacacg gtcacttaca aatgccccca    600
cattaccgaa gtggagcctg aagacattga ctgctggtgc aaccttacat cgacatgggt    660
gacttatgga acatgcaatc aagctggaga gcatagacgc gataagagat cagtggcgtt    720
agctccccat gttggcatgg gactggacac acgcactcaa acctggatgt cggctgaagg    780
agcttggaga caagtcgaga aggtagagac atgggccctt aggcacccag ggtttaccat    840
actagcccta tttcttgccc attacatagg cacttcctg acccagaaag tggttatttt    900
tatactatta atgctggtta ccccatccat gacaatgaga tgtgtaggag taggaaacag    960
agattttgtg gaaggcctat cgggagctac gtgggttgac gtggtgctcg agcacggtgg   1020
gtgtgtgact accatggcta agaacaagcc cacgctggac atagagcttc agaagaccga   1080
ggccacccaa ctggcgaccc taaggaagct atgcattgag ggaaaaatta ccaacataac   1140
aaccgactca agatgtccca cccaagggga agcgattta cctgaggagc aggaccagaa    1200
ctacgtgtgt aagcatacat acgtggacag aggctgggga acggttgtg gtttgtttgg   1260 caagggaagc ttggtgacat gcgcgaaatt tcaatgttta gaatcaatag agggaaaagt   1320 ggtgcaaacat gagaacctca aatacaccgt catcatcaca gtgcacacag agaccaaca    1380 ccaggtggga aatgaaacgc agggagtcac ggctgagata acaccccagg catcaaccgc   1440
```

```
tgaagccatt ttacctgaat atggaaccct cgggctagaa tgctcaccac ggacaggttt    1500
ggatttcaat gaaatgatct cattgacaat gaagaacaaa gcatggatgg tacatagaca    1560
atggttcttt gacttacccc taccatggac atcaggagct acagcagaaa caccaacttg    1620
gaacaggaaa gagcttcttg tgacatttaa aaatgcacat gcaaaaaagc aagaagtagt    1680
tgttcttgga tcacaagagg gagcaatgca tacagcactg acaggagcta cagagatcca    1740
aacctcagga ggcacaagta tctttgcggg gcacttaaaa tgtagactca agatggacaa    1800
attggaactc aagggatga gctatgcaat gtgcttgagt agctttgtgt tgaagaaaga     1860
agtctccgaa acgcagcatg ggacaatact cattaaggtt gagtacaaag gggaagatgc    1920
accctgcaag attcctttct ccacggagga tggacaagga aaagctcaca atggcagact    1980
gatcacagcc aatccagtgg tgaccaagaa ggaggagcct gtcaacattg aggctgaacc    2040
tccttttgga gaaagtaaca tagtaattgg aattggagac aaagccctga aaatcaactg    2100
gtacaagaag ggaagctcga ttgggaagat gttcgaggcc actgccagag gtgcaaggcg    2160
catggccatc ttgggagaca cagcctggga ctttggatca gtgggtggtg ttttgaattc    2220
attagggaaa atggtccacc aaatatttgg gagtgcttac acagccctat ttggtggagt    2280
ctcctggatg atgaaaattg gaataggtgt cctcttaacc tggataggt tgaactcaaa     2340 aaatacttct atgtcatttt catgcatcgc gataggaatc attacactct atctgggagc    2400
cgtggtgcaa gctgacatgg ggtgtgtcat aaactggaaa ggcaaagaac tcaaatgtgg    2460
aagtggaatt ttcgtcacta atgaggtcca cacctggaca gagcaataca aatttcaagc    2520
agactccccc aagagactgg caacagccat tgcaggcgct tgggaaaatg gagtgtgcgg    2580
aattaggtca acaaccagaa tggagaacct cttgtggaag caaatagcca atgaactgaa    2640
ttacatatta tgggaaaaca cattaaatt aacggtagtt gtaggcgaca taactggggt     2700
cttagagcaa gggaaaagaa cactaacacc acaacccatg gagctaaaat attcttggaa    2760
aacatgggga aaggcaaaaa tagtgacagc tgaaacacaa aattcctctt tcataataga    2820
tgggccaagc acaccggagt gtccaagtgc ctcaagagca tggaatgtgt gggaggtgga    2880
ggattacggg ttcggagttt tcacaaccaa catatggctg aaactccgag aggtgtacac    2940
ccaactatgt gaccataggc taatgtcggc agccgtcaag gatgagaggg ctgtacatgc    3000
cgacatgggc tattgataga aaagccaaaa gaatgggagt tggaagctag aaaaagcatc    3060
cttcatagag gtgaaaacct gcacatggcc aaaatcacac actctctgga gcaatggtgt    3120
gctagagagt gacatgatta tcccaaagag tctagctggt cccattcgc aacacaacca     3180 caggcccggg taccacaccc aaacggcagg accctggcac ttaggaaaat tggagctgga    3240
cttcaactat tgtgaaggaa caacagttgt catctcagaa aactgtggga caagaggccc    3300
atcattgaga caacaacgg tgtcaggga gttgatacac gaatggtgct gccgctcgtg      3360
cacacttcct cccctacgat acatgggaga agacggctgc tggtatgca tggaaatcag     3420 acccattaat gagaaagaag agaatatggt aaagtctcta gcctcagcag ggagtggaaa    3480
ggtggacaac ttcacaatgg gtgtcttgtg tttggcaatc ctctttgaag aggtgatgag    3540
aggaaaattt gggaaaaaac acatgattgc aggggttctc ttcacgtttg tgctcctcct    3600
ctcagggcaa ataacatgga gagacatggc gcacacactc ataatgattg ggtccaacgc    3660
ctctgacaga atggggatgg gcgtcactta cctagctcta attgcaacat ttaaaattca    3720
gccattcctg gctttgggat tcttcctgag gaaactgaca tctagagaaa atttattgct    3780
```

```
gggagttggg ttggccatgg cagcaacgtt acgactgcca gaggacattg aacagatggc    3840
gaatggaatt gctttggggc tcatggctct taaactgata acacaatttg aaacatacca    3900
actatggacg gcattagttt ccctaacgtg ttcaaataca attttcacgt tgactgttgc    3960
ctggagaaca gccactctga ttttagccgg aatttcgctt ttgccagtgt gccagtcttc    4020
gagcatgagg aaaacagatt ggctcccaat gactgtggca gctatgggag ctcaacccct    4080 accactttt attttcagtc tgaaagatac actcaaaagg agaagctggc cactgaatga    4140
gggggtgatg gcagttggac ttgtgagcat tctagctagt tctctcctta ggaatgatgt    4200
gcctatggct ggaccattag tggctggggg cttgctgata gcgtgctacg tcataactgg    4260
cacgtcagca gacctcactg tagaaaaagc agcagatgta catgggagg aagaggccga    4320 gcaaacagga gtgtcccaca atttaatggt cacagttgat gatgatgaa caatgagaat    4380 aaaagatgac gagactgaga acatcttaac agtgcttta aaaacagcac tactaatagt    4440
atcaggcatc tttccatact ccatacccgc aacactgttg gtctggcata cttggcaaaa    4500
gcaaacccaa agatccggcg tcctatggga cgtacccagc cccccagaga cacagaaagc    4560
ggaactggaa aaggggtct ataggatcaa acagcaagga attttggga aacccaagt    4620 ggggttgga gtacagaaag aaggagtttt ccacaccatg tggcatgtca caagaggggc    4680
agtgttgaca cacaatggga aaagactgga accaaactgg gctagcgtga aaaaagatct    4740
gatttcatac ggaggaggat ggagattgag tgcacaatgg caaagggggg aggaggtgca    4800
ggttattgcc gtagagcctg ggaagaaccc aaagaacttt caaaccatgc caggcatttt    4860
tcagacaaca cagggaaa taggagcaat tgcactggat tcaagcctg aacttcagg    4920 atctcccatc ataaacagag agggaaggt agtgggactg tatggcaatg gagtggttac    4980
aaagaatgga ggctatgtca gtggaatagc gcaaacaaat gcagaaccag atggaccgac    5040
accagagttg gaagaagaga tgttcaaaaa gcgaaatcta accataatgg atctccatcc    5100
tgggtcagga aagacgcgga aatatcttcc agctattgtt agagaggcaa tcaagagacg    5160
cttaaggact ctaattttgg caccaacaag ggtagttgca gctgagatgg aagaagcatt    5220
gaaagggctc ccaataaggt atcaaacaac tgcaacaaaa tctgaacaca caggaagaga    5280
gattgttgat ctaatgtgtc acgcaacgtt cacaatgcgc ttgctgtcac cagtcagggt    5340
tccaaactac aacttgataa taatggatga ggcccatttc acagaccag ccagtatagc    5400 ggctagaggg tacatatcaa ctcgtgtagg aatgggagag gcagccgcaa ttttcatgac    5460
agcaacaccc cctggaacag ctgatgcctt tcctcagagc aacgctccaa ttcaagatga    5520
agagagagac ataccggaac gctcatggaa ttcaggcaat gaatggatta ctgactttgt    5580
tgggaagaca gtgtggtttg tccctagcat caaagccgga aatgacatag caaactgctt    5640
gcggaaaaat ggaaaaaagg ttattcaact cagcaggaag accctttgaca cagaatatca    5700 aaagaccaaa ctgaatgatt gggacttttgt ggtgacaaca gacatttcag aaatgggagc    5760
caatttcaaa gcagatagag tgatcgaccc aagaagatgt ctcaagccgg tgattttgac    5820
agatggaccc gagcgggtga tcctggctgg accaatgcca gtcaccgtag cgagcgctgc    5880
gcaaaggaga gggagagttg gcaggaaccc acaaaaagaa aatgaccagt acatattcat    5940
gggccagcct ctcaacaatg atgaagacca tgctcactgg acagaagcaa aatgctgct    6000 ggacaacatc aacacaccag aagggattat accagctctc tttgaaccag aaagggagaa    6060
gtcagccgcc atagacggcg aataccgcct gaagggtgag tccaggaaga ctttcgtgga    6120
actcatgagg agggggtgacc tcccagtttg gctagcccat aaagtagcat cagaagggat    6180
```

```
caaatataca gatagaaaat ggtgctttga tggagaacgt aataatcaaa ttttagagga     6240
gaatatggat gtggaaatct ggacaaagga aggagaaaag aaaaaactga gacctaggtg     6300
gcttgatgcc cgcacttatt cagatccttt agcactcaaa gaattcaagg attttgcagc     6360
tggcagaaag tcaatcgccc ttgatcttgt gacagaaata ggaagagtgc cttcacactt     6420
agcccacaga acgagaaacg ccctggataa tttggtgatg ctgcacacgt cagaacatgg     6480
cggtagggcc tacaggcatg cagtggagga actaccagaa cgatggaaaa cactcttact     6540
cctgggactg atgatcttgt taacaggtgg agcaatgctc ttcttgatat caggtaaagg     6600
gattggaaag acttcaatag gactcatttg tgtaattgct tccagcggca tgttatggat     6660
ggctgatgtc ccactccaat ggatcgcatc ggctatagtc ctggagtttt ttatgatggt     6720
gttgctcata ccagaaccag aaaagcagag aactccccaa gacaaccaac tcgcatatgt     6780
cgtgataggc atacttacat tggctgcaat agtagcggcc aatgaaatgg gactgttgga     6840
aactacaaag agagatttag gaatgtctaa agaaccaggt gttgtttctc caaccagcta     6900
tttggatgtg gacttgcacc cagcatcagc ctggacattg tacgccgtgg ccacaacagt     6960
aataacacca atgttgagac acaccataga gaattccaca gcaaatgtgt ctctggcagc     7020
catagctaac caggcagtgg tcctgatggg tttagacaaa ggatggccga tatcgaaaat     7080
ggacttgggc gtaccactat tggcactggg ttgctattca caagtgaacc cactaactct     7140
tgcagcggca gtacttttgc tagtcacaca ttatgcaatt ataggtccag gattgcaggc     7200
aaaagccacc cgtgaagctc agaaaaggac agctgctgga ataatgaaga tccaacggt     7260 ggatggaata atgacaatag acctagatcc tgtaatatat gattcaaaat ttgaaaagca     7320
actaggacag gtcatgctcc tggttctgtg tgcagtccaa cttttattga tgagaacatc     7380
atgggccttg tgtgaagttc taaccctagc cacaggacca ataacaacac tctgggaagg     7440
atcacctggg aagttctgga acaccacgat agctgtttcc atggcgaaca tctttagagg     7500 gagctatta gcaggagctg ggcttgcttt ttctatcatg aaatcagttg gaacaggaaa     7560
gagaggaaca gggtcacaag gtgaaaacct aggagaaaag tggaaaaaga attaaatca     7620 gttatcccgg aaagagtttg acctttacaa gaaatccgga atcaccgaag tggatagaac     7680
agaagccaaa gaagggttaa aaagaggaga ataacacac catgccgtgt ccagaggcag     7740
cgcaaaactt caatggttcg tggagagaaa catggtcatt cctgaaggaa gagtcataga     7800
cctaggctgt ggaagaggag ctggtcata ttactgtgca ggactgaaaa aagttacaga     7860
agtgcgagga tacacaaaag gcggcccagg acacgaagaa ccagtaccta tgtctacata     7920
cggatggaac atagtcaagt taatgagtgg aaaggatgtt ttttatctgc cacctgaaaa     7980
gtgtgatacc ctattgtgtg acattggaga atcttcacca gcccaacag tggaagaaag     8040 cagaaccata agagttttga gatggttga accatggcta agaacaacc agttttgcat     8100 taaagtattg aacccataca tgccaactgt gattgagcac ttagaaagac tacaaaggaa     8160
acatggagga atgcttgtga gaaatccact ctcacgaaac tccacgcacg aaatgtattg     8220
gatatccaat ggtacaggca atatcgtctc ttcagtcaac atggtatcca gattgctact     8280
gaacagattc acaatgacac acaggagacc caccatagag aaagatgtgg atctaggagc     8340
aggaacccga catgtcaatg cggaaccaga aacacccaac atggatgtca ttggggaaag     8400
aataaaaagg atcaaagagg agcatagttc aacatgcac tatgatgatg aaatccttta     8460 caaacgtgg gcttaccatg gatcctatga agtaaaagcc acaggctcag cctcctccat     8520
```

```
gataaatgga gtcgtgaaac tcctcacaaa accatgggat gtggtgccca tggtgacaca    8580
gatggcaatg acagatacaa ctccattcgg ccagcaaaga gttttttaaag agaaagtgga    8640
caccaggaca cctaggccca tgccaggaac aagaaaggtt atggagatca cagcggagtg    8700
gctttggagg accctgggaa ggaacaaaag acccagatta tgcacaaggg aggaattcac    8760
aaagaaggtc agaaccaacg cagctatggg cgctgtcttc acagaagaga accaatggga    8820
cagtgcgaga gctgctgttg aggacgaaga attttggaaa cttgtggaca gagaacgtga    8880
actccacaaa ctgggcaagt gtggaagctg cgtttacaac atgatgggca agagagagaa    8940
aaaacttgga gagtttggta agcaaaaggc agtagggct atatggtaca tgtggttggg    9000
agccaggtac cttgagttcg aggcgctcgg attcctcaat gaagaccact ggttctcgcg    9060
tgaaaactct tacagtggag tagaaggaga aggactgcac aagctgggat acatcttgag    9120
agatatttcc aagataccccg gaggagccat gtatgctgat gacacagccg gttgggacac    9180
aagaataaca gaagatgacc tgcacaatga ggaaaaaatc acacagcaga tggacccctga    9240
acacaggcag ctagcgaacg ctatattcaa gctcacatac caaaacaaag tggtcaaagt    9300
ccaacgacca actccaaagg gcacggtaat ggacatcata tctaggaaag accaaagagg    9360
cagtggacag gtgggaactt atggtctgaa cacattcacc aacatggaag cccagctaat    9420
cagacaaatg gaaggagaag gcgtgttgtc aaaggcagac ctcgagaacc cccatccgct    9480
agagaagaaa attacacaat ggttggaaac taaggagtg gaaaggttaa aagaatggc    9540
catcagcggg gatgattgcg ttgtgaaacc aatcgacgac agattcgcca atgccctgct    9600
tgccctgaac gatatgggaa aggttagaaa ggacatacct caatggcagc catcaaaggg    9660
atggcatgat tggcaacagg tccccttctg ctcccaccac tttcatgaat tgatcatgaa    9720
agatggaaga aagttggtag ttccctgcag accccaggac gaactaatag gaagagcgag    9780
aatctcccaa ggagcaggat ggagccttag agaaactgca tgtctaggga agcctacgc    9840
tcaaatgtgg gctctcatgt atttccacag aagagatctt agactagcat ccaacgccat    9900
atgttcagca gtaccagtcc actgggtccc cacgagcaga acgacatggt ctattcatgc    9960
tcaccatcag tggatgacta cagaagacat gcttactgtc tggaacagg tgtggatagga   10020
ggacaatcca tggatggaag acaaaactcc agtcacaacg tgggaagatg ttccatatct   10080
agggaagaga gaagaccaat ggtgcggatc actcatagg ctcacttcca gagcaacctg   10140
ggcccagaac atactcacag caatccaaca ggtgagaagc ctcataggca atgaagagtt   10200
tctggactac atgccttcga tgaagagatt caggaaggag gaggagtcag agggagccat   10260
ttggtaaaag caggaggtaa actgtcaggc cacattaagc cacagtacgg aagaagctgt   10320
gcagcctgtg agccccgtcc aaggacgtta aagaagaag tcaggcccaa aagccacggt   10380
ttgagcaaac cgtgctgcct gtagctccgt cgtggggacg taaagcctgg gaggctgcaa   10440
accgtggaag ctgtacgcac ggtgtagcag actagtggtt agaggagacc ctcccatga   10500
cacaacgcag cagcggggcc cgagcactga gggaagctgt acctccttgc aaaggactag   10560
aggttagagg agacccccg caaacaaaaa cagcatattg acgctgggag agaccagaga   10620
tcctgctgtc tcctcagcat cattccaggc acagaacgcc agaaaatgga atggtgctgt   10680
tgaatcaaca ggttctagt                                                10699
```

<210> SEQ ID NO 11
<211> LENGTH: 3390
<212> TYPE: PRT
<213> ORGANISM: Artificial
<220> FEATURE:
<223> OTHER INFORMATION: Synthetic construct

<400> SEQUENCE: 11

```
Met Asn Asn Gln Arg Lys Lys Thr Gly Lys Pro Ser Ile Asn Met Leu
1               5                   10                  15

Lys Arg Val Arg Asn Arg Val Ser Thr Gly Ser Gln Leu Ala Lys Arg
            20                  25                  30

Phe Ser Arg Gly Leu Leu Asn Gly Gln Gly Pro Met Lys Leu Val Met
        35                  40                  45

Ala Phe Ile Ala Phe Leu Arg Phe Leu Ala Ile Pro Pro Thr Ala Gly
50                  55                  60

Val Leu Ala Arg Trp Gly Thr Phe Lys Lys Ser Gly Ala Ile Lys Val
65                  70                  75                  80

Leu Lys Gly Phe Lys Lys Glu Ile Ser Asn Met Leu Ser Ile Ile Asn
            85                  90                  95

Lys Arg Lys Lys Thr Ser Leu Cys Leu Met Met Met Leu Pro Ala Thr
            100                 105                 110

Leu Ala Phe His Leu Thr Ser Arg Asp Gly Glu Pro Arg Met Ile Val
            115                 120                 125

Gly Lys Asn Glu Arg Gly Lys Ser Leu Leu Phe Lys Thr Ala Ser Gly
        130                 135                 140

Ile Asn Met Cys Thr Leu Ile Ala Met Asp Leu Gly Glu Met Cys Asp
145                 150                 155                 160

Asp Thr Val Thr Tyr Lys Cys Pro His Ile Thr Glu Val Glu Pro Glu
                165                 170                 175

Asp Ile Asp Cys Trp Cys Asn Leu Thr Ser Thr Trp Val Thr Tyr Gly
            180                 185                 190

Thr Cys Asn Gln Ala Gly Glu His Arg Arg Asp Lys Arg Ser Val Ala
        195                 200                 205

Leu Ala Pro His Val Gly Met Gly Leu Asp Thr Arg Thr Gln Thr Trp
210                 215                 220

Met Ser Ala Glu Gly Ala Trp Arg Gln Val Glu Lys Val Glu Thr Trp
225                 230                 235                 240

Ala Leu Arg His Pro Gly Phe Thr Ile Leu Ala Leu Phe Leu Ala His
            245                 250                 255

Tyr Ile Gly Thr Ser Leu Thr Gln Lys Val Val Ile Phe Ile Leu Leu
            260                 265                 270

Met Leu Val Thr Pro Ser Met Thr Met Arg Cys Val Gly Val Gly Asn
            275                 280                 285

Arg Asp Phe Val Glu Gly Leu Ser Gly Ala Thr Trp Val Asp Val Val
        290                 295                 300

Leu Glu His Gly Gly Cys Val Thr Thr Met Ala Lys Asn Lys Pro Thr
305                 310                 315                 320

Leu Asp Ile Glu Leu Gln Lys Thr Glu Ala Thr Gln Leu Ala Thr Leu
            325                 330                 335

Arg Lys Leu Cys Ile Glu Gly Lys Ile Thr Asn Ile Thr Thr Asp Ser
            340                 345                 350

Arg Cys Pro Thr Gln Gly Glu Ala Ile Leu Pro Glu Glu Gln Asp Gln
        355                 360                 365

Asn Tyr Val Cys Lys His Thr Tyr Val Asp Arg Gly Trp Gly Asn Gly
    370                 375                 380

Cys Gly Leu Phe Gly Lys Gly Ser Leu Val Thr Cys Ala Lys Phe Gln
385                 390                 395                 400
```

```
Cys Leu Glu Ser Ile Glu Gly Lys Val Val Gln His Glu Asn Leu Lys
                405                 410                 415

Tyr Thr Val Ile Ile Thr Val His Thr Gly Asp Gln His Gln Val Gly
                420                 425                 430

Asn Glu Thr Gln Gly Val Thr Ala Glu Ile Thr Pro Gln Ala Ser Thr
                435                 440                 445

Ala Glu Ala Ile Leu Pro Glu Tyr Gly Thr Leu Gly Leu Glu Cys Ser
450                 455                 460

Pro Arg Thr Gly Leu Asp Phe Asn Glu Met Ile Ser Leu Thr Met Lys
465                 470                 475                 480

Asn Lys Ala Trp Met Val His Arg Gln Trp Phe Phe Asp Leu Pro Leu
                485                 490                 495

Pro Trp Thr Ser Gly Ala Thr Ala Glu Thr Pro Thr Trp Asn Arg Lys
                500                 505                 510

Glu Leu Leu Val Thr Phe Lys Asn Ala His Ala Lys Lys Gln Glu Val
                515                 520                 525

Val Val Leu Gly Ser Gln Glu Gly Ala Met His Thr Ala Leu Thr Gly
                530                 535                 540

Ala Thr Glu Ile Gln Thr Ser Gly Gly Thr Ser Ile Phe Ala Gly His
545                 550                 555                 560

Leu Lys Cys Arg Leu Lys Met Asp Lys Leu Glu Leu Lys Gly Met Ser
                565                 570                 575

Tyr Ala Met Cys Leu Ser Ser Phe Val Leu Lys Lys Glu Val Ser Glu
                580                 585                 590

Thr Gln His Gly Thr Ile Leu Ile Lys Val Glu Tyr Lys Gly Glu Asp
                595                 600                 605

Ala Pro Cys Lys Ile Pro Phe Ser Thr Glu Asp Gly Gln Gly Lys Ala
610                 615                 620

His Asn Gly Arg Leu Ile Thr Ala Asn Pro Val Val Thr Lys Lys Glu
625                 630                 635                 640

Glu Pro Val Asn Ile Glu Ala Glu Pro Pro Phe Gly Glu Ser Asn Ile
                645                 650                 655

Val Ile Gly Ile Gly Asp Lys Ala Leu Lys Ile Asn Trp Tyr Lys Lys
                660                 665                 670

Gly Ser Ser Ile Gly Lys Met Phe Glu Ala Thr Ala Arg Gly Ala Arg
                675                 680                 685

Arg Met Ala Ile Leu Gly Asp Thr Ala Trp Asp Phe Gly Ser Val Gly
690                 695                 700

Gly Val Leu Asn Ser Leu Gly Lys Met Val His Gln Ile Phe Gly Ser
705                 710                 715                 720

Ala Tyr Thr Ala Leu Phe Gly Gly Val Ser Trp Met Met Lys Ile Gly
                725                 730                 735

Ile Gly Val Leu Leu Thr Trp Ile Gly Leu Asn Ser Lys Asn Thr Ser
                740                 745                 750

Met Ser Phe Ser Cys Ile Ala Ile Gly Ile Ile Thr Leu Tyr Leu Gly
                755                 760                 765

Ala Val Val Gln Ala Asp Met Gly Cys Val Ile Asn Trp Lys Gly Lys
                770                 775                 780

Glu Leu Lys Cys Gly Ser Gly Ile Phe Val Thr Asn Glu Val His Thr
785                 790                 795                 800

Trp Thr Glu Gln Tyr Lys Phe Gln Ala Asp Ser Pro Lys Arg Leu Ala
                805                 810                 815
```

-continued

```
Thr Ala Ile Ala Gly Ala Trp Glu Asn Gly Val Cys Gly Ile Arg Ser
            820                 825                 830

Thr Thr Arg Met Glu Asn Leu Leu Trp Lys Gln Ile Ala Asn Glu Leu
            835                 840                 845

Asn Tyr Ile Leu Trp Glu Asn Asn Ile Lys Leu Thr Val Val Val Gly
            850                 855                 860

Asp Ile Thr Gly Val Leu Glu Gln Gly Lys Arg Thr Leu Thr Pro Gln
865                 870                 875                 880

Pro Met Glu Leu Lys Tyr Ser Trp Lys Thr Trp Gly Lys Ala Lys Ile
            885                 890                 895

Val Thr Ala Glu Thr Gln Asn Ser Ser Phe Ile Ile Asp Gly Pro Ser
            900                 905                 910

Thr Pro Glu Cys Pro Ser Ala Ser Arg Ala Trp Asn Val Trp Glu Val
            915                 920                 925

Glu Asp Tyr Gly Phe Gly Val Phe Thr Thr Asn Ile Trp Leu Lys Leu
            930                 935                 940

Arg Glu Val Tyr Thr Gln Leu Cys Asp His Arg Leu Met Ser Ala Ala
945                 950                 955                 960

Val Lys Asp Glu Arg Ala Val His Ala Asp Met Gly Tyr Trp Ile Glu
            965                 970                 975

Ser Gln Lys Asn Gly Ser Trp Lys Leu Glu Lys Ala Ser Phe Ile Glu
            980                 985                 990

Val Lys Thr Cys Thr Trp Pro Lys Ser His Thr Leu Trp Ser Asn Gly
            995                1000                1005

Val Leu Glu Ser Asp Met Ile Ile Pro Lys Ser Leu Ala Gly Pro
            1010                1015                1020

Ile Ser Gln His Asn His Arg Pro Gly Tyr His Thr Gln Thr Ala
            1025                1030                1035

Gly Pro Trp His Leu Gly Lys Leu Glu Leu Asp Phe Asn Tyr Cys
            1040                1045                1050

Glu Gly Thr Thr Val Val Ile Ser Glu Asn Cys Gly Thr Arg Gly
            1055                1060                1065

Pro Ser Leu Arg Thr Thr Thr Val Ser Gly Lys Leu Ile His Glu
            1070                1075                1080

Trp Cys Cys Arg Ser Cys Thr Leu Pro Pro Leu Arg Tyr Met Gly
            1085                1090                1095

Glu Asp Gly Cys Trp Tyr Gly Met Glu Ile Arg Pro Ile Asn Glu
            1100                1105                1110

Lys Glu Glu Asn Met Val Lys Ser Leu Ala Ser Ala Gly Ser Gly
            1115                1120                1125

Lys Val Asp Asn Phe Thr Met Gly Val Leu Cys Leu Ala Ile Leu
            1130                1135                1140

Phe Glu Glu Val Met Arg Gly Lys Phe Gly Lys His Met Ile
            1145                1150                1155

Ala Gly Val Leu Phe Thr Phe Val Leu Leu Leu Ser Gly Gln Ile
            1160                1165                1170

Thr Trp Arg Asp Met Ala His Thr Leu Ile Met Ile Gly Ser Asn
            1175                1180                1185

Ala Ser Asp Arg Met Gly Met Gly Val Thr Tyr Leu Ala Leu Ile
            1190                1195                1200

Ala Thr Phe Lys Ile Gln Pro Phe Leu Ala Leu Gly Phe Phe Leu
            1205                1210                1215

Arg Lys Leu Thr Ser Arg Glu Asn Leu Leu Leu Gly Val Gly Leu
```

-continued

```
         1220            1225            1230
Ala Met  Ala Ala Thr Leu Arg Leu Pro Glu Asp Ile Glu Gln Met
    1235            1240            1245
Ala Asn  Gly Ile Ala Leu Gly Leu Met Ala Leu Lys Leu Ile Thr
    1250            1255            1260
Gln Phe  Glu Thr Tyr Gln Leu Trp Thr Ala Leu Val Ser Leu Thr
    1265            1270            1275
Cys Ser  Asn Thr Ile Phe Thr Leu Thr Val Ala Trp Arg Thr Ala
    1280            1285            1290
Thr Leu  Ile Leu Ala Gly Ile Ser Leu Leu Pro Val Cys Gln Ser
    1295            1300            1305
Ser Ser  Met Arg Lys Thr Asp Trp Leu Pro Met Thr Val Ala Ala
    1310            1315            1320
Met Gly  Ala Gln Pro Leu Pro Leu Phe Ile Phe Ser Leu Lys Asp
    1325            1330            1335
Thr Leu  Lys Arg Arg Ser Trp Pro Leu Asn Glu Gly Val Met Ala
    1340            1345            1350
Val Gly  Leu Val Ser Ile Leu Ala Ser Ser Leu Leu Arg Asn Asp
    1355            1360            1365
Val Pro  Met Ala Gly Pro Leu Val Ala Gly Gly Leu Leu Ile Ala
    1370            1375            1380
Cys Tyr  Val Ile Thr Gly Thr Ser Ala Asp Leu Thr Val Glu Lys
    1385            1390            1395
Ala Ala  Asp Val Thr Trp Glu Glu Ala Glu Gln Thr Gly Val
    1400            1405            1410
Ser His  Asn Leu Met Val Thr Val Asp Asp Gly Thr Met Arg
    1415            1420            1425
Ile Lys  Asp Asp Glu Thr Glu Asn Ile Leu Thr Val Leu Leu Lys
    1430            1435            1440
Thr Ala  Leu Leu Ile Val Ser Gly Ile Phe Pro Tyr Ser Ile Pro
    1445            1450            1455
Ala Thr  Leu Leu Val Trp His Thr Trp Gln Lys Gln Thr Gln Arg
    1460            1465            1470
Ser Gly  Val Leu Trp Asp Val Pro Ser Pro Glu Thr Gln Lys
    1475            1480            1485
Ala Glu  Leu Glu Glu Gly Val Tyr Arg Ile Lys Gln Gln Gly Ile
    1490            1495            1500
Phe Gly  Lys Thr Gln Val Gly Val Gly Val Gln Lys Glu Gly Val
    1505            1510            1515
Phe His  Thr Met Trp His Val Thr Arg Gly Ala Val Leu Thr His
    1520            1525            1530
Asn Gly  Lys Arg Leu Glu Pro Asn Trp Ala Ser Val Lys Lys Asp
    1535            1540            1545
Leu Ile  Ser Tyr Gly Gly Gly Trp Arg Leu Ser Ala Gln Trp Gln
    1550            1555            1560
Lys Gly  Glu Glu Val Gln Val Ile Ala Val Glu Pro Gly Lys Asn
    1565            1570            1575
Pro Lys  Asn Phe Gln Thr Met Pro Gly Ile Phe Gln Thr Thr Thr
    1580            1585            1590
Gly Glu  Ile Gly Ala Ile Ala Leu Asp Phe Lys Pro Gly Thr Ser
    1595            1600            1605
Gly Ser  Pro Ile Ile Asn Arg Glu Gly Lys Val Val Gly Leu Tyr
    1610            1615            1620
```

```
Gly Asn Gly Val Val Thr Lys Asn Gly Gly Tyr Val Ser Gly Ile
    1625              1630                1635

Ala Gln Thr Asn Ala Glu Pro Asp Gly Pro Thr Pro Glu Leu Glu
    1640              1645                1650

Glu Glu Met Phe Lys Lys Arg Asn Leu Thr Ile Met Asp Leu His
    1655              1660                1665

Pro Gly Ser Gly Lys Thr Arg Lys Tyr Leu Pro Ala Ile Val Arg
    1670              1675                1680

Glu Ala Ile Lys Arg Arg Leu Arg Thr Leu Ile Leu Ala Pro Thr
    1685              1690                1695

Arg Val Val Ala Ala Glu Met Glu Glu Ala Leu Lys Gly Leu Pro
    1700              1705                1710

Ile Arg Tyr Gln Thr Thr Ala Thr Lys Ser Glu His Thr Gly Arg
    1715              1720                1725

Glu Ile Val Asp Leu Met Cys His Ala Thr Phe Thr Met Arg Leu
    1730              1735                1740

Leu Ser Pro Val Arg Val Pro Asn Tyr Asn Leu Ile Ile Met Asp
    1745              1750                1755

Glu Ala His Phe Thr Asp Pro Ala Ser Ile Ala Ala Arg Gly Tyr
    1760              1765                1770

Ile Ser Thr Arg Val Gly Met Gly Glu Ala Ala Ala Ile Phe Met
    1775              1780                1785

Thr Ala Thr Pro Pro Gly Thr Ala Asp Ala Phe Pro Gln Ser Asn
    1790              1795                1800

Ala Pro Ile Gln Asp Glu Glu Arg Asp Ile Pro Glu Arg Ser Trp
    1805              1810                1815

Asn Ser Gly Asn Glu Trp Ile Thr Asp Phe Val Gly Lys Thr Val
    1820              1825                1830

Trp Phe Val Pro Ser Ile Lys Ala Gly Asn Asp Ile Ala Asn Cys
    1835              1840                1845

Leu Arg Lys Asn Gly Lys Lys Val Ile Gln Leu Ser Arg Lys Thr
    1850              1855                1860

Phe Asp Thr Glu Tyr Gln Lys Thr Lys Leu Asn Asp Trp Asp Phe
    1865              1870                1875

Val Val Thr Thr Asp Ile Ser Glu Met Gly Ala Asn Phe Lys Ala
    1880              1885                1890

Asp Arg Val Ile Asp Pro Arg Arg Cys Leu Lys Pro Val Ile Leu
    1895              1900                1905

Thr Asp Gly Pro Glu Arg Val Ile Leu Ala Gly Pro Met Pro Val
    1910              1915                1920

Thr Val Ala Ser Ala Ala Gln Arg Arg Gly Arg Val Gly Arg Asn
    1925              1930                1935

Pro Gln Lys Glu Asn Asp Gln Tyr Ile Phe Met Gly Gln Pro Leu
    1940              1945                1950

Asn Asn Asp Glu Asp His Ala His Trp Thr Glu Ala Lys Met Leu
    1955              1960                1965

Leu Asp Asn Ile Asn Thr Pro Glu Gly Ile Ile Pro Ala Leu Phe
    1970              1975                1980

Glu Pro Glu Arg Glu Lys Ser Ala Ala Ile Asp Gly Glu Tyr Arg
    1985              1990                1995

Leu Lys Gly Glu Ser Arg Lys Thr Phe Val Glu Leu Met Arg Arg
    2000              2005                2010
```

```
Gly Asp Leu Pro Val Trp Leu Ala His Lys Val Ala Ser Glu Gly
    2015                2020                2025

Ile Lys Tyr Thr Asp Arg Lys Trp Cys Phe Asp Gly Glu Arg Asn
    2030                2035                2040

Asn Gln Ile Leu Glu Glu Asn Met Asp Val Glu Ile Trp Thr Lys
    2045                2050                2055

Glu Gly Glu Lys Lys Lys Leu Arg Pro Arg Trp Leu Asp Ala Arg
    2060                2065                2070

Thr Tyr Ser Asp Pro Leu Ala Leu Lys Glu Phe Lys Asp Phe Ala
    2075                2080                2085

Ala Gly Arg Lys Ser Ile Ala Leu Asp Leu Val Thr Glu Ile Gly
    2090                2095                2100

Arg Val Pro Ser His Leu Ala His Arg Thr Arg Asn Ala Leu Asp
    2105                2110                2115

Asn Leu Val Met Leu His Thr Ser Glu His Gly Gly Arg Ala Tyr
    2120                2125                2130

Arg His Ala Val Glu Glu Leu Pro Glu Thr Met Glu Thr Leu Leu
    2135                2140                2145

Leu Leu Gly Leu Met Ile Leu Leu Thr Gly Gly Ala Met Leu Phe
    2150                2155                2160

Leu Ile Ser Gly Lys Gly Ile Gly Lys Thr Ser Ile Gly Leu Ile
    2165                2170                2175

Cys Val Ile Ala Ser Ser Gly Met Leu Trp Met Ala Asp Val Pro
    2180                2185                2190

Leu Gln Trp Ile Ala Ser Ala Ile Val Leu Glu Phe Phe Met Met
    2195                2200                2205

Val Leu Leu Ile Pro Glu Pro Glu Lys Gln Arg Thr Pro Gln Asp
    2210                2215                2220

Asn Gln Leu Ala Tyr Val Val Ile Gly Ile Leu Thr Leu Ala Ala
    2225                2230                2235

Ile Val Ala Ala Asn Glu Met Gly Leu Leu Glu Thr Thr Lys Arg
    2240                2245                2250

Asp Leu Gly Met Ser Lys Glu Pro Gly Val Val Ser Pro Thr Ser
    2255                2260                2265

Tyr Leu Asp Val Asp Leu His Pro Ala Ser Ala Trp Thr Leu Tyr
    2270                2275                2280

Ala Val Ala Thr Thr Val Ile Thr Pro Met Leu Arg His Thr Ile
    2285                2290                2295

Glu Asn Ser Thr Ala Asn Val Ser Leu Ala Ala Ile Ala Asn Gln
    2300                2305                2310

Ala Val Val Leu Met Gly Leu Asp Lys Gly Trp Pro Ile Ser Lys
    2315                2320                2325

Met Asp Leu Gly Val Pro Leu Leu Ala Leu Gly Cys Tyr Ser Gln
    2330                2335                2340

Val Asn Pro Leu Thr Leu Ala Ala Ala Val Leu Leu Leu Val Thr
    2345                2350                2355

His Tyr Ala Ile Ile Gly Pro Gly Leu Gln Ala Lys Ala Thr Arg
    2360                2365                2370

Glu Ala Gln Lys Arg Thr Ala Ala Gly Ile Met Lys Asn Pro Thr
    2375                2380                2385

Val Asp Gly Ile Met Thr Ile Asp Leu Asp Pro Val Ile Tyr Asp
    2390                2395                2400

Ser Lys Phe Glu Lys Gln Leu Gly Gln Val Met Leu Leu Val Leu
```

```
                2405                2410                2415
Cys Ala Val Gln Leu Leu Met Arg Thr Ser Trp Ala Leu Cys
        2420            2425                2430
Glu Val Leu Thr Leu Ala Thr Gly Pro Ile Thr Thr Leu Trp Glu
2435            2440                2445
Gly Ser Pro Gly Lys Phe Trp Asn Thr Thr Ile Ala Val Ser Met
2450                2455                2460
Ala Asn Ile Phe Arg Gly Ser Tyr Leu Ala Gly Gly Leu Ala
2465                2470                2475
Phe Ser Ile Met Lys Ser Val Gly Thr Gly Lys Arg Gly Thr Gly
2480                2485                2490
Ser Gln Gly Glu Thr Leu Gly Glu Lys Trp Lys Lys Leu Asn
2495                2500                2505
Gln Leu Ser Arg Lys Glu Phe Asp Leu Tyr Lys Lys Ser Gly Ile
2510                2515                2520
Thr Glu Val Asp Arg Thr Glu Ala Lys Glu Gly Leu Lys Arg Gly
2525                2530                2535
Glu Ile Thr His His Ala Val Ser Arg Gly Ser Ala Lys Leu Gln
2540                2545                2550
Trp Phe Val Glu Arg Asn Met Val Ile Pro Glu Gly Arg Val Ile
2555                2560                2565
Asp Leu Gly Cys Gly Arg Gly Gly Trp Ser Tyr Tyr Cys Ala Gly
2570                2575                2580
Leu Lys Lys Val Thr Glu Val Arg Gly Tyr Thr Lys Gly Gly Pro
2585                2590                2595
Gly His Glu Glu Pro Val Pro Met Ser Thr Tyr Gly Trp Asn Ile
2600                2605                2610
Val Lys Leu Met Ser Gly Lys Asp Val Phe Tyr Leu Pro Pro Glu
2615                2620                2625
Lys Cys Asp Thr Leu Leu Cys Asp Ile Gly Glu Ser Ser Pro Ser
2630                2635                2640
Pro Thr Val Glu Glu Ser Arg Thr Ile Arg Val Leu Lys Met Val
2645                2650                2655
Glu Pro Trp Leu Lys Asn Asn Gln Phe Cys Ile Lys Val Leu Asn
2660                2665                2670
Pro Tyr Met Pro Thr Val Ile Glu His Leu Glu Arg Leu Gln Arg
2675                2680                2685
Lys His Gly Gly Met Leu Val Arg Asn Pro Leu Ser Arg Asn Ser
2690                2695                2700
Thr His Glu Met Tyr Trp Ile Ser Asn Gly Thr Gly Asn Ile Val
2705                2710                2715
Ser Ser Val Asn Met Val Ser Arg Leu Leu Leu Asn Arg Phe Thr
2720                2725                2730
Met Thr His Arg Arg Pro Thr Ile Glu Lys Asp Val Asp Leu Gly
2735                2740                2745
Ala Gly Thr Arg His Val Asn Ala Glu Pro Glu Thr Pro Asn Met
2750                2755                2760
Asp Val Ile Gly Glu Arg Ile Lys Arg Ile Lys Glu Glu His Ser
2765                2770                2775
Ser Thr Trp His Tyr Asp Asp Glu Asn Pro Tyr Lys Thr Trp Ala
2780                2785                2790
Tyr His Gly Ser Tyr Glu Val Lys Ala Thr Gly Ser Ala Ser Ser
2795                2800                2805
```

```
Met Ile Asn Gly Val Val Lys Leu Leu Thr Lys Pro Trp Asp Val
2810                2815                2820

Val Pro Met Val Thr Gln Met Ala Met Thr Asp Thr Thr Pro Phe
2825                2830                2835

Gly Gln Gln Arg Val Phe Lys Glu Lys Val Asp Thr Arg Thr Pro
2840                2845                2850

Arg Pro Met Pro Gly Thr Arg Lys Val Met Glu Ile Thr Ala Glu
2855                2860                2865

Trp Leu Trp Arg Thr Leu Gly Arg Asn Lys Arg Pro Arg Leu Cys
2870                2875                2880

Thr Arg Glu Glu Phe Thr Lys Lys Val Arg Thr Asn Ala Ala Met
2885                2890                2895

Gly Ala Val Phe Thr Glu Glu Asn Gln Trp Asp Ser Ala Arg Ala
2900                2905                2910

Ala Val Glu Asp Glu Glu Phe Trp Lys Leu Val Asp Arg Glu Arg
2915                2920                2925

Glu Leu His Lys Leu Gly Lys Cys Gly Ser Cys Val Tyr Asn Met
2930                2935                2940

Met Gly Lys Arg Glu Lys Lys Leu Gly Glu Phe Gly Lys Ala Lys
2945                2950                2955

Gly Ser Arg Ala Ile Trp Tyr Met Trp Leu Gly Ala Arg Tyr Leu
2960                2965                2970

Glu Phe Glu Ala Leu Gly Phe Leu Asn Glu Asp His Trp Phe Ser
2975                2980                2985

Arg Glu Asn Ser Tyr Ser Gly Val Glu Gly Glu Gly Leu His Lys
2990                2995                3000

Leu Gly Tyr Ile Leu Arg Asp Ile Ser Lys Ile Pro Gly Gly Ala
3005                3010                3015

Met Tyr Ala Asp Asp Thr Ala Gly Trp Asp Thr Arg Ile Thr Glu
3020                3025                3030

Asp Asp Leu His Asn Glu Glu Lys Ile Thr Gln Gln Met Asp Pro
3035                3040                3045

Glu His Arg Gln Leu Ala Asn Ala Ile Phe Lys Leu Thr Tyr Gln
3050                3055                3060

Asn Lys Val Val Lys Val Gln Arg Pro Thr Pro Lys Gly Thr Val
3065                3070                3075

Met Asp Ile Ile Ser Arg Lys Asp Gln Arg Gly Ser Gly Gln Val
3080                3085                3090

Gly Thr Tyr Gly Leu Asn Thr Phe Thr Asn Met Glu Ala Gln Leu
3095                3100                3105

Ile Arg Gln Met Glu Gly Glu Gly Val Leu Ser Lys Ala Asp Leu
3110                3115                3120

Glu Asn Pro His Pro Leu Glu Lys Lys Ile Thr Gln Trp Leu Glu
3125                3130                3135

Thr Lys Gly Val Glu Arg Leu Lys Arg Met Ala Ile Ser Gly Asp
3140                3145                3150

Asp Cys Val Val Lys Pro Ile Asp Asp Arg Phe Ala Asn Ala Leu
3155                3160                3165

Leu Ala Leu Asn Asp Met Gly Lys Val Arg Lys Asp Ile Pro Gln
3170                3175                3180

Trp Gln Pro Ser Lys Gly Trp His Asp Trp Gln Gln Val Pro Phe
3185                3190                3195
```

```
Cys Ser  His His Phe His Glu  Leu Ile Met Lys Asp  Gly Arg Lys
    3200                 3205                 3210

Leu Val  Val Pro Cys Arg Pro  Gln Asp Glu Leu Ile  Gly Arg Ala
    3215                 3220                 3225

Arg Ile  Ser Gln Gly Ala Gly  Trp Ser Leu Arg Glu  Thr Ala Cys
    3230                 3235                 3240

Leu Gly  Lys Ala Tyr Ala Gln  Met Trp Ala Leu Met  Tyr Phe His
    3245                 3250                 3255

Arg Arg  Asp Leu Arg Leu Ala  Ser Asn Ala Ile Cys  Ser Ala Val
    3260                 3265                 3270

Pro Val  His Trp Val Pro Thr  Ser Arg Thr Thr Trp  Ser Ile His
    3275                 3280                 3285

Ala His  His Gln Trp Met Thr  Thr Glu Asp Met Leu  Thr Val Trp
    3290                 3295                 3300

Asn Arg  Val Trp Ile Glu Asp  Asn Pro Trp Met Glu  Asp Lys Thr
    3305                 3310                 3315

Pro Val  Thr Thr Trp Glu Asp  Val Pro Tyr Leu Gly  Lys Arg Glu
    3320                 3325                 3330

Asp Gln  Trp Cys Gly Ser Leu  Ile Gly Leu Thr Ser  Arg Ala Thr
    3335                 3340                 3345

Trp Ala  Gln Asn Ile Leu Thr  Ala Ile Gln Gln Val  Arg Ser Leu
    3350                 3355                 3360

Ile Gly  Asn Glu Glu Phe Leu  Asp Tyr Met Pro Ser  Met Lys Arg
    3365                 3370                 3375

Phe Arg  Lys Glu Glu Glu Ser  Glu Gly Ala Ile Trp
    3380                 3385                 3390

<210> SEQ ID NO 12
<211> LENGTH: 5
<212> TYPE: PRT
<213> ORGANISM: Artificial
<220> FEATURE:
<223> OTHER INFORMATION: Synthetic construct

<400> SEQUENCE: 12

Gly Ala Gly Lys Thr
1               5

<210> SEQ ID NO 13
<211> LENGTH: 5
<212> TYPE: PRT
<213> ORGANISM: Artificial
<220> FEATURE:
<223> OTHER INFORMATION: Synthetic construct

<400> SEQUENCE: 13

Gly Arg Ile Gly Arg
1               5

<210> SEQ ID NO 14
<211> LENGTH: 10723
<212> TYPE: DNA
<213> ORGANISM: Artificial Sequence
<220> FEATURE:
<223> OTHER INFORMATION: Derived from Dengue virus serotype 2/Dengue
      virus serotype 1, MVS

<400> SEQUENCE: 14
agttgttagt ctacgtggac cgacaaagac agattctttg agggagctaa gctcaatgta      60
gttctaacag tttttaatt agagagcaga tctctgatga ataaccaacg gaaaaaggcg      120
```

```
aaaaacacgc ctttcaatat gctgaaacgc gagagaaacc gcgtgtcgac tgtgcaacag      180
ctgacaaaga gattctcact tggaatgctg cagggacgag gaccattaaa actgttcatg      240
gccctggtgg cgttccttcg tttcctaaca atcccaccaa cagcagggat attgaagaga      300
tggggaacaa ttaaaaaatc aaaagctatt aatgttttga gagggttcag gaaagagatt      360
ggaaggatgc tgaacatctt gaataggaga cgcagatctg caggcatgat cattatgctg      420
attccaacag tgatggcgtt ccatttaacc acgcgtgggg gagagccgca tatgatagtt      480
agcaagcagg aaagaggaaa gtcacttttg ttcaagacct ctgcaggtgt caacatgtgc      540
accctcattg cgatggattt gggagagttg tgtgaggaca cgatgaccta caatgcccc      600 cggatcactg aggcggaacc agatgacgtt gactgttggt gcaatgccac ggacacatgg      660
gtgacctatg aacgtgctc tcaaactggc aacaccgac gagacaaacg ttccgtcgca      720
ttggccccac acgtggggct tggcctagaa acaagagccg aaacgtggat gtcctctgaa      780
ggtgcttgga acagataca aaaagtagag acttgggctc tgagacatcc aggattcacg      840
gtgatagccc ttttctagc acatgccata ggaacatcca tcacccagaa agggatcatt      900
ttcattttgc tgatgctggt aacaccatct atggccatgc gatgcgtggg aataggcaac      960
agagacttcg tggaaggact gtcaggagca acatgggtgg atgtggtact ggagcatgga     1020
agttgcgtca ccaccatggc aaaaaacaaa ccaacactgg acattgaact cttgaagacg     1080
gaggtcacaa accctgcagt tctgcgtaaa ttgtgcattg aagctaaaat atcaaacacc     1140
accaccgatt cgagatgtcc aacacaagga gaagccacac tggtggaaga caagacgcg     1200 aactttgtgt gccgacgaac gttcgtggac agaggctggg gcaatggctg tgggctattc     1260
ggaaaaggta gtctaataac gtgtgccaag tttaagtgtg tgacaaaact agaaggaaag     1320
atagttcaat atgaaaacct aaaatattca gtgatagtca ccgtccacac tggagatcag     1380
caccaggtgg gaaatgagac tacagaacat ggaacaactg caaccataac acctcaagct     1440
cctacgtcgg aaatacagct gaccgactac ggaacccta cattagattg ttcacctagg     1500
acagggctag attttaacga gatggtgttg ctgacaatga agaaagatc atggcttgtc     1560 cacaaacaat ggttcctaga cttaccactg ccttggacct ctgggcttc aacatcccaa     1620 gagacttgga acagacaaga tttactggtc acatttaaga cagctcatgc aaagaagcag     1680
gaagtagtcg tactaggatc acaagaagga gcaatgcaca ctgcgctgac tggagcgaca     1740
gaaatccaaa cgtcaggaac gacaacaatt ttcgcaggac acctaaaatg cagactaaaa     1800
atggacaaac taacttaa agggatgtca tatgtgatgt gcacaggctc attcaagtta     1860
gagaaagaag tggctgagac ccagcatgga actgttctgg tgcaggttaa atatgaagga     1920
acagacgcac catgcaagat tcccttttcg acccaagatg agaaaggagc aacccagaat     1980
gggagattaa taacagccaa ccccatagtc actgacaaag aaaaaccagt caatattgag     2040
gcagaaccac cctttggtga gagctacatc gtggtaggag caggtgaaaa agctttgaaa     2100
ctaagctggt tcaagaaagg aagcagcata gggaaaatgt ttgaagcaac tgcccgagga     2160
gcacgaagga tggccattct gggagacacc gcatgggact tcggttctat aggaggagtg     2220
ttcacgtcta tgggaaaact ggtacaccag ttttttggaa ctgcatatgg agttttgttt     2280
agcggagttt cttggaccat gaaaatagga ataggattc tgctgacatg gctaggatta     2340
aattcaagga acacgtccct ttcgatgatg tgcatcgcag ccggcattgt gacactgtat     2400
ttgggagtca tggtgcaggc cgatagtggt tgcgttgtga gctggaaaaa caaagaactg     2460
```

```
aaatgtggca gtgggatttt catcacagac aacgtgcaca catggacaga acaatacaag    2520
ttccaaccag aatcccttc aaaactagct tcagctatcc agaaagccca tgaagaggac     2580
atttgtggaa tccgctcagt aacaagactg gagaatctga tgtggaaaca aataacacca    2640
gaattgaatc acattctatc agaaaatgag gtgaagttaa ctattatgac aggagacatc    2700
aaaggaatca tgcaggcagg aaaacgatct ctgcggcctc agcccactga gctgaagtat    2760
tcatggaaaa catggggcaa agcaaaaatg ctctctacag agtctcataa ccagacctt     2820 ctcattgatg cccccgaaac agcagaatgc cccaacacaa atagagcttg gaattcgttg    2880
gaagttgaag actatggctt tggagtattc accaccaata tatggctaaa attgaaagaa    2940
aaacaggatg tattctgcga ctcaaaactc atgtcagcgg ccataaaaga caacagagcc    3000
gtccatgccg atatgggtta ttggatagaa agtgcactca atgacacatg gaagatagag    3060
aaagcctctt tcattgaagt taaaaactgc cactggccaa aatcacacac cctctggagc    3120
aatggagtgc tagaaagtga gatgataatt ccaagaatc tcgctggacc agtgtctcaa    3180
cacaactata gaccaggcta ccatacacaa ataacggac catggcatct aggtaagctt    3240
gagatggact ttgatttctg tgatggaaca acagtggtag tgactgagga ctgcggaaat    3300
agaggaccct ctttgagaac aaccactgcc tctggaaaac tcataacaga atggtgctgc    3360
cgatcttgca cattccacc gctaagatac agaggtgagg atgggtgctg gtacgggatg    3420
gaaatcagac cattgaagga gaagaagag aatttggtca actccttggt cacagctgga    3480
catgggcagg tcgacaactt ttcactagga gtcttgggaa tggcattgtt cctggaggaa    3540
atgcttagga cccgagtagg aacgaaacat gcaatactac tagttgcagt ttcttttgtg    3600
acattgatca caggaacat gtcctttaga gacctgggaa gagtgatggt tatggtaggc    3660
gccactatga cggatgacat aggtatgggc gtgacttatc ttgccctact agcagccttc    3720
aaagtcagac aactttttgc agctggacta ctcttgagaa gctgaccctc caaggaattg    3780
atgatgacta ctataggaat tgtactcctc tcccagagca ccctaccaga gaccattctt    3840
gagttgactg atgcgttagc cttaggcatg atggtcctca aaatggtgag aaatatggaa    3900
aagtatcaat tggcagtgac tatcatggct atcttgtgcg tcccaaacgc agtgatatta    3960
caaaacgcat ggaaagtgag ttgcacaata ttggcagtgg tgtccgtttc cccactgttc    4020
ttaacatcct cacagcaaaa aacagattgg ataccattag cattgacgat caaaggtctc    4080
aatccaacag ctatttttct aacaaccctc tcaagaacca gcaagaaaag gagctggcca    4140
ttaaatgagg ctatcatggc agtcgggatg gtgagcattt tagccagttc tctcctaaaa    4200
aatgatattc ccatgacagg accattagtg gctggagggc tcctcactgt gtgctacgtg    4260
ctcactggac gatcggccga tttggaactg gagagagcag ccgatgtcaa atgggaagac    4320
caggcagaga tatcaggaag cagtccaatc ctgtcaataa caatatcaga agatggtagc    4380
atgtcgataa aaatgaaga ggaagatcaa acactgacca tactcattag aacaggattg    4440
ctggtgatct caggactttt tcctgtatca ataccaatca cggcagcagc atggtacctg    4500
tgggaagtga agaaacaacg ggccggagta ttgtgggatg ttccttcacc cccacccatg    4560
ggaaaggctg aactgaaga tggagcctat agaattaagc aaaaagggat tcttggatat    4620
tcccagatcg gagccggagt ttacaaagaa ggaacattcc atacaatgtg gcatgtcaca    4680
cgtggcgctg ttctaatgca taaggaaag aggattgaac catcatgggc ggacgtcaag    4740
aaagacctaa tatcatatgg aggaggctgg aagttagaag gagaatggaa ggaaggagaa    4800
gaagtccagg tattggcact ggagcctgga aaaaatccaa gagccgtcca aacgaaacct    4860
```

```
ggtcttttca aaaccaacgc cggaacaata ggtgctgtat ctctggactt ttctcctgga    4920
acgtcaggat ctccaattat cgacaaaaaa ggaaaagttg tgggtcttta tggtaatggt    4980
gttgttacaa ggagtggagc atatgtgagt gctatagccc agactgaaaa aagcattgaa    5040
gacaacccag agatcgaaga tgacattttc gaaagagaa gactgaccat catggacctc    5100
cacccaggag cgggaaagac gaagagatac cttccggcca tagtcagaga agctataaaa    5160
cggggtttga gaacattaat cttggccccc actagagttg tggcagctga aatggaggaa    5220
gcccttagag gacttccaat aagataccag accccagcca tcagagctgt gcacaccggg    5280
cgggagattg tggacctaat gtgtcatgcc acatttacca tgaggctgct atcaccagtt    5340
agagtgccaa actacaacct gattatcatg gacgaagccc atttcacaga cccagcaagt    5400
atagcagcta gaggatacat ctcaactcga gtggagatgg gtgaggcagc tgggattttt    5460
atgacagcca ctcccccggg aagcagagac ccatttcctc agagcaatgc accaatcata    5520
gatgaagaaa gagaaatccc tgaacgctcg tggaattccg gacatgaatg ggtcacggat    5580
tttaaaggga agactgtttg gttcgttcca agtataaaag caggaaatga tatagcagct    5640
tgcctgagga aaaatggaaa gaaagtgata caactcagta ggaagacctt tgattctgag    5700
tatgtcaaga ctagaaccaa tgattgggac ttcgtggtta caactgacat ttcagaaatg    5760
ggtgccaatt tcaaggctga gagggttata gaccccagac gctgcatgaa accagtcata    5820
ctaacagatg gtgaagagcg ggtgattctg gcaggaccta tgccagtgac ccactctagt    5880
gcagcacaaa aagagggag aataggaaga aatccaaaaa atgagaatga ccagtacata    5940
tacatggggg aacctctgga aaatgatgaa gactgtgcac actggaaaga agctaaaatg    6000
ctcctagata acatcaacac gccagaagga atcattccta gcatgttcga accagagcgt    6060
gaaaaggtgg atgccattga tggcgaatac cgcttgagag gagaagcaag gaaaaccttt    6120
gtagacttaa tgagaagagg agacctacca gtctggttgg cctacagagt ggcagctgaa    6180
ggcatcaact acgcagacag aaggtggtgt tttgatggag tcaagaacaa ccaaatccta    6240
gaagaaaacg tggaagttga atctggaca aaagaagggg aaaggaagaa attgaaaccc    6300
agatggttgg atgctaggat ctattctgac ccactggcgc taaagaatt taaggaattt    6360 gcagccggaa gaaagtctct gacccctgaac ctaatcacag aaatgggtag gctcccaacc    6420
ttcatgactc agaaggcaag agacgcactg gacaacttag cagtgctgca cacggctgag    6480
gcaggtggaa gggcgtacaa ccatgctctc agtgaactgc cggagaccct ggagacattg    6540
cttttactga cacttctggc tacagtcacg gagggatct ttttattctt gatgagcgca    6600
aggggcatag ggaagatgac cctgggaatg tgctgcataa tcacggctag catcctccta    6660
tggtacgcac aaatacagcc acactggata gcagcttcaa taatactgga gttttttctc    6720
atagttttgc ttattccaga acctgaaaaa cagagaacac cccaagacaa ccaactgacc    6780
tacgttgtca tagccatcct cacagtggtg gccgcaacca tggcaaacga gatgggtttc    6840
ctagaaaaaa cgaagaaaga tctcggattg ggaagcattg caacccagca acccgagagc    6900
aacatcctgg acatagatct acgtcctgca tcagcatgga cgctgtatgc cgtggccaca    6960
acatttgtta caccaatgtt gagacatagc attgaaaatt cctcagtgaa tgtgtcccta    7020
acagctatag ccaaccaagc cacagtgtta atgggtctcg ggaaaggatg gccattgtca    7080
aagatggaca tcggagttcc ccttctcgcc attggatgct actcacaagt caaccccata    7140
actctcacag cagctcttttt cttattggta gcacattatg ccatcatagg gccaggactc    7200
```

```
caagcaaaag caaccagaga agctcagaaa agagcagcgg cgggcatcat gaaaaaccca   7260
actgtcgatg gaataacagt gattgaccta gatccaatac cttatgatcc gaagtttgaa   7320
aagcagttgg gacaagtaat gctcctagtc ctctgcgtga ctcaagtatt gatgatgagg   7380
actacatggg ctctgtgtga ggctttaacc ttagctaccg ggcccatctc acattgtgg    7440
gaaggaaatc cagggaggtt ttggaacact accattgcgg tgtcaatggc taacattttt   7500
agagggagtt acttggccgg agctggactt ctcttttcta ttatgaagaa cacaaccaac   7560
acaagaaggg gaactggcaa cataggagag acgcttggag agaaatggaa aagccgattg   7620
aacgcattgg gaaaaagtga attccagatc tacaagaaaa gtggaatcca ggaagtggat   7680
agaaccttag caaaagaagg cattaaaaga ggagaaacgg accatcacgc tgtgtcgcga   7740
ggctcagcaa aactgagatg gttcgttgag agaaacatgg tcacaccaga agggaaagta   7800
gtggacctcg gttgtggcag aggaggctgg tcatactatt gtggaggact aaagaatgta   7860
agagaagtca aaggcctaac aaaaggagga ccaggacacg aagaacccat ccccatgtca   7920
acatatgggt ggaatctagt gcgtcttcaa agtggagttg acgttttctt catcccgcca   7980
gaaaagtgtg acacattatt gtgtgacata ggggagtcat caccaaatcc cacagtggaa   8040
gcaggacgaa cactcagagt ccttaactta gtagaaaatt ggttgaacaa caacactcaa   8100
ttttgcataa aggttctcaa cccatatatg ccctcagtca tagaaaaaat ggaagcacta   8160
caaaggaaat atggaggagc cttagtgagg aatccactct cacgaaactc cacacatgag   8220
atgtactggg tatccaatgc ttccgggaac atagtgtcat cagtgaacat gatttcaagg   8280
atgttgatca acagatttac aatgagatac aagaaagcca cttacgagcc ggatgttgac   8340
ctcggaagcg gaacccgtaa catcgggatt gaaagtgaga taccaaacct agatataatt   8400
gggaaaagaa tagaaaaaat aaagcaagag catgaaacat catggcacta tgaccaagac   8460
cacccataca aaacgtgggc ataccatggt agctatgaaa caaaacagac tggatcagca   8520
tcatccatgt caacggagt ggtcaggctg ctgacaaaac cttgggacgt cgtccccatg   8580
gtgacacaga tggcaatgac agacacgact ccatttggac aacagcgcgt ttttaaagag   8640
aaagtggaca cgagaaccca agaaccgaaa gaaggcacga agaaactaat gaaaataaca   8700
gcagagtggc tttggaaaga attagggaag aaaaagacac ccaggatgtg caccagagaa   8760
gaattcacaa gaaaggtgag aagcaatgca gccttggggg ccatattcac tgatgagaac   8820
aagtggaagt cggcacgtga ggctgttgaa gatagtaggt tttgggagct ggttgacaag   8880
gaaaggaatc tccatcttga aggaaagtgt gaaacatgtg tgtacaacat gatgggaaaa   8940
agagagaaga agctagggga attcggcaag gcaaaggca gcagagccat atggtacatg   9000
tggcttggag cacgcttctt agagtttgaa gccctaggat tcttaaatga agatcactgg   9060
ttctccagag agaactccct gagtggagtg aaggagaag ggctgcacaa gctaggttac   9120
attctaagag acgtgagcaa gaaagaggga ggagcaatgt atgccgatga caccgcagga   9180
tgggatacaa gaatcacact agaagaccta aaaaatgaag aaatggtaac aaaccacatg   9240
gaaggagaac acaagaaact agccgaggcc attttcaaac taacgtacca aaacaaggtg   9300
gtgcgtgtgc aaagaccaac accaagaggc acagtaatgg acatcatatc gagaagagac   9360
caaagaggta gtggacaagt tggcacctat ggactcaata ctttcaccaa tatggaagcc   9420
caactaatca gacagatgga gggagaagga gtctttaaaa gcattcagca cctaacaatc   9480
acagaagaaa tcgctgtgca aaactggtta gcaagagtgg ggcgcgaaag gttatcaaga   9540
atggccatca gtgagatga ttgtgttgtg aaacctttag atgacaggtt cgcaagcgct   9600
```

```
ttaacagctc taaatgacat gggaaagatt aggaaagaca tacaacaatg ggaaccttca  9660
agaggatgga atgattggac acaagtgccc ttctgttcac accatttcca tgagttaatc  9720
atgaaagacg tcgcgtact cgttgttcca tgtagaaacc aagatgaact gattggcaga  9780
gcccgaatct cccaaggagc agggtggtct ttgcgggaga cggcctgttt ggggaagtct  9840
tacgcccaaa tgtggagctt gatgtacttc cacagacgcg acctcaggct ggcggcaaat  9900
gctatttgct cggcagtacc atcacattgg gttccaacaa gtcgaacaac ctggtccata  9960
catgctaaac atgaatggat gacaacggaa gacatgctga cagtctggaa cagggtgtgg 10020
attcaagaaa acccatggat ggaagacaaa actccagtgg aatcatggga ggaaatccca 10080
tacttgggga aaagagaaga ccaatggtgc ggctcattga ttgggttaac aagcagggcc 10140
acctgggcaa agaacatcca agcagcaata aatcaagtta gatcccttat aggcaatgaa 10200
gaatacacag attacatgcc atccatgaaa agattcagaa gagaagagga agaagcagga 10260
gttctgtggt agaaagcaaa actaacatga acaaggcta gaagtcaggt cggattaagc 10320
catagtacgg aaaaaactat gctacctgtg agccccgtcc aaggacgtta aaagaagtca 10380
ggccatcata aatgccatag cttgagtaaa ctatgcagcc tgtagctcca cctgagaagg 10440
tgtaaaaaat ccgggaggcc acaaaccatg gaagctgtac gcatggcgta gtggactagc 10500
ggttagagga gaccccctccc ttacaaatcg cagcaacaat gggggcccaa ggcgagatga 10560
agctgtagtc tcgctggaag gactagaggt tagaggagac cccccgaaa caaaaaacag 10620
catattgacg ctgggaaaga ccagagatcc tgctgtctcc tcagcatcat tccaggcaca 10680
gaacgccaga aaatggaatg gtgctgttga atcaacaggt tct                   10723
```

<210> SEQ ID NO 15
<211> LENGTH: 3391
<212> TYPE: PRT
<213> ORGANISM: Artificial Sequence
<220> FEATURE:
<223> OTHER INFORMATION: Polypeptide, Derived from Dengue virus serotype 2/Dengue virus serotype 1, MVS

<400> SEQUENCE: 15

```
Met Asn Asn Gln Arg Lys Lys Ala Lys Asn Thr Pro Phe Asn Met Leu
1               5                   10                  15

Lys Arg Glu Arg Asn Arg Val Ser Thr Val Gln Gln Leu Thr Lys Arg
            20                  25                  30

Phe Ser Leu Gly Met Leu Gln Gly Arg Gly Pro Leu Lys Leu Phe Met
        35                  40                  45

Ala Leu Val Ala Phe Leu Arg Phe Leu Thr Ile Pro Pro Thr Ala Gly
    50                  55                  60

Ile Leu Lys Arg Trp Gly Thr Ile Lys Lys Ser Lys Ala Ile Asn Val
65                  70                  75                  80

Leu Arg Gly Phe Arg Lys Glu Ile Gly Arg Met Leu Asn Ile Leu Asn
                85                  90                  95

Arg Arg Arg Arg Ser Ala Gly Met Ile Ile Met Leu Ile Pro Thr Val
            100                 105                 110

Met Ala Phe His Leu Thr Thr Arg Gly Gly Glu Pro His Met Ile Val
        115                 120                 125

Ser Lys Gln Glu Arg Gly Lys Ser Leu Leu Phe Lys Thr Ser Ala Gly
    130                 135                 140

Val Asn Met Cys Thr Leu Ile Ala Met Asp Leu Gly Glu Leu Cys Glu
145                 150                 155                 160
```

```
Asp Thr Met Thr Tyr Lys Cys Pro Arg Ile Thr Glu Ala Glu Pro Asp
                165                 170                 175

Asp Val Asp Cys Trp Cys Asn Ala Thr Asp Thr Trp Val Thr Tyr Gly
            180                 185                 190

Thr Cys Ser Gln Thr Gly Glu His Arg Arg Asp Lys Arg Ser Val Ala
        195                 200                 205

Leu Ala Pro His Val Gly Leu Gly Leu Glu Thr Arg Ala Glu Thr Trp
    210                 215                 220

Met Ser Ser Glu Gly Ala Trp Lys Gln Ile Gln Lys Val Glu Thr Trp
225                 230                 235                 240

Ala Leu Arg His Pro Gly Phe Thr Val Ile Ala Leu Phe Leu Ala His
                245                 250                 255

Ala Ile Gly Thr Ser Ile Thr Gln Lys Gly Ile Ile Phe Ile Leu Leu
            260                 265                 270

Met Leu Val Thr Pro Ser Met Ala Met Arg Cys Val Gly Ile Gly Asn
        275                 280                 285

Arg Asp Phe Val Glu Gly Leu Ser Gly Ala Thr Trp Val Asp Val Val
    290                 295                 300

Leu Glu His Gly Ser Cys Val Thr Thr Met Ala Lys Asn Lys Pro Thr
305                 310                 315                 320

Leu Asp Ile Glu Leu Leu Lys Thr Glu Val Thr Asn Pro Ala Val Leu
                325                 330                 335

Arg Lys Leu Cys Ile Glu Ala Lys Ile Ser Asn Thr Thr Thr Asp Ser
            340                 345                 350

Arg Cys Pro Thr Gln Gly Glu Ala Thr Leu Val Glu Glu Gln Asp Ala
        355                 360                 365

Asn Phe Val Cys Arg Arg Thr Phe Val Asp Arg Gly Trp Gly Asn Gly
    370                 375                 380

Cys Gly Leu Phe Gly Lys Gly Ser Leu Ile Thr Cys Ala Lys Phe Lys
385                 390                 395                 400

Cys Val Thr Lys Leu Glu Gly Lys Ile Val Gln Tyr Glu Asn Leu Lys
                405                 410                 415

Tyr Ser Val Ile Val Thr Val His Thr Gly Asp Gln His Gln Val Gly
            420                 425                 430

Asn Glu Thr Thr Glu His Gly Thr Thr Ala Thr Ile Thr Pro Gln Ala
        435                 440                 445

Pro Thr Ser Glu Ile Gln Leu Thr Asp Tyr Gly Thr Leu Thr Leu Asp
    450                 455                 460

Cys Ser Pro Arg Thr Gly Leu Asp Phe Asn Glu Met Val Leu Leu Thr
465                 470                 475                 480

Met Lys Glu Arg Ser Trp Leu Val His Lys Gln Trp Phe Leu Asp Leu
                485                 490                 495

Pro Leu Pro Trp Thr Ser Gly Ala Ser Thr Ser Gln Glu Thr Trp Asn
            500                 505                 510

Arg Gln Asp Leu Leu Val Thr Phe Lys Thr Ala His Ala Lys Lys Gln
        515                 520                 525

Glu Val Val Val Leu Gly Ser Gln Glu Gly Ala Met His Thr Ala Leu
    530                 535                 540

Thr Gly Ala Thr Glu Ile Gln Thr Ser Gly Thr Thr Thr Ile Phe Ala
545                 550                 555                 560

Gly His Leu Lys Cys Arg Leu Lys Met Asp Lys Leu Thr Leu Lys Gly
                565                 570                 575
```

-continued

```
Met Ser Tyr Val Met Cys Thr Gly Ser Phe Lys Leu Glu Lys Glu Val
            580                 585                 590

Ala Glu Thr Gln His Gly Thr Val Leu Val Gln Val Lys Tyr Glu Gly
        595                 600                 605

Thr Asp Ala Pro Cys Lys Ile Pro Phe Ser Thr Gln Asp Glu Lys Gly
    610                 615                 620

Ala Thr Gln Asn Gly Arg Leu Ile Thr Ala Asn Pro Ile Val Thr Asp
625                 630                 635                 640

Lys Glu Lys Pro Val Asn Ile Glu Ala Glu Pro Pro Phe Gly Glu Ser
                645                 650                 655

Tyr Ile Val Val Gly Ala Gly Glu Lys Ala Leu Lys Leu Ser Trp Phe
            660                 665                 670

Lys Lys Gly Ser Ser Ile Gly Lys Met Phe Glu Ala Thr Ala Arg Gly
        675                 680                 685

Ala Arg Arg Met Ala Ile Leu Gly Asp Thr Ala Trp Asp Phe Gly Ser
    690                 695                 700

Ile Gly Gly Val Phe Thr Ser Met Gly Lys Leu Val His Gln Val Phe
705                 710                 715                 720

Gly Thr Ala Tyr Gly Val Leu Phe Ser Gly Val Ser Trp Thr Met Lys
                725                 730                 735

Ile Gly Ile Gly Ile Leu Leu Thr Trp Leu Gly Leu Asn Ser Arg Asn
            740                 745                 750

Thr Ser Leu Ser Met Met Cys Ile Ala Ala Gly Ile Val Thr Leu Tyr
        755                 760                 765

Leu Gly Val Met Val Gln Ala Asp Ser Gly Cys Val Val Ser Trp Lys
    770                 775                 780

Asn Lys Glu Leu Lys Cys Gly Ser Gly Ile Phe Ile Thr Asp Asn Val
785                 790                 795                 800

His Thr Trp Thr Glu Gln Tyr Lys Phe Gln Pro Glu Ser Pro Ser Lys
                805                 810                 815

Leu Ala Ser Ala Ile Gln Lys Ala His Glu Glu Asp Ile Cys Gly Ile
            820                 825                 830

Arg Ser Val Thr Arg Leu Glu Asn Leu Met Trp Lys Gln Ile Thr Pro
        835                 840                 845

Glu Leu Asn His Ile Leu Ser Glu Asn Glu Val Lys Leu Thr Ile Met
    850                 855                 860

Thr Gly Asp Ile Lys Gly Ile Met Gln Ala Gly Lys Arg Ser Leu Arg
865                 870                 875                 880

Pro Gln Pro Thr Glu Leu Lys Tyr Ser Trp Lys Thr Trp Gly Lys Ala
                885                 890                 895

Lys Met Leu Ser Thr Glu Ser His Asn Gln Thr Phe Leu Ile Asp Gly
            900                 905                 910

Pro Glu Thr Ala Glu Cys Pro Asn Thr Asn Arg Ala Trp Asn Ser Leu
        915                 920                 925

Glu Val Glu Asp Tyr Gly Phe Gly Val Phe Thr Thr Asn Ile Trp Leu
    930                 935                 940

Lys Leu Lys Glu Lys Gln Asp Val Phe Cys Asp Ser Lys Leu Met Ser
945                 950                 955                 960

Ala Ala Ile Lys Asp Asn Arg Ala Val His Ala Asp Met Gly Tyr Trp
                965                 970                 975

Ile Glu Ser Ala Leu Asn Asp Thr Trp Lys Ile Glu Lys Ala Ser Phe
            980                 985                 990

Ile Glu Val Lys Asn Cys His Trp  Pro Lys Ser His Thr  Leu Trp Ser
```

-continued

```
             995                 1000                1005
Asn Gly Val Leu Glu Ser Glu Met Ile Ile Pro Lys Asn Leu Ala
            1010                1015                1020
Gly Pro Val Ser Gln His Asn Tyr Arg Pro Gly Tyr His Thr Gln
            1025                1030                1035
Ile Thr Gly Pro Trp His Leu Gly Lys Leu Glu Met Asp Phe Asp
            1040                1045                1050
Phe Cys Asp Gly Thr Thr Val Val Val Thr Glu Asp Cys Gly Asn
            1055                1060                1065
Arg Gly Pro Ser Leu Arg Thr Thr Thr Ala Ser Gly Lys Leu Ile
            1070                1075                1080
Thr Glu Trp Cys Cys Arg Ser Cys Thr Leu Pro Pro Leu Arg Tyr
            1085                1090                1095
Arg Gly Glu Asp Gly Cys Trp Tyr Gly Met Glu Ile Arg Pro Leu
            1100                1105                1110
Lys Glu Lys Glu Glu Asn Leu Val Asn Ser Leu Val Thr Ala Gly
            1115                1120                1125
His Gly Gln Val Asp Asn Phe Ser Leu Gly Val Leu Gly Met Ala
            1130                1135                1140
Leu Phe Leu Glu Glu Met Leu Arg Thr Arg Val Gly Thr Lys His
            1145                1150                1155
Ala Ile Leu Leu Val Ala Val Ser Phe Val Thr Leu Ile Thr Gly
            1160                1165                1170
Asn Met Ser Phe Arg Asp Leu Gly Arg Val Met Val Met Val Gly
            1175                1180                1185
Ala Thr Met Thr Asp Asp Ile Gly Met Gly Val Thr Tyr Leu Ala
            1190                1195                1200
Leu Leu Ala Ala Phe Lys Val Arg Pro Thr Phe Ala Ala Gly Leu
            1205                1210                1215
Leu Leu Arg Lys Leu Thr Ser Lys Glu Leu Met Met Thr Thr Ile
            1220                1225                1230
Gly Ile Val Leu Leu Ser Gln Ser Thr Leu Pro Glu Thr Ile Leu
            1235                1240                1245
Glu Leu Thr Asp Ala Leu Ala Leu Gly Met Met Val Leu Lys Met
            1250                1255                1260
Val Arg Asn Met Glu Lys Tyr Gln Leu Ala Val Thr Ile Met Ala
            1265                1270                1275
Ile Leu Cys Val Pro Asn Ala Val Ile Leu Gln Asn Ala Trp Lys
            1280                1285                1290
Val Ser Cys Thr Ile Leu Ala Val Val Ser Val Ser Pro Leu Phe
            1295                1300                1305
Leu Thr Ser Ser Gln Gln Lys Thr Asp Trp Ile Pro Leu Ala Leu
            1310                1315                1320
Thr Ile Lys Gly Leu Asn Pro Thr Ala Ile Phe Leu Thr Thr Leu
            1325                1330                1335
Ser Arg Thr Ser Lys Lys Arg Ser Trp Pro Leu Asn Glu Ala Ile
            1340                1345                1350
Met Ala Val Gly Met Val Ser Ile Leu Ala Ser Ser Leu Leu Lys
            1355                1360                1365
Asn Asp Ile Pro Met Thr Gly Pro Leu Val Ala Gly Gly Leu Leu
            1370                1375                1380
Thr Val Cys Tyr Val Leu Thr Gly Arg Ser Ala Asp Leu Glu Leu
            1385                1390                1395
```

```
Glu Arg Ala Ala Asp Val Lys Trp Glu Asp Gln Ala Glu Ile Ser
    1400            1405                1410
Gly Ser Ser Pro Ile Leu Ser Ile Thr Ile Ser Glu Asp Gly Ser
    1415            1420                1425
Met Ser Ile Lys Asn Glu Glu Glu Asp Gln Thr Leu Thr Ile Leu
    1430            1435                1440
Ile Arg Thr Gly Leu Leu Val Ile Ser Gly Leu Phe Pro Val Ser
    1445            1450                1455
Ile Pro Ile Thr Ala Ala Ala Trp Tyr Leu Trp Glu Val Lys Lys
    1460            1465                1470
Gln Arg Ala Gly Val Leu Trp Asp Val Pro Ser Pro Pro Pro Met
    1475            1480                1485
Gly Lys Ala Glu Leu Glu Asp Gly Ala Tyr Arg Ile Lys Gln Lys
    1490            1495                1500
Gly Ile Leu Gly Tyr Ser Gln Ile Gly Ala Gly Val Tyr Lys Glu
    1505            1510                1515
Gly Thr Phe His Thr Met Trp His Val Thr Arg Gly Ala Val Leu
    1520            1525                1530
Met His Lys Gly Lys Arg Ile Glu Pro Ser Trp Ala Asp Val Lys
    1535            1540                1545
Lys Asp Leu Ile Ser Tyr Gly Gly Gly Trp Lys Leu Glu Gly Glu
    1550            1555                1560
Trp Lys Glu Gly Glu Glu Val Gln Val Leu Ala Leu Glu Pro Gly
    1565            1570                1575
Lys Asn Pro Arg Ala Val Gln Thr Lys Pro Gly Leu Phe Lys Thr
    1580            1585                1590
Asn Ala Gly Thr Ile Gly Ala Val Ser Leu Asp Phe Ser Pro Gly
    1595            1600                1605
Thr Ser Gly Ser Pro Ile Ile Asp Lys Lys Gly Lys Val Val Gly
    1610            1615                1620
Leu Tyr Gly Asn Gly Val Val Thr Arg Ser Gly Ala Tyr Val Ser
    1625            1630                1635
Ala Ile Ala Gln Thr Glu Lys Ser Ile Glu Asp Asn Pro Glu Ile
    1640            1645                1650
Glu Asp Asp Ile Phe Arg Lys Arg Arg Leu Thr Ile Met Asp Leu
    1655            1660                1665
His Pro Gly Ala Gly Lys Thr Lys Arg Tyr Leu Pro Ala Ile Val
    1670            1675                1680
Arg Glu Ala Ile Lys Arg Gly Leu Arg Thr Leu Ile Leu Ala Pro
    1685            1690                1695
Thr Arg Val Val Ala Ala Glu Met Glu Glu Ala Leu Arg Gly Leu
    1700            1705                1710
Pro Ile Arg Tyr Gln Thr Pro Ala Ile Arg Ala Val His Thr Gly
    1715            1720                1725
Arg Glu Ile Val Asp Leu Met Cys His Ala Thr Phe Thr Met Arg
    1730            1735                1740
Leu Leu Ser Pro Val Arg Val Pro Asn Tyr Asn Leu Ile Ile Met
    1745            1750                1755
Asp Glu Ala His Phe Thr Asp Pro Ala Ser Ile Ala Ala Arg Gly
    1760            1765                1770
Tyr Ile Ser Thr Arg Val Glu Met Gly Glu Ala Ala Gly Ile Phe
    1775            1780                1785
```

-continued

```
Met Thr Ala Thr Pro Pro Gly Ser Arg Asp Pro Phe Pro Gln Ser
1790                1795                1800

Asn Ala Pro Ile Ile Asp Glu Glu Arg Glu Ile Pro Glu Arg Ser
    1805                1810                1815

Trp Asn Ser Gly His Glu Trp Val Thr Asp Phe Lys Gly Lys Thr
1820                1825                1830

Val Trp Phe Val Pro Ser Ile Lys Ala Gly Asn Asp Ile Ala Ala
    1835                1840                1845

Cys Leu Arg Lys Asn Gly Lys Lys Val Ile Gln Leu Ser Arg Lys
1850                1855                1860

Thr Phe Asp Ser Glu Tyr Val Lys Thr Arg Thr Asn Asp Trp Asp
    1865                1870                1875

Phe Val Val Thr Thr Asp Ile Ser Glu Met Gly Ala Asn Phe Lys
1880                1885                1890

Ala Glu Arg Val Ile Asp Pro Arg Arg Cys Met Lys Pro Val Ile
    1895                1900                1905

Leu Thr Asp Gly Glu Glu Arg Val Ile Leu Ala Gly Pro Met Pro
1910                1915                1920

Val Thr His Ser Ser Ala Ala Gln Arg Arg Gly Arg Ile Gly Arg
    1925                1930                1935

Asn Pro Lys Asn Glu Asn Asp Gln Tyr Ile Tyr Met Gly Glu Pro
1940                1945                1950

Leu Glu Asn Asp Glu Asp Cys Ala His Trp Lys Glu Ala Lys Met
    1955                1960                1965

Leu Leu Asp Asn Ile Asn Thr Pro Glu Gly Ile Ile Pro Ser Met
1970                1975                1980

Phe Glu Pro Glu Arg Glu Lys Val Asp Ala Ile Asp Gly Glu Tyr
    1985                1990                1995

Arg Leu Arg Gly Glu Ala Arg Lys Thr Phe Val Asp Leu Met Arg
2000                2005                2010

Arg Gly Asp Leu Pro Val Trp Leu Ala Tyr Arg Val Ala Ala Glu
    2015                2020                2025

Gly Ile Asn Tyr Ala Asp Arg Arg Trp Cys Phe Asp Gly Val Lys
2030                2035                2040

Asn Asn Gln Ile Leu Glu Glu Asn Val Glu Val Glu Ile Trp Thr
    2045                2050                2055

Lys Glu Gly Glu Arg Lys Lys Leu Lys Pro Arg Trp Leu Asp Ala
2060                2065                2070

Arg Ile Tyr Ser Asp Pro Leu Ala Leu Lys Glu Phe Lys Glu Phe
    2075                2080                2085

Ala Ala Gly Arg Lys Ser Leu Thr Leu Asn Leu Ile Thr Glu Met
2090                2095                2100

Gly Arg Leu Pro Thr Phe Met Thr Gln Lys Ala Arg Asp Ala Leu
    2105                2110                2115

Asp Asn Leu Ala Val Leu His Thr Ala Glu Ala Gly Gly Arg Ala
2120                2125                2130

Tyr Asn His Ala Leu Ser Glu Leu Pro Glu Thr Leu Glu Thr Leu
    2135                2140                2145

Leu Leu Leu Thr Leu Leu Ala Thr Val Thr Gly Gly Ile Phe Leu
2150                2155                2160

Phe Leu Met Ser Ala Arg Gly Ile Gly Lys Met Thr Leu Gly Met
    2165                2170                2175

Cys Cys Ile Ile Thr Ala Ser Ile Leu Leu Trp Tyr Ala Gln Ile
```

```
                2180                2185                2190
Gln Pro His Trp Ile Ala Ala Ser Ile Ile Leu Glu Phe Phe Leu
        2195                2200                2205
Ile Val Leu Leu Ile Pro Glu Pro Glu Lys Gln Arg Thr Pro Gln
        2210                2215                2220
Asp Asn Gln Leu Thr Tyr Val Ile Ala Ile Leu Thr Val Val
        2225                2230                2235
Ala Ala Thr Met Ala Asn Glu Met Gly Phe Leu Glu Lys Thr Lys
        2240                2245                2250
Lys Asp Leu Gly Leu Gly Ser Ile Ala Thr Gln Gln Pro Glu Ser
        2255                2260                2265
Asn Ile Leu Asp Ile Asp Leu Arg Pro Ala Ser Ala Trp Thr Leu
        2270                2275                2280
Tyr Ala Val Ala Thr Thr Phe Val Thr Pro Met Leu Arg His Ser
        2285                2290                2295
Ile Glu Asn Ser Ser Val Asn Val Ser Leu Thr Ala Ile Ala Asn
        2300                2305                2310
Gln Ala Thr Val Leu Met Gly Leu Gly Lys Gly Trp Pro Leu Ser
        2315                2320                2325
Lys Met Asp Ile Gly Val Pro Leu Leu Ala Ile Gly Cys Tyr Ser
        2330                2335                2340
Gln Val Asn Pro Ile Thr Leu Thr Ala Ala Leu Phe Leu Leu Val
        2345                2350                2355
Ala His Tyr Ala Ile Ile Gly Pro Gly Leu Gln Ala Lys Ala Thr
        2360                2365                2370
Arg Glu Ala Gln Lys Arg Ala Ala Gly Ile Met Lys Asn Pro
        2375                2380                2385
Thr Val Asp Gly Ile Thr Val Ile Asp Leu Asp Pro Ile Pro Tyr
        2390                2395                2400
Asp Pro Lys Phe Glu Lys Gln Leu Gly Gln Val Met Leu Leu Val
        2405                2410                2415
Leu Cys Val Thr Gln Val Leu Met Met Arg Thr Thr Trp Ala Leu
        2420                2425                2430
Cys Glu Ala Leu Thr Leu Ala Thr Gly Pro Ile Ser Thr Leu Trp
        2435                2440                2445
Glu Gly Asn Pro Gly Arg Phe Trp Asn Thr Thr Ile Ala Val Ser
        2450                2455                2460
Met Ala Asn Ile Phe Arg Gly Ser Tyr Leu Ala Gly Ala Gly Leu
        2465                2470                2475
Leu Phe Ser Ile Met Lys Asn Thr Thr Asn Thr Arg Arg Gly Thr
        2480                2485                2490
Gly Asn Ile Gly Glu Thr Leu Gly Glu Lys Trp Lys Ser Arg Leu
        2495                2500                2505
Asn Ala Leu Gly Lys Ser Glu Phe Gln Ile Tyr Lys Lys Ser Gly
        2510                2515                2520
Ile Gln Glu Val Asp Arg Thr Leu Ala Lys Glu Gly Ile Lys Arg
        2525                2530                2535
Gly Glu Thr Asp His His Ala Val Ser Arg Gly Ser Ala Lys Leu
        2540                2545                2550
Arg Trp Phe Val Glu Arg Asn Met Val Thr Pro Glu Gly Lys Val
        2555                2560                2565
Val Asp Leu Gly Cys Gly Arg Gly Gly Trp Ser Tyr Tyr Cys Gly
        2570                2575                2580
```

```
Gly Leu Lys Asn Val Arg Glu Val Lys Gly Leu Thr Lys Gly Gly
2585                2590                2595

Pro Gly His Glu Glu Pro Ile Pro Met Ser Thr Tyr Gly Trp Asn
2600                2605                2610

Leu Val Arg Leu Gln Ser Gly Val Asp Val Phe Phe Ile Pro Pro
2615                2620                2625

Glu Lys Cys Asp Thr Leu Leu Cys Asp Ile Gly Glu Ser Ser Pro
2630                2635                2640

Asn Pro Thr Val Glu Ala Gly Arg Thr Leu Arg Val Leu Asn Leu
2645                2650                2655

Val Glu Asn Trp Leu Asn Asn Thr Gln Phe Cys Ile Lys Val
2660                2665                2670

Leu Asn Pro Tyr Met Pro Ser Val Ile Glu Lys Met Glu Ala Leu
2675                2680                2685

Gln Arg Lys Tyr Gly Gly Ala Leu Val Arg Asn Pro Leu Ser Arg
2690                2695                2700

Asn Ser Thr His Glu Met Tyr Trp Val Ser Asn Ala Ser Gly Asn
2705                2710                2715

Ile Val Ser Ser Val Asn Met Ile Ser Arg Met Leu Ile Asn Arg
2720                2725                2730

Phe Thr Met Arg Tyr Lys Lys Ala Thr Tyr Glu Pro Asp Val Asp
2735                2740                2745

Leu Gly Ser Gly Thr Arg Asn Ile Gly Ile Glu Ser Glu Ile Pro
2750                2755                2760

Asn Leu Asp Ile Ile Gly Lys Arg Ile Glu Lys Ile Lys Gln Glu
2765                2770                2775

His Glu Thr Ser Trp His Tyr Asp Gln Asp His Pro Tyr Lys Thr
2780                2785                2790

Trp Ala Tyr His Gly Ser Tyr Glu Thr Lys Gln Thr Gly Ser Ala
2795                2800                2805

Ser Ser Met Val Asn Gly Val Val Arg Leu Leu Thr Lys Pro Trp
2810                2815                2820

Asp Val Val Pro Met Val Thr Gln Met Ala Met Thr Asp Thr Thr
2825                2830                2835

Pro Phe Gly Gln Gln Arg Val Phe Lys Glu Lys Val Asp Thr Arg
2840                2845                2850

Thr Gln Glu Pro Lys Glu Gly Thr Lys Lys Leu Met Lys Ile Thr
2855                2860                2865

Ala Glu Trp Leu Trp Lys Glu Leu Gly Lys Lys Lys Thr Pro Arg
2870                2875                2880

Met Cys Thr Arg Glu Glu Phe Thr Arg Lys Val Arg Ser Asn Ala
2885                2890                2895

Ala Leu Gly Ala Ile Phe Thr Asp Glu Asn Lys Trp Lys Ser Ala
2900                2905                2910

Arg Glu Ala Val Glu Asp Ser Arg Phe Trp Glu Leu Val Asp Lys
2915                2920                2925

Glu Arg Asn Leu His Leu Glu Gly Lys Cys Glu Thr Cys Val Tyr
2930                2935                2940

Asn Met Met Gly Lys Arg Glu Lys Lys Leu Gly Glu Phe Gly Lys
2945                2950                2955

Ala Lys Gly Ser Arg Ala Ile Trp Tyr Met Trp Leu Gly Ala Arg
2960                2965                2970
```

```
Phe Leu Glu Phe Glu Ala Leu Gly Phe Leu Asn Glu Asp His Trp
2975             2980                 2985

Phe Ser Arg Glu Asn Ser Leu Ser Gly Val Glu Gly Glu Gly Leu
2990             2995                 3000

His Lys Leu Gly Tyr Ile Leu Arg Asp Val Ser Lys Lys Glu Gly
3005             3010                 3015

Gly Ala Met Tyr Ala Asp Asp Thr Ala Gly Trp Asp Thr Arg Ile
3020             3025                 3030

Thr Leu Glu Asp Leu Lys Asn Glu Glu Met Val Thr Asn His Met
3035             3040                 3045

Glu Gly Glu His Lys Lys Leu Ala Glu Ala Ile Phe Lys Leu Thr
3050             3055                 3060

Tyr Gln Asn Lys Val Val Arg Val Gln Arg Pro Thr Pro Arg Gly
3065             3070                 3075

Thr Val Met Asp Ile Ile Ser Arg Arg Asp Gln Arg Gly Ser Gly
3080             3085                 3090

Gln Val Gly Thr Tyr Gly Leu Asn Thr Phe Thr Asn Met Glu Ala
3095             3100                 3105

Gln Leu Ile Arg Gln Met Glu Gly Glu Gly Val Phe Lys Ser Ile
3110             3115                 3120

Gln His Leu Thr Ile Thr Glu Glu Ile Ala Val Gln Asn Trp Leu
3125             3130                 3135

Ala Arg Val Gly Arg Glu Arg Leu Ser Arg Met Ala Ile Ser Gly
3140             3145                 3150

Asp Asp Cys Val Val Lys Pro Leu Asp Asp Arg Phe Ala Ser Ala
3155             3160                 3165

Leu Thr Ala Leu Asn Asp Met Gly Lys Ile Arg Lys Asp Ile Gln
3170             3175                 3180

Gln Trp Glu Pro Ser Arg Gly Trp Asn Asp Trp Thr Gln Val Pro
3185             3190                 3195

Phe Cys Ser His His Phe His Glu Leu Ile Met Lys Asp Gly Arg
3200             3205                 3210

Val Leu Val Val Pro Cys Arg Asn Gln Asp Glu Leu Ile Gly Arg
3215             3220                 3225

Ala Arg Ile Ser Gln Gly Ala Gly Trp Ser Leu Arg Glu Thr Ala
3230             3235                 3240

Cys Leu Gly Lys Ser Tyr Ala Gln Met Trp Ser Leu Met Tyr Phe
3245             3250                 3255

His Arg Arg Asp Leu Arg Leu Ala Ala Asn Ala Ile Cys Ser Ala
3260             3265                 3270

Val Pro Ser His Trp Val Pro Thr Ser Arg Thr Thr Trp Ser Ile
3275             3280                 3285

His Ala Lys His Glu Trp Met Thr Thr Glu Asp Met Leu Thr Val
3290             3295                 3300

Trp Asn Arg Val Trp Ile Gln Glu Asn Pro Trp Met Glu Asp Lys
3305             3310                 3315

Thr Pro Val Glu Ser Trp Glu Glu Ile Pro Tyr Leu Gly Lys Arg
3320             3325                 3330

Glu Asp Gln Trp Cys Gly Ser Leu Ile Gly Leu Thr Ser Arg Ala
3335             3340                 3345

Thr Trp Ala Lys Asn Ile Gln Ala Ala Ile Asn Gln Val Arg Ser
3350             3355                 3360

Leu Ile Gly Asn Glu Glu Tyr Thr Asp Tyr Met Pro Ser Met Lys
```

```
                3365              3370              3375
Arg Phe  Arg Arg Glu Glu  Glu  Glu Ala Gly Val Leu  Trp
      3380              3385              3390

<210> SEQ ID NO 16
<211> LENGTH: 10723
<212> TYPE: DNA
<213> ORGANISM: Artificial Sequence
<220> FEATURE:
<223> OTHER INFORMATION: Derived from Dengue virus serotype 2, PDK-53
      derivative, MVS

<400> SEQUENCE: 16
agttgttagt ctacgtggac cgacaaagac agattctttg agggagctaa gctcaatgta      60
gttctaacag tttttaatt  agagagcaga tctctgatga ataaccaacg gaaaaaggcg     120
aaaaacacgc ctttcaatat gctgaaacgc gagagaaacc gcgtgtcgac tgtgcaacag     180
ctgacaaaga gattctcact tggaatgctg cagggacgag gaccattaaa actgttcatg     240
gccctggtgg cgttccttcg tttcctaaca atcccaccaa cagcagggat attgaagaga     300
tggggaacaa ttaaaaaatc aaaagctatt aatgttttga gagggttcag gaaagagatt     360
ggaaggatgc tgaacatctt gaataggaga gcagatctg  caggcatgat cattatgctg     420
attccaacag tgatggcgtt ccatttaacc acacgtaacg gagaaccaca catgatcgtc     480
agcagacaag agaagggaa  aagtcttctg tttaaaacag aggttggcgt gaacatgtgt     540
accctcatgg ccatggacct tggtgaattg tgtgaagaca caatcacgta cgagtgtccc     600
cttctcaggc agaatgagcc agaagacata gactgttggt gcaactctac gtccacgtgg     660
gtaacttatg gacgtgtac  caccatggga gaacatagaa gagaaaaaag atcagtggca     720
ctcgttccac atgtgggaat gggactggag acacgaactg aaacatggat gtcatcagaa     780
ggggcctgga acatgtcca  gagaattgaa acttggatct tgagacatcc aggcttcacc     840
atgatggcag caatcctggc atacaccata ggaacgacac atttccaaag agccctgatc     900
ttcatcttac tgacagctgt cactccttca atgacaatgc gttgcatagg aatgtcaaat     960
agagactttg tggaaggggt ttcaggagga gctgggttg  acatagtctt agaacatgga    1020
agctgtgtga cgacgatggc aaaaaacaaa ccaacattgg attttgaact gataaaaaca    1080
gaagccaaac agcctgccac cctaaggaag tactgtatag aggcaaagct aaccaacaca    1140
acaacagaat ctcgctgccc aacacaaggg gaacccagcc taaatgaaga gcaggacaaa    1200
aggttcgtct gcaaacactc catggtagac agaggatggg gaaatggatg tggactattt    1260
ggaaagggag gcattgtgac ctgtgctatg ttcagatgca aaaagaacat ggaaggaaaa    1320
gttgtgcaac cagaaaactt ggaatacacc attgtgataa cacctcactc agggggaagag    1380 catgcagtcg gaaatgacac aggaaaacat ggcaaggaaa tcaaaataac accacagagt    1440
tccatcacag aagcagaatt gacaggttat ggcactgtca caatggagtg ctctccaaga    1500
acgggcctcg acttcaatga gatggtgttg ctgcagatga aaataaagc  ttggctggtg    1560 cacaggcaat ggttcctaga cctgccgtta ccatggttgc ccggagcgga cacacaaggg    1620
tcaaattgga tacagaaaga gacattggtc actttcaaaa atcccatgc  gaagaaacag    1680 gatgttgttg ttttaggatc ccaagaaggg gccatgcaca cagcacttac aggggccaca    1740
gaaatccaaa tgtcatcagg aaacttactc ttcacaggac atctcaagtg caggctgaga    1800
atggacaagc tacagctcaa aggaatgtca tactctatgt gcacaggaaa gtttaaagtt    1860
gtgaaggaaa tagcagaaac acaacatgga acaatagtta tcagagtgca atatgaaggg    1920
```

```
gacggctctc catgcaagat ccctttgag  ataatggatt tggaaaaaag acatgtctta    1980
ggtcgcctga ttacagtcaa cccaattgtg acagaaaaag atagcccagt caacatagaa    2040
gcagaacctc catttggaga cagctacatc atcataggag tagagccggg acaactgaag    2100
ctcaactggt ttaagaaagg aagttctatc ggccaaatgt tgagacaac  aatgaggggg    2160 gcgaagagaa tggccatttt aggtgacaca gcctgggatt ttggatcctt gggaggagtg    2220
tttacatcta taggaaaggc tctccaccaa gtctttggag caatctatgg agctgccttc    2280
agtggggttt catggactat gaaaatcctc ataggagtca ttatcacatg gataggaatg    2340
aattcacgca gcacctcact gtctgtgaca ctagtattgg tgggaattgt gacactgtat    2400
ttgggagtca tggtgcaggc cgatagtggt tgcgttgtga gctggaaaaa caagaactg    2460 aaatgtggca gtgggatttt catcacagac aacgtgcaca catggacaga acaatacaag    2520
ttccaaccag aatccccttc aaaactagct tcagctatcc agaaagccca tgaagaggac    2580
atttgtggaa tccgctcagt aacaagactg gagaatctga tgtggaaaca aataacacca    2640
gaattgaatc acattctatc agaaaatgag gtgaagttaa ctattatgac aggagacatc    2700
aaaggaatca tgcaggcagg aaaacgatct ctgcggcctc agcccactga gctgaagtat    2760
tcatggaaaa catggggcaa agcaaaaatg ctctctacag agtctcataa ccagaccttt    2820
ctcattgatg cccccgaaac agcagaatgc cccaacacaa atagagcttg gaattcgttg    2880
gaagttgaag actatggctt tggagtattc accaccaata tatggctaaa attgaaagaa    2940
aaacaggatg tattctgcga ctcaaaactc atgtcagcgg ccataaaaga caacagagcc    3000
gtccatgccg atatgggtta ttggatagaa agtgcactca atgacacatg gaagatagag    3060
aaagcctctt tcattgaagt taaaaactgc cactggccaa aatcacacac cctctggagc    3120
aatggagtgc tagaaagtga gatgataatt ccaaagaatc tcgctggacc agtgtctcaa    3180
cacaactata taccaggcta ccatacacaa ataacaggac catggcatct aggtaagctt    3240
gagatggact ttgatttctg tgatggaaca acagtggtag tgactgagga ctgcggaaat    3300
agaggaccct cttttgagaa caaccactgc ctctggaaaac tcataacaga atggtgctgc    3360
cgatcttgca cattaccacc gctaagatac agaggtgagg atgggtgctg gtacgggatg    3420
gaaatcagac cattgaagga aaagaagag  aatttggtca actccttggt cacagctgga    3480
catgggcagg tcgacaactt ttcactagga gtcttggaa  tggcattgtt cctgaggaa     3540 atgcttagga cccgagtagg aacgaaacat gcaatactac tagttgcagt ttcttttgtg    3600
acattgatca cagggaacat gtcctttaga gacctgggaa gagtgatggt tatggtaggc    3660
gccactatga cggatgacat aggtatgggc gtgacttatc ttgccctact agcagccttc    3720
aaagtcagac caacttttgc agctggacta ctcttgagaa agctgacctc aaggaattg    3780 atgatgacta ctataggaat tgtactcctc tcccagagca ccataccaga gaccattctt    3840
gagttgactg atgcgttagc cttaggcatg atggtcctca aaatggtgag aaatatggaa    3900
aagtatcaat tggcagtgac tatcatggct atcttgtgcg tcccaaacgc agtgatatta    3960
caaaacgcat ggaaagtgag ttgcacaata ttggcagtgg tgtccgtttc cccactgttc    4020
ttaacatcct cacagcaaaa aacagattgg ataccattag cattgacgat caaaggtctc    4080
aatccaacag ctattttct  aacaacccte tcaagaacca gcaagaaaag gagctggcca    4140
ttaaatgagg ctatcatggc agtcgggatg gtgagcattt tagccagttc tctcctaaaa    4200
aatgatattc ccatgacagg accattagtg gctggagggc tcctcactgt gtgctacgtg    4260
```

```
ctcactggac gatcggccga tttggaactg gagagagcag ccgatgtcaa atgggaagac   4320
caggcagaga tatcaggaag cagtccaatc ctgtcaataa caatatcaga agatggtagc   4380
atgtcgataa aaaatgaaga ggaagaacaa acactgacca tactcattag aacaggattg   4440
ctggtgatct caggactttt tcctgtatca ataccaatca cggcagcagc atggtacctg   4500
tgggaagtga agaaacaacg ggccggagta ttgtgggatg ttccttcacc cccacccatg   4560
ggaaaggctg aactggaaga tggagcctat agaattaagc aaaaagggat tcttggatat   4620
tcccagatcg gagccggagt ttacaaagaa ggaacattcc atacaatgtg gcatgtcaca   4680
cgtggcgctg ttctaatgca taaaggaaag aggattgaac catcatgggc ggacgtcaag   4740
aaagacctaa tatcatatgg aggaggctgg aagttagaag gagaatggaa ggaaggagaa   4800
gaagtccagg tattggcact ggagcctgga aaaaatccaa gagccgtcca aacgaaacct   4860
ggtcttttca aaccaacgc cggaacaata ggtgctgtat ctctggactt ttctcctgga   4920
acgtcaggat ctccaattat cgacaaaaaa ggaaaagttg tgggtcttta tggtaatggt   4980
gttgttacaa ggagtggagc atatgtgagt gctatagccc agactgaaaa aagcattgaa   5040
gacaacccag atcgaagga tgacattttc cgaaagagaa gactgaccat catggacctc   5100
cacccaggag cggaaaagac gaagagatac cttccggcca tagtcagaga agctataaaa   5160
cggggtttga acattaat cttggccccc actagagttg tggcagctga atggaggaa   5220
gcccttagag gacttccaat aagataccag accccagcca tcagagctgt gcacaccggg   5280
cgggagattg tggacctaat gtgtcatgcc acatttacca tgaggctgct atcaccagtt   5340
agagtgccaa actacaacct gattatcatg gacgaagccc atttcacaga cccagcaagt   5400
atagcagcta gaggatacat ctcaactcga gtggagatgg gtgaggcagc tgggatttt   5460
atgcagcca ctcccccggg aagcagagac ccatttcctc agagcaatgc accaatcata   5520
gatgaagaaa gagaaatccc tgaacgctcg tggaattccg acatgaatg ggtcacggat   5580
tttaagggga agactgtttg gttcgttcca agtataaaag caggaaatga tatagcagct   5640
tgcctgagga aaaatggaaa gaaagtgata caactcagta ggaagacctt gattctgag   5700
tatgtcaaga ctagaaccaa tgattgggac ttcgtggtta caactgacat ttcagaaatg   5760
ggtgccaatt tcaaggctga gagggttata daccccagac gctgcatgaa accagtcata   5820
ctaacagatg gtgaagagcg ggtgattctg gcaggaccta tgccagtgac ccactctagt   5880
gcagcacaaa gaagagggag aataggaaga aatccaaaaa atgagaatga ccagtacata   5940
tacatggggg aacctctgga aaatgatgaa gactgtgcac actggaaaga agctaaaatg   6000
ctcctagata acatcaacac gccagaagga atcattccta gcatgttcga accagagcgt   6060
gaaaaggtgg atgccattga tggcgaatac cgcttgagag agaagcaag gaaaaccttt   6120
gtagacttaa tgagaagagg agacctacca gtctggttgg cctacagagt ggcagctgaa   6180
ggcatcaact acgcagacag aaggtggtgt tttgatggag tcaagaacaa ccaaatccta   6240
gaagaaaacg tggaagttga atctggaca aaagaagggg aaaggaagaa attgaaaccc   6300
agatggttgg atgctaggat ctattctgac ccactggcgc taaagaatt taaggaattt   6360
gcagccggaa gaaagtctct gaccctgaac ctaatcacag aaatgggtag ctcccaacc   6420
ttcatgactc agaaggcaag agacgcactg gacaacttag cagtgctgca cacggctgag   6480
gcaggtggaa gggcgtacaa ccatgctctc agtgaactgc cggagaccct ggagacattg   6540
cttttactga cacttctggc tacagtcacg ggagggatct ttttattctt gatgagcgca   6600
aggggcatag ggaagatgac cctgggaatg tgctgcataa tcacggctag catcctccta   6660
```

```
tggtacgcac aaatacagcc acactggata gcagcttcaa taatactgga gttttttctc    6720
atagttttgc ttattccaga acctgaaaaa cagagaacac cccaagacaa ccaactgacc    6780
tacgttgtca tagccatcct cacagtggtg ccgcaaccca tggcaaacga tgggtttc     6840
ctagaaaaaa cgaagaaaga tctcggattg ggaagcattg caacccagca acccgagagc    6900
aacatcctgg acatagatct acgtcctgca tcagcatgga cgctgtatgc cgtggccaca    6960
acatttgtta caccaatgtt gagacatagc attgaaaatt cctcagtgaa tgtgtcccta    7020
acagctatag ccaaccaagc cacagtgtta atgggtctcg ggaaggatg gccattgtca     7080
aagatggaca tcggagttcc ccttctcgcc attggatgct actcacaagt caaccccata    7140
actctcacag cagctctttt cttattggta gcacattatg ccatcatagg gccaggactc    7200
caagcaaaag caaccagaga agctcagaaa agagcagcgg cgggcatcat gaaaaaccca    7260
actgtcgatg aataacagt gattgaccta gatccaatac cttatgatcc aaagtttgaa     7320
aagcagttgg acaagtaat gctcctagtc ctctgcgtga ctcaagtatt gatgatgagg     7380
actacatggg ctctgtgtga ggctttaacc ttagctaccg ggcccatctc cacattgtgg    7440
gaaggaaatc cagggaggtt ttggaacact accattgcgg tgtcaatggc taacattttt    7500
agagggagtt acttggccgg agctggactt ctctttttcta ttatgaagaa cacaaccaac    7560
acaagaaggg gaactggcaa cataggagag acgcttggag agaaatggaa aagccgattg    7620
aacgcattgg gaaaagtga attccagatc tacaagaaaa gtggaatcca ggaagtggat     7680
agaaccttag caaagaagg cattaaaaga ggagaaacgg accatcacgc tgtgtcgcga     7740
ggctcagcaa aactgagatg gttcgttgag agaaacatgg tcacaccaga agggaaagta    7800
gtggacctcg gttgtggcag aggaggctgg tcatactatt gtggaggact aaagaatgta    7860
agagaagtca aaggcctaac aaaaggagga ccaggacacg aagaacccat ccccatgtca    7920
acatatgggt ggaatctagt gcgtcttcaa agtggagttg acgttttctt catcccgcca    7980
gaaaagtgtg acacattatt gtgtgacata ggggagtcat caccaaatcc cacagtggaa    8040
gcaggacgaa cactcagagt ccttaactta gtagaaaatt ggttgaacaa caacactcaa    8100
ttttgcataa aggttctcaa cccatatatg ccctcagtca tagaaaaaat ggaagcacta    8160
caaaggaaat atggaggagc cttagtgagg aatccactct cacgaaactc cacacatgag    8220
atgtactggg tatccaatgc ttccgggaac atagtgtcat cagtgaacat gatttcaagg    8280
atgttgatca acagatttac aatgagatac aagaaagcca cttacgagcc ggatgttgac    8340
ctcggaagcg gaacccgtaa catcgggatt gaaagtgaga taccaaacct agatataatt    8400
gggaaaagaa tagaaaaaat aaagcaagag catgaaacat catggcacta tgaccaagac    8460
cacccataca aaacgtggcc ataccatggt agctatgaaa caaacagac tggatcagca    8520
tcatccatgg tcaacggagt ggtcaggctg ctgacaaaac cttgggacgt cgtccccatg    8580
gtgacacaga tggcaatgac agacacgact ccatttggac aacagcgcgt ttttaaagag    8640
aaagtggaca cgagaacca agaaccgaaa gaaggcacga gaaactaat gaaaataaca    8700
gcagagtggc tttggaaaga attagggaag aaaaagacac ccaggatgtg caccagagaa    8760
gaattcacaa gaaaggtgag aagcaatgca gccttggggg ccgtattcac tgatgagaac    8820
aagtggaagt cggcacgtga ggctgttgaa gatagtaggt tttgggagct ggttgacaag    8880
gaaaggaatc tccatcttga aggaaagtgt gaaacatgtg tgtacaacat gatgggaaaa    8940
agagagaaga agctagggga attcggcaag gcaaaaggca gcagagccat atggtacatg    9000
```

-continued

```
tggcttggag cacgcttctt agagtttgaa gccctaggat tcttaaatga agatcactgg    9060
ttctccagag agaactccct gagtggagtg aaggagaag gctgcacaa gctaggttac      9120 attctaagag acgtgagcaa gaaagaggga ggagcaatgt atgccgatga caccgcagga   9180
tgggatacaa gaatcacact agaagaccta aaaaatgaag aaatggtaac aaaccacatg   9240
gaaggagaac acaagaaact agccgaggcc atttcaaac taacgtacca aaacaaggtg    9300
gtgcgtgtgc aaagaccaac accaagaggc acagtaatgg acatcatatc gagaagagac   9360
caaagaggta gtggacaagt tggcacctat ggactcaata ctttcaccaa tatggaagcc   9420
caactaatca gacagatgga gggagaagga gtctttaaaa gcattcagca cctaacaatc   9480
acagaagaaa tcgctgtgca aactggtta gcaagagtgg ggcgcgaaag gttatcaaga    9540
atggccatca gtggagatga ttgtgttgtg aaacctttag atgacaggtt cgcaagcgct   9600
ttaacagctc taatgacat gggaaagatt aggaaagaca tacaacaatg gaaccttca    9660 agaggatgga atgattggac aagtgccc ttctgttcac accatttcca tgagttaatc     9720
atgaaagacg gtcgcgtact cgttgttcca tgtagaaacc aagatgaact gattggcaga   9780
gcccgaatct cccaaggagc agggtggtct ttgcgggaga cggcctgttt ggggaagtct   9840
tacgcccaaa tgtggagctt gatgtacttc cacagacgcg acctcaggct ggcggcaaat   9900
gctatttgct cggcagtacc atcacattgg gttccaacaa gtcgaacaac ctggtccata   9960
catgctaaac atgaatggat gacaacggaa gacatgctga cagtctggaa cagggtgtgg  10020
attcaagaaa acccatggat ggaagacaaa actccagtgg aatcatggga ggaaatccca  10080
tacttgggga aagagaaga ccaatggtgc ggctcattga ttgggttaac aagcagggcc   10140
acctgggcaa gaacatcca agcagcaata atcaagtta gatcccttat aggcaatgaa   10200
gaatacacag attacatgcc atccatgaaa agattcagaa gagaagagga gaagcagga   10260 gttctgtggt agaaagcaaa actaacatga acaaggcta gaagtcaggt cggattaagc   10320
catagtacgg aaaaaactat gctacctgtg agccccgtcc aaggacgtta aaagaagtca  10380
ggccatcata atgccatag cttgagtaaa ctatgcagcc tgtagctcca cctgagaagg   10440
tgtaaaaaat ccgggaggcc acaaaccatg gaagctgtac gcatggcgta gtggactagc  10500
ggttagagga gacccctccc ttacaaatcg cagcaacaat ggggggccaa ggcgagatga  10560
agctgtagtc tcgctggaag gactagaggt tagaggagac cccccgaaa caaaaaacag   10620 catattgacg ctgggaaaga ccagagatcc tgctgtctcc tcagcatcat tccaggcaca  10680
gaacgccaga aatggaatg tgctgttga atcaacaggt tct                      10723
```

```
<210> SEQ ID NO 17
<211> LENGTH: 3391
<212> TYPE: PRT
<213> ORGANISM: Artificial Sequence
<220> FEATURE:
<223> OTHER INFORMATION: Derived from Dengue virus serotype 2, PDK-53
      derivative, MVS

<400> SEQUENCE: 17
```

```
Met Asn Asn Gln Arg Lys Lys Ala Lys Asn Thr Pro Phe Asn Met Leu
1               5                   10                  15

Lys Arg Glu Arg Asn Arg Val Ser Thr Val Gln Gln Leu Thr Lys Arg
                20                  25                  30

Phe Ser Leu Gly Met Leu Gln Gly Arg Gly Pro Leu Lys Leu Phe Met
            35                  40                  45

Ala Leu Val Ala Phe Leu Arg Phe Leu Thr Ile Pro Pro Thr Ala Gly
```

```
            50                  55                  60
Ile Leu Lys Arg Trp Gly Thr Ile Lys Ser Lys Ala Ile Asn Val
 65                  70                  75                  80

Leu Arg Gly Phe Arg Lys Glu Ile Gly Arg Met Leu Asn Ile Leu Asn
                 85                  90                  95

Arg Arg Arg Arg Ser Ala Gly Met Ile Ile Met Leu Ile Pro Thr Val
             100                 105                 110

Met Ala Phe His Leu Thr Thr Arg Asn Gly Glu Pro His Met Ile Val
             115                 120                 125

Ser Arg Gln Glu Lys Gly Lys Ser Leu Leu Phe Lys Thr Glu Val Gly
         130                 135                 140

Val Asn Met Cys Thr Leu Met Ala Met Asp Leu Gly Glu Leu Cys Glu
145                 150                 155                 160

Asp Thr Ile Thr Tyr Glu Cys Pro Leu Leu Arg Gln Asn Glu Pro Glu
                165                 170                 175

Asp Ile Asp Cys Trp Cys Asn Ser Thr Ser Thr Trp Val Thr Tyr Gly
            180                 185                 190

Thr Cys Thr Thr Met Gly Glu His Arg Arg Glu Lys Arg Ser Val Ala
        195                 200                 205

Leu Val Pro His Val Gly Met Gly Leu Glu Thr Arg Thr Glu Thr Trp
210                 215                 220

Met Ser Glu Gly Ala Trp Lys His Val Gln Arg Ile Glu Thr Trp
225                 230                 235                 240

Ile Leu Arg His Pro Gly Phe Thr Met Met Ala Ala Ile Leu Ala Tyr
                245                 250                 255

Thr Ile Gly Thr Thr His Phe Gln Arg Ala Leu Ile Phe Ile Leu Leu
            260                 265                 270

Thr Ala Val Thr Pro Ser Met Thr Met Arg Cys Ile Gly Met Ser Asn
        275                 280                 285

Arg Asp Phe Val Glu Gly Val Ser Gly Gly Ser Trp Val Asp Ile Val
290                 295                 300

Leu Glu His Gly Ser Cys Val Thr Thr Met Ala Lys Asn Lys Pro Thr
305                 310                 315                 320

Leu Asp Phe Glu Leu Ile Lys Thr Glu Ala Lys Gln Pro Ala Thr Leu
                325                 330                 335

Arg Lys Tyr Cys Ile Glu Ala Lys Leu Thr Asn Thr Thr Thr Glu Ser
            340                 345                 350

Arg Cys Pro Thr Gln Gly Glu Pro Ser Leu Asn Glu Glu Gln Asp Lys
        355                 360                 365

Arg Phe Val Cys Lys His Ser Met Val Asp Arg Gly Trp Gly Asn Gly
370                 375                 380

Cys Gly Leu Phe Gly Lys Gly Ile Val Thr Cys Ala Met Phe Arg
385                 390                 395                 400

Cys Lys Lys Asn Met Glu Gly Lys Val Val Gln Pro Glu Asn Leu Glu
                405                 410                 415

Tyr Thr Ile Val Ile Thr Pro His Ser Gly Glu Glu His Ala Val Gly
            420                 425                 430

Asn Asp Thr Gly Lys His Gly Lys Glu Ile Lys Ile Thr Pro Gln Ser
        435                 440                 445

Ser Ile Thr Glu Ala Glu Leu Thr Gly Tyr Gly Thr Val Thr Met Glu
        450                 455                 460

Cys Ser Pro Arg Thr Gly Leu Asp Phe Asn Glu Met Val Leu Leu Gln
465                 470                 475                 480
```

```
Met Glu Asn Lys Ala Trp Leu Val His Arg Gln Trp Phe Leu Asp Leu
            485                 490                 495

Pro Leu Pro Trp Leu Pro Gly Ala Asp Thr Gln Gly Ser Asn Trp Ile
            500                 505                 510

Gln Lys Glu Thr Leu Val Thr Phe Lys Asn Pro His Ala Lys Lys Gln
            515                 520                 525

Asp Val Val Leu Gly Ser Gln Glu Gly Ala Met His Thr Ala Leu
            530                 535                 540

Thr Gly Ala Thr Glu Ile Gln Met Ser Ser Gly Asn Leu Leu Phe Thr
545                 550                 555                 560

Gly His Leu Lys Cys Arg Leu Arg Met Asp Lys Leu Gln Leu Lys Gly
            565                 570                 575

Met Ser Tyr Ser Met Cys Thr Gly Lys Phe Lys Val Val Lys Glu Ile
            580                 585                 590

Ala Glu Thr Gln His Gly Thr Ile Val Ile Arg Val Gln Tyr Glu Gly
            595                 600                 605

Asp Gly Ser Pro Cys Lys Ile Pro Phe Glu Ile Met Asp Leu Glu Lys
            610                 615                 620

Arg His Val Leu Gly Arg Leu Ile Thr Val Asn Pro Ile Val Thr Glu
625                 630                 635                 640

Lys Asp Ser Pro Val Asn Ile Glu Ala Glu Pro Pro Phe Gly Asp Ser
            645                 650                 655

Tyr Ile Ile Ile Gly Val Glu Pro Gly Gln Leu Lys Leu Asn Trp Phe
            660                 665                 670

Lys Lys Gly Ser Ser Ile Gly Gln Met Phe Glu Thr Thr Met Arg Gly
            675                 680                 685

Ala Lys Arg Met Ala Ile Leu Gly Asp Thr Ala Trp Asp Phe Gly Ser
            690                 695                 700

Leu Gly Gly Val Phe Thr Ser Ile Gly Lys Ala Leu His Gln Val Phe
705                 710                 715                 720

Gly Ala Ile Tyr Gly Ala Ala Phe Ser Gly Val Ser Trp Thr Met Lys
            725                 730                 735

Ile Leu Ile Gly Val Ile Ile Thr Trp Ile Gly Met Asn Ser Arg Ser
            740                 745                 750

Thr Ser Leu Ser Val Thr Leu Val Leu Val Gly Ile Val Thr Leu Tyr
            755                 760                 765

Leu Gly Val Met Val Gln Ala Asp Ser Gly Cys Val Val Ser Trp Lys
            770                 775                 780

Asn Lys Glu Leu Lys Cys Gly Ser Gly Ile Phe Ile Thr Asp Asn Val
785                 790                 795                 800

His Thr Trp Thr Glu Gln Tyr Lys Phe Gln Pro Glu Ser Pro Ser Lys
            805                 810                 815

Leu Ala Ser Ala Ile Gln Lys Ala His Glu Glu Asp Ile Cys Gly Ile
            820                 825                 830

Arg Ser Val Thr Arg Leu Glu Asn Leu Met Trp Lys Gln Ile Thr Pro
            835                 840                 845

Glu Leu Asn His Ile Leu Ser Glu Asn Glu Val Lys Leu Thr Ile Met
            850                 855                 860

Thr Gly Asp Ile Lys Gly Ile Met Gln Ala Gly Lys Arg Ser Leu Arg
865                 870                 875                 880

Pro Gln Pro Thr Glu Leu Lys Tyr Ser Trp Lys Thr Trp Gly Lys Ala
            885                 890                 895
```

```
Lys Met Leu Ser Thr Glu Ser His Asn Gln Thr Phe Leu Ile Asp Gly
                900                 905                 910

Pro Glu Thr Ala Glu Cys Pro Asn Thr Asn Arg Ala Trp Asn Ser Leu
            915                 920                 925

Glu Val Glu Asp Tyr Gly Phe Gly Val Phe Thr Asn Ile Trp Leu
        930                 935                 940

Lys Leu Lys Glu Lys Gln Asp Val Phe Cys Asp Ser Lys Leu Met Ser
945                 950                 955                 960

Ala Ala Ile Lys Asp Asn Arg Ala Val His Ala Asp Met Gly Tyr Trp
                965                 970                 975

Ile Glu Ser Ala Leu Asn Asp Thr Trp Lys Ile Glu Lys Ala Ser Phe
            980                 985                 990

Ile Glu Val Lys Asn Cys His Trp Pro Lys Ser His Thr Leu Trp Ser
        995                 1000                1005

Asn Gly Val Leu Glu Ser Glu Met Ile Ile Pro Lys Asn Leu Ala
    1010                1015                1020

Gly Pro Val Ser Gln His Asn Tyr Arg Pro Gly Tyr His Thr Gln
    1025                1030                1035

Ile Thr Gly Pro Trp His Leu Gly Lys Leu Glu Met Asp Phe Asp
    1040                1045                1050

Phe Cys Asp Gly Thr Thr Val Val Thr Glu Asp Cys Gly Asn
    1055                1060                1065

Arg Gly Pro Ser Leu Arg Thr Thr Ala Ser Gly Lys Leu Ile
    1070                1075                1080

Thr Glu Trp Cys Cys Arg Ser Cys Thr Leu Pro Pro Leu Arg Tyr
    1085                1090                1095

Arg Gly Glu Asp Gly Cys Trp Tyr Gly Met Glu Ile Arg Pro Leu
    1100                1105                1110

Lys Glu Lys Glu Glu Asn Leu Val Asn Ser Leu Val Thr Ala Gly
    1115                1120                1125

His Gly Gln Val Asp Asn Phe Ser Leu Gly Val Leu Gly Met Ala
    1130                1135                1140

Leu Phe Leu Glu Glu Met Leu Arg Thr Arg Val Gly Thr Lys His
    1145                1150                1155

Ala Ile Leu Leu Val Ala Val Ser Phe Val Thr Leu Ile Thr Gly
    1160                1165                1170

Asn Met Ser Phe Arg Asp Leu Gly Arg Val Met Val Met Val Gly
    1175                1180                1185

Ala Thr Met Thr Asp Asp Ile Gly Met Gly Val Thr Tyr Leu Ala
    1190                1195                1200

Leu Leu Ala Ala Phe Lys Val Arg Pro Thr Phe Ala Ala Gly Leu
    1205                1210                1215

Leu Leu Arg Lys Leu Thr Ser Lys Glu Leu Met Met Thr Thr Ile
    1220                1225                1230

Gly Ile Val Leu Leu Ser Gln Ser Thr Ile Pro Glu Thr Ile Leu
    1235                1240                1245

Glu Leu Thr Asp Ala Leu Ala Leu Gly Met Met Val Leu Lys Met
    1250                1255                1260

Val Arg Asn Met Glu Lys Tyr Gln Leu Ala Val Thr Ile Met Ala
    1265                1270                1275

Ile Leu Cys Val Pro Asn Ala Val Ile Leu Gln Asn Ala Trp Lys
    1280                1285                1290

Val Ser Cys Thr Ile Leu Ala Val Val Ser Val Ser Pro Leu Phe
```

```
            1295                1300                1305
Leu Thr Ser Ser Gln Gln Lys Thr Asp Trp Ile Pro Leu Ala Leu
        1310                1315                1320

Thr Ile Lys Gly Leu Asn Pro Thr Ala Ile Phe Leu Thr Thr Leu
        1325                1330                1335

Ser Arg Thr Ser Lys Lys Arg Ser Trp Pro Leu Asn Glu Ala Ile
        1340                1345                1350

Met Ala Val Gly Met Val Ser Ile Leu Ala Ser Ser Leu Leu Lys
        1355                1360                1365

Asn Asp Ile Pro Met Thr Gly Pro Leu Val Ala Gly Gly Leu Leu
        1370                1375                1380

Thr Val Cys Tyr Val Leu Thr Gly Arg Ser Ala Asp Leu Glu Leu
        1385                1390                1395

Glu Arg Ala Ala Asp Val Lys Trp Glu Asp Gln Ala Glu Ile Ser
        1400                1405                1410

Gly Ser Ser Pro Ile Leu Ser Ile Thr Ile Ser Glu Asp Gly Ser
        1415                1420                1425

Met Ser Ile Lys Asn Glu Glu Glu Gln Thr Leu Thr Ile Leu
        1430                1435                1440

Ile Arg Thr Gly Leu Leu Val Ile Ser Gly Leu Phe Pro Val Ser
        1445                1450                1455

Ile Pro Ile Thr Ala Ala Ala Trp Tyr Leu Trp Glu Val Lys Lys
        1460                1465                1470

Gln Arg Ala Gly Val Leu Trp Asp Val Pro Ser Pro Pro Pro Met
        1475                1480                1485

Gly Lys Ala Glu Leu Glu Asp Gly Ala Tyr Arg Ile Lys Gln Lys
        1490                1495                1500

Gly Ile Leu Gly Tyr Ser Gln Ile Gly Ala Gly Val Tyr Lys Glu
        1505                1510                1515

Gly Thr Phe His Thr Met Trp His Val Thr Arg Gly Ala Val Leu
        1520                1525                1530

Met His Lys Gly Lys Arg Ile Glu Pro Ser Trp Ala Asp Val Lys
        1535                1540                1545

Lys Asp Leu Ile Ser Tyr Gly Gly Gly Trp Lys Leu Glu Gly Glu
        1550                1555                1560

Trp Lys Glu Gly Glu Glu Val Gln Val Leu Ala Leu Glu Pro Gly
        1565                1570                1575

Lys Asn Pro Arg Ala Val Gln Thr Lys Pro Gly Leu Phe Lys Thr
        1580                1585                1590

Asn Ala Gly Thr Ile Gly Ala Val Ser Leu Asp Phe Ser Pro Gly
        1595                1600                1605

Thr Ser Gly Ser Pro Ile Ile Asp Lys Lys Gly Lys Val Val Gly
        1610                1615                1620

Leu Tyr Gly Asn Gly Val Val Thr Arg Ser Gly Ala Tyr Val Ser
        1625                1630                1635

Ala Ile Ala Gln Thr Glu Lys Ser Ile Glu Asp Asn Pro Glu Ile
        1640                1645                1650

Glu Asp Asp Ile Phe Arg Lys Arg Arg Leu Thr Ile Met Asp Leu
        1655                1660                1665

His Pro Gly Ala Gly Lys Thr Lys Arg Tyr Leu Pro Ala Ile Val
        1670                1675                1680

Arg Glu Ala Ile Lys Arg Gly Leu Arg Thr Leu Ile Leu Ala Pro
        1685                1690                1695
```

-continued

```
Thr Arg Val Val Ala Ala Glu Met Glu Ala Leu Arg Gly Leu
    1700            1705            1710

Pro Ile Arg Tyr Gln Thr Pro Ala Ile Arg Ala Val His Thr Gly
    1715            1720            1725

Arg Glu Ile Val Asp Leu Met Cys His Ala Thr Phe Thr Met Arg
    1730            1735            1740

Leu Leu Ser Pro Val Arg Val Pro Asn Tyr Asn Leu Ile Ile Met
    1745            1750            1755

Asp Glu Ala His Phe Thr Asp Pro Ala Ser Ile Ala Ala Arg Gly
    1760            1765            1770

Tyr Ile Ser Thr Arg Val Glu Met Gly Glu Ala Ala Gly Ile Phe
    1775            1780            1785

Met Thr Ala Thr Pro Pro Gly Ser Arg Asp Pro Phe Pro Gln Ser
    1790            1795            1800

Asn Ala Pro Ile Ile Asp Glu Glu Arg Glu Ile Pro Glu Arg Ser
    1805            1810            1815

Trp Asn Ser Gly His Glu Trp Val Thr Asp Phe Lys Gly Lys Thr
    1820            1825            1830

Val Trp Phe Val Pro Ser Ile Lys Ala Gly Asn Asp Ile Ala Ala
    1835            1840            1845

Cys Leu Arg Lys Asn Gly Lys Lys Val Ile Gln Leu Ser Arg Lys
    1850            1855            1860

Thr Phe Asp Ser Glu Tyr Val Lys Thr Arg Thr Asn Asp Trp Asp
    1865            1870            1875

Phe Val Val Thr Thr Asp Ile Ser Glu Met Gly Ala Asn Phe Lys
    1880            1885            1890

Ala Glu Arg Val Ile Asp Pro Arg Arg Cys Met Lys Pro Val Ile
    1895            1900            1905

Leu Thr Asp Gly Glu Glu Arg Val Ile Leu Ala Gly Pro Met Pro
    1910            1915            1920

Val Thr His Ser Ser Ala Ala Gln Arg Arg Gly Arg Ile Gly Arg
    1925            1930            1935

Asn Pro Lys Asn Glu Asn Asp Gln Tyr Ile Tyr Met Gly Glu Pro
    1940            1945            1950

Leu Glu Asn Asp Glu Asp Cys Ala His Trp Lys Glu Ala Lys Met
    1955            1960            1965

Leu Leu Asp Asn Ile Asn Thr Pro Glu Gly Ile Ile Pro Ser Met
    1970            1975            1980

Phe Glu Pro Glu Arg Glu Lys Val Asp Ala Ile Asp Gly Glu Tyr
    1985            1990            1995

Arg Leu Arg Gly Glu Ala Arg Lys Thr Phe Val Asp Leu Met Arg
    2000            2005            2010

Arg Gly Asp Leu Pro Val Trp Leu Ala Tyr Arg Val Ala Ala Glu
    2015            2020            2025

Gly Ile Asn Tyr Ala Asp Arg Arg Trp Cys Phe Asp Gly Val Lys
    2030            2035            2040

Asn Asn Gln Ile Leu Glu Glu Asn Val Glu Val Glu Ile Trp Thr
    2045            2050            2055

Lys Glu Gly Glu Arg Lys Lys Leu Lys Pro Arg Trp Leu Asp Ala
    2060            2065            2070

Arg Ile Tyr Ser Asp Pro Leu Ala Leu Lys Glu Phe Lys Glu Phe
    2075            2080            2085
```

-continued

| | | | | | | | | | | | |
|---|---|---|---|---|---|---|---|---|---|---|---|
|Ala|Ala|Gly|Arg|Lys|Ser|Leu|Thr|Leu|Asn|Leu|Ile|Thr|Glu|Met
| | |2090| | | |2095| | | |2100| | | | |

Ala Ala Gly Arg Lys Ser Leu Thr Leu Asn Leu Ile Thr Glu Met
    2090                2095             2100

Gly Arg Leu Pro Thr Phe Met Thr Gln Lys Ala Arg Asp Ala Leu
    2105                2110             2115

Asp Asn Leu Ala Val Leu His Thr Ala Glu Ala Gly Gly Arg Ala
    2120                2125             2130

Tyr Asn His Ala Leu Ser Glu Leu Pro Glu Thr Leu Glu Thr Leu
    2135                2140             2145

Leu Leu Leu Thr Leu Leu Ala Thr Val Thr Gly Gly Ile Phe Leu
    2150                2155             2160

Phe Leu Met Ser Ala Arg Gly Ile Gly Lys Met Thr Leu Gly Met
    2165                2170             2175

Cys Cys Ile Ile Thr Ala Ser Ile Leu Leu Trp Tyr Ala Gln Ile
    2180                2185             2190

Gln Pro His Trp Ile Ala Ala Ser Ile Ile Leu Glu Phe Phe Leu
    2195                2200             2205

Ile Val Leu Leu Ile Pro Glu Pro Glu Lys Gln Arg Thr Pro Gln
    2210                2215             2220

Asp Asn Gln Leu Thr Tyr Val Val Ile Ala Ile Leu Thr Val Val
    2225                2230             2235

Ala Ala Thr Met Ala Asn Glu Met Gly Phe Leu Glu Lys Thr Lys
    2240                2245             2250

Lys Asp Leu Gly Leu Gly Ser Ile Ala Thr Gln Gln Pro Glu Ser
    2255                2260             2265

Asn Ile Leu Asp Ile Asp Leu Arg Pro Ala Ser Ala Trp Thr Leu
    2270                2275             2280

Tyr Ala Val Ala Thr Thr Phe Val Thr Pro Met Leu Arg His Ser
    2285                2290             2295

Ile Glu Asn Ser Ser Val Asn Val Ser Leu Thr Ala Ile Ala Asn
    2300                2305             2310

Gln Ala Thr Val Leu Met Gly Leu Gly Lys Gly Trp Pro Leu Ser
    2315                2320             2325

Lys Met Asp Ile Gly Val Pro Leu Leu Ala Ile Gly Cys Tyr Ser
    2330                2335             2340

Gln Val Asn Pro Ile Thr Leu Thr Ala Ala Leu Phe Leu Leu Val
    2345                2350             2355

Ala His Tyr Ala Ile Ile Gly Pro Gly Leu Gln Ala Lys Ala Thr
    2360                2365             2370

Arg Glu Ala Gln Lys Arg Ala Ala Ala Gly Ile Met Lys Asn Pro
    2375                2380             2385

Thr Val Asp Gly Ile Thr Val Ile Asp Leu Asp Pro Ile Pro Tyr
    2390                2395             2400

Asp Pro Lys Phe Glu Lys Gln Leu Gly Gln Val Met Leu Leu Val
    2405                2410             2415

Leu Cys Val Thr Gln Val Leu Met Met Arg Thr Thr Trp Ala Leu
    2420                2425             2430

Cys Glu Ala Leu Thr Leu Ala Thr Gly Pro Ile Ser Thr Leu Trp
    2435                2440             2445

Glu Gly Asn Pro Gly Arg Phe Trp Asn Thr Thr Ile Ala Val Ser
    2450                2455             2460

Met Ala Asn Ile Phe Arg Gly Ser Tyr Leu Ala Gly Ala Gly Leu
    2465                2470             2475

Leu Phe Ser Ile Met Lys Asn Thr Thr Asn Thr Arg Arg Gly Thr

-continued

```
            2480                2485                2490
Gly Asn Ile Gly Glu Thr Leu Gly Glu Lys Trp Lys Ser Arg Leu
            2495                2500                2505
Asn Ala Leu Gly Lys Ser Glu Phe Gln Ile Tyr Lys Lys Ser Gly
            2510                2515                2520
Ile Gln Glu Val Asp Arg Thr Leu Ala Lys Glu Gly Ile Lys Arg
            2525                2530                2535
Gly Glu Thr Asp His His Ala Val Ser Arg Gly Ser Ala Lys Leu
            2540                2545                2550
Arg Trp Phe Val Glu Arg Asn Met Val Thr Pro Glu Gly Lys Val
            2555                2560                2565
Val Asp Leu Gly Cys Gly Arg Gly Gly Trp Ser Tyr Tyr Cys Gly
            2570                2575                2580
Gly Leu Lys Asn Val Arg Glu Val Lys Gly Leu Thr Lys Gly Gly
            2585                2590                2595
Pro Gly His Glu Glu Pro Ile Pro Met Ser Thr Tyr Gly Trp Asn
            2600                2605                2610
Leu Val Arg Leu Gln Ser Gly Val Asp Val Phe Phe Ile Pro Pro
            2615                2620                2625
Glu Lys Cys Asp Thr Leu Leu Cys Asp Ile Gly Glu Ser Ser Pro
            2630                2635                2640
Asn Pro Thr Val Glu Ala Gly Arg Thr Leu Arg Val Leu Asn Leu
            2645                2650                2655
Val Glu Asn Trp Leu Asn Asn Asn Thr Gln Phe Cys Ile Lys Val
            2660                2665                2670
Leu Asn Pro Tyr Met Pro Ser Val Ile Glu Lys Met Glu Ala Leu
            2675                2680                2685
Gln Arg Lys Tyr Gly Gly Ala Leu Val Arg Asn Pro Leu Ser Arg
            2690                2695                2700
Asn Ser Thr His Glu Met Tyr Trp Val Ser Asn Ala Ser Gly Asn
            2705                2710                2715
Ile Val Ser Ser Val Asn Met Ile Ser Arg Met Leu Ile Asn Arg
            2720                2725                2730
Phe Thr Met Arg Tyr Lys Lys Ala Thr Tyr Glu Pro Asp Val Asp
            2735                2740                2745
Leu Gly Ser Gly Thr Arg Asn Ile Gly Ile Glu Ser Glu Ile Pro
            2750                2755                2760
Asn Leu Asp Ile Ile Gly Lys Arg Ile Glu Lys Ile Lys Gln Glu
            2765                2770                2775
His Glu Thr Ser Trp His Tyr Asp Gln Asp His Pro Tyr Lys Thr
            2780                2785                2790
Trp Ala Tyr His Gly Ser Tyr Glu Thr Lys Gln Thr Gly Ser Ala
            2795                2800                2805
Ser Ser Met Val Asn Gly Val Val Arg Leu Leu Thr Lys Pro Trp
            2810                2815                2820
Asp Val Val Pro Met Val Thr Gln Met Ala Met Thr Asp Thr Thr
            2825                2830                2835
Pro Phe Gly Gln Gln Arg Val Phe Lys Glu Lys Val Asp Thr Arg
            2840                2845                2850
Thr Gln Glu Pro Lys Glu Gly Thr Lys Lys Leu Met Lys Ile Thr
            2855                2860                2865
Ala Glu Trp Leu Trp Lys Glu Leu Gly Lys Lys Lys Thr Pro Arg
            2870                2875                2880
```

-continued

```
Met Cys Thr Arg Glu Glu Phe Thr Arg Lys Val Arg Ser Asn Ala
2885                 2890                2895

Ala Leu Gly Ala Val Phe Thr Asp Glu Asn Lys Trp Lys Ser Ala
2900                 2905                2910

Arg Glu Ala Val Glu Asp Ser Arg Phe Trp Glu Leu Val Asp Lys
2915                 2920                2925

Glu Arg Asn Leu His Leu Glu Gly Lys Cys Glu Thr Cys Val Tyr
2930                 2935                2940

Asn Met Met Gly Lys Arg Glu Lys Lys Leu Gly Glu Phe Gly Lys
2945                 2950                2955

Ala Lys Gly Ser Arg Ala Ile Trp Tyr Met Trp Leu Gly Ala Arg
2960                 2965                2970

Phe Leu Glu Phe Glu Ala Leu Gly Phe Leu Asn Glu Asp His Trp
2975                 2980                2985

Phe Ser Arg Glu Asn Ser Leu Ser Gly Val Glu Gly Glu Gly Leu
2990                 2995                3000

His Lys Leu Gly Tyr Ile Leu Arg Asp Val Ser Lys Lys Glu Gly
3005                 3010                3015

Gly Ala Met Tyr Ala Asp Asp Thr Ala Gly Trp Asp Thr Arg Ile
3020                 3025                3030

Thr Leu Glu Asp Leu Lys Asn Glu Glu Met Val Thr Asn His Met
3035                 3040                3045

Glu Gly Glu His Lys Lys Leu Ala Glu Ala Ile Phe Lys Leu Thr
3050                 3055                3060

Tyr Gln Asn Lys Val Val Arg Val Gln Arg Pro Thr Pro Arg Gly
3065                 3070                3075

Thr Val Met Asp Ile Ile Ser Arg Arg Asp Gln Arg Gly Ser Gly
3080                 3085                3090

Gln Val Gly Thr Tyr Gly Leu Asn Thr Phe Thr Asn Met Glu Ala
3095                 3100                3105

Gln Leu Ile Arg Gln Met Glu Gly Glu Gly Val Phe Lys Ser Ile
3110                 3115                3120

Gln His Leu Thr Ile Thr Glu Glu Ile Ala Val Gln Asn Trp Leu
3125                 3130                3135

Ala Arg Val Gly Arg Glu Arg Leu Ser Arg Met Ala Ile Ser Gly
3140                 3145                3150

Asp Asp Cys Val Val Lys Pro Leu Asp Asp Arg Phe Ala Ser Ala
3155                 3160                3165

Leu Thr Ala Leu Asn Asp Met Gly Lys Ile Arg Lys Asp Ile Gln
3170                 3175                3180

Gln Trp Glu Pro Ser Arg Gly Trp Asn Asp Trp Thr Gln Val Pro
3185                 3190                3195

Phe Cys Ser His His Phe His Glu Leu Ile Met Lys Asp Gly Arg
3200                 3205                3210

Val Leu Val Val Pro Cys Arg Asn Gln Asp Glu Leu Ile Gly Arg
3215                 3220                3225

Ala Arg Ile Ser Gln Gly Ala Gly Trp Ser Leu Arg Glu Thr Ala
3230                 3235                3240

Cys Leu Gly Lys Ser Tyr Ala Gln Met Trp Ser Leu Met Tyr Phe
3245                 3250                3255

His Arg Arg Asp Leu Arg Leu Ala Ala Asn Ala Ile Cys Ser Ala
3260                 3265                3270
```

| | | | | | | | | | | |
|---|---|---|---|---|---|---|---|---|---|---|
| Val | Pro | Ser | His | Trp | Val | Pro | Thr | Ser | Arg | Thr | Thr | Trp | Ser | Ile |
| | 3275 | | | | 3280 | | | | 3285 | |

Val Pro Ser His Trp Val Pro Thr Ser Arg Thr Thr Trp Ser Ile
    3275                3280                3285

His Ala Lys His Glu Trp Met Thr Thr Glu Asp Met Leu Thr Val
    3290                3295                3300

Trp Asn Arg Val Trp Ile Gln Glu Asn Pro Trp Met Glu Asp Lys
    3305                3310                3315

Thr Pro Val Glu Ser Trp Glu Glu Ile Pro Tyr Leu Gly Lys Arg
    3320                3325                3330

Glu Asp Gln Trp Cys Gly Ser Leu Ile Gly Leu Thr Ser Arg Ala
    3335                3340                3345

Thr Trp Ala Lys Asn Ile Gln Ala Ala Ile Asn Gln Val Arg Ser
    3350                3355                3360

Leu Ile Gly Asn Glu Glu Tyr Thr Asp Tyr Met Pro Ser Met Lys
    3365                3370                3375

Arg Phe Arg Arg Glu Glu Glu Ala Gly Val Leu Trp
    3380                3385                3390

<210> SEQ ID NO 18
<211> LENGTH: 10717
<212> TYPE: DNA
<213> ORGANISM: Artificial Sequence
<220> FEATURE:
<223> OTHER INFORMATION: Derived from Dengue virus serotype 2/Dengue
      virus serotype 3, MVS

<400> SEQUENCE: 18

```
agttgttagt ctacgtggac cgacaaagac agattctttg agggagctaa gctcaatgta    60
gttctaacag ttttttaatt agagagcaga tctctgatga ataaccaacg gaaaaggcg    120 aaaaacacgc ctttcaatat gctgaaacgc gagagaaacc gcgtgtcgac tgtgcaacag    180
ctgacaaaga gattctcact tggaatgctg cagggacgag gaccattaaa actgttcatg    240
gccctggtgg cgttccttcg tttcctaaca atcccaccaa cagcaggat attgaagaga    300 tggggaacaa ttaaaaaatc aaaagctatt aatgtttga gagggttcag gaaagagatt    360
ggaaggatgc tgaacatctt gaataggaga cgcagatctg caggcatgat cattatgctg    420
attccaacag tgatggcgtt ccatttaacc acgcgtgatg gagagccgcg catgattgtg    480
gggaagaatg aaagaggaaa atccctactt ttcaagacag cctctggaat caacatgtgc    540
acactcatag ctatggatct gggagagatg tgtgatgaca cggtcactta caatgcccc    600 cacattaccg aagtggagcc tgaagacatt gactgctggt gcaaccttac atcgacatgg    660
gtgacttatg gaacatgcaa tcaagctgga gagcatagac gcgataagag atcagtggcg    720
ttagctcccc atgttggcat gggactggac acacgcactc aaacctggat gtcggctgaa    780
ggagcttgga gacaagtcga gaaggtagag acatgggccc ttaggcaccc agggtttacc    840
atactagccc tatttcttgc ccattacata ggcacttcct tgacccagaa agtggttatt    900
tttatactat taatgctggt tacccccatcc atgacaatga atgtgtagg agtaggaaac    960 agagattttg tggaaggcct atcgggagct acgtgggttg acgtggtgct cgagcacggt   1020
gggtgtgtga ctaccatggc taagaacaag cccacgctgg acatagagct tcagaagacc   1080
gaggccaccc aactggcgac cctaaggaag ctatgcattg agggaaaaat taccaacata   1140
acaaccgact caagatgtcc cacccaaggg gaagcgattt acctgagga gcaggaccag   1200 aactacgtgt gtaagcatac atacgtggac agaggctggg gaaacggttg tggtttgttt   1260
ggcaagggaa gcttggtgac atgcgcgaaa tttcaatgtt tagaatcaat agagggaaaa   1320
```

```
gtggtgcaac atgagaacct caaatacacc gtcatcatca cagtgcacac aggagaccaa    1380
caccaggtgg gaaatgaaac gcagggagtc acggctgaga taacacccca ggcatcaacc    1440
gctgaagcca ttttacctga atatggaacc ctcgggctag aatgctcacc acggacaggt    1500
ttggatttca atgaaatgat ctcattgaca atgaagaaca aagcatggat ggtacataga    1560
caatggttct ttgacttacc cctaccatgg acatcaggag cttcagcaga aacaccaact    1620
tggaacagga aagagcttct tgtgacattt aaaaatgcac atgcaaaaaa gcaagaagta    1680
gttgttcttg gatcacaaga gggagcaatg catacagcac tgacaggagc tacagagatc    1740
caaacctcag gaggcacaag tatctttgcg gggcacttaa aatgtagact caagatggac    1800
aaattggaac tcaaggggat gagctatgca atgtgcttga gtagctttgt gttgaagaaa    1860
gaagtctccg aaacgcagca tgggacaata ctcattaagg ttgagtacaa aggggaagat    1920
gcaccctgca agattccttt ctccacggag gatggacaag gaaaagctct caatggcaga    1980
ctgatcacag ccaatccagt ggtgaccaag aaggaggagc tgtcaacat tgaggctgaa    2040 cctcctttg gagaaagtaa catagtaatt ggaattggag acaaagccct gaaaatcaac    2100
tggtacaaga agggaagctc gattgggaag atgttcgagg ccactgccag aggtgcaagg    2160
cgcatggcca tcttgggaga cacagcctgg gactttggat cagtgggtgg tgttttgaat    2220
tcattaggga aaatggtcca ccaaatattt ggagtgctt acacagccct atttggtgga    2280
gtctcctgga tgatgaaaat tggaatagg gtcctcttaa cctggatagg gttgaactca    2340
aaaaatactt ctatgtcatt ttcatgcatc gcggccggca ttgtgacact gtatttggga    2400
gtcatggtgc aggccgatag tggttgcgtt gtgagctgga aaaacaaaga actgaaatgt    2460
ggcagtggga ttttcatcac agacaacgtg cacacatgga cagaacaata caagttccaa    2520
ccagaatccc cttcaaaact agcttcagct atccagaaag cccatgaaga ggacatttgt    2580
ggaatccgct cagtaacaag actggagaat ctgatgtgga acaaataac accagaattg    2640 aatcacattc tatcagaaaa tgaggtgaag ttaactatta tgacaggaga catcaaagga    2700
atcatgcagg caggaaaacg atctctgcgg cctcagccca ctgagctgaa gtattcatgg    2760
aaaacatggg gcaaagcaaa aatgctctct acagagtctc ataaccagac ctttctcatt    2820
gatggccccg aaacagcaga atgccccaac acaaatagag cttggaattc gttggaagtt    2880
gaagactatg ctttggagt attcaccacc aatatatggc taaaattgaa agaaaaacag    2940
gatgtattct gcgactcaaa actcatgtca gcggccataa aagacaacag agccgtccat    3000
gccgatatgg gttattggat agaaagtgca ctcaatgaca catggaagat agagaaagcc    3060
tctttcattg aagttaaaaa ctgccactgg ccaaaatcac acaccctctg gagcaatgga    3120
gtgctagaaa gtgagatgat aattccaaag aatctcgctg gaccagtgtc tcaacacaac    3180
tatagaccag gctaccatac acaaataaca ggaccatggc atctaggtaa gcttgagatg    3240
gactttgatt tctgtgatgg aacaacagtg gtagtgactg aggactgcgg aaatagagga    3300
ccctctttga gaacaaccac tgcctctgga aaactcataa cagaatggtg ctgccgatct    3360
tgcacattac caccgctaag atacagaggt gaggatgggt gctggtacgg gatggaaatc    3420
agaccattga aggagaaaga agagaatttg gtcaactcct tggtcacagc tggacatggg    3480
caggtcgaca actttttcact aggagtcttg ggaatggcat tgttcctgga ggaaatgctt    3540 aggaccccgag taggaacgaa acatgcaata ctactagttg cagtttcttt tgtgacattg    3600
atcacaggga acatgtcctt tagagacctg ggaagagtga tggttatggt aggcgccact    3660
atgacggatg acataggtat gggcgtgact tatcttgccc tactagcagc cttcaaagtc    3720
```

```
agaccaactt ttgcagctgg actactcttg agaaagctga cctccaagga attgatgatg    3780
actactatag gaattgtact cctctcccag agcaccatac cagagaccat tcttgagttg    3840
actgatgcgt tagccttagg catgatggtc ctcaaaatgg tgagaaatat ggaaaagtat    3900
caattggcag tgactatcat ggctatcttg tgcgtcccaa acgcagtgat attacaaaac    3960
gcatggaaag tgagttgcac aatattggca gtggtgtccg tttccccact gttcttaaca    4020
tcctcacagc aaaaaacaga ttggatacca ttagcattga cgatcaaagg tctcaatcca    4080
acagctattt ttctaacaac cctctcaaga accagcaaga aaaggagctg ccattaaat     4140 gaggctatca tggcagtcgg gatggtgagc attttagcca gttctctcct aaaaaatgat    4200
attcccatga caggaccatt agtggctgga gggctcctca ctgtgtgcta cgtgctcact    4260
ggacgatcgg ccgatttgga actggagaga gcagccgatg tcaaatggga agaccaggca    4320
gagatatcag gaagcagtcc aatcctgtca ataacaatat cagaagatgg tagcatgtcg    4380 ataaaaatg aagaggaaga acaaacactg accatactca ttagaacagg attgctggtg    4440
atctcaggac ttttcctgt atcaatacca atcacggcag cagcatggta cctgtgggaa    4500
gtgaagaaac aacgggccgg agtattgtgg gatgttcctt cacccccacc catgggaaag    4560
gctgaactgg aagatggagc ctatagaatt aagcaaaaag ggattcttgg atattcccag    4620
atcggagccg gagtttacaa agaaggaaca ttccatacaa tgtggcatgt cacacgtggc    4680
gctgttctaa tgcataaagg aaagaggatt gaaccatcat gggcggacgt caagaaagac    4740
ctaatatcat atggaggagg ctggaagtta gaaggagaat ggaaggaagg agaagaagtc    4800
caggtattgg cactggagcc tggaaaaaat ccaagagccg tccaaacgaa acctggtctt    4860
ttcaaaacca cgccggaac aataggtgct gtatctctgg acttttctcc tggaacgtca    4920
ggatctccaa ttatcgacaa aaaaggaaaa gttgtgggtc tttatggtaa tggtgttgtt    4980
acaaggagtg gagcatatgt gagtgctata gcccagactg aaaaaagcat tgaagacaac    5040
ccagagatcg aagatgacat tttccgaaag agaagactga ccatcatgga cctccaccca    5100
ggagcgggaa agacgaagag ataccttccg gccatagtca gagaagctat aaaacggggt    5160
ttgagaacat taatcttggc ccccactaga gttgtggcag ctgaaatgga ggaagccctt    5220
agaggacttc caataagata ccagacccca gccatcagag ctgtgcacac cgggcgggag    5280
attgtggacc taatgtgtca tgccacattt accatgagge tgctatcacc agttagagtg    5340
ccaaactaca acctgattat catggacgaa gcccatttca cagacccagc aagtatagca    5400
gctagaggat acatctcaac tcgagtggag atgggtgagg cagctgggat tttatgaca    5460 gccactcccc cgggaagcag agacccattt cctcagagca atgcaccaat catagatgaa    5520
gaaagagaaa tccctgaacg ctcgtggaat tccggacatg aatgggtcac ggatttaaa    5580 gggaagactg tttggttcgt tccaagtata aaagcaggaa atgatatagc agcttgcctg    5640
aggaaaaatg gaaagaaagt gatacaactc agtaggaaga cctttgattc tgagtatgtc    5700
aagactagaa ccaatgattg ggacttcgtg gttacaactg acatttcaga aatgggtgcc    5760
aatttcaagg ctgagagggt tatagacccc agacgctgca tgaaaccagt catactaaca    5820
gatggtgaag agcgggtgat tctggcagga cctatgccag tgacccactc tagtgcagca    5880
caaagaagag ggagaatagg aagaaatcca aaaaatgaga atgaccagta catatacatg    5940
ggggaacctc tggaaaatga tgaagactgt gcacactgga agaagctaa aatgctccta    6000 gataacatca acacgccaga aggaatcatt cctagcatgt tcgaaccaga gcgtgaaaag    6060
```

```
gtggatgcca ttgatggcga ataccgcttg agaggagaag caaggaaaac ctttgtagac    6120
ttaatgagaa gaggagacct accagtctgg ttggcctaca gagtggcagc tgaaggcatc    6180
aactacgcag acagaaggtg gtgttttgat ggagtcaaga acaaccaaat cctagaagaa    6240
aacgtggaag ttgaaatctg acaaaagaa ggggaaagga agaaattgaa acccagatgg    6300
ttggatgcta ggatctattc tgacccactg gcgctaaaag aatttaagga atttgcagcc    6360
ggaagaaagt ctctgaccct gaacctaatc acagaaatgg gtaggctccc aaccttcatg    6420
actcagaagg caagagacgc actggacaac ttagcagtgc tgcacacggc tgaggcaggt    6480
ggaagggcgt acaaccatgc tctcagtgaa ctgccggaga ccctggagac attgctttta    6540
ctgacacttc tggctacagt cacgggaggg atctttttat tcttgatgag cgcaaggggc    6600
atagggaaga tgaccctggg aatgtgctgc ataatcacgg ctagcatcct cctatggtac    6660
gcacaaatac agccacactg gatagcagct tcaataatac tggagttttt tctcatagtt    6720
ttgcttattc cagaacctga aaacagaga cacccccaag acaaccaact gacctacgtt    6780
gtcatagcca tcctcacagt ggtggccgca accatggcaa cgagatgggt ttcctagaa    6840 aaaacgaaga aagatctcgg attgggaagc attgcaaccc agcaacccga gagcaacatc    6900
ctggacatag atctacgtcc tgcatcagca tggacgctgt atgccgtggc cacaacattt    6960
gttacaccaa tgttgagaca tagcattgaa aattcctcag tgaatgtgtc cctaacagct    7020
atagccaacc aagccacagt gttaatgggt ctcgggaaag gatggccatt gtcaaagatg    7080
gacatcggag ttccccttct cgccattgga tgctactcac aagtcaaccc cataactctc    7140
acagcagctc ttttcttatt ggtagcacat tatgccatca tagggccagg actccaagca    7200
aaagcaacca gagaagctca gaaaagagca gcggcgggca tcatgaaaaa cccaactgtc    7260 gatgaataa cagtgattga cctagatcca ataccttatg atccaaagtt tgaaaagcag    7320
ttgggacaag taatgctcct agtcctctgc gtgactcaag tattgatgat gaggactaca    7380
tgggctctgt gtgaggcttt aaccttagct accgggccca tctccacatt gtgggaagga    7440
aatccaggga ggttttggaa cactaccatt gcggtgtcaa tggctaacat ttttagaggg    7500
agttacttgg ccggagctgg acttctcttt tctattatga agaacacaac caacacaaga    7560
aggggaactg gcaacatagg agagacgctt ggagagaaat ggaaaagccg attgaacgcg    7620
ttgggaaaaa gtgaattcca gatctacaag aaaagtggaa tccaggaagt ggatagaacc    7680
ttagcaaaag aaggcattaa agaggagaaa acggaccatc acgctgtgtc gcgaggctca    7740
gcaaaactga gatggttcgt tgagagaaac atggtcacac cagaagggaa agtagtggac    7800
ctcggttgtg gcagaggagg ctggtcatac tattgtggag gactaaagaa tgtaagagaa    7860
gtcaaaggcc taacaaaagg aggaccagga cacgaagaac ccatccccat gtcaacatat    7920
gggtggaatc tagtgcgtct tcaaagtgga gttgacgttt tcttcatccc gccagaaaag    7980
tgtgacacat tattgtgtga catagggag tcatcaccaa atccacagt ggaagcagga    8040 cgaacactca gagtccttaa cttagtagaa aattggttga caacaacac tcaattttgc    8100 ataaaggttc tcaacccata tatgcccctca gtcatagaaa aaatggaagc actacaaagg    8160
aaatatggag gagccttagt gaggaatcca ctctcacgaa actccacaca tgagatgtac    8220
tgggtatcca atgcttccgg gaacatagtg tcatcagtga acatgattc aaggatgttg    8280 atcaacagat ttacaatgag atacaagaaa gccacttacg agccggatgt tgacctcgga    8340
agcggaaccc gtaacatcgg gattgaaagt gagataccaa acctagatat aattgggaaa    8400
agaatagaaa aaataaagca agagcatgaa acatcatggc actatgacca agaccaccca    8460
```

```
tacaaaacgt gggcatacca tggtagctat gaaacaaaac agactggatc agcatcatcc    8520
atggtcaacg gagtggtcag gctgctgaca aaaccttggg acgtcgtccc catggtgaca    8580
cagatggcaa tgacagacac gactccattt ggacaacagc gcgtttttaa agagaaagtg    8640
gacacgagaa cccaagaacc gaaagaaggc acgaagaaac taatgaaaat aacagcagag    8700
tggctttgga agaattagg gaagaaaaag acacccagga tgtgcaccag agaagaattc     8760
acaagaaagg tgagaagcaa tgcagccttg ggggccatat tcactgatga gaacaagtgg    8820
aagtcggcac gtgaggctgt tgaagatagt aggttttggg agctggttga caaggaaagg    8880
aatctccatc ttgaaggaaa gtgtgaaaca tgtgtgtaca acatgatggg aaaaagagag    8940
aagaagctag gggaattcgg caaggcaaaa ggcagcagag ccatatggta catgtggctt    9000
ggagcacgct tcttagagtt tgaagcccta ggattcttaa atgaagatca ctggttctcc    9060
agagagaact ccctgagtgg agtggaagga aagggctgc acaagctagg ttacattcta     9120
agagacgtga gcaagaaaga gggaggagca atgtatgccg atgacaccgc aggatgggat    9180
acaagaatca cactagaaga cctaaaaaat gaagaaatgg taacaaacca catggaagga    9240
gaacacaaga aactagccga ggccattttc aaactaacgt accaaaacaa ggtggtgcgt    9300
gtgcaaagac caacaccaag aggcacagta atggacatca tatcgagaag agaccaaaga    9360
ggtagtggac aagttggcac ctatggactc aatactttca ccaatatgga agcccaacta    9420
atcagacaga tggagggaga aggagtcttt aaaagcattc agcacctaac aatcacagaa    9480
gaaatcgctg tgcaaaactg gttagcaaga gtggggcgcg aaaggttatc aagaatggcc    9540
atcagtggag atgattgtgt tgtgaaacct ttagatgaca ggttcgcaag cgctttaaca    9600
gctctaaatg acatgggaaa gattaggaaa gacatacaac aatgggaacc ttcaagagga    9660
tggaatgatt ggacacaagt gcccttctgt tcacaccatt tccatgagtt aatcatgaaa    9720
gacggtcgcg tactcgttgt tccatgtaga accaagatg aactgattgg cagagcccga    9780
atctcccaag gagcagggtg gtcttttgcg gagacggcct gtttgggaa gtcttacgcc     9840 caaatgtgga gcttgatgta cttccacaga cgcgacctca ggctggcggc aaatgctatt    9900
tgctcggcag taccatcaca ttgggttcca acaagtcgaa caacctggtc catacatgct    9960
aaacatgaat ggatgacaac ggaagacatg ctgacagtct ggaacagggt gtggattcaa    10020
gaaaacccat ggatgaaga caaaactcca gtggaatcat gggaggaaat cccatacttg    10080
gggaaaagag aagaccaatg gtgcggctca ttgattgggt taacaagcag gccacctgg    10140 gcaaagaaca tccaagcagc aataaatcaa gttagatccc ttataggcaa tgaagaatac    10200
acagattaca tgccatccat gaaaagattc agaagagaag aggaagaagc aggagttctg    10260
tggtagaaag caaaactaac atgaaacaag gctagaagtc aggtcggatt aagccatagt    10320
acggaaaaaa ctatgctacc tgtgagcccc gtccaaggac gttaaaagaa gtcaggccat    10380
cataaatgcc atagcttgag taaactatgc agcctgtagc tccacctgag aaggtgtaaa    10440
aaatccggga ggccacaaac catggaagct gtacgcatgg cgtagtggac tagcggttag    10500
aggagacccc tcccttacaa atcgcagcaa caatgggggc ccaaggcgag atgaagctgt    10560
agtctcgctg gaaggactag aggttagagg agaccccccc gaaacaaaaa acagcatatt    10620
gacgctggga agaccagag atcctgctgt ctcctcagca tcattccagg cacagaacgc     10680
cagaaaatgg aatggtgctg ttgaatcaac aggttct                             10717
```

<210> SEQ ID NO 19

-continued

```
<211> LENGTH: 3389
<212> TYPE: PRT
<213> ORGANISM: Artificial Sequence
<220> FEATURE:
<223> OTHER INFORMATION: Derived from Dengue virus serotype 2/Dengue
      virus serotype 3, MVS

<400> SEQUENCE: 19
```

Met Asn Asn Gln Arg Lys Lys Ala Lys Asn Thr Pro Phe Asn Met Leu
1               5                   10                  15

Lys Arg Glu Arg Asn Arg Val Ser Thr Val Gln Gln Leu Thr Lys Arg
            20                  25                  30

Phe Ser Leu Gly Met Leu Gln Gly Arg Gly Pro Leu Lys Leu Phe Met
        35                  40                  45

Ala Leu Val Ala Phe Leu Arg Phe Leu Thr Ile Pro Pro Thr Ala Gly
    50                  55                  60

Ile Leu Lys Arg Trp Gly Thr Ile Lys Lys Ser Lys Ala Ile Asn Val
65                  70                  75                  80

Leu Arg Gly Phe Arg Lys Glu Ile Gly Arg Met Leu Asn Ile Leu Asn
                85                  90                  95

Arg Arg Arg Arg Ser Ala Gly Met Ile Ile Met Leu Ile Pro Thr Val
            100                 105                 110

Met Ala Phe His Leu Thr Thr Arg Asp Gly Glu Pro Arg Met Ile Val
        115                 120                 125

Gly Lys Asn Glu Arg Gly Lys Ser Leu Leu Phe Lys Thr Ala Ser Gly
    130                 135                 140

Ile Asn Met Cys Thr Leu Ile Ala Met Asp Leu Gly Glu Met Cys Asp
145                 150                 155                 160

Asp Thr Val Thr Tyr Lys Cys Pro His Ile Thr Glu Val Glu Pro Glu
                165                 170                 175

Asp Ile Asp Cys Trp Cys Asn Leu Thr Ser Thr Trp Val Thr Tyr Gly
            180                 185                 190

Thr Cys Asn Gln Ala Gly Glu His Arg Arg Asp Lys Arg Ser Val Ala
        195                 200                 205

Leu Ala Pro His Val Gly Met Gly Leu Asp Thr Arg Thr Gln Thr Trp
    210                 215                 220

Met Ser Ala Glu Gly Ala Trp Arg Gln Val Glu Lys Val Glu Thr Trp
225                 230                 235                 240

Ala Leu Arg His Pro Gly Phe Thr Ile Leu Ala Leu Phe Leu Ala His
                245                 250                 255

Tyr Ile Gly Thr Ser Leu Thr Gln Lys Val Val Ile Phe Ile Leu Leu
            260                 265                 270

Met Leu Val Thr Pro Ser Met Thr Met Arg Cys Val Gly Val Gly Asn
        275                 280                 285

Arg Asp Phe Val Glu Gly Leu Ser Gly Ala Thr Trp Val Asp Val Val
    290                 295                 300

Leu Glu His Gly Gly Cys Val Thr Met Ala Lys Asn Lys Pro Thr
305                 310                 315                 320

Leu Asp Ile Glu Leu Gln Lys Thr Glu Ala Thr Gln Leu Ala Thr Leu
                325                 330                 335

Arg Lys Leu Cys Ile Glu Gly Lys Ile Thr Asn Ile Thr Thr Asp Ser
            340                 345                 350

Arg Cys Pro Thr Gln Gly Glu Ala Ile Leu Pro Glu Glu Gln Asp Gln
        355                 360                 365

Asn Tyr Val Cys Lys His Thr Tyr Val Asp Arg Gly Trp Gly Asn Gly

```
                370             375             380
Cys Gly Leu Phe Gly Lys Gly Ser Leu Val Thr Cys Ala Lys Phe Gln
385             390             395             400

Cys Leu Glu Ser Ile Glu Gly Lys Val Val Gln His Glu Asn Leu Lys
            405             410             415

Tyr Thr Val Ile Ile Thr Val His Thr Gly Asp Gln His Gln Val Gly
            420             425             430

Asn Glu Thr Gln Gly Val Thr Ala Glu Ile Thr Pro Gln Ala Ser Thr
        435             440             445

Ala Glu Ala Ile Leu Pro Glu Tyr Gly Thr Leu Gly Leu Glu Cys Ser
450             455             460

Pro Arg Thr Gly Leu Asp Phe Asn Glu Met Ile Ser Leu Thr Met Lys
465             470             475             480

Asn Lys Ala Trp Met Val His Arg Gln Trp Phe Phe Asp Leu Pro Leu
            485             490             495

Pro Trp Thr Ser Gly Ala Ser Ala Glu Thr Pro Thr Trp Asn Arg Lys
            500             505             510

Glu Leu Leu Val Thr Phe Lys Asn Ala His Ala Lys Lys Gln Glu Val
            515             520             525

Val Val Leu Gly Ser Gln Glu Gly Ala Met His Thr Ala Leu Thr Gly
        530             535             540

Ala Thr Glu Ile Gln Thr Ser Gly Gly Thr Ser Ile Phe Ala Gly His
545             550             555             560

Leu Lys Cys Arg Leu Lys Met Asp Lys Leu Glu Leu Lys Gly Met Ser
            565             570             575

Tyr Ala Met Cys Leu Ser Ser Phe Val Leu Lys Lys Glu Val Ser Glu
            580             585             590

Thr Gln His Gly Thr Ile Leu Ile Lys Val Glu Tyr Lys Gly Glu Asp
        595             600             605

Ala Pro Cys Lys Ile Pro Phe Ser Thr Glu Asp Gly Gln Gly Lys Ala
610             615             620

Leu Asn Gly Arg Leu Ile Thr Ala Asn Pro Val Val Thr Lys Lys Glu
625             630             635             640

Glu Pro Val Asn Ile Glu Ala Glu Pro Pro Phe Gly Glu Ser Asn Ile
            645             650             655

Val Ile Gly Ile Gly Asp Lys Ala Leu Lys Ile Asn Trp Tyr Lys Lys
            660             665             670

Gly Ser Ser Ile Gly Lys Met Phe Glu Ala Thr Ala Arg Gly Ala Arg
        675             680             685

Arg Met Ala Ile Leu Gly Asp Thr Ala Trp Asp Phe Gly Ser Val Gly
690             695             700

Gly Val Leu Asn Ser Leu Gly Lys Met Val His Gln Ile Phe Gly Ser
705             710             715             720

Ala Tyr Thr Ala Leu Phe Gly Gly Val Ser Trp Met Met Lys Ile Gly
            725             730             735

Ile Gly Val Leu Leu Thr Trp Ile Gly Leu Asn Ser Lys Asn Thr Ser
            740             745             750

Met Ser Phe Ser Cys Ile Ala Ala Gly Ile Val Thr Leu Tyr Leu Gly
        755             760             765

Val Met Val Gln Ala Asp Ser Gly Cys Val Val Ser Trp Lys Asn Lys
        770             775             780

Glu Leu Lys Cys Gly Ser Gly Ile Phe Ile Thr Asp Asn Val His Thr
785             790             795             800
```

-continued

Trp Thr Glu Gln Tyr Lys Phe Gln Pro Glu Ser Pro Ser Lys Leu Ala
            805                 810                 815

Ser Ala Ile Gln Lys Ala His Glu Glu Asp Ile Cys Gly Ile Arg Ser
            820                 825                 830

Val Thr Arg Leu Glu Asn Leu Met Trp Lys Gln Ile Thr Pro Glu Leu
            835                 840                 845

Asn His Ile Leu Ser Glu Asn Glu Val Lys Leu Thr Ile Met Thr Gly
            850                 855                 860

Asp Ile Lys Gly Ile Met Gln Ala Gly Lys Arg Ser Leu Arg Pro Gln
865                 870                 875                 880

Pro Thr Glu Leu Lys Tyr Ser Trp Lys Thr Trp Gly Lys Ala Lys Met
            885                 890                 895

Leu Ser Thr Glu Ser His Asn Gln Thr Phe Leu Ile Asp Gly Pro Glu
            900                 905                 910

Thr Ala Glu Cys Pro Asn Thr Asn Arg Ala Trp Asn Ser Leu Glu Val
            915                 920                 925

Glu Asp Tyr Gly Phe Gly Val Phe Thr Thr Asn Ile Trp Leu Lys Leu
            930                 935                 940

Lys Glu Lys Gln Asp Val Phe Cys Asp Ser Lys Leu Met Ser Ala Ala
945                 950                 955                 960

Ile Lys Asp Asn Arg Ala Val His Ala Asp Met Gly Tyr Trp Ile Glu
            965                 970                 975

Ser Ala Leu Asn Asp Thr Trp Lys Ile Glu Lys Ala Ser Phe Ile Glu
            980                 985                 990

Val Lys Asn Cys His Trp Pro Lys Ser His Thr Leu Trp Ser Asn Gly
            995                 1000                1005

Val Leu Glu Ser Glu Met Ile Ile Pro Lys Asn Leu Ala Gly Pro
    1010                1015                1020

Val Ser Gln His Asn Tyr Arg Pro Gly Tyr His Thr Gln Ile Thr
    1025                1030                1035

Gly Pro Trp His Leu Gly Lys Leu Glu Met Asp Phe Asp Phe Cys
    1040                1045                1050

Asp Gly Thr Thr Val Val Thr Glu Asp Cys Gly Asn Arg Gly
    1055                1060                1065

Pro Ser Leu Arg Thr Thr Ala Ser Gly Lys Leu Ile Thr Glu
    1070                1075                1080

Trp Cys Cys Arg Ser Cys Thr Leu Pro Pro Leu Arg Tyr Arg Gly
    1085                1090                1095

Glu Asp Gly Cys Trp Tyr Gly Met Glu Ile Arg Pro Leu Lys Glu
    1100                1105                1110

Lys Glu Glu Asn Leu Val Asn Ser Leu Val Thr Ala Gly His Gly
    1115                1120                1125

Gln Val Asp Asn Phe Ser Leu Gly Val Leu Gly Met Ala Leu Phe
    1130                1135                1140

Leu Glu Glu Met Leu Arg Thr Arg Val Gly Thr Lys His Ala Ile
    1145                1150                1155

Leu Leu Val Ala Val Ser Phe Val Thr Leu Ile Thr Gly Asn Met
    1160                1165                1170

Ser Phe Arg Asp Leu Gly Arg Val Met Val Met Val Gly Ala Thr
    1175                1180                1185

Met Thr Asp Asp Ile Gly Met Gly Val Thr Tyr Leu Ala Leu Leu
    1190                1195                1200

```
Ala Ala Phe Lys Val Arg Pro Thr Phe Ala Gly Leu Leu Leu
1205                1210                1215

Arg Lys Leu Thr Ser Lys Glu Leu Met Met Thr Thr Ile Gly Ile
1220                1225                1230

Val Leu Leu Ser Gln Ser Thr Ile Pro Glu Thr Ile Leu Glu Leu
1235                1240                1245

Thr Asp Ala Leu Ala Leu Gly Met Met Val Leu Lys Met Val Arg
1250                1255                1260

Asn Met Glu Lys Tyr Gln Leu Ala Val Thr Ile Met Ala Ile Leu
1265                1270                1275

Cys Val Pro Asn Ala Val Ile Leu Gln Asn Ala Trp Lys Val Ser
1280                1285                1290

Cys Thr Ile Leu Ala Val Val Ser Val Ser Pro Leu Phe Leu Thr
1295                1300                1305

Ser Ser Gln Gln Lys Thr Asp Trp Ile Pro Leu Ala Leu Thr Ile
1310                1315                1320

Lys Gly Leu Asn Pro Thr Ala Ile Phe Leu Thr Thr Leu Ser Arg
1325                1330                1335

Thr Ser Lys Lys Arg Ser Trp Pro Leu Asn Glu Ala Ile Met Ala
1340                1345                1350

Val Gly Met Val Ser Ile Leu Ala Ser Ser Leu Leu Lys Asn Asp
1355                1360                1365

Ile Pro Met Thr Gly Pro Leu Val Ala Gly Gly Leu Leu Thr Val
1370                1375                1380

Cys Tyr Val Leu Thr Gly Arg Ser Ala Asp Leu Glu Leu Glu Arg
1385                1390                1395

Ala Ala Asp Val Lys Trp Glu Asp Gln Ala Glu Ile Ser Gly Ser
1400                1405                1410

Ser Pro Ile Leu Ser Ile Thr Ile Ser Glu Asp Gly Ser Met Ser
1415                1420                1425

Ile Lys Asn Glu Glu Glu Gln Thr Leu Thr Ile Leu Ile Arg
1430                1435                1440

Thr Gly Leu Leu Val Ile Ser Gly Leu Phe Pro Val Ser Ile Pro
1445                1450                1455

Ile Thr Ala Ala Ala Trp Tyr Leu Trp Glu Val Lys Lys Gln Arg
1460                1465                1470

Ala Gly Val Leu Trp Asp Val Pro Ser Pro Pro Met Gly Lys
1475                1480                1485

Ala Glu Leu Glu Asp Gly Ala Tyr Arg Ile Lys Gln Lys Gly Ile
1490                1495                1500

Leu Gly Tyr Ser Gln Ile Gly Ala Gly Val Tyr Lys Glu Gly Thr
1505                1510                1515

Phe His Thr Met Trp His Val Thr Arg Gly Ala Val Leu Met His
1520                1525                1530

Lys Gly Lys Arg Ile Glu Pro Ser Trp Ala Asp Val Lys Lys Asp
1535                1540                1545

Leu Ile Ser Tyr Gly Gly Gly Trp Lys Leu Glu Gly Glu Trp Lys
1550                1555                1560

Glu Gly Glu Glu Val Gln Val Leu Ala Leu Glu Pro Gly Lys Asn
1565                1570                1575

Pro Arg Ala Val Gln Thr Lys Pro Gly Leu Phe Lys Thr Asn Ala
1580                1585                1590

Gly Thr Ile Gly Ala Val Ser Leu Asp Phe Ser Pro Gly Thr Ser
```

```
                  1595                1600                1605
Gly Ser Pro Ile Ile Asp Lys Lys Gly Lys Val Val Gly Leu Tyr
    1610                1615                1620

Gly Asn Gly Val Val Thr Arg Ser Gly Ala Tyr Val Ser Ala Ile
    1625                1630                1635

Ala Gln Thr Glu Lys Ser Ile Glu Asp Asn Pro Glu Ile Glu Asp
    1640                1645                1650

Asp Ile Phe Arg Lys Arg Leu Thr Ile Met Asp Leu His Pro
    1655                1660                1665

Gly Ala Gly Lys Thr Lys Arg Tyr Leu Pro Ala Ile Val Arg Glu
    1670                1675                1680

Ala Ile Lys Arg Gly Leu Arg Thr Leu Ile Leu Ala Pro Thr Arg
    1685                1690                1695

Val Val Ala Ala Glu Met Glu Glu Ala Leu Arg Gly Leu Pro Ile
    1700                1705                1710

Arg Tyr Gln Thr Pro Ala Ile Arg Ala Val His Thr Gly Arg Glu
    1715                1720                1725

Ile Val Asp Leu Met Cys His Ala Thr Phe Thr Met Arg Leu Leu
    1730                1735                1740

Ser Pro Val Arg Val Pro Asn Tyr Asn Leu Ile Ile Met Asp Glu
    1745                1750                1755

Ala His Phe Thr Asp Pro Ala Ser Ile Ala Ala Arg Gly Tyr Ile
    1760                1765                1770

Ser Thr Arg Val Glu Met Gly Glu Ala Ala Gly Ile Phe Met Thr
    1775                1780                1785

Ala Thr Pro Pro Gly Ser Arg Asp Pro Phe Pro Gln Ser Asn Ala
    1790                1795                1800

Pro Ile Ile Asp Glu Glu Arg Glu Ile Pro Glu Arg Ser Trp Asn
    1805                1810                1815

Ser Gly His Glu Trp Val Thr Asp Phe Lys Gly Lys Thr Val Trp
    1820                1825                1830

Phe Val Pro Ser Ile Lys Ala Gly Asn Asp Ile Ala Ala Cys Leu
    1835                1840                1845

Arg Lys Asn Gly Lys Lys Val Ile Gln Leu Ser Arg Lys Thr Phe
    1850                1855                1860

Asp Ser Glu Tyr Val Lys Thr Arg Thr Asn Asp Trp Asp Phe Val
    1865                1870                1875

Val Thr Thr Asp Ile Ser Glu Met Gly Ala Asn Phe Lys Ala Glu
    1880                1885                1890

Arg Val Ile Asp Pro Arg Arg Cys Met Lys Pro Val Ile Leu Thr
    1895                1900                1905

Asp Gly Glu Glu Arg Val Ile Leu Ala Gly Pro Met Pro Val Thr
    1910                1915                1920

His Ser Ser Ala Ala Gln Arg Arg Gly Arg Ile Gly Arg Asn Pro
    1925                1930                1935

Lys Asn Glu Asn Asp Gln Tyr Ile Tyr Met Gly Glu Pro Leu Glu
    1940                1945                1950

Asn Asp Glu Asp Cys Ala His Trp Lys Glu Ala Lys Met Leu Leu
    1955                1960                1965

Asp Asn Ile Asn Thr Pro Glu Gly Ile Ile Pro Ser Met Phe Glu
    1970                1975                1980

Pro Glu Arg Glu Lys Val Asp Ala Ile Asp Gly Glu Tyr Arg Leu
    1985                1990                1995
```

-continued

Arg Gly Glu Ala Arg Lys Thr Phe Val Asp Leu Met Arg Arg Gly
2000                2005                2010

Asp Leu Pro Val Trp Leu Ala Tyr Arg Val Ala Ala Glu Gly Ile
2015                2020                2025

Asn Tyr Ala Asp Arg Arg Trp Cys Phe Asp Gly Val Lys Asn Asn
2030                2035                2040

Gln Ile Leu Glu Glu Asn Val Glu Val Glu Ile Trp Thr Lys Glu
2045                2050                2055

Gly Glu Arg Lys Lys Leu Lys Pro Arg Trp Leu Asp Ala Arg Ile
2060                2065                2070

Tyr Ser Asp Pro Leu Ala Leu Lys Glu Phe Lys Glu Phe Ala Ala
2075                2080                2085

Gly Arg Lys Ser Leu Thr Leu Asn Leu Ile Thr Glu Met Gly Arg
2090                2095                2100

Leu Pro Thr Phe Met Thr Gln Lys Ala Arg Asp Ala Leu Asp Asn
2105                2110                2115

Leu Ala Val Leu His Thr Ala Glu Ala Gly Gly Arg Ala Tyr Asn
2120                2125                2130

His Ala Leu Ser Glu Leu Pro Glu Thr Leu Glu Thr Leu Leu Leu
2135                2140                2145

Leu Thr Leu Leu Ala Thr Val Thr Gly Gly Ile Phe Leu Phe Leu
2150                2155                2160

Met Ser Ala Arg Gly Ile Gly Lys Met Thr Leu Gly Met Cys Cys
2165                2170                2175

Ile Ile Thr Ala Ser Ile Leu Leu Trp Tyr Ala Gln Ile Gln Pro
2180                2185                2190

His Trp Ile Ala Ala Ser Ile Ile Leu Glu Phe Phe Leu Ile Val
2195                2200                2205

Leu Leu Ile Pro Glu Pro Glu Lys Gln Arg Thr Pro Gln Asp Asn
2210                2215                2220

Gln Leu Thr Tyr Val Val Ile Ala Ile Leu Thr Val Val Ala Ala
2225                2230                2235

Thr Met Ala Asn Glu Met Gly Phe Leu Glu Lys Thr Lys Lys Asp
2240                2245                2250

Leu Gly Leu Gly Ser Ile Ala Thr Gln Gln Pro Glu Ser Asn Ile
2255                2260                2265

Leu Asp Ile Asp Leu Arg Pro Ala Ser Ala Trp Thr Leu Tyr Ala
2270                2275                2280

Val Ala Thr Thr Phe Val Thr Pro Met Leu Arg His Ser Ile Glu
2285                2290                2295

Asn Ser Ser Val Asn Val Ser Leu Thr Ala Ile Ala Asn Gln Ala
2300                2305                2310

Thr Val Leu Met Gly Leu Gly Lys Gly Trp Pro Leu Ser Lys Met
2315                2320                2325

Asp Ile Gly Val Pro Leu Leu Ala Ile Gly Cys Tyr Ser Gln Val
2330                2335                2340

Asn Pro Ile Thr Leu Thr Ala Ala Leu Phe Leu Leu Val Ala His
2345                2350                2355

Tyr Ala Ile Ile Gly Pro Gly Leu Gln Ala Lys Ala Thr Arg Glu
2360                2365                2370

Ala Gln Lys Arg Ala Ala Ala Gly Ile Met Lys Asn Pro Thr Val
2375                2380                2385

```
Asp Gly Ile Thr Val Ile Asp Leu Asp Pro Ile Pro Tyr Asp Pro
    2390            2395            2400

Lys Phe Glu Lys Gln Leu Gly Gln Val Met Leu Leu Val Leu Cys
    2405            2410            2415

Val Thr Gln Val Leu Met Met Arg Thr Thr Trp Ala Leu Cys Glu
    2420            2425            2430

Ala Leu Thr Leu Ala Thr Gly Pro Ile Ser Thr Leu Trp Glu Gly
    2435            2440            2445

Asn Pro Gly Arg Phe Trp Asn Thr Thr Ile Ala Val Ser Met Ala
    2450            2455            2460

Asn Ile Phe Arg Gly Ser Tyr Leu Ala Gly Ala Gly Leu Leu Phe
    2465            2470            2475

Ser Ile Met Lys Asn Thr Thr Asn Thr Arg Arg Gly Thr Gly Asn
    2480            2485            2490

Ile Gly Glu Thr Leu Gly Glu Lys Trp Lys Ser Arg Leu Asn Ala
    2495            2500            2505

Leu Gly Lys Ser Glu Phe Gln Ile Tyr Lys Lys Ser Gly Ile Gln
    2510            2515            2520

Glu Val Asp Arg Thr Leu Ala Lys Glu Gly Ile Lys Arg Gly Glu
    2525            2530            2535

Thr Asp His His Ala Val Ser Arg Gly Ser Ala Lys Leu Arg Trp
    2540            2545            2550

Phe Val Glu Arg Asn Met Val Thr Pro Glu Gly Lys Val Val Asp
    2555            2560            2565

Leu Gly Cys Gly Arg Gly Gly Trp Ser Tyr Tyr Cys Gly Gly Leu
    2570            2575            2580

Lys Asn Val Arg Glu Val Lys Gly Leu Thr Lys Gly Gly Pro Gly
    2585            2590            2595

His Glu Glu Pro Ile Pro Met Ser Thr Tyr Gly Trp Asn Leu Val
    2600            2605            2610

Arg Leu Gln Ser Gly Val Asp Val Phe Phe Ile Pro Pro Glu Lys
    2615            2620            2625

Cys Asp Thr Leu Leu Cys Asp Ile Gly Glu Ser Ser Pro Asn Pro
    2630            2635            2640

Thr Val Glu Ala Gly Arg Thr Leu Arg Val Leu Asn Leu Val Glu
    2645            2650            2655

Asn Trp Leu Asn Asn Asn Thr Gln Phe Cys Ile Lys Val Leu Asn
    2660            2665            2670

Pro Tyr Met Pro Ser Val Ile Glu Lys Met Glu Ala Leu Gln Arg
    2675            2680            2685

Lys Tyr Gly Gly Ala Leu Val Arg Asn Pro Leu Ser Arg Asn Ser
    2690            2695            2700

Thr His Glu Met Tyr Trp Val Ser Asn Ala Ser Gly Asn Ile Val
    2705            2710            2715

Ser Ser Val Asn Met Ile Ser Arg Met Leu Ile Asn Arg Phe Thr
    2720            2725            2730

Met Arg Tyr Lys Lys Ala Thr Tyr Glu Pro Asp Val Asp Leu Gly
    2735            2740            2745

Ser Gly Thr Arg Asn Ile Gly Ile Glu Ser Glu Ile Pro Asn Leu
    2750            2755            2760

Asp Ile Ile Gly Lys Arg Ile Glu Lys Ile Lys Gln Glu His Glu
    2765            2770            2775

Thr Ser Trp His Tyr Asp Gln Asp His Pro Tyr Lys Thr Trp Ala
```

```
             2780                2785                2790
Tyr His Gly Ser Tyr Glu Thr Lys Gln Thr Gly Ser Ala Ser Ser
     2795                2800                2805

Met Val Asn Gly Val Val Arg Leu Leu Thr Lys Pro Trp Asp Val
     2810                2815                2820

Val Pro Met Val Thr Gln Met Ala Met Thr Asp Thr Thr Pro Phe
     2825                2830                2835

Gly Gln Gln Arg Val Phe Lys Glu Lys Val Asp Thr Arg Thr Gln
     2840                2845                2850

Glu Pro Lys Glu Gly Thr Lys Lys Leu Met Lys Ile Thr Ala Glu
     2855                2860                2865

Trp Leu Trp Lys Glu Leu Gly Lys Lys Thr Pro Arg Met Cys
     2870                2875                2880

Thr Arg Glu Glu Phe Thr Arg Lys Val Arg Ser Asn Ala Ala Leu
     2885                2890                2895

Gly Ala Ile Phe Thr Asp Glu Asn Lys Trp Lys Ser Ala Arg Glu
     2900                2905                2910

Ala Val Glu Asp Ser Arg Phe Trp Glu Leu Val Asp Lys Glu Arg
     2915                2920                2925

Asn Leu His Leu Glu Gly Lys Cys Glu Thr Cys Val Tyr Asn Met
     2930                2935                2940

Met Gly Lys Arg Glu Lys Lys Leu Gly Glu Phe Gly Lys Ala Lys
     2945                2950                2955

Gly Ser Arg Ala Ile Trp Tyr Met Trp Leu Gly Ala Arg Phe Leu
     2960                2965                2970

Glu Phe Glu Ala Leu Gly Phe Leu Asn Glu Asp His Trp Phe Ser
     2975                2980                2985

Arg Glu Asn Ser Leu Ser Gly Val Glu Gly Glu Gly Leu His Lys
     2990                2995                3000

Leu Gly Tyr Ile Leu Arg Asp Val Ser Lys Lys Glu Gly Gly Ala
     3005                3010                3015

Met Tyr Ala Asp Asp Thr Ala Gly Trp Asp Thr Arg Ile Thr Leu
     3020                3025                3030

Glu Asp Leu Lys Asn Glu Glu Met Val Thr Asn His Met Glu Gly
     3035                3040                3045

Glu His Lys Lys Leu Ala Glu Ala Ile Phe Lys Leu Thr Tyr Gln
     3050                3055                3060

Asn Lys Val Val Arg Val Gln Arg Pro Thr Pro Arg Gly Thr Val
     3065                3070                3075

Met Asp Ile Ile Ser Arg Arg Asp Gln Arg Gly Ser Gly Gln Val
     3080                3085                3090

Gly Thr Tyr Gly Leu Asn Thr Phe Thr Asn Met Glu Ala Gln Leu
     3095                3100                3105

Ile Arg Gln Met Glu Gly Glu Gly Val Phe Lys Ser Ile Gln His
     3110                3115                3120

Leu Thr Ile Thr Glu Glu Ile Ala Val Gln Asn Trp Leu Ala Arg
     3125                3130                3135

Val Gly Arg Glu Arg Leu Ser Arg Met Ala Ile Ser Gly Asp Asp
     3140                3145                3150

Cys Val Val Lys Pro Leu Asp Asp Arg Phe Ala Ser Ala Leu Thr
     3155                3160                3165

Ala Leu Asn Asp Met Gly Lys Ile Arg Lys Asp Ile Gln Gln Trp
     3170                3175                3180
```

| | | | | | | | | | | |
|---|---|---|---|---|---|---|---|---|---|---|
| Glu | Pro | Ser | Arg | Gly | Trp | Asn | Asp | Trp | Thr | Gln | Val | Pro | Phe | Cys |
| | 3185 | | | | 3190 | | | | 3195 | |

Glu Pro Ser Arg Gly Trp Asn Asp Trp Thr Gln Val Pro Phe Cys
  3185            3190            3195

Ser His His Phe His Glu Leu Ile Met Lys Asp Gly Arg Val Leu
  3200            3205            3210

Val Val Pro Cys Arg Asn Gln Asp Glu Leu Ile Gly Arg Ala Arg
  3215            3220            3225

Ile Ser Gln Gly Ala Gly Trp Ser Leu Arg Glu Thr Ala Cys Leu
  3230            3235            3240

Gly Lys Ser Tyr Ala Gln Met Trp Ser Leu Met Tyr Phe His Arg
  3245            3250            3255

Arg Asp Leu Arg Leu Ala Ala Asn Ala Ile Cys Ser Ala Val Pro
  3260            3265            3270

Ser His Trp Val Pro Thr Ser Arg Thr Thr Trp Ser Ile His Ala
  3275            3280            3285

Lys His Glu Trp Met Thr Thr Glu Asp Met Leu Thr Val Trp Asn
  3290            3295            3300

Arg Val Trp Ile Gln Glu Asn Pro Trp Met Glu Asp Lys Thr Pro
  3305            3310            3315

Val Glu Ser Trp Glu Glu Ile Pro Tyr Leu Gly Lys Arg Glu Asp
  3320            3325            3330

Gln Trp Cys Gly Ser Leu Ile Gly Leu Thr Ser Arg Ala Thr Trp
  3335            3340            3345

Ala Lys Asn Ile Gln Ala Ala Ile Asn Gln Val Arg Ser Leu Ile
  3350            3355            3360

Gly Asn Glu Glu Tyr Thr Asp Tyr Met Pro Ser Met Lys Arg Phe
  3365            3370            3375

Arg Arg Glu Glu Glu Glu Ala Gly Val Leu Trp
  3380            3385

<210> SEQ ID NO 20
<211> LENGTH: 10723
<212> TYPE: DNA
<213> ORGANISM: Artificial Sequence
<220> FEATURE:
<223> OTHER INFORMATION: Derived from Dengue virus serotype 2/Dengue
      virus serotype 4, MVS

<400> SEQUENCE: 20

```
agttgttagt ctacgtggac cgacaaagac agattctttg agggagctaa gctcaatgta      60
gttctaacag ttttttaatt agagagcaga tctctgatga ataaccaacg aaaaaggcg      120
aaaaacacgc ctttcaatat gctgaaacgc gagagaaacc gcgtgtcgac tgtgcaacag      180
ctgacaaaga gattctcact tggaatgctg cagggacgag gaccttttaaa actgttcatg      240
gccctggtgg cgttccttcg tttcctaaca atcccaccaa cagcagggat attgaagaga      300
tggggaacaa ttaaaaaatc aaaagctatt aatgttttga gagggttcag gaaagagatt      360
ggaaggatgc tgaacatctt gaataggaga cgcagctctg caggcatgat cattatgctg      420
attccaacag tgatggcgtt ccatttaacc acgcgtgatg gcgaacccct catgatagtg      480
gcaaaacatg aaaggggag acctctcttg tttaagacaa cagaggggat caacaaatgc      540
actctcattg ccatggactt gggtgaaatg tgtgaggaca ctgtcacgta taatgcccc      600
ttactggtca ataccgaacc tgaagacatt gattgctggt gcaatctcac gtctacctgg      660
gtcatgtatg gaacatgcac ccagagcgga gaacggagac gagagaagcg ctcagtagct      720
ttaacaccac attcaggaat gggattggaa acaagagctg agacatggat gtcatcggaa      780
```

```
ggggcttgga agcatgctca gagagtagag agctggatac tcagaaaccc aggattcgcg    840
ctcttggcag gatttatggc ttatatgatt gggcaaacag gaatccagcg aactgtcttc    900
tttgtcctaa tgatgctggt cgccccatcc tacggaatgc gatgcgtagg agtaggaaac    960
agagactttg tggaaggagt ctcaggtgga gcatgggtcg atctggtgct agaacatgga   1020
ggatgcgtca caaccatggc ccagggaaaa ccaaccttgg attttgaact gactaagaca   1080
acagccaagg aagtggctct gttaagaacc tattgcattg aagcctcaat atcaaacata   1140
accacggcaa caagatgtcc aacgcaagga gagccttatc taaaagagga acaagaccaa   1200
cagtacattt gccggagaga tgtgtagac agagggtggg gcaatggctg tggcttgttt   1260
ggaaaaggag gagttgtgac atgtgcgaag ttttcatgtt cggggaagat aacaggcaat   1320
ttggtccaaa ttgagaacct tgaatacaca gtggttgtaa cagtccacaa tggagacacc   1380
catgcagtag gaaatgacac gtccaatcat ggagttacag ccacgataac tcccaggtca   1440
ccatcggtgg aagtcaaatt gccggactat ggagaactaa cactcgattg tgaacccagg   1500
tctggaattg actttaatga gatgattctg atgaaaatga aaagaaaac atggcttgtg   1560 cataagcaat ggtttttgga tctacctcta ccatggacag caggagcaga cacatcagag   1620
gttcactgga attacaaaga gagaatggtg acatttaagg ttcctcatgc caagagacag   1680
gatgtgacag tgctgggatc tcaggaagga gccatgcatt ctgccctcgc tggagccaca   1740
gaagtggact ccggtgatgg aaatcacatg tttgcaggac atctcaagtg caaagtccgt   1800
atggagaaat tgagaatcaa gggaatgtca tacacgatgt gttcaggaaa gttctcaatt   1860
gacaaagaga tggcagaaac acagcatggg acaacagtgg tgaaagtcaa gtatgaaggt   1920
gctggagctc cgtgtaaagt ccccatagag ataagagatg tgaacaagga aaaagtggtt   1980
gggcgtatca tctcatccac cccctttggct gagaatacca acagtgtaac caacatagag   2040
ttagaacccc cctttgggga cagctacata gtgataggtg ttggaaacag tgcattaaca   2100
ctccattggt tcaggaaagg gagttccatt ggcaagatgt ttgagtccac atacagaggt   2160
gcaaaacgaa tggccattct aggtgaaaca gcttgggatt ttggttccgt tggtggactg   2220
ttcacatcat gggaaggc tgtgcaccag ttttttggaa gtgtgtatac aaccctgttt   2280
ggaggagtct catggatgat tagaatccta attgggttcc tagtgttgtg gattggcacg   2340
aactcaagga acacttcaat ggctatgacg tgcatagctg ccggcattgt gacactgtat   2400
ttgggagtca tggtgcaggc cgatagtggt tgcgttgtga gctggaaaaa caagaactg   2460 aaaatgtggca gtgggatttt catcacagac aacgtgcaca catggacaga acaatacaag   2520
ttccaaccag aatccccttc aaaactagct tcagctatcc agaaagccca tgaagaggac   2580
atttgtggaa tccgctcagt aacaagactg gagaatctga tgtggaaca aataacacca   2640 gaattgaatc acattctatc agaaaatgag gtgaagttaa ctattatgac aggagacatc   2700
aaaggaatca tgcaggcagg aaaacgatct ctgcggcctc agcccactga gctgaagtat   2760
tcatggaaaa catggggcaa agcaaaaatg ctctctacag agtctcataa ccagacccttt   2820 ctcattgatg gccccgaaac agcagaatgc cccaacacaa atagagcttg aattcgttg   2880 gaagttgaag actatggctt tggagtattc accaccaata tatggctaaa attgaaagaa   2940
aaacaggatg tattctgcga ctcaaaactc atgtcagcgg ccataaaaga caacagagcc   3000
gtccatgccg atatgggtta ttggatagaa agtgcactca atgacacatg gaagatagag   3060
aaagcctctt tcattgaagt taaaaactgc cactggccaa aatcacacac cctctggagc   3120
```

|  |  |
|---|---|
| aatggagtgc tagaaagtga gatgataatt ccaaagaatc tcgctggacc agtgtctcaa | 3180 |
| cacaactata gaccaggcta ccatacacaa ataacaggac catggcatct aggtaagctt | 3240 |
| gagatggact ttgatttctg tgatggaaca acagtggtag tgactgagga ctgcggaaat | 3300 |
| agaggaccct ctttgagaac aaccactgcc tctggaaaac tcataacaga atggtgctgc | 3360 |
| cgatcttgca cattaccacc gctaagatac agaggtgagg atgggtgctg gtacgggatg | 3420 |
| gaaatcagac cattgaagga gaaagaagag aatttggtca actccttggt cacagctgga | 3480 |
| catgggcagg tcgacaactt ttcactagga gtcttgggaa tggcattgtt cctggaggaa | 3540 |
| atgcttagga cccgagtagg aacgaaacat gcaatactac tagttgcagt ttcttttgtg | 3600 |
| acattgatca cagggaacat gtcctttaga gacctgggaa gagtgatggt tatggtaggc | 3660 |
| gccactatga cgggtgacat aggtatgggc gtgacttatc ttgccctact agcagccttc | 3720 |
| aaagtcagac caacttttgc agctggacta ctcttgagaa agctgacctc cagggaattg | 3780 |
| atgatgacta ctataggaat tgtactcctc tcccagagca ccataccaga gaccattctt | 3840 |
| gagttgactg atgcgttagc cttaggcatg atggtcctca aaatggtgag aaatatggaa | 3900 |
| aagtatcaat ggcagtgac tatcatggct atcttgtgcg tcccaaacgc agtgatatta | 3960 |
| caaaacgcat ggaaagtgag ttgcacaata ttggcagtgg tgtccgtttc cccactgttc | 4020 |
| ttaacatcct cacagcaaaa aacagattgg ataccattag cattgacgat caaaggtctc | 4080 |
| aatccaacag ctattttct aacaaccctc tcaagaacca gcaagaaaag gagctggcca | 4140 |
| ttaaatgagg ctatcatggc agtcgggatg gtgagcattt tagccagttc tctcctaaaa | 4200 |
| aatgatattc ccatgacagg accattagtg gctggagggc tcctcactgt gtgctacgtg | 4260 |
| ctcactggac gatcggccga tttggaactg gagagagcag ccgatgtcaa atgggaagac | 4320 |
| caggcagaga tatcaggaag cagtccaatc ctgtcaataa caatatcaga agatggtagc | 4380 |
| atgtcgataa aaatgaaga ggaagaacaa acactgacca tactcattag aacaggattg | 4440 |
| ctggtgatct caggactttt tcctgtatca ataccaatca cggcagcagc atggtacctg | 4500 |
| tgggaagtga agaaacaacg ggccggagta ttgtgggatg ttccttcacc cccacccatg | 4560 |
| ggaaaggctg aactgaaga tggagcctat agaattaagc aaaaagggat tcttggatat | 4620 |
| tcccagatcg gagccggagt ttacaaagaa ggaacattcc atacaatgtg gcatgtcaca | 4680 |
| cgtggcgctg ttctaatgca taaggaaag aggattgaac catcatgggc ggacgtcaag | 4740 |
| aaagacctaa tatcatatgg aggaggctgg aagttagaag gagaatggaa ggaaggagaa | 4800 |
| gaagtccagg tattggcact ggagcctgga aaaaatccaa gagccgtcca aacgaaacct | 4860 |
| ggtcttttca aaaccaacgc cggaacaata ggtgctgtat ctctggactt ttctcctgga | 4920 |
| acgtcaggat ctccaattat cgacaaaaaa ggaaaagttg tgggtcttta tggtaatggt | 4980 |
| gttgttacaa ggagtggagc atatgtgagt gctatagccc agactgaaaa aagcattgaa | 5040 |
| gacaacccag atcgaagaa tgacattttc cgaaagagaa gactgaccat catggaccct | 5100 |
| cacccaggag cgggaaagac gaagagatac cttccggcca tagtcagaga agctataaaa | 5160 |
| cggggtttga gaacattaat cttggccccc actagagttg tggcagctga atggaggaa | 5220 |
| gcccttagag gacttccaat aagataccag accccagcca tcagagctgt gcacaccggg | 5280 |
| cgggagattg tggacctaat gtgtcatgcc acatttacca tgaggctgct atcaccagtt | 5340 |
| agagtgccaa actacaacct gattatcatg gacgaagccc atttcacaga tccagcaagt | 5400 |
| atagcagcta gaggatacat ctcaactcga gtggagatgg gtgaggcagc tgggattttt | 5460 |
| atgacagcca ctcccccggg aagcagagac ccatttcctc agagcaatgc accaatcata | 5520 |

```
gatgaagaaa gagaaatccc tgaacgctcg tggaattccg gacatgaatg ggtcacggat      5580
tttaaaggga agactgtttg gttcgttcca agtataaaag caggaaatga tatagcagct      5640
tgcctgagga aaaatggaaa gaaagtgata caactcagta ggaagacctt tgattctgag      5700
tatgtcaaga ctagaaccaa tgattgggac ttcgtggtta caactgacat ttcagaaatg      5760
ggtgccaatt tcaaggctga gagggttata daccccagac gctgcatgaa accagtcata      5820
ctaacagatg tgaagagcg ggtgattctg caggaccta tgccagtgac ccactctagt       5880
gcagcacaaa aagagggag aataggaaga aatccaaaaa atgagaatga ccagtacata       5940
tacatggggg aacctctgga aaatgatgaa gactgtgcac actggaaaga agctaaaatg      6000
ctcctagata acatcaacac gccagaagga atcattccta gcatgttcga accagagcgt      6060
gaaaaggtgg atgccattga tggcgaatac cgcttgagag gagaagcaag gaaaaccttt      6120
gtagacttaa tgaagagagg agacctacca gtctggttgg cctacagagt ggcagctgaa      6180
ggcatcaact acgcagacag aaggtggtgt tttgatggag tcaagaacaa ccaaatccta      6240
gaagaaaacg tggaagttga aatctggaca aaagaagggg aaaggaagaa attgaaaccc      6300
agatggttgg atgctaggat ctattctgac ccactggcgc taaaagaatt taaggaattt      6360
gcagccggaa gaaagtctct gaccctgaac ctaatcacag aaatgggtag gctcccaacc      6420
ttcatgactc agaaggtaag agacgcactg gacaacttag cagtgctgca cacggctgag      6480
gcaggtggaa gggcgtacaa ccatgctctc agtgaactgc cggagaccct ggagacattg      6540
cttttactga cacttctggc tacagtcacg gagggatct tttattctt gatgagcgca       6600 agggggcatag ggaagatgac cctgggaatg tgctgcataa tcacggctag catcctccta      6660
tggtacgcac aaatacagcc acactggata gcagcttcaa taatactgga gttttttctc      6720
atagttttgc ttattccaga acctgaaaaa cagagaacac cccaagacaa ccaactgacc      6780
tacgttgtca tagccatcct cacagtggtg gccgcaacca tggcaaacga gatgggtttc      6840
ctagaaaaaa cgaagaaaga tctcggattg ggaagcattg caacccagca acccgagagc      6900
aacatcctgg acatagatct acgtcctgca tcagcatgga cgctgtatgc cgtggccaca      6960
acatttgtta caccaatgtt gagacatagc attgaaaatt cctcagtgaa tgtgtcccta      7020
acagccatag ccaaccaagc cacagtgtta atgggtctcg ggaaaggatg gccattgtca      7080
aagatggaca tcggagttcc ccttctcgcc attggatgct actcacaagt caaccccata      7140
actctcacag cagctcttt cttattggta gcacattatg ccatcatagg gccaggactc      7200
caagcaaaag caaccagaga agctcagaaa agagcagcgg cgggcatcat gaaaaaccca      7260
actgtcgatg gaataacagt gattgaccta gatccaatac cttatgatcc aaagtttgaa      7320
aagcagttgg gacaagtaat gctcctagtc ctctgcgtga ctcaagtatt gatgatgagg      7380
actacatggg ctctgtgtga ggctttaacc ttagctaccg ggcccatctc cacattgtgg      7440
gaaggaaatc cagggaggtt ttggaacact accattgcgg tgtcaatggc taacattttt      7500
agagggagtt acttggccgg agctggactt ctcttttcta ttatgaagaa cacaaccaac      7560
acaagaaggg gaactggcaa cataggagag acgcttggag agaaatggaa agccgattg       7620 aacgcattgg gaaaagtgaa attccagatc tacaagaaaa gtggaatcca ggaagtggat      7680
agaaccttag caaagaagg cattaaaaga ggagaaacgg accatcacgc tgtgtcgcga      7740
ggctcagcaa aactgagatg gttcgttgag agaaacatgg tcacaccaga agggaaagta      7800 gtggaccctcg gttgtggcag aggaggctgg tcatactatt gtggaggact aaagaatgta      7860
```

```
agagaagtca aaggcctaac aaaaggagga ccaggacacg aagaacccat ccccatgtca   7920
acatatgggt ggaatctagt gcgtcttcaa agtggagttg acgttttctt catcccgcca   7980
gaaaagtgtg acacattatt gtgtgacata ggggagtcat caccaaatcc cacagtggaa   8040
gcaggacgaa cactcagagt ccttaactta gtagaaaatt ggttgaacaa caacactcaa   8100
ttttgcataa aggttctcaa cccatatatg ccctcagtca tagaaaaaat ggaagcacta   8160
caaaggaaat atggaggagc cttagtgagg aatccactct cacgaaactc cacacatgag   8220
atgtactggg tatccaatgc ttccgggaac atagtgtcat cagtgaacat gatttcaagg   8280
atgttgatca acagatttac aatgagatac aagaaagcca cttacgagcc ggatgttgac   8340
ctcggaagcg gaacccgtaa catcgggatt gaaagtgaga taccaaacct agatataatt   8400
gggaaaagaa tagaaaaaat aaagcaagag catgaaacat catggcacta tgaccaagac   8460
cacccataca aaacgtgggc ataccatggt agctatgaaa caaaacagac tggatcagca   8520
tcatccatgg tcaacggagt ggtcaggctg ctgacaaaac cttgggacgt cgtccccatg   8580
gtgacacaga tggcaatgac agacacgact ccatttggac aacagcgcgt ttttaaagag   8640
aaagtggaca cgagaaccca agaaccgaaa gaaggcacga agaaactaat gaaaataaca   8700
gcagagtggc tttggaaaga attagggaag aaaaagacac caggatgtg caccagagaa   8760 gaattcacaa gaaggtgag aagcaatgca gccttggggg ccatattcac tgatgagaac   8820
aagtggaagt cggcacgtga ggctgttgaa gatagtaggt tttgggagct ggttgacaag   8880
gaaaggaatc tccatcttga aggaaagtgt gaaacatgtg tgtacaacat gatgggaaaa   8940
agagagaaga agctagggga attcggcaag gcaaaggca gcagagccat atggtacatg   9000
tggcttggag cacgcttctt agagtttgaa gccctaggat tcttaaatga agatcactgg   9060
ttctccagag agaactccct gagtggagtg aaggagaaag gctgcacaa gctaggttac   9120 attctaagag acgtgagcaa aaagaggga ggagcaatgt atgccgatga caccgcagga   9180
tgggataaca gaatcacact agaagaccta aaaaatgaag aaatggtaac aaaccacatg   9240
gaaggagaac acaagaaact agccgaggcc attttcaaac taacgtacca aaacaaggtg   9300
gtgcgtgtgc aaagaccaac accaagaggc acagtaatgg acatcatatc gagaagagac   9360
caaagaggta gtggacaagt tggcacctat ggactcaata ctttcaccaa tatggaagcc   9420
caactaatca gacagatgga gggagaagga gtcttaaaa gcattcagca cctaacaatc   9480
acagaagaaa tcgctgtgca aaactggtta gcaagagtgg ggcgcgaaag gttatcaaga   9540
atggccatca gtggagatga ttgtgttgtg aaaccttag atgacaggtt cgcaagcgct   9600
ttaacagctc taaatgacat gggaaagatt aggaaagaca tacaacaatg gaaccttca   9660 agaggatgga atgattggac acaagtgccc ttctgttcac accatttcca tgagttaatc   9720
atgaaagacg gtcgcgtact cgttgttccc tgtagaaacc aagatgaact gattggcaga   9780
gcccgaatct cccaaggagc agggtggtct ttgcgggaga cggcctgttt ggggaagtct   9840
tacgcccaaa tgtggagctt gatgtacttc cacagacgcg acctcaggct ggcggcaaat   9900
gctatttgct cggcagtacc atcacattgg gttccaacaa gtcgaacaac ctggtccata   9960
catgctaaac atgaatggat gacaacggaa gacatgctga cagtctggaa cagggtgtgg  10020
attcaagaaa acccatggat ggaagacaaa actccagtgg aatcatggga ggaaatccca  10080
tacttgggga aaagaagaga ccaatggtgc ggctcattga ttgggttaac aagcagggcc  10140
acctgggcaa agaacatcca agcagcaata aatcaagtta gatccctat aggcaatgaa  10200 gaatacacag attacatgcc atccatgaaa agattcagaa gagaagagga agaagcagga  10260
```

-continued

```
gttctgtggt agaaagcaaa actaacatga acaaggcta gaagtcaggt cggattaagc   10320
catagtacgg aaaaaactat gctacctgtg agccccgtcc aaggacgtta aaagaagtca   10380
ggccatcata aatgccatag cttgagtaaa ctatgcagcc tgtagctcca cctgagaagg   10440
tgtaaaaaat ccgggaggcc acaaaccatg gaagctgtac gcatggcgta gtggactagc   10500
ggttagagga gacccctccc ttacaaatcg cagcaacaat gggggcccaa ggcgagatga   10560
agctgtagtc tcgctggaag gactagaggt tagaggagac cccccgaaa caaaaaacag   10620 catattgacg ctgggaaaga ccagagatcc tgctgtctcc tcagcatcat tccaggcaca   10680
gaacgccaga aaatggaatg gtgctgttga atcaacaggt tct                   10723
```

<210> SEQ ID NO 21
<211> LENGTH: 3391
<212> TYPE: PRT
<213> ORGANISM: Artificial Sequence
<220> FEATURE:
<223> OTHER INFORMATION: Derived from Dengue virus serotype 2/Dengue
      virus serotype 4, MVS

<400> SEQUENCE: 21

```
Met Asn Asn Gln Arg Lys Lys Ala Lys Asn Thr Pro Phe Asn Met Leu
1               5                   10                  15

Lys Arg Glu Arg Asn Arg Val Ser Thr Val Gln Gln Leu Thr Lys Arg
            20                  25                  30

Phe Ser Leu Gly Met Leu Gln Gly Arg Gly Pro Leu Lys Leu Phe Met
        35                  40                  45

Ala Leu Val Ala Phe Leu Arg Phe Leu Thr Ile Pro Pro Thr Ala Gly
    50                  55                  60

Ile Leu Lys Arg Trp Gly Thr Ile Lys Lys Ser Lys Ala Ile Asn Val
65                  70                  75                  80

Leu Arg Gly Phe Arg Lys Glu Ile Gly Arg Met Leu Asn Ile Leu Asn
                85                  90                  95

Arg Arg Arg Ser Ser Ala Gly Met Ile Ile Met Leu Ile Pro Thr Val
            100                 105                 110

Met Ala Phe His Leu Thr Thr Arg Asp Gly Glu Pro Leu Met Ile Val
        115                 120                 125

Ala Lys His Glu Arg Gly Arg Pro Leu Leu Phe Lys Thr Thr Glu Gly
    130                 135                 140

Ile Asn Lys Cys Thr Leu Ile Ala Met Asp Leu Gly Glu Met Cys Glu
145                 150                 155                 160

Asp Thr Val Thr Tyr Lys Cys Pro Leu Leu Val Asn Thr Glu Pro Glu
                165                 170                 175

Asp Ile Asp Cys Trp Cys Asn Leu Thr Ser Thr Trp Val Met Tyr Gly
            180                 185                 190

Thr Cys Thr Gln Ser Gly Glu Arg Arg Glu Lys Arg Ser Val Ala
        195                 200                 205

Leu Thr Pro His Ser Gly Met Gly Leu Glu Thr Arg Ala Glu Thr Trp
    210                 215                 220

Met Ser Ser Glu Gly Ala Trp Lys His Ala Gln Arg Val Glu Ser Trp
225                 230                 235                 240

Ile Leu Arg Asn Pro Gly Phe Ala Leu Leu Ala Gly Phe Met Ala Tyr
                245                 250                 255

Met Ile Gly Gln Thr Gly Ile Gln Arg Thr Val Phe Phe Val Leu Met
            260                 265                 270
```

```
Met Leu Val Ala Pro Ser Tyr Gly Met Arg Cys Val Gly Val Gly Asn
                275                 280                 285

Arg Asp Phe Val Glu Gly Val Ser Gly Gly Ala Trp Val Asp Leu Val
290                 295                 300

Leu Glu His Gly Gly Cys Val Thr Thr Met Ala Gln Gly Lys Pro Thr
305                 310                 315                 320

Leu Asp Phe Glu Leu Thr Lys Thr Thr Ala Lys Glu Val Ala Leu Leu
                325                 330                 335

Arg Thr Tyr Cys Ile Glu Ala Ser Ile Ser Asn Ile Thr Thr Ala Thr
                340                 345                 350

Arg Cys Pro Thr Gln Gly Glu Pro Tyr Leu Lys Glu Glu Gln Asp Gln
                355                 360                 365

Gln Tyr Ile Cys Arg Arg Asp Val Val Asp Arg Gly Trp Gly Asn Gly
                370                 375                 380

Cys Gly Leu Phe Gly Lys Gly Val Val Thr Cys Ala Lys Phe Ser
385                 390                 395                 400

Cys Ser Gly Lys Ile Thr Gly Asn Leu Val Gln Ile Glu Asn Leu Glu
                405                 410                 415

Tyr Thr Val Val Val Thr Val His Asn Gly Asp Thr His Ala Val Gly
                420                 425                 430

Asn Asp Thr Ser Asn His Gly Val Thr Ala Thr Ile Thr Pro Arg Ser
                435                 440                 445

Pro Ser Val Glu Val Lys Leu Pro Asp Tyr Gly Glu Leu Thr Leu Asp
                450                 455                 460

Cys Glu Pro Arg Ser Gly Ile Asp Phe Asn Glu Met Ile Leu Met Lys
465                 470                 475                 480

Met Lys Lys Lys Thr Trp Leu Val His Lys Gln Trp Phe Leu Asp Leu
                485                 490                 495

Pro Leu Pro Trp Thr Ala Gly Ala Asp Thr Ser Glu Val His Trp Asn
                500                 505                 510

Tyr Lys Glu Arg Met Val Thr Phe Lys Val Pro His Ala Lys Arg Gln
                515                 520                 525

Asp Val Thr Val Leu Gly Ser Gln Glu Gly Ala Met His Ser Ala Leu
530                 535                 540

Ala Gly Ala Thr Glu Val Asp Ser Gly Asp Gly Asn His Met Phe Ala
545                 550                 555                 560

Gly His Leu Lys Cys Lys Val Arg Met Glu Lys Leu Arg Ile Lys Gly
                565                 570                 575

Met Ser Tyr Thr Met Cys Ser Gly Lys Phe Ser Ile Asp Lys Glu Met
                580                 585                 590

Ala Glu Thr Gln His Gly Thr Thr Val Val Lys Val Lys Tyr Glu Gly
                595                 600                 605

Ala Gly Ala Pro Cys Lys Val Pro Ile Glu Ile Arg Asp Val Asn Lys
                610                 615                 620

Glu Lys Val Val Gly Arg Ile Ile Ser Ser Thr Pro Leu Ala Glu Asn
625                 630                 635                 640

Thr Asn Ser Val Thr Asn Ile Glu Leu Glu Pro Pro Phe Gly Asp Ser
                645                 650                 655

Tyr Ile Val Ile Gly Val Gly Asn Ser Ala Leu Thr Leu His Trp Phe
                660                 665                 670

Arg Lys Gly Ser Ser Ile Gly Lys Met Phe Glu Ser Thr Tyr Arg Gly
                675                 680                 685

Ala Lys Arg Met Ala Ile Leu Gly Glu Thr Ala Trp Asp Phe Gly Ser
```

-continued

```
            690                 695                 700
Val Gly Gly Leu Phe Thr Ser Leu Gly Lys Ala Val His Gln Val Phe
705                     710                 715                 720

Gly Ser Val Tyr Thr Thr Leu Phe Gly Val Ser Trp Met Ile Arg
                    725                 730                 735

Ile Leu Ile Gly Phe Leu Val Leu Trp Ile Gly Thr Asn Ser Arg Asn
                740                 745                 750

Thr Ser Met Ala Met Thr Cys Ile Ala Ala Gly Ile Val Thr Leu Tyr
                    755                 760                 765

Leu Gly Val Met Val Gln Ala Asp Ser Gly Cys Val Val Ser Trp Lys
        770                 775                 780

Asn Lys Glu Leu Lys Cys Gly Ser Gly Ile Phe Ile Thr Asp Asn Val
785                 790                 795                 800

His Thr Trp Thr Glu Gln Tyr Lys Phe Gln Pro Glu Ser Pro Ser Lys
                    805                 810                 815

Leu Ala Ser Ala Ile Gln Lys Ala His Glu Glu Asp Ile Cys Gly Ile
                820                 825                 830

Arg Ser Val Thr Arg Leu Glu Asn Leu Met Trp Lys Gln Ile Thr Pro
        835                 840                 845

Glu Leu Asn His Ile Leu Ser Glu Asn Glu Val Lys Leu Thr Ile Met
850                 855                 860

Thr Gly Asp Ile Lys Gly Ile Met Gln Ala Gly Lys Arg Ser Leu Arg
865                 870                 875                 880

Pro Gln Pro Thr Glu Leu Lys Tyr Ser Trp Lys Thr Trp Gly Lys Ala
                    885                 890                 895

Lys Met Leu Ser Thr Glu Ser His Asn Gln Thr Phe Leu Ile Asp Gly
                900                 905                 910

Pro Glu Thr Ala Glu Cys Pro Asn Thr Asn Arg Ala Trp Asn Ser Leu
                915                 920                 925

Glu Val Glu Asp Tyr Gly Phe Gly Val Phe Thr Thr Asn Ile Trp Leu
        930                 935                 940

Lys Leu Lys Glu Lys Gln Asp Val Phe Cys Asp Ser Lys Leu Met Ser
945                 950                 955                 960

Ala Ala Ile Lys Asp Asn Arg Ala Val His Ala Asp Met Gly Tyr Trp
                965                 970                 975

Ile Glu Ser Ala Leu Asn Asp Thr Trp Lys Ile Glu Lys Ala Ser Phe
                980                 985                 990

Ile Glu Val Lys Asn Cys His Trp Pro Lys Ser His Thr Leu Trp Ser
            995                 1000                1005

Asn Gly Val Leu Glu Ser Glu Met Ile Ile Pro Lys Asn Leu Ala
    1010                1015                1020

Gly Pro Val Ser Gln His Asn Tyr Arg Pro Gly Tyr His Thr Gln
    1025                1030                1035

Ile Thr Gly Pro Trp His Leu Gly Lys Leu Glu Met Asp Phe Asp
    1040                1045                1050

Phe Cys Asp Gly Thr Thr Val Val Val Thr Glu Asp Cys Gly Asn
    1055                1060                1065

Arg Gly Pro Ser Leu Arg Thr Thr Thr Ala Ser Gly Lys Leu Ile
    1070                1075                1080

Thr Glu Trp Cys Cys Arg Ser Cys Thr Leu Pro Pro Leu Arg Tyr
    1085                1090                1095

Arg Gly Glu Asp Gly Cys Trp Tyr Gly Met Glu Ile Arg Pro Leu
    1100                1105                1110
```

-continued

```
Lys Glu Lys Glu Glu Asn Leu Val Asn Ser Leu Val Thr Ala Gly
    1115                1120                1125

His Gly Gln Val Asp Asn Phe Ser Leu Gly Val Leu Gly Met Ala
    1130                1135                1140

Leu Phe Leu Glu Glu Met Leu Arg Thr Arg Val Gly Thr Lys His
    1145                1150                1155

Ala Ile Leu Leu Val Ala Val Ser Phe Val Thr Leu Ile Thr Gly
    1160                1165                1170

Asn Met Ser Phe Arg Asp Leu Gly Arg Val Met Val Met Val Gly
    1175                1180                1185

Ala Thr Met Thr Gly Asp Ile Gly Met Gly Val Thr Tyr Leu Ala
    1190                1195                1200

Leu Leu Ala Ala Phe Lys Val Arg Pro Thr Phe Ala Ala Gly Leu
    1205                1210                1215

Leu Leu Arg Lys Leu Thr Ser Arg Glu Leu Met Met Thr Thr Ile
    1220                1225                1230

Gly Ile Val Leu Leu Ser Gln Ser Thr Ile Pro Glu Thr Ile Leu
    1235                1240                1245

Glu Leu Thr Asp Ala Leu Ala Leu Gly Met Met Val Leu Lys Met
    1250                1255                1260

Val Arg Asn Met Glu Lys Tyr Gln Leu Ala Val Thr Ile Met Ala
    1265                1270                1275

Ile Leu Cys Val Pro Asn Ala Val Ile Leu Gln Asn Ala Trp Lys
    1280                1285                1290

Val Ser Cys Thr Ile Leu Ala Val Val Ser Val Ser Pro Leu Phe
    1295                1300                1305

Leu Thr Ser Ser Gln Gln Lys Thr Asp Trp Ile Pro Leu Ala Leu
    1310                1315                1320

Thr Ile Lys Gly Leu Asn Pro Thr Ala Ile Phe Leu Thr Thr Leu
    1325                1330                1335

Ser Arg Thr Ser Lys Lys Arg Ser Trp Pro Leu Asn Glu Ala Ile
    1340                1345                1350

Met Ala Val Gly Met Val Ser Ile Leu Ala Ser Ser Leu Leu Lys
    1355                1360                1365

Asn Asp Ile Pro Met Thr Gly Pro Leu Val Ala Gly Gly Leu Leu
    1370                1375                1380

Thr Val Cys Tyr Val Leu Thr Gly Arg Ser Ala Asp Leu Glu Leu
    1385                1390                1395

Glu Arg Ala Ala Asp Val Lys Trp Glu Asp Gln Ala Glu Ile Ser
    1400                1405                1410

Gly Ser Ser Pro Ile Leu Ser Ile Thr Ile Ser Glu Asp Gly Ser
    1415                1420                1425

Met Ser Ile Lys Asn Glu Glu Glu Gln Thr Leu Thr Ile Leu
    1430                1435                1440

Ile Arg Thr Gly Leu Leu Val Ile Ser Gly Leu Phe Pro Val Ser
    1445                1450                1455

Ile Pro Ile Thr Ala Ala Ala Trp Tyr Leu Trp Glu Val Lys Lys
    1460                1465                1470

Gln Arg Ala Gly Val Leu Trp Asp Val Pro Ser Pro Pro Pro Met
    1475                1480                1485

Gly Lys Ala Glu Leu Glu Asp Gly Ala Tyr Arg Ile Lys Gln Lys
    1490                1495                1500
```

-continued

Gly Ile Leu Gly Tyr Ser Gln Ile Gly Ala Gly Val Tyr Lys Glu
1505                1510                1515

Gly Thr Phe His Thr Met Trp His Val Thr Arg Gly Ala Val Leu
1520                1525                1530

Met His Lys Gly Lys Arg Ile Glu Pro Ser Trp Ala Asp Val Lys
1535                1540                1545

Lys Asp Leu Ile Ser Tyr Gly Gly Trp Lys Leu Glu Gly Glu
1550                1555                1560

Trp Lys Glu Gly Glu Glu Val Gln Val Leu Ala Leu Glu Pro Gly
1565                1570                1575

Lys Asn Pro Arg Ala Val Gln Thr Lys Pro Gly Leu Phe Lys Thr
1580                1585                1590

Asn Ala Gly Thr Ile Gly Ala Val Ser Leu Asp Phe Ser Pro Gly
1595                1600                1605

Thr Ser Gly Ser Pro Ile Ile Asp Lys Lys Gly Lys Val Val Gly
1610                1615                1620

Leu Tyr Gly Asn Gly Val Val Thr Arg Ser Gly Ala Tyr Val Ser
1625                1630                1635

Ala Ile Ala Gln Thr Glu Lys Ser Ile Glu Asp Asn Pro Glu Ile
1640                1645                1650

Glu Asp Asp Ile Phe Arg Lys Arg Arg Leu Thr Ile Met Asp Leu
1655                1660                1665

His Pro Gly Ala Gly Lys Thr Lys Arg Tyr Leu Pro Ala Ile Val
1670                1675                1680

Arg Glu Ala Ile Lys Arg Gly Leu Arg Thr Leu Ile Leu Ala Pro
1685                1690                1695

Thr Arg Val Val Ala Ala Glu Met Glu Glu Ala Leu Arg Gly Leu
1700                1705                1710

Pro Ile Arg Tyr Gln Thr Pro Ala Ile Arg Ala Val His Thr Gly
1715                1720                1725

Arg Glu Ile Val Asp Leu Met Cys His Ala Thr Phe Thr Met Arg
1730                1735                1740

Leu Leu Ser Pro Val Arg Val Pro Asn Tyr Asn Leu Ile Ile Met
1745                1750                1755

Asp Glu Ala His Phe Thr Asp Pro Ala Ser Ile Ala Ala Arg Gly
1760                1765                1770

Tyr Ile Ser Thr Arg Val Glu Met Gly Glu Ala Ala Gly Ile Phe
1775                1780                1785

Met Thr Ala Thr Pro Pro Gly Ser Arg Asp Pro Phe Pro Gln Ser
1790                1795                1800

Asn Ala Pro Ile Ile Asp Glu Glu Arg Glu Ile Pro Glu Arg Ser
1805                1810                1815

Trp Asn Ser Gly His Glu Trp Val Thr Asp Phe Lys Gly Lys Thr
1820                1825                1830

Val Trp Phe Val Pro Ser Ile Lys Ala Gly Asn Asp Ile Ala Ala
1835                1840                1845

Cys Leu Arg Lys Asn Gly Lys Lys Val Ile Gln Leu Ser Arg Lys
1850                1855                1860

Thr Phe Asp Ser Glu Tyr Val Lys Thr Arg Thr Asn Asp Trp Asp
1865                1870                1875

Phe Val Val Thr Thr Asp Ile Ser Glu Met Gly Ala Asn Phe Lys
1880                1885                1890

Ala Glu Arg Val Ile Asp Pro Arg Arg Cys Met Lys Pro Val Ile

-continued

```
            1895                1900                1905

Leu Thr Asp Gly Glu Glu Arg Val Ile Leu Ala Gly Pro Met Pro
            1910                1915                1920

Val Thr His Ser Ser Ala Ala Gln Arg Arg Gly Arg Ile Gly Arg
            1925                1930                1935

Asn Pro Lys Asn Glu Asn Asp Gln Tyr Ile Tyr Met Gly Glu Pro
            1940                1945                1950

Leu Glu Asn Asp Glu Asp Cys Ala His Trp Lys Glu Ala Lys Met
            1955                1960                1965

Leu Leu Asp Asn Ile Asn Thr Pro Glu Gly Ile Ile Pro Ser Met
            1970                1975                1980

Phe Glu Pro Glu Arg Glu Lys Val Asp Ala Ile Asp Gly Glu Tyr
            1985                1990                1995

Arg Leu Arg Gly Glu Ala Arg Lys Thr Phe Val Asp Leu Met Arg
            2000                2005                2010

Arg Gly Asp Leu Pro Val Trp Leu Ala Tyr Arg Val Ala Ala Glu
            2015                2020                2025

Gly Ile Asn Tyr Ala Asp Arg Arg Trp Cys Phe Asp Gly Val Lys
            2030                2035                2040

Asn Asn Gln Ile Leu Glu Glu Asn Val Glu Val Glu Ile Trp Thr
            2045                2050                2055

Lys Glu Gly Glu Arg Lys Lys Leu Lys Pro Arg Trp Leu Asp Ala
            2060                2065                2070

Arg Ile Tyr Ser Asp Pro Leu Ala Leu Lys Glu Phe Lys Glu Phe
            2075                2080                2085

Ala Ala Gly Arg Lys Ser Leu Thr Leu Asn Leu Ile Thr Glu Met
            2090                2095                2100

Gly Arg Leu Pro Thr Phe Met Thr Gln Lys Val Arg Asp Ala Leu
            2105                2110                2115

Asp Asn Leu Ala Val Leu His Thr Ala Glu Ala Gly Gly Arg Ala
            2120                2125                2130

Tyr Asn His Ala Leu Ser Glu Leu Pro Glu Thr Leu Glu Thr Leu
            2135                2140                2145

Leu Leu Leu Thr Leu Leu Ala Thr Val Thr Gly Gly Ile Phe Leu
            2150                2155                2160

Phe Leu Met Ser Ala Arg Gly Ile Gly Lys Met Thr Leu Gly Met
            2165                2170                2175

Cys Cys Ile Ile Thr Ala Ser Ile Leu Leu Trp Tyr Ala Gln Ile
            2180                2185                2190

Gln Pro His Trp Ile Ala Ala Ser Ile Ile Leu Glu Phe Phe Leu
            2195                2200                2205

Ile Val Leu Leu Ile Pro Glu Pro Glu Lys Gln Arg Thr Pro Gln
            2210                2215                2220

Asp Asn Gln Leu Thr Tyr Val Val Ile Ala Ile Leu Thr Val Val
            2225                2230                2235

Ala Ala Thr Met Ala Asn Glu Met Gly Phe Leu Glu Lys Thr Lys
            2240                2245                2250

Lys Asp Leu Gly Leu Gly Ser Ile Ala Thr Gln Gln Pro Glu Ser
            2255                2260                2265

Asn Ile Leu Asp Ile Asp Leu Arg Pro Ala Ser Ala Trp Thr Leu
            2270                2275                2280

Tyr Ala Val Ala Thr Thr Phe Val Thr Pro Met Leu Arg His Ser
            2285                2290                2295
```

```
Ile Glu Asn Ser Ser Val Asn Val Ser Leu Thr Ala Ile Ala Asn
                2300                2305                2310

Gln Ala Thr Val Leu Met Gly Leu Gly Lys Gly Trp Pro Leu Ser
                2315                2320                2325

Lys Met Asp Ile Gly Val Pro Leu Leu Ala Ile Gly Cys Tyr Ser
                2330                2335                2340

Gln Val Asn Pro Ile Thr Leu Thr Ala Ala Leu Phe Leu Leu Val
                2345                2350                2355

Ala His Tyr Ala Ile Ile Gly Pro Gly Leu Gln Ala Lys Ala Thr
                2360                2365                2370

Arg Glu Ala Gln Lys Arg Ala Ala Ala Gly Ile Met Lys Asn Pro
                2375                2380                2385

Thr Val Asp Gly Ile Thr Val Ile Asp Leu Asp Pro Ile Pro Tyr
                2390                2395                2400

Asp Pro Lys Phe Glu Lys Gln Leu Gly Gln Val Met Leu Leu Val
                2405                2410                2415

Leu Cys Val Thr Gln Val Leu Met Met Arg Thr Thr Trp Ala Leu
                2420                2425                2430

Cys Glu Ala Leu Thr Leu Ala Thr Gly Pro Ile Ser Thr Leu Trp
                2435                2440                2445

Glu Gly Asn Pro Gly Arg Phe Trp Asn Thr Thr Ile Ala Val Ser
                2450                2455                2460

Met Ala Asn Ile Phe Arg Gly Ser Tyr Leu Ala Gly Ala Gly Leu
                2465                2470                2475

Leu Phe Ser Ile Met Lys Asn Thr Thr Asn Thr Arg Arg Gly Thr
                2480                2485                2490

Gly Asn Ile Gly Glu Thr Leu Gly Glu Lys Trp Lys Ser Arg Leu
                2495                2500                2505

Asn Ala Leu Gly Lys Ser Glu Phe Gln Ile Tyr Lys Lys Ser Gly
                2510                2515                2520

Ile Gln Glu Val Asp Arg Thr Leu Ala Lys Glu Gly Ile Lys Arg
                2525                2530                2535

Gly Glu Thr Asp His His Ala Val Ser Arg Gly Ser Ala Lys Leu
                2540                2545                2550

Arg Trp Phe Val Glu Arg Asn Met Val Thr Pro Glu Gly Lys Val
                2555                2560                2565

Val Asp Leu Gly Cys Gly Arg Gly Gly Trp Ser Tyr Tyr Cys Gly
                2570                2575                2580

Gly Leu Lys Asn Val Arg Glu Val Lys Gly Leu Thr Lys Gly Gly
                2585                2590                2595

Pro Gly His Glu Glu Pro Ile Pro Met Ser Thr Tyr Gly Trp Asn
                2600                2605                2610

Leu Val Arg Leu Gln Ser Gly Val Asp Val Phe Phe Ile Pro Pro
                2615                2620                2625

Glu Lys Cys Asp Thr Leu Leu Cys Asp Ile Gly Glu Ser Ser Pro
                2630                2635                2640

Asn Pro Thr Val Glu Ala Gly Arg Thr Leu Arg Val Leu Asn Leu
                2645                2650                2655

Val Glu Asn Trp Leu Asn Asn Asn Thr Gln Phe Cys Ile Lys Val
                2660                2665                2670

Leu Asn Pro Tyr Met Pro Ser Val Ile Glu Lys Met Glu Ala Leu
                2675                2680                2685
```

```
Gln Arg Lys Tyr Gly Gly Ala Leu Val Arg Asn Pro Leu Ser Arg
2690                2695                2700

Asn Ser Thr His Glu Met Tyr Trp Val Ser Asn Ala Ser Gly Asn
2705                2710                2715

Ile Val Ser Ser Val Asn Met Ile Ser Arg Met Leu Ile Asn Arg
2720                2725                2730

Phe Thr Met Arg Tyr Lys Lys Ala Thr Tyr Glu Pro Asp Val Asp
2735                2740                2745

Leu Gly Ser Gly Thr Arg Asn Ile Gly Ile Glu Ser Glu Ile Pro
2750                2755                2760

Asn Leu Asp Ile Ile Gly Lys Arg Ile Glu Lys Ile Lys Gln Glu
2765                2770                2775

His Glu Thr Ser Trp His Tyr Asp Gln Asp His Pro Tyr Lys Thr
2780                2785                2790

Trp Ala Tyr His Gly Ser Tyr Glu Thr Lys Gln Thr Gly Ser Ala
2795                2800                2805

Ser Ser Met Val Asn Gly Val Val Arg Leu Leu Thr Lys Pro Trp
2810                2815                2820

Asp Val Val Pro Met Val Thr Gln Met Ala Met Thr Asp Thr Thr
2825                2830                2835

Pro Phe Gly Gln Gln Arg Val Phe Lys Glu Lys Val Asp Thr Arg
2840                2845                2850

Thr Gln Glu Pro Lys Glu Gly Thr Lys Lys Leu Met Lys Ile Thr
2855                2860                2865

Ala Glu Trp Leu Trp Lys Glu Leu Gly Lys Lys Lys Thr Pro Arg
2870                2875                2880

Met Cys Thr Arg Glu Glu Phe Thr Arg Lys Val Arg Ser Asn Ala
2885                2890                2895

Ala Leu Gly Ala Ile Phe Thr Asp Glu Asn Lys Trp Lys Ser Ala
2900                2905                2910

Arg Glu Ala Val Glu Asp Ser Arg Phe Trp Glu Leu Val Asp Lys
2915                2920                2925

Glu Arg Asn Leu His Leu Glu Gly Lys Cys Glu Thr Cys Val Tyr
2930                2935                2940

Asn Met Met Gly Lys Arg Glu Lys Lys Leu Gly Glu Phe Gly Lys
2945                2950                2955

Ala Lys Gly Ser Arg Ala Ile Trp Tyr Met Trp Leu Gly Ala Arg
2960                2965                2970

Phe Leu Glu Phe Glu Ala Leu Gly Phe Leu Asn Glu Asp His Trp
2975                2980                2985

Phe Ser Arg Glu Asn Ser Leu Ser Gly Val Glu Gly Glu Gly Leu
2990                2995                3000

His Lys Leu Gly Tyr Ile Leu Arg Asp Val Ser Lys Lys Glu Gly
3005                3010                3015

Gly Ala Met Tyr Ala Asp Asp Thr Ala Gly Trp Asp Thr Arg Ile
3020                3025                3030

Thr Leu Glu Asp Leu Lys Asn Glu Glu Met Val Thr Asn His Met
3035                3040                3045

Glu Gly Glu His Lys Lys Leu Ala Glu Ala Ile Phe Lys Leu Thr
3050                3055                3060

Tyr Gln Asn Lys Val Val Arg Val Gln Arg Pro Thr Pro Arg Gly
3065                3070                3075

Thr Val Met Asp Ile Ile Ser Arg Arg Asp Gln Arg Gly Ser Gly
```

```
                3080                3085                3090
Gln Val Gly Thr Tyr Gly Leu Asn Thr Phe Thr Asn Met Glu Ala
        3095                3100                3105
Gln Leu Ile Arg Gln Met Glu Gly Glu Gly Val Phe Lys Ser Ile
        3110                3115                3120
Gln His Leu Thr Ile Thr Glu Glu Ile Ala Val Gln Asn Trp Leu
        3125                3130                3135
Ala Arg Val Gly Arg Glu Arg Leu Ser Arg Met Ala Ile Ser Gly
        3140                3145                3150
Asp Asp Cys Val Val Lys Pro Leu Asp Asp Arg Phe Ala Ser Ala
        3155                3160                3165
Leu Thr Ala Leu Asn Asp Met Gly Lys Ile Arg Lys Asp Ile Gln
        3170                3175                3180
Gln Trp Glu Pro Ser Arg Gly Trp Asn Asp Trp Thr Gln Val Pro
        3185                3190                3195
Phe Cys Ser His His Phe His Glu Leu Ile Met Lys Asp Gly Arg
        3200                3205                3210
Val Leu Val Val Pro Cys Arg Asn Gln Asp Glu Leu Ile Gly Arg
        3215                3220                3225
Ala Arg Ile Ser Gln Gly Ala Gly Trp Ser Leu Arg Glu Thr Ala
        3230                3235                3240
Cys Leu Gly Lys Ser Tyr Ala Gln Met Trp Ser Leu Met Tyr Phe
        3245                3250                3255
His Arg Arg Asp Leu Arg Leu Ala Ala Asn Ala Ile Cys Ser Ala
        3260                3265                3270
Val Pro Ser His Trp Val Pro Thr Ser Arg Thr Thr Trp Ser Ile
        3275                3280                3285
His Ala Lys His Glu Trp Met Thr Thr Glu Asp Met Leu Thr Val
        3290                3295                3300
Trp Asn Arg Val Trp Ile Gln Glu Asn Pro Trp Met Glu Asp Lys
        3305                3310                3315
Thr Pro Val Glu Ser Trp Glu Glu Ile Pro Tyr Leu Gly Lys Arg
        3320                3325                3330
Glu Asp Gln Trp Cys Gly Ser Leu Ile Gly Leu Thr Ser Arg Ala
        3335                3340                3345
Thr Trp Ala Lys Asn Ile Gln Ala Ala Ile Asn Gln Val Arg Ser
        3350                3355                3360
Leu Ile Gly Asn Glu Glu Tyr Thr Asp Tyr Met Pro Ser Met Lys
        3365                3370                3375
Arg Phe Arg Arg Glu Glu Glu Glu Ala Gly Val Leu Trp
        3380                3385                3390

<210> SEQ ID NO 22
<211> LENGTH: 10723
<212> TYPE: DNA
<213> ORGANISM: Artificial Sequence
<220> FEATURE:
<223> OTHER INFORMATION: Derived from Dengue virus serotype 2/Dengue
      virus serotype 4, DENV-4e

<400> SEQUENCE: 22
agttgttagt ctacgtggac cgacaaagac agattctttg agggagctaa gctcaatgta      60
gttctaacag ttttttaatt agagagcaga tctctgatga ataaccaacg gaaaaggcg      120 aaaacacgc ctttcaatat gctgaaacgc gagagaaacc gcgtgtcgac tgtgcaacag     180
```

```
ctgacaaaga gattctcact tggaatgctg cagggacgag gaccattaaa actgttcatg      240
gccctggtgg cgttccttcg tttcctaaca atcccaccaa cagcaggat attgaagaga      300
```

```
ctgacaaaga gattctcact tggaatgctg cagggacgag gaccattaaa actgttcatg      240
gccctggtgg cgttccttcg tttcctaaca atcccaccaa cagcaggat attgaagaga      300
tggggaacaa ttaaaaaatc aaaagctatt aatgttttga gagggttcag gaaagagatt      360
ggaaggatgc tgaacatctt gaataggaga cgcagctcaa cgataacatt gctgtacttg      420
attcccaccg taatggcgtt tcacttgtca acgcgtgatg gcgaaccccct catgatagtg      480
gcaaaacatg aaaggggag acctctcttg tttaagacaa cagaggggat caacaaatgc      540
actctcattg ccatggactt gggtgaaatg tgtgaggaca ctgtcacgta taaatgcccc      600
ttactggtca ataccgaacc tgaagacatt gattgctggt gcaatctcac gtctacctgg      660
gtcatgtatg ggacatgcac ccagagcgga gaacggagac gagagaagcg ctcagtagct      720
ttaacaccac attcaggaat gggattggaa acaagagctg agacatggat gtcatcggaa      780
ggggcttgga agcatgctca gagagtagag agctggatac tcagaaaccc aggattcgcg      840
ctcttggcag gatttatggc ttatatgatt gggcaaacag gaatccagcg aactgtcttc      900
tttgtcctaa tgatgctggt cgccccatcc tacggaatgc gatgcgtagg agtaggaaac      960
agagactttg tggaaggagt ctcaggtgga gcatgggtcg atctggtgct agaacatgga     1020
ggatgcgtca caaccatggc ccagggaaaa ccaaccttgg attttgaact gactaagaca     1080
acagccaagg aagtggctct gttaagaacc tattgcattg aagcctcaat atcaaacata     1140
accacggcaa caagatgtcc aacgcaagga gagccttatc taaaagagga caagaccaa     1200
cagtacattt gccggagaga tgtggtagac agagggtggg gcaatggctg tggcttgttt     1260
ggaaaaggag gagttgtgac atgtgcgaag ttttcatgtt cggggaagat aacaggcaat     1320
ttggtccaaa ttgagaacct tgaatacaca gtggttgtaa cagtccacaa tggagacacc     1380
catgcagtag gaaatgacac gtccaatcat ggagttacag ccacgataac tcccaggtca     1440
ccatcggtgg aagtcaaatt gccggactat ggagaactaa cactcgattg tgaacccagg     1500
tctggaattg actttaatga gatgattctg atgaaaatga aaagaaaac atggcttgtg     1560
cataagcaat ggtttttgga tctacctcta ccatggacag caggagcaga cacatcagag     1620
gttcactgga attacaaaga gagaatggtg acatttaagg ttcctcatgc caagagacag     1680
gatgtgacag tgctgggatc tcaggaagga gccatgcatt ctgccctcgc tggagccaca     1740
gaagtggact ccgtgatggg aaatcacatg tttgcaggac atctcaagtg caaagtccgt     1800
atggagaaat tgagaatcaa gggaatgtca tacacgatgt gttcaggaaa gttctcaatt     1860
gacaaagaga tggcagaaac acagcatggg acaacagtgg tgaaagtcaa gtatgaaggt     1920
gctggagctc cgtgtaaagt ccccatagag ataagagatg tgaacaagga aaaagtggtt     1980
gggcgtatca tctcatccac ccctttggct gagaatacca acagtgtaac caacatagag     2040
ttagaacccc ccttttggga cagctacata gtgataggtg ttggaaacag tgcattaaca     2100
ctccattggt tcaggaaagg gagttccatt ggcaagatgt ttgagtccac atacagaggt     2160
gcaaaacgaa tggccattct aggtgaaaca gcttgggatt ttggttccgt tggtggactg     2220
ttcacatcat tgggaaaggc tgtgcaccag gttttttggaa gtgtgtatac aaccctgttt     2280
ggaggagtct catggatgat tagaatccta attgggttcc tagtgttgtg gattggcacg     2340
aactcaagga acacttcaat ggctatgacg tgcatagctg ccggcattgt gacactgtat     2400
ttgggagtca tggtgcaggc cgatagtggt tgcgttgtga gctggaaaaa caaagaactg     2460
aaatgtggca gtgggatttt catcacagac aacgtgcaca catggacaga acaatacaag     2520
ttccaaccag aatccccttc aaaactagct tcagctatcc agaaagccca tgaagaggac     2580
```

```
atttgtggaa tccgctcagt aacaagactg gagaatctga tgtggaaaca aataacacca    2640
gaattgaatc acattctatc agaaaatgag gtgaagttaa ctattatgac aggagacatc    2700
aaaggaatca tgcaggcagg aaaacgatct ctgcggcctc agcccactga gctgaagtat    2760
tcatggaaaa catggggcaa agcaaaaatg ctctctacag agtctcataa ccagaccttt    2820
ctcattgatg gccccgaaac agcagaatgc cccaacacaa atagagcttg gaattcgttg    2880
gaagttgaag actatggctt tggagtattc accaccaata tatggctaaa attgaaagaa    2940
aaacaggatg tattctgcga ctcaaaactc atgtcagcgg ccataaaaga caacagagcc    3000
gtccatgccg atatgggtta ttggatagaa agtgcactca atgacacatg gaagatagag    3060
aaagcctctt tcattgaagt taaaaactgc cactggccaa atcacacac cctctggagc    3120 aatggagtgc tagaaagtga gatgataatt ccaaagaatc tcgctggacc agtgtctcaa    3180
cacaactata gaccaggcta ccatacacaa ataacaggac catggcatct aggtaagctt    3240
gagatggact ttgatttctg tgatggaaca acagtggtag tgactgagga ctgcggaaat    3300
agaggaccct cttttgagaac aaccactgcc tctggaaaac tcataacaga atggtgctgc    3360
cgatcttgca cattaccacc gctaagatac agaggtgagg atgggtgctg gtacgggatg    3420
gaaatcagac cattgaagga gaaagaagag aatttggtca actccttggt cacagctgga    3480
catgggcagg tcgacaactt ttcactagga gtcttgggaa tggcattgtt cctgaggaa    3540 atgcttagga cccgagtagg aacgaaacat gcaatactac tagttgcagt ttcttttgtg    3600
acattgatca cagggaacat gtcctttaga gacctgggaa gagtgatggt tatggtaggc    3660
gccactatga cggatgacat aggtatgggc gtgacttatc ttgccctact agcagccttc    3720
aaagtcagac caactttttgc agctggacta ctcttgagaa agctgacctc caaggaattg    3780
atgatgacta ctataggaat tgtactcctc tcccagagca ccataccaga gaccattctt    3840
gagttgactg atgcgttagc cttaggcatg atggtcctca aaatggtgag aaatatggaa    3900
aagtatcaat tggcagtgac tatcatggct atcttgtgcg tcccaaacgc agtgatatta    3960
caaaacgcat ggaaagtgag ttgcacaata ttggcagtgg tgtccgtttc cccactgttc    4020
ttaacatcct cacagcaaaa aacagattgg ataccattag cattgacgat caaaggtctc    4080
aatccaacag ctatttttct aacaacccct caagaaccca gcaagaaaag gagctggcca    4140
ttaaatgagg ctatcatggc agtcgggatg gtgagcattt tagccagttc tctcctaaaa    4200
aatgatattc ccatgacagg accattagtg gctggagggc tcctcactgt gtgctacgtg    4260
ctcactggac gatcggccga tttgaactg gagagagcag ccgatgtcaa atgggaagac    4320
caggcagaga tatcaggaag cagtccaatc ctgtcaataa caatatcaga agatggtagc    4380
atgtcgataa aaatgaaga ggaagaacaa acactgacca tactcattag aacaggattg    4440
ctggtgatct caggactttt tcctgtatca ataccaatca cggcagcagc atggtacctg    4500
tgggaagtga gaaacaacg ggccggagta ttgtgggatg ttccttcacc cccacccatg    4560
ggaaaggctg aactggaaga tggagcctat agaattaagc aaaaagggat tcttggatat    4620
tcccagatcg gagccggagt ttacaaagaa ggaacattcc atacaatgtg gcatgtcaca    4680
cgtggcgctg ttctaatgca taaggaaag aggattgaac catcatgggc ggacgtcaag    4740
aaagacctaa tatcatatgg aggaggctgg aagttagaag gagaatggaa ggaaggagaa    4800
gaagtccagg tattggcact ggagcctgga aaaaatccaa gagccgtcca aacgaaacct    4860 ggtctttca aaaccaacgc cggaacaata ggtgctgtat ctctggactt ttctcctgga    4920
```

```
acgtcaggat ctccaattat cgacaaaaaa ggaaaagttg tgggtctttta tggtaatggt    4980
gttgttacaa ggagtggagc atatgtgagt gctatagccc agactgaaaa aagcattgaa    5040
gacaacccag agatcgaaga tgacattttc cgaaagagaa gactgaccat catggacctc    5100
cacccaggag cgggaaagac gaagagatac cttccggcca tagtcagaga agctataaaa    5160
cggggtttga gaacattaat cttggccccc actagagttg tggcagctga aatggaggaa    5220
gcccttagag gacttccaat aagataccag accccagcca tcagagctgt gcacaccggg    5280
cgggagattg tggacctaat gtgtcatgcc acatttacca tgaggctgct atcaccagtt    5340
agagtgccaa actacaacct gattatcatg gacgaagccc atttcacaga cccagcaagt    5400
atagcagcta gaggatacat ctcaactcga gtggagatgg gtgaggcagc tgggattttt    5460
atgacagcca ctccccccgg aagcagagac ccatttcctc agcaatgc accaatcata    5520
gatgaagaaa gagaaatccc tgaacgctcg tggaattccg acatgaatg ggtcacggat    5580
tttaagggaa agactgtttg gttcgttcca agtataaaag caggaaatga tatagcagct    5640
tgcctgagga aaaatggaaa gaaagtgata caactcagta ggaagacctt tgattctgag    5700
tatgtcaaga ctagaaccaa tgattgggac ttcgtggtta caactgacat ttcagaaatg    5760
ggtgccaatt tcaaggctga gagggttata daccccagac gctgcatgaa accagtcata    5820
ctaacagatg gtgaagagcg ggtgattctg gcaggaccta tgccagtgac ccactctagt    5880
gcagcacaaa aagagggag aataggaaga aatccaaaaa atgagaatga ccagtacata    5940
tacatggggg aacctctgga aaatgatgaa gactgtgcac actggaaaga agctaaaatg    6000
ctcctagata acatcaacac gccagaagga atcattccta gcatgttcga accagagcgt    6060
gaaaaggtgg atgccattga tggcgaatac cgcttgagag gagaagcaag gaaaaccttt    6120
gtagacttaa tgagaagagg agacctacca gtctggttgg cctacagagt ggcagctgaa    6180
ggcatcaact acgcagacag aaggtggtgt tttgatggag tcaagaacaa ccaaatccta    6240
gaagaaaacg tggaagttga atctggaca aaagaagggg aaaggaagaa attgaaaccc    6300
agatggttgg atgctaggat ctattctgac ccactggcgc taaaagaatt taaggaattt    6360
gcagccggaa gaaagtctct gaccctgaac ctaatcacag aaatgggtag gctcccaacc    6420
ttcatgactc agaaggcaag agacgcactg gacaacttag cagtgctgca cacggctgag    6480
gcaggtggaa gggcgtacaa ccatgctctc agtgaactgc cggagaccct ggagacattg    6540
cttttactga cacttctggc tacagtcacg ggagggatct ttttattctt gatgagcgca    6600
aggggcatag gaagatgac cctgggaatg tgctgcataa tcacggctag catcctccta    6660
tggtacgcac aaatacagcc acactggata gcagcttcaa taatactgga gttttttctc    6720
atagttttgc ttattccaga acctgaaaaa cagagaacac cccaagacaa ccaactgacc    6780
tacgttgtca tagccatcct cacagtggtg gccgcaacca tggcaaacga gatgggtttc    6840
ctagaaaaaa cgaagaaaga tctcggattg ggaagcattg caacccagca acccgagagc    6900
aacatcctgg acatagatct acgtcctgca tcagcatgga cgctgtatgc cgtggccaca    6960
acatttgtta caccaatgtt gagacatagc attgaaaatt cctcagtgaa tgtgtcccta    7020
acagctatag ccaaccaagc cacagtgtta atgggtctcg ggaaaggatg ccattgtca    7080
aagatggaca tcggagttcc ccttctcgcc attggatgct actcacaagt caaccccata    7140
actctcacag cagctctttt cttattggta gcacattatg ccatcatagg gccaggactc    7200
caagcaaaag caaccagaga agctcagaaa agagcagcgg cgggcatcat gaaaaaccca    7260
actgtcgatg gaataacagt gattgaccta gatccaatac cttatgatcc aaagtttgaa    7320
```

-continued

```
aagcagttgg gacaagtaat gctcctagtc ctctgcgtga ctcaagtatt gatgatgagg   7380
actacatggg ctctgtgtga ggctttaacc ttagctaccg ggcccatctc cacattgtgg   7440
gaaggaaatc cagggaggtt ttggaacact accattgcgg tgtcaatggc taacattttt   7500
agagggagtt acttggccgg agctggactt ctcttttcta ttatgaagaa cacaaccaac   7560
acaagaaggg gaactggcaa cataggagag acgcttggag agaaatggaa aagccgattg   7620
aacgcattgg gaaaagtga attccagatc tacaagaaaa gtggaatcca ggaagtggat   7680
agaaccttag caaagaagg cattaaaaga ggagaaacgg accatcacgc tgtgtcgcga   7740
ggctcagcaa aactgagatg gttcgttgag agaaacatgg tcacaccaga agggaaagta   7800
gtggacctcg gttgtggcag aggaggctgg tcatactatt gtggaggact aaagaatgta   7860
agagaagtca aaggcctaac aaaaggagga ccaggcacg aagaacccat ccccatgtca   7920
acatatgggt ggaatctagt gcgtcttcaa agtggagttg acgttttctt catcccgcca   7980
gaaaagtgtg acacattatt gtgtgacata ggggagtcat caccaaatcc cacagtggaa   8040
gcaggacgaa cactcagagt ccttaactta gtagaaaatt ggttgaacaa caacactcaa   8100
ttttgcataa aggttctcaa cccatatatg ccctcagtca tagaaaaaat ggaagcacta   8160
caaaggaaat atggaggagc cttagtgagg aatccactct cacgaaactc cacacatgag   8220
atgtactggg tatccaatgc ttccgggaac atagtgtcat cagtgaacat gatttcaagg   8280
atgttgatca acagatttac aatgagatac aagaaagcca cttacgagcc ggatgttgac   8340
ctcggaagcg gaacccgtaa catcgggatt gaaagtgaga taccaaacct agatataatt   8400
gggaaaagaa tagaaaaaat aaagcaagag catgaaacat catggcacta tgaccaagac   8460
cacccataca aaacgtggc ataccatggt agctatgaaa caaaacagac tggatcagca   8520
tcatccatgg tcaacggagt ggtcaggctg ctgacaaaac cttgggacgt cgtccccatg   8580
gtgacacaga tggcaatgac agacacgact ccatttggac aacagcgcgt ttttaaagag   8640
aaagtggaca cgagaaccca agaaccgaaa gaaggcacga agaaactaat gaaaataaca   8700
gcagagtggc tttggaaaga attagggaag aaaaagacac ccaggatgtg caccagagaa   8760
gaattcacaa gaaaggtgag aagcaatgca gccttggggg ccatattcac tgatgagaac   8820
aagtggaagt cggcacgtga ggctgttgaa gatagtaggt tttgggagct ggttgacaag   8880
gaaaggaatc tccatcttga aggaaagtgt gaaacatgtg tgtacaacat gatgggaaaa   8940
agagagaaga agctagggga attcggcaag gcaaaaggca gcagagccat atggtacatg   9000
tggcttggag cacgcttctt agagtttgaa gccctaggat tcttaaatga agatcactgg   9060
ttctccagag agaactccct gagtggagtg aaggagaag ggctgcacaa gctaggttac   9120
attctaagag acgtgagcaa gaaagaggga ggagcaatgt atgccgatga caccgcagga   9180
tgggatacaa gaatcacact agaagaccta aaaaatgaag aaatggtaac aaaccacatg   9240
gaaggagaac acaagaaact agccgaggcc atttttcaaac taacgtacca aaacaaggtg   9300
gtgcgtgtgc aaagaccaac accaagaggc acagtaatgg acatcatatc gagaagagac   9360
caaagaggta gtggacaagt tggcacctat ggactcaata ctttcaccaa tatggaagcc   9420
caactaatca gacagatgga gggagaagga gtctttaaaa gcattcagca cctaacaatc   9480
acagaagaaa tcgctgtgca aaactggtta gcaagagtgg ggcgcgaaag gttatcaaga   9540
atggccatca gtgagatga ttgtgttgtg aaacctttag atgacaggtt cgcaagcgct   9600
ttaacagctc taatgacat gggaaagatt aggaaagaca tacaacaatg gaaccttca   9660
```

-continued

```
agaggatgga atgattggac acaagtgccc ttctgttcac accatttcca tgagttaatc   9720
atgaaagacg tcgcgtact cgttgttcca tgtagaaacc aagatgaact gattggcaga   9780
gcccgaatct cccaaggagc agggtggtct ttgcgggaga cggcctgttt ggggaagtct   9840
tacgcccaaa tgtggagctt gatgtacttc cacagacgcg acctcaggct ggcggcaaat   9900
gctatttgct cggcagtacc atcacattgg gttccaacaa gtcgaacaac ctggtccata   9960
catgctaaac atgaatggat gacaacggaa gacatgctga cagtctggaa cagggtgtgg  10020
attcaagaaa acccatggat ggaagacaaa actccagtgg aatcatggga ggaaatccca  10080
tacttgggga aaagagaaga ccaatggtgc ggctcattga ttgggttaac aagcagggcc  10140
acctgggcaa agaacatcca agcagcaata aatcaagtta gatcccttat aggcaatgaa  10200
gaatacacag attacatgcc atccatgaaa agattcagaa gagaagagga agaagcagga  10260
gttctgtggt agaaagcaaa actaacatga acaaggcta gaagtcaggt cggattaagc  10320
catagtacgg aaaaaactat gctacctgtg agccccgtcc aaggacgtta aagaagtca   10380
ggccatcata aatgccatag cttgagtaaa ctatgcagcc tgtagctcca cctgagaagg  10440
tgtaaaaaat ccgggaggcc acaaaccatg gaagctgtac gcatggcgta gtggactagc  10500
ggttagagga gaccccctccc ttacaaatcg cagcaacaat gggggcccaa ggcgagatga  10560
agctgtagtc tcgctggaag gactagaggt tagaggagac cccccgaaa caaaaaacag  10620
catattgacg ctgggaaaga ccagagatcc tgctgtctcc tcagcatcat tccaggcaca  10680
gaacgccaga aaatggaatg gtgctgttga atcaacaggt tct                    10723
```

<210> SEQ ID NO 23
<211> LENGTH: 3391
<212> TYPE: PRT
<213> ORGANISM: Artificial Sequence
<220> FEATURE:
<223> OTHER INFORMATION: Derived from Dengue virus serotype 2/Dengue
    virus serotype 4, DEN-4e

<400> SEQUENCE: 23

```
Met Asn Asn Gln Arg Lys Lys Ala Lys Asn Thr Pro Phe Asn Met Leu
1               5                   10                  15

Lys Arg Glu Arg Asn Arg Val Ser Thr Val Gln Gln Leu Thr Lys Arg
            20                  25                  30

Phe Ser Leu Gly Met Leu Gln Gly Arg Gly Pro Leu Lys Leu Phe Met
        35                  40                  45

Ala Leu Val Ala Phe Leu Arg Phe Leu Thr Ile Pro Pro Thr Ala Gly
    50                  55                  60

Ile Leu Lys Arg Trp Gly Thr Ile Lys Lys Ser Lys Ala Ile Asn Val
65                  70                  75                  80

Leu Arg Gly Phe Arg Lys Glu Ile Gly Arg Met Leu Asn Ile Leu Asn
                85                  90                  95

Arg Arg Arg Ser Ser Thr Ile Thr Leu Leu Tyr Leu Ile Pro Thr Val
            100                 105                 110

Met Ala Phe His Leu Ser Thr Arg Asp Gly Glu Pro Leu Met Ile Val
        115                 120                 125

Ala Lys His Glu Arg Gly Arg Pro Leu Leu Phe Lys Thr Thr Glu Gly
    130                 135                 140

Ile Asn Lys Cys Thr Leu Ile Ala Met Asp Leu Gly Glu Met Cys Glu
145                 150                 155                 160

Asp Thr Val Thr Tyr Lys Cys Pro Leu Leu Val Asn Thr Glu Pro Glu
                165                 170                 175
```

```
Asp Ile Asp Cys Trp Cys Asn Leu Thr Ser Thr Trp Val Met Tyr Gly
                180                 185                 190

Thr Cys Thr Gln Ser Gly Glu Arg Arg Glu Lys Arg Ser Val Ala
            195                 200                 205

Leu Thr Pro His Ser Gly Met Gly Leu Glu Thr Arg Ala Glu Thr Trp
210                 215                 220

Met Ser Ser Glu Gly Ala Trp Lys His Ala Gln Arg Val Glu Ser Trp
225                 230                 235                 240

Ile Leu Arg Asn Pro Gly Phe Ala Leu Leu Ala Gly Phe Met Ala Tyr
                245                 250                 255

Met Ile Gly Gln Thr Gly Ile Gln Arg Thr Val Phe Phe Val Leu Met
                260                 265                 270

Met Leu Val Ala Pro Ser Tyr Gly Met Arg Cys Val Gly Val Gly Asn
                275                 280                 285

Arg Asp Phe Val Glu Gly Val Ser Gly Gly Ala Trp Val Asp Leu Val
290                 295                 300

Leu Glu His Gly Gly Cys Val Thr Thr Met Ala Gln Gly Lys Pro Thr
305                 310                 315                 320

Leu Asp Phe Glu Leu Thr Lys Thr Thr Ala Lys Glu Val Ala Leu Leu
                325                 330                 335

Arg Thr Tyr Cys Ile Glu Ala Ser Ile Ser Asn Ile Thr Thr Ala Thr
                340                 345                 350

Arg Cys Pro Thr Gln Gly Glu Pro Tyr Leu Lys Glu Glu Gln Asp Gln
                355                 360                 365

Gln Tyr Ile Cys Arg Arg Asp Val Val Asp Arg Gly Trp Gly Asn Gly
                370                 375                 380

Cys Gly Leu Phe Gly Lys Gly Val Val Thr Cys Ala Lys Phe Ser
385                 390                 395                 400

Cys Ser Gly Lys Ile Thr Gly Asn Leu Val Gln Ile Glu Asn Leu Glu
                405                 410                 415

Tyr Thr Val Val Val Thr Val His Asn Gly Asp Thr His Ala Val Gly
                420                 425                 430

Asn Asp Thr Ser Asn His Gly Val Thr Ala Thr Ile Thr Pro Arg Ser
                435                 440                 445

Pro Ser Val Glu Val Lys Leu Pro Asp Tyr Gly Glu Leu Thr Leu Asp
450                 455                 460

Cys Glu Pro Arg Ser Gly Ile Asp Phe Asn Glu Met Ile Leu Met Lys
465                 470                 475                 480

Met Lys Lys Lys Thr Trp Leu Val His Lys Gln Trp Phe Leu Asp Leu
                485                 490                 495

Pro Leu Pro Trp Thr Ala Gly Ala Asp Thr Ser Glu Val His Trp Asn
                500                 505                 510

Tyr Lys Glu Arg Met Val Thr Phe Lys Val Pro His Ala Lys Arg Gln
                515                 520                 525

Asp Val Thr Val Leu Gly Ser Gln Glu Gly Ala Met His Ser Ala Leu
                530                 535                 540

Ala Gly Ala Thr Glu Val Asp Ser Gly Asp Gly Asn His Met Phe Ala
545                 550                 555                 560

Gly His Leu Lys Cys Lys Val Arg Met Glu Lys Leu Arg Ile Lys Gly
                565                 570                 575

Met Ser Tyr Thr Met Cys Ser Gly Lys Phe Ser Ile Asp Lys Glu Met
                580                 585                 590
```

```
Ala Glu Thr Gln His Gly Thr Thr Val Val Lys Val Lys Tyr Glu Gly
            595                 600                 605

Ala Gly Ala Pro Cys Lys Val Pro Ile Glu Ile Arg Asp Val Asn Lys
    610                 615                 620

Glu Lys Val Val Gly Arg Ile Ile Ser Ser Thr Pro Leu Ala Glu Asn
625                 630                 635                 640

Thr Asn Ser Val Thr Asn Ile Glu Leu Glu Pro Pro Phe Gly Asp Ser
                645                 650                 655

Tyr Ile Val Ile Gly Val Gly Asn Ser Ala Leu Thr Leu His Trp Phe
            660                 665                 670

Arg Lys Gly Ser Ser Ile Gly Lys Met Phe Glu Ser Thr Tyr Arg Gly
    675                 680                 685

Ala Lys Arg Met Ala Ile Leu Gly Glu Thr Ala Trp Asp Phe Gly Ser
    690                 695                 700

Val Gly Gly Leu Phe Thr Ser Leu Gly Lys Ala Val His Gln Val Phe
705                 710                 715                 720

Gly Ser Val Tyr Thr Thr Leu Phe Gly Gly Val Ser Trp Met Ile Arg
                725                 730                 735

Ile Leu Ile Gly Phe Leu Val Leu Trp Ile Gly Thr Asn Ser Arg Asn
            740                 745                 750

Thr Ser Met Ala Met Thr Cys Ile Ala Ala Gly Ile Val Thr Leu Tyr
    755                 760                 765

Leu Gly Val Met Val Gln Ala Asp Ser Gly Cys Val Val Ser Trp Lys
    770                 775                 780

Asn Lys Glu Leu Lys Cys Gly Ser Gly Ile Phe Ile Thr Asp Asn Val
785                 790                 795                 800

His Thr Trp Thr Glu Gln Tyr Lys Phe Gln Pro Glu Ser Pro Ser Lys
                805                 810                 815

Leu Ala Ser Ala Ile Gln Lys Ala His Glu Glu Asp Ile Cys Gly Ile
            820                 825                 830

Arg Ser Val Thr Arg Leu Glu Asn Leu Met Trp Lys Gln Ile Thr Pro
    835                 840                 845

Glu Leu Asn His Ile Leu Ser Glu Asn Glu Val Lys Leu Thr Ile Met
    850                 855                 860

Thr Gly Asp Ile Lys Gly Ile Met Gln Ala Gly Lys Arg Ser Leu Arg
865                 870                 875                 880

Pro Gln Pro Thr Glu Leu Lys Tyr Ser Trp Lys Thr Trp Gly Lys Ala
                885                 890                 895

Lys Met Leu Ser Thr Glu Ser His Asn Gln Thr Phe Leu Ile Asp Gly
            900                 905                 910

Pro Glu Thr Ala Glu Cys Pro Asn Thr Asn Arg Ala Trp Asn Ser Leu
    915                 920                 925

Glu Val Glu Asp Tyr Gly Phe Gly Val Phe Thr Thr Asn Ile Trp Leu
    930                 935                 940

Lys Leu Lys Glu Lys Gln Asp Val Phe Cys Asp Ser Lys Leu Met Ser
945                 950                 955                 960

Ala Ala Ile Lys Asp Asn Arg Ala Val His Ala Asp Met Gly Tyr Trp
                965                 970                 975

Ile Glu Ser Ala Leu Asn Asp Thr Trp Lys Ile Glu Lys Ala Ser Phe
            980                 985                 990

Ile Glu Val Lys Asn Cys His Trp Pro Lys Ser His Thr Leu Trp Ser
    995                 1000                1005

Asn Gly Val Leu Glu Ser Glu Met Ile Ile Pro Lys Asn Leu Ala
```

```
            1010                1015                1020
Gly Pro Val Ser Gln His Asn Tyr Arg Pro Gly Tyr His Thr Gln
        1025                1030                1035
Ile Thr Gly Pro Trp His Leu Gly Lys Leu Glu Met Asp Phe Asp
        1040                1045                1050
Phe Cys Asp Gly Thr Thr Val Val Thr Glu Asp Cys Gly Asn
        1055                1060                1065
Arg Gly Pro Ser Leu Arg Thr Thr Ala Ser Gly Lys Leu Ile
        1070                1075                1080
Thr Glu Trp Cys Cys Arg Ser Cys Thr Leu Pro Pro Leu Arg Tyr
        1085                1090                1095
Arg Gly Glu Asp Gly Cys Trp Tyr Gly Met Glu Ile Arg Pro Leu
        1100                1105                1110
Lys Glu Lys Glu Glu Asn Leu Val Asn Ser Leu Val Thr Ala Gly
        1115                1120                1125
His Gly Gln Val Asp Asn Phe Ser Leu Gly Val Leu Gly Met Ala
        1130                1135                1140
Leu Phe Leu Glu Glu Met Leu Arg Thr Arg Val Gly Thr Lys His
        1145                1150                1155
Ala Ile Leu Leu Val Ala Val Ser Phe Val Thr Leu Ile Thr Gly
        1160                1165                1170
Asn Met Ser Phe Arg Asp Leu Gly Arg Val Met Val Met Val Gly
        1175                1180                1185
Ala Thr Met Thr Asp Asp Ile Gly Met Gly Val Thr Tyr Leu Ala
        1190                1195                1200
Leu Leu Ala Ala Phe Lys Val Arg Pro Thr Phe Ala Ala Gly Leu
        1205                1210                1215
Leu Leu Arg Lys Leu Thr Ser Lys Glu Leu Met Met Thr Thr Ile
        1220                1225                1230
Gly Ile Val Leu Leu Ser Gln Ser Thr Ile Pro Glu Thr Ile Leu
        1235                1240                1245
Glu Leu Thr Asp Ala Leu Ala Leu Gly Met Met Val Leu Lys Met
        1250                1255                1260
Val Arg Asn Met Glu Lys Tyr Gln Leu Ala Val Thr Ile Met Ala
        1265                1270                1275
Ile Leu Cys Val Pro Asn Ala Val Ile Leu Gln Asn Ala Trp Lys
        1280                1285                1290
Val Ser Cys Thr Ile Leu Ala Val Val Ser Val Ser Pro Leu Phe
        1295                1300                1305
Leu Thr Ser Ser Gln Gln Lys Thr Asp Trp Ile Pro Leu Ala Leu
        1310                1315                1320
Thr Ile Lys Gly Leu Asn Pro Thr Ala Ile Phe Leu Thr Thr Leu
        1325                1330                1335
Ser Arg Thr Ser Lys Lys Arg Ser Trp Pro Leu Asn Glu Ala Ile
        1340                1345                1350
Met Ala Val Gly Met Val Ser Ile Leu Ala Ser Ser Leu Leu Lys
        1355                1360                1365
Asn Asp Ile Pro Met Thr Gly Pro Leu Val Ala Gly Gly Leu Leu
        1370                1375                1380
Thr Val Cys Tyr Val Leu Thr Gly Arg Ser Ala Asp Leu Glu Leu
        1385                1390                1395
Glu Arg Ala Ala Asp Val Lys Trp Glu Asp Gln Ala Glu Ile Ser
        1400                1405                1410
```

```
Gly Ser Ser Pro Ile Leu Ser Ile Thr Ile Ser Glu Asp Gly Ser
    1415                1420                1425

Met Ser Ile Lys Asn Glu Glu Glu Gln Thr Leu Thr Ile Leu
    1430                1435                1440

Ile Arg Thr Gly Leu Leu Val Ile Ser Gly Leu Phe Pro Val Ser
    1445                1450                1455

Ile Pro Ile Thr Ala Ala Ala Trp Tyr Leu Trp Glu Val Lys Lys
    1460                1465                1470

Gln Arg Ala Gly Val Leu Trp Asp Val Pro Ser Pro Pro Met
    1475                1480                1485

Gly Lys Ala Glu Leu Glu Asp Gly Ala Tyr Arg Ile Lys Gln Lys
    1490                1495                1500

Gly Ile Leu Gly Tyr Ser Gln Ile Gly Ala Gly Val Tyr Lys Glu
    1505                1510                1515

Gly Thr Phe His Thr Met Trp His Val Thr Arg Gly Ala Val Leu
    1520                1525                1530

Met His Lys Gly Lys Arg Ile Glu Pro Ser Trp Ala Asp Val Lys
    1535                1540                1545

Lys Asp Leu Ile Ser Tyr Gly Gly Gly Trp Lys Leu Glu Gly Glu
    1550                1555                1560

Trp Lys Glu Gly Glu Glu Val Gln Val Leu Ala Leu Glu Pro Gly
    1565                1570                1575

Lys Asn Pro Arg Ala Val Gln Thr Lys Pro Gly Leu Phe Lys Thr
    1580                1585                1590

Asn Ala Gly Thr Ile Gly Ala Val Ser Leu Asp Phe Ser Pro Gly
    1595                1600                1605

Thr Ser Gly Ser Pro Ile Ile Asp Lys Lys Gly Lys Val Val Gly
    1610                1615                1620

Leu Tyr Gly Asn Gly Val Val Thr Arg Ser Gly Ala Tyr Val Ser
    1625                1630                1635

Ala Ile Ala Gln Thr Glu Lys Ser Ile Glu Asp Asn Pro Glu Ile
    1640                1645                1650

Glu Asp Asp Ile Phe Arg Lys Arg Arg Leu Thr Ile Met Asp Leu
    1655                1660                1665

His Pro Gly Ala Gly Lys Thr Lys Arg Tyr Leu Pro Ala Ile Val
    1670                1675                1680

Arg Glu Ala Ile Lys Arg Gly Leu Arg Thr Leu Ile Leu Ala Pro
    1685                1690                1695

Thr Arg Val Val Ala Ala Glu Met Glu Glu Ala Leu Arg Gly Leu
    1700                1705                1710

Pro Ile Arg Tyr Gln Thr Pro Ala Ile Arg Ala Val His Thr Gly
    1715                1720                1725

Arg Glu Ile Val Asp Leu Met Cys His Ala Thr Phe Thr Met Arg
    1730                1735                1740

Leu Leu Ser Pro Val Arg Val Pro Asn Tyr Asn Leu Ile Ile Met
    1745                1750                1755

Asp Glu Ala His Phe Thr Asp Pro Ala Ser Ile Ala Ala Arg Gly
    1760                1765                1770

Tyr Ile Ser Thr Arg Val Glu Met Gly Glu Ala Ala Gly Ile Phe
    1775                1780                1785

Met Thr Ala Thr Pro Pro Gly Ser Arg Asp Pro Phe Pro Gln Ser
    1790                1795                1800
```

-continued

Asn Ala Pro Ile Ile Asp Glu Arg Glu Ile Pro Glu Arg Ser
    1805            1810            1815

Trp Asn Ser Gly His Glu Trp Val Thr Asp Phe Lys Gly Lys Thr
    1820            1825            1830

Val Trp Phe Val Pro Ser Ile Lys Ala Gly Asn Asp Ile Ala Ala
    1835            1840            1845

Cys Leu Arg Lys Asn Gly Lys Lys Val Ile Gln Leu Ser Arg Lys
    1850            1855            1860

Thr Phe Asp Ser Glu Tyr Val Lys Thr Arg Thr Asn Asp Trp Asp
    1865            1870            1875

Phe Val Val Thr Thr Asp Ile Ser Glu Met Gly Ala Asn Phe Lys
    1880            1885            1890

Ala Glu Arg Val Ile Asp Pro Arg Arg Cys Met Lys Pro Val Ile
    1895            1900            1905

Leu Thr Asp Gly Glu Glu Arg Val Ile Leu Ala Gly Pro Met Pro
    1910            1915            1920

Val Thr His Ser Ser Ala Ala Gln Arg Arg Gly Arg Ile Gly Arg
    1925            1930            1935

Asn Pro Lys Asn Glu Asn Asp Gln Tyr Ile Tyr Met Gly Glu Pro
    1940            1945            1950

Leu Glu Asn Asp Glu Asp Cys Ala His Trp Lys Glu Ala Lys Met
    1955            1960            1965

Leu Leu Asp Asn Ile Asn Thr Pro Glu Gly Ile Ile Pro Ser Met
    1970            1975            1980

Phe Glu Pro Glu Arg Glu Lys Val Asp Ala Ile Asp Gly Glu Tyr
    1985            1990            1995

Arg Leu Arg Gly Glu Ala Arg Lys Thr Phe Val Asp Leu Met Arg
    2000            2005            2010

Arg Gly Asp Leu Pro Val Trp Leu Ala Tyr Arg Val Ala Ala Glu
    2015            2020            2025

Gly Ile Asn Tyr Ala Asp Arg Arg Trp Cys Phe Asp Gly Val Lys
    2030            2035            2040

Asn Asn Gln Ile Leu Glu Glu Asn Val Glu Val Glu Ile Trp Thr
    2045            2050            2055

Lys Glu Gly Glu Arg Lys Lys Leu Lys Pro Arg Trp Leu Asp Ala
    2060            2065            2070

Arg Ile Tyr Ser Asp Pro Leu Ala Leu Lys Glu Phe Lys Glu Phe
    2075            2080            2085

Ala Ala Gly Arg Lys Ser Leu Thr Leu Asn Leu Ile Thr Glu Met
    2090            2095            2100

Gly Arg Leu Pro Thr Phe Met Thr Gln Lys Ala Arg Asp Ala Leu
    2105            2110            2115

Asp Asn Leu Ala Val Leu His Thr Ala Glu Ala Gly Gly Arg Ala
    2120            2125            2130

Tyr Asn His Ala Leu Ser Glu Leu Pro Glu Thr Leu Glu Thr Leu
    2135            2140            2145

Leu Leu Leu Thr Leu Leu Ala Thr Val Thr Gly Gly Ile Phe Leu
    2150            2155            2160

Phe Leu Met Ser Ala Arg Gly Ile Gly Lys Met Thr Leu Gly Met
    2165            2170            2175

Cys Cys Ile Ile Thr Ala Ser Ile Leu Leu Trp Tyr Ala Gln Ile
    2180            2185            2190

Gln Pro His Trp Ile Ala Ala Ser Ile Ile Leu Glu Phe Phe Leu

-continued

|  | 2195 |  |  |  | 2200 |  |  |  | 2205 |  |
|---|---|---|---|---|---|---|---|---|---|---|
| Ile | Val | Leu | Leu | Ile | Pro | Glu | Pro | Glu | Lys | Gln | Arg | Thr | Pro | Gln |
|  | 2210 |  |  |  | 2215 |  |  |  | 2220 |  |

Asp Asn Gln Leu Thr Tyr Val Val Ile Ala Ile Leu Thr Val Val
    2225                2230                2235

Ala Ala Thr Met Ala Asn Glu Met Gly Phe Leu Glu Lys Thr Lys
    2240                2245                2250

Lys Asp Leu Gly Leu Gly Ser Ile Ala Thr Gln Gln Pro Glu Ser
    2255                2260                2265

Asn Ile Leu Asp Ile Asp Leu Arg Pro Ala Ser Ala Trp Thr Leu
    2270                2275                2280

Tyr Ala Val Ala Thr Thr Phe Val Thr Pro Met Leu Arg His Ser
    2285                2290                2295

Ile Glu Asn Ser Ser Val Asn Val Ser Leu Thr Ala Ile Ala Asn
    2300                2305                2310

Gln Ala Thr Val Leu Met Gly Leu Gly Lys Gly Trp Pro Leu Ser
    2315                2320                2325

Lys Met Asp Ile Gly Val Pro Leu Leu Ala Ile Gly Cys Tyr Ser
    2330                2335                2340

Gln Val Asn Pro Ile Thr Leu Thr Ala Ala Leu Phe Leu Leu Val
    2345                2350                2355

Ala His Tyr Ala Ile Ile Gly Pro Gly Leu Gln Ala Lys Ala Thr
    2360                2365                2370

Arg Glu Ala Gln Lys Arg Ala Ala Ala Gly Ile Met Lys Asn Pro
    2375                2380                2385

Thr Val Asp Gly Ile Thr Val Ile Asp Leu Asp Pro Ile Pro Tyr
    2390                2395                2400

Asp Pro Lys Phe Glu Lys Gln Leu Gly Gln Val Met Leu Leu Val
    2405                2410                2415

Leu Cys Val Thr Gln Val Leu Met Met Arg Thr Thr Trp Ala Leu
    2420                2425                2430

Cys Glu Ala Leu Thr Leu Ala Thr Gly Pro Ile Ser Thr Leu Trp
    2435                2440                2445

Glu Gly Asn Pro Gly Arg Phe Trp Asn Thr Thr Ile Ala Val Ser
    2450                2455                2460

Met Ala Asn Ile Phe Arg Gly Ser Tyr Leu Ala Gly Ala Gly Leu
    2465                2470                2475

Leu Phe Ser Ile Met Lys Asn Thr Thr Asn Thr Arg Arg Gly Thr
    2480                2485                2490

Gly Asn Ile Gly Glu Thr Leu Gly Glu Lys Trp Lys Ser Arg Leu
    2495                2500                2505

Asn Ala Leu Gly Lys Ser Glu Phe Gln Ile Tyr Lys Lys Ser Gly
    2510                2515                2520

Ile Gln Glu Val Asp Arg Thr Leu Ala Lys Glu Gly Ile Lys Arg
    2525                2530                2535

Gly Glu Thr Asp His His Ala Val Ser Arg Gly Ser Ala Lys Leu
    2540                2545                2550

Arg Trp Phe Val Glu Arg Asn Met Val Thr Pro Glu Gly Lys Val
    2555                2560                2565

Val Asp Leu Gly Cys Gly Arg Gly Gly Trp Ser Tyr Tyr Cys Gly
    2570                2575                2580

Gly Leu Lys Asn Val Arg Glu Val Lys Gly Leu Thr Lys Gly Gly
    2585                2590                2595

```
Pro Gly His Glu Pro Ile Pro Met Ser Thr Tyr Gly Trp Asn
    2600            2605            2610

Leu Val Arg Leu Gln Ser Gly Val Asp Val Phe Phe Ile Pro Pro
    2615            2620            2625

Glu Lys Cys Asp Thr Leu Leu Cys Asp Ile Gly Glu Ser Ser Pro
    2630            2635            2640

Asn Pro Thr Val Glu Ala Gly Arg Thr Leu Arg Val Leu Asn Leu
    2645            2650            2655

Val Glu Asn Trp Leu Asn Asn Thr Gln Phe Cys Ile Lys Val
    2660            2665            2670

Leu Asn Pro Tyr Met Pro Ser Val Ile Glu Lys Met Glu Ala Leu
    2675            2680            2685

Gln Arg Lys Tyr Gly Gly Ala Leu Val Arg Asn Pro Leu Ser Arg
    2690            2695            2700

Asn Ser Thr His Glu Met Tyr Trp Val Ser Asn Ala Ser Gly Asn
    2705            2710            2715

Ile Val Ser Ser Val Asn Met Ile Ser Arg Met Leu Ile Asn Arg
    2720            2725            2730

Phe Thr Met Arg Tyr Lys Lys Ala Thr Tyr Glu Pro Asp Val Asp
    2735            2740            2745

Leu Gly Ser Gly Thr Arg Asn Ile Gly Ile Glu Ser Glu Ile Pro
    2750            2755            2760

Asn Leu Asp Ile Ile Gly Lys Arg Ile Glu Lys Ile Lys Gln Glu
    2765            2770            2775

His Glu Thr Ser Trp His Tyr Asp Gln Asp His Pro Tyr Lys Thr
    2780            2785            2790

Trp Ala Tyr His Gly Ser Tyr Glu Thr Lys Gln Thr Gly Ser Ala
    2795            2800            2805

Ser Ser Met Val Asn Gly Val Val Arg Leu Leu Thr Lys Pro Trp
    2810            2815            2820

Asp Val Val Pro Met Val Thr Gln Met Ala Met Thr Asp Thr Thr
    2825            2830            2835

Pro Phe Gly Gln Gln Arg Val Phe Lys Glu Lys Val Asp Thr Arg
    2840            2845            2850

Thr Gln Glu Pro Lys Glu Gly Thr Lys Lys Leu Met Lys Ile Thr
    2855            2860            2865

Ala Glu Trp Leu Trp Lys Glu Leu Gly Lys Lys Lys Thr Pro Arg
    2870            2875            2880

Met Cys Thr Arg Glu Glu Phe Thr Arg Lys Val Arg Ser Asn Ala
    2885            2890            2895

Ala Leu Gly Ala Ile Phe Thr Asp Glu Asn Lys Trp Lys Ser Ala
    2900            2905            2910

Arg Glu Ala Val Glu Asp Ser Arg Phe Trp Glu Leu Val Asp Lys
    2915            2920            2925

Glu Arg Asn Leu His Leu Glu Gly Lys Cys Glu Thr Cys Val Tyr
    2930            2935            2940

Asn Met Met Gly Lys Arg Glu Lys Lys Leu Gly Glu Phe Gly Lys
    2945            2950            2955

Ala Lys Gly Ser Arg Ala Ile Trp Tyr Met Trp Leu Gly Ala Arg
    2960            2965            2970

Phe Leu Glu Phe Glu Ala Leu Gly Phe Leu Asn Glu Asp His Trp
    2975            2980            2985
```

-continued

```
Phe Ser Arg Glu Asn Ser Leu Ser Gly Val Glu Gly Glu Gly Leu
2990                2995                3000

His Lys Leu Gly Tyr Ile Leu Arg Asp Val Ser Lys Lys Glu Gly
3005                3010                3015

Gly Ala Met Tyr Ala Asp Asp Thr Ala Gly Trp Asp Thr Arg Ile
3020                3025                3030

Thr Leu Glu Asp Leu Lys Asn Glu Glu Met Val Thr Asn His Met
3035                3040                3045

Glu Gly Glu His Lys Lys Leu Ala Glu Ala Ile Phe Lys Leu Thr
3050                3055                3060

Tyr Gln Asn Lys Val Val Arg Val Gln Arg Pro Thr Pro Arg Gly
3065                3070                3075

Thr Val Met Asp Ile Ile Ser Arg Arg Asp Gln Arg Gly Ser Gly
3080                3085                3090

Gln Val Gly Thr Tyr Gly Leu Asn Thr Phe Thr Asn Met Glu Ala
3095                3100                3105

Gln Leu Ile Arg Gln Met Glu Gly Glu Gly Val Phe Lys Ser Ile
3110                3115                3120

Gln His Leu Thr Ile Thr Glu Glu Ile Ala Val Gln Asn Trp Leu
3125                3130                3135

Ala Arg Val Gly Arg Glu Arg Leu Ser Arg Met Ala Ile Ser Gly
3140                3145                3150

Asp Asp Cys Val Val Lys Pro Leu Asp Asp Arg Phe Ala Ser Ala
3155                3160                3165

Leu Thr Ala Leu Asn Asp Met Gly Lys Ile Arg Lys Asp Ile Gln
3170                3175                3180

Gln Trp Glu Pro Ser Arg Gly Trp Asn Asp Trp Thr Gln Val Pro
3185                3190                3195

Phe Cys Ser His His Phe His Glu Leu Ile Met Lys Asp Gly Arg
3200                3205                3210

Val Leu Val Val Pro Cys Arg Asn Gln Asp Glu Leu Ile Gly Arg
3215                3220                3225

Ala Arg Ile Ser Gln Gly Ala Gly Trp Ser Leu Arg Glu Thr Ala
3230                3235                3240

Cys Leu Gly Lys Ser Tyr Ala Gln Met Trp Ser Leu Met Tyr Phe
3245                3250                3255

His Arg Arg Asp Leu Arg Leu Ala Ala Asn Ala Ile Cys Ser Ala
3260                3265                3270

Val Pro Ser His Trp Val Pro Thr Ser Arg Thr Thr Trp Ser Ile
3275                3280                3285

His Ala Lys His Glu Trp Met Thr Thr Glu Asp Met Leu Thr Val
3290                3295                3300

Trp Asn Arg Val Trp Ile Gln Glu Asn Pro Trp Met Glu Asp Lys
3305                3310                3315

Thr Pro Val Glu Ser Trp Glu Glu Ile Pro Tyr Leu Gly Lys Arg
3320                3325                3330

Glu Asp Gln Trp Cys Gly Ser Leu Ile Gly Leu Thr Ser Arg Ala
3335                3340                3345

Thr Trp Ala Lys Asn Ile Gln Ala Ala Ile Asn Gln Val Arg Ser
3350                3355                3360

Leu Ile Gly Asn Glu Glu Tyr Thr Asp Tyr Met Pro Ser Met Lys
3365                3370                3375

Arg Phe Arg Arg Glu Glu Glu Ala Gly Val Leu Trp
```

<210> SEQ ID NO 24
<211> LENGTH: 10723
<212> TYPE: DNA
<213> ORGANISM: Artificial Sequence
<220> FEATURE:
<223> OTHER INFORMATION: Derived from Dengue virus serotype 2/Dengue virus serotype 4, DEN, 4h

<400> SEQUENCE: 24

```
agttgttagt ctacgtggac cgacaaagac agattctttg agggagctaa gctcaatgta      60
gttctaacag tttttttaatt agagagcaga tctctgatga ataaccaacg aaaaaggcg     120
aaaaacacgc ctttcaatat gctgaaacgc gagagaaacc gcgtgtcgac tgtgcaacag     180
ctgacaaaga gattctcact tggaatgctg cagggacgag gaccattaaa actgttcatg     240
gccctggtgg cgttccttcg tttcctaaca atcccaccaa cagcagggat attgaagaga     300
tggggaacaa ttaaaaaatc aaaagctatt aatgttttga gagggttcag aaagagaatt     360
ggaaggatgc tgaacatctt gaataggaga cgcagctctg caggcatgat cattatgctg     420
attccaacag tgatggcgtt ccatttaacc acgcgtgatg cgaacccct catgatagtg     480
gcaaaacatg aaagggggag acctctcttg tttaagacaa cagaggggat caacaaatgc     540
actctcattg ccatggactt gggtgaaatg tgtgaggaca ctgtcacgta taatgccccc     600
ttactggtca ataccgaacc tgaagacatt gattgctggt gcaatctcac gtctacctgg     660
gtcatgtatg gacatgcac ccagagcgga gaacggagac gagagaagcg ctcagtagct     720
ttaacaccac attcaggaat gggattggaa acaagagctg agacatggat gtcatcggaa     780
gggctggga agcatgctca gagagtagag agctggatac tcagaaaccc aggattcgcg     840
ctcttggcag gatttatggc ttatatgatt gggcaaacag gaatccagcg aactgtcttc     900
tttgtcctaa tgatgctggt cgccccatcc tacggaatgc gatgcgtagg agtaggaaac     960
agagacttg tggaaggagt ctcaggtgga gcatgggtcg atctggtgct agaacatgga    1020
ggatgcgtca acatggc ccagggaaaa ccaaccttgg attttgaact gactaagaca    1080
acagccaagg aagtggctct gttaagaacc tattgcattg aagcctcaat atcaaacata    1140
accacggcaa caagatgtcc aacgcaagga gagccttatc taaaagagga acaagaccaa    1200
cagtacattt gccggagaga tgtggtagac agaggtgggg gcaatggctg tggcttgttt    1260
ggaaaaggag gagttgtgac atgtgcgaag tttttcatgtt cggggaagat aacaggcaat    1320
ttggtccaaa ttgagaacct tgaatacaca gtggttgtaa cagtcacaa tggagacacc    1380
catgcagtag gaaatgacac gtccaatcat ggagttacag ccacgataac tcccaggtca    1440
ccatcggtgg aagtcaaatt gccggactat ggagaactaa cactcgattg tgaacccag    1500
tctggaattg actttaatga gatgattctg atgaaaatga aaaagaaaac atggcttgtg    1560
cataagcaat ggtttttgga tctacctcta ccatggacag caggagcaga cacatcagag    1620
gttcactgga attacaaaga gagaatggtg acatttaagg ttcctcatgc caagagacag    1680
gatgtgacag tgctgggatc tcaggaagga gccatgcatt ctgccctcgc tggagccaca    1740
gaagtggact ccgtgatgg aaatcacatg tttgcaggac atctcaagtg caaagtccgt    1800
atggagaaat tgagaatcaa gggaatgtca tacacgatgt gttcaggaaa gttctcaatt    1860
gacaaagaga tggcagaaac acagcatggg acaacagtgg tgaaagtcaa gtatgaaggt    1920
gctggagctc cgtgtaaagt ccccatagag ataagagatg tgaacaagga aaaagtggtt    1980
```

```
gggcgtatca tctcatccac cccttttggct gagaatacca acagtgtaac caacatagag    2040
ttagaacccc cctttgggga cagctacata gtgataggtg ttggaaacag tgcattaaca    2100
ctccattggt tcaggaaagg gagttccatt ggcaagatgt ttgagtccac atacagaggt    2160
gcaaaacgaa tggccattct aggtaaaaca gcttgggatt ttggttccgt tggtggactg    2220
ttcacatcat tgggaaaggc tgtgcaccag gttttttggaa gtgtgtatac aaccctgttt    2280
ggaggagtct catggatgat tagaatccta attgggttcc tagtgttgtg gattggcacg    2340
aactcaagga acacttcaat ggctatgacg tgcatagctg ccggcattgt gacactgtat    2400
ttgggagtca tggtgcaggc cgatagtggt tgcgttgtga gctggaaaaa caaagaactg    2460
aaatgtggca gtgggatttt catcacagac aacgtgcaca catggacaga acaatacaag    2520
ttccaaccag aatcccttc aaaactagct tcagctatcc agaaagccca tgaagaggac    2580
atttgtggaa tccgctcagt aacaagactg gagaatctga tgtggaaaca aataacacca    2640
gaattgaatc acattctatc agaaaatgag gtgaagttaa ctattatgac aggagacatc    2700
aaaggaatca tgcaggcagg aaaacgatct ctgcggcctc agcccactga gctgaagtat    2760
tcatggaaaa catggggcaa agcaaaaatg ctctctacag agtctcataa ccagaccttt    2820
ctcattgatg gcccccgaaac agcagaatgc cccaacacaa atagagcttg gaattcgttg    2880
gaagttgaag actatggctt tggagtattc accaccaata tatggctaaa attgaaagaa    2940
aaacaggatg tattctgcga ctcaaaactc atgtcagcgg ccataaaaga caacagagcc    3000
gtccatgccg atatgggtta ttggatagaa agtgcactca atgacacatg gaagatagag    3060
aaagcctctt tcattgaagt taaaaactgc cactggccaa aatcacacac cctctggagc    3120
aatggagtgc tagaaagtga aatgataat ccaaagaatc tcgctggacc agtgtctcaa    3180
cacaactata gaccaggcta ccatacacaa ataacaggac catggcatct aggtaagctt    3240
gagatggact ttgatttctg tgatggaaca acagtggtag tgactgagga ctgcggaaat    3300
agaggaccct ctttgagaac aaccactgcc tctggaaaaac tcataacaga atggtgctgc    3360
cgatcttgca cattaccacc gctaagatac agaggtgagg atgggtgctg gtacgggatg    3420
gaaatcagac cattgaagga gaagaagag aatttggtca actccttggt cacagctgga    3480
catgggcagg tcgacaactt ttcactagga gtcttgggaa tggcattgtt cctggaggaa    3540
atgcttagga cccgagtagg aacgaaacat gcaatactac tagttgcagt ttcttttgtg    3600
acattgatca cagggaacat gtcctttaga gacctgggaa gagtgatggt tatggtaggc    3660
gccactatga cggatgacat aggtatgggc gtgacttatc ttgccctact agcagccttc    3720
aaagtcagac caacttttgc agctggacta ctcttgagaa agctgacctc caaggaattg    3780
atgatgacta ctataggaat tgtactcctc tcccagagca ccataccaga gaccattctt    3840
gagttgactg atgcgttagc cttaggcatg atggtcctca aaatggtgag aaatatggaa    3900
aagtatcaat tggcagtgac tatcatggct atcttgtgcg tcccaaacgc agtgatatta    3960
caaaacgcat ggaaagtgag ttgcacaata ttggcagtgg tgtccgtttc cccactgttc    4020
ttaacatcct cacagcaaaa aacagattgg ataccattag cattgacgat caaaggtctc    4080
aatccaacag ctatttttct aacaaccctc tcaagaacca gcaagaaaag gagctggcca    4140
ttaaatgagg ctatcatggc agtcgggatg gtgagcattt tagccagttc tctcctaaaa    4200
aatgatattc ccatgacagg accattagtg gctggagggc tcctcactgt gtgctacgtg    4260
ctcactggac gatcggccga tttgaactg gagagagcag ccgatgtcaa atgggaagac    4320
caggcagaga tatcaggaag cagtccaatc ctgtcaataa caatatcaga agatggtagc    4380
```

```
atgtcgataa aaaatgaaga ggaagaacaa acactgacca tactcattag aacaggattg    4440
ctggtgatct caggactttt tcctgtatca ataccaatca cggcagcagc atggtacctg    4500
tgggaagtga agaaacaacg ggccggagta ttgtgggatg ttccttcacc cccacccatg    4560
ggaaaggctg aactgaaga tggagcctat agaattaagc aaaaagggat tcttggatat    4620
tcccagatcg gagccggagt ttacaaagaa ggaacattcc atacaatgtg gcatgtcaca    4680
cgtggcgctg ttctaatgca taaaggaaag aggattgaac catcatgggc ggacgtcaag    4740
aaagacctaa tatcatatgg aggaggctgg aagttagaag gagaatggaa ggaaggagaa    4800
gaagtccagg tattggcact ggagcctgga aaaaatccaa gagccgtcca aacgaaacct    4860
ggtcttttca aaaccaacgc cggaacaata ggtgctgtat ctctggactt ttctcctgga    4920
acgtcaggat ctccaattat cgacaaaaaa ggaaaagttg tgggtcttta tggtaatggt    4980
gttgttacaa ggagtggagc atatgtgagt gctatagccc agactgaaaa aagcattgaa    5040
gacaacccag atcgaagaa tgacattttc cgaaagagaa gactgaccat catggacctc    5100
cacccaggag cgggaaagac gaagagatac cttccggcca tagtcagaga agctataaaa    5160
cggggtttga acattaat cttggccccc actagagttg tggcagctga atgaggaa    5220 gcccttagag gacttccaat aagataccag accccagcca tcagagctgt gcacaccggg    5280
cgggagattg tggacctaat gtgtcatgcc acatttacca tgaggctgct atcaccagtt    5340
agagtgccaa actacaacct gattatcatg gacgaagccc atttcacaga cccagcaagt    5400
atagcagcta gaggatacat ctcaactcga gtggagatgg gtgaggcagc tgggattttt    5460
atgacagcca ctccccggg aagcagagac ccatttcctc agagcaatgc accaatcata    5520
gatgaagaaa gagaaatccc tgaacgctcg tggaattccg gacatgaatg ggtcacggat    5580
tttaaaggga gactgtttg gttcgttcca agtataaaag caggaaatga tatagcagct    5640
tgcctgagga aaaatggaaa gaaagtgata caactcagta ggaagacctt tgattctgag    5700
tatgtcaaga ctagaaccaa tgattgggac ttcgtggtta caactgacat ttcagaaatg    5760
ggtgccaatt tcaaggctga gagggttata gaccccagac gctgcatgaa accagtcata    5820
ctaacagatg gtgaagagcg ggtgattctg gcaggaccta tgccagtgac ccactctagt    5880
gcagcacaaa aagagggag aataggaaga aatccaaaaa atgagaatga ccagtacata    5940
tacatggggg aacctctgga aaatgatgaa gactgtgcac actggaaaga agctaaaatg    6000
ctcctagata acatcaacac gccagaagga atcattccta gcatgttcga accagagcgt    6060
gaaaaggtgg atgccattga tggcgaatac cgcttgagag agaagcaag gaaaacccttt    6120 gtagacttaa tgagaagagg agacctacca gtctggttgg cctacagagt ggcagctgaa    6180
ggcatcaact acgcagacag aaggtggtgt tttgatggag tcaagaacaa ccaaatccta    6240
gaagaaaacg tggaagttga atctggaca aaagaagggg aaaggaagaa attgaacccc    6300
agatggttgg atgctaggat ctattctgac ccactggcgc taaaagaatt taaggaattt    6360
gcagccggaa gaaagtctct gaccctgaac ctaatcacag aaatgggtag gctcccaacc    6420
ttcatgactc agaaggcaag agacgcactg gacaacttag cagtgctgca cacggctgag    6480
gcaggtggaa gggcgtacaa ccatgctctc agtgaactgc cggagaccct ggagacattg    6540
cttttactga cacttctggc tacagtcacg ggagggatct ttttattctt gatgagcgca    6600 agggcatag gaagatgac cctgggaatg tgctgcataa tcacggctag catcctccta    6660
tggtacgcac aaatacagcc acactggata gcagcttcaa taatactgga gttttttctc    6720
```

| | |
|---|---|
| atagttttgc ttattccaga acctgaaaaa cagagaacac cccaagacaa ccaactgacc | 6780 |
| tacgttgtca tagccatcct cacagtggtg gccgcaacca tggcaaacga gatgggtttc | 6840 |
| ctagaaaaaa cgaagaaaga tctcggattg ggaagcattg caacccagca acccgagagc | 6900 |
| aacatcctgg acatagatct acgtcctgca tcagcatgga cgctgtatgc cgtggccaca | 6960 |
| acatttgtta caccaatgtt gagacatagc attgaaaatt cctcagtgaa tgtgtccta | 7020 |
| acagctatag ccaaccaagc cacagtgtta atgggtctcg ggaaaggatg gccattgtca | 7080 |
| aagatggaca tcggagttcc ccttctcgcc attggatgct actcacaagt caaccccata | 7140 |
| actctcacag cagctctttt cttattggta gcacattatg ccatcatagg gccaggactc | 7200 |
| caagcaaaag caaccagaga agctcagaaa agagcagcgg cgggcatcat gaaaaaccca | 7260 |
| actgtcgatg gaataacagt gattgaccta gatccaatac cttatgatcc aaagtttgaa | 7320 |
| aagcagttgg gacaagtaat gctcctagtc ctctgcgtga ctcaagtatt gatgatgagg | 7380 |
| actacatggg ctctgtgtga ggctttaacc ttagctaccg ggcccatctc acattgtgg | 7440 |
| gaaggaaatc cagggaggtt ttggaacact accattgcgg tgtcaatggc taacattttt | 7500 |
| agagggagtt acttggccgg agctggactt ctctttttcta ttatgaagaa cacaaccaac | 7560 |
| acaagaaggg gaactggcaa catagagag acgcttggag agaaatggaa aagccgattg | 7620 |
| aacgcattgg gaaaaagtga attccagatc tacaagaaaa gtggaatcca ggaagtggat | 7680 |
| agaaccttag caaagaagg cattaaaaga ggagaaacgg accatcacgc tgtgtcgcga | 7740 |
| ggctcagcaa aactgagatg gttcgttgag agaaacatgg tcacaccaga agggaaagta | 7800 |
| gtggacctcg gttgtggcag aggaggctgg tcatactatt gtggaggact aaagaatgta | 7860 |
| agagaagtca aaggcctaac aaaaggagga ccaggacacg aagaacccat ccccatgtca | 7920 |
| acatatgggt ggaatctagt gcgtcttcaa agtggagttg acgttttctt catcccgcca | 7980 |
| gaaaagtgtg acacattatt gtgtgacata ggggagtcat caccaaatcc cacagtggaa | 8040 |
| gcaggacgaa cactcagagt ccttaactta gtagaaaatt ggttgaacaa caacactcaa | 8100 |
| ttttgcataa aggttctcaa cccatatatg ccctcagtca tagaaaaaat ggaagcacta | 8160 |
| caaaggaaat atggaggagc cttagtgagg aatccactct cacgaaactc cacacatgag | 8220 |
| atgtactggg tatccaatgc ttccgggaac atagtgtcat cagtgaacat gatttcaagg | 8280 |
| atgttgatca acagatttac aatgagatac aagaaagcca cttacagcc ggatgttgac | 8340 |
| ctcggaagcg gaacccgtaa catcgggatt gaaagtgaga taccaaacct agatataatt | 8400 |
| gggaaagaa tagaaaaaat aaagcaagag catgaaacat catggcacta tgaccaagac | 8460 |
| caccataca aaacgtgggc ataccatggt agctatgaaa caaaacagac tggatcagca | 8520 |
| tcatccatgg tcaacggagt ggtcaggctg ctgacaaaac cttgggacgt cgtccccatg | 8580 |
| gtgacacaga tggcaatgac agacacgact ccatttggac aacagcgcgt ttttaaagag | 8640 |
| aaagtggaca cgagaaccca agaaccgaaa gaaggcacga gaaactaat gaaaataaca | 8700 |
| gcagagtggc tttggaaaga attagggaag aaaaagacac ccaggatgtg caccagagaa | 8760 |
| gaattcacaa gaaaggtgag aagcaatgca gccttggggg ccatattcac tgatgagaac | 8820 |
| aagtggaagt cggcacgtga ggctgttgaa gatagtaggt tgggagct ggttgacaag | 8880 |
| gaaaggaatc tccatcttga aggaaagtgt gaaacatgtg tgtacaacat gatgggaaaa | 8940 |
| agagagaaga agctagggga attcggcaag gcaaaaggca gcagagccat atggtacatg | 9000 |
| tggcttggag cacgcttctt agagtttgaa gccctaggat tcttaaatga agatcactgg | 9060 |
| ttctccagag agaactccct gagtggagtg gaaggagaag ggctgcacaa gctaggttac | 9120 |

-continued

```
attctaagag acgtgagcaa gaaagaggga ggagcaatgt atgccgatga caccgcagga    9180
tgggatacaa gaatcacact agaagaccta aaaaatgaag aaatggtaac aaaccacatg    9240
gaaggagaac acaagaaact agccgaggcc attttcaaac taacgtacca aaacaaggtg    9300
gtgcgtgtgc aaagaccaac accaagaggc acagtaatgg acatcatatc gagaagagac    9360
caaagaggta gtggacaagt tggcacctat ggactcaata ctttcaccaa tatggaagcc    9420
caactaatca gacagatgga gggagaagga gtctttaaaa gcattcagca cctaacaatc    9480
acagaagaaa tcgctgtgca aaactggtta gcaagagtgg ggcgcgaaag gttatcaaga    9540
atggccatca gtggagatga ttgtgttgtg aaacctttag atgacaggtt cgcaagcgct    9600
ttaacagctc taaatgacat gggaaagatt aggaaagaca taacaatgg gaaccttca     9660 agaggatgga atgattggac acaagtgccc ttctgttcac accatttcca tgagttaatc    9720
atgaaagacg gtcgcgtact cgttgttcca tgtagaaacc aagatgaact gattggcaga    9780
gcccgaatct cccaaggagc agggtggtct ttgcgggaga cggcctgttt ggggaagtct    9840
tacgcccaaa tgtggagctt gatgtacttc cacagacgcg acctcaggct ggcggcaaat    9900
gctatttgct cggcagtacc atcacattgg gttccaacaa gtcgaacaac ctggtccata    9960
catgctaaac atgaatggat gacaacggaa gacatgctga cagtctggaa cagggtgtgg   10020
attcaagaaa acccatggat ggaagacaaa actccagtgg aatcatggga ggaaatccca   10080
tacttgggga aagagaaga ccaatggtgc ggctcattga ttgggttaac aagcagggcc    10140
acctgggcaa agaacatcca agcagcaata aatcaagtta gatcccttat aggcaatgaa   10200
gaatacacag attacatgcc atccatgaaa agattcagaa gagaagagga agaagcagga    10260
gttctgtggt agaaagcaaa actaacatga aacaaggcta gaagtcaggt cggattaagc    10320
catagtacgg aaaaaactat gctacctgtg agccccgtcc aaggacgtta aaagaagtca   10380
ggccatcata aatgccatag cttgagtaaa ctatgcagcc tgtagctcca cctgagaagg    10440
tgtaaaaaat ccgggaggcc acaaaccatg gaagctgtac gcatggcgta gtggactagc    10500
ggttagagga gacccctccc ttacaaatcg cagcaacaat gggggcccaa ggcgagatga   10560
agctgtagtc tcgctggaag gactagaggt tagaggagac ccccccgaaa caaaaaacag   10620
catattgacg ctgggaaaga ccagagatcc tgctgtctcc tcagcatcat tccaggcaca   10680
gaacgccaga aaatggaatg gtgctgttga atcaacaggt tct                     10723
```

<210> SEQ ID NO 25
<211> LENGTH: 3391
<212> TYPE: PRT
<213> ORGANISM: Artificial Sequence
<220> FEATURE:
<223> OTHER INFORMATION: Derived from Dengue virus serotype 2/Dengue
      virus serotype 4, DEN4h

<400> SEQUENCE: 25

```
Met Asn Asn Gln Arg Lys Lys Ala Lys Asn Thr Pro Phe Asn Met Leu
1               5                   10                  15

Lys Arg Glu Arg Asn Arg Val Ser Thr Val Gln Gln Leu Thr Lys Arg
                20                  25                  30

Phe Ser Leu Gly Met Leu Gln Gly Arg Gly Pro Leu Lys Leu Phe Met
            35                  40                  45

Ala Leu Val Ala Phe Leu Arg Phe Leu Thr Ile Pro Pro Thr Ala Gly
        50                  55                  60

Ile Leu Lys Arg Trp Gly Thr Ile Lys Lys Ser Lys Ala Ile Asn Val
```

-continued

```
              65                  70                  75                  80
Leu Arg Gly Phe Arg Lys Glu Ile Gly Arg Met Leu Asn Ile Leu Asn
                 85                  90                  95

Arg Arg Arg Ser Ser Ala Gly Met Ile Ile Met Leu Ile Pro Thr Val
            100                 105                 110

Met Ala Phe His Leu Thr Thr Arg Asp Gly Glu Pro Leu Met Ile Val
            115                 120                 125

Ala Lys His Glu Arg Gly Arg Pro Leu Leu Phe Lys Thr Thr Glu Gly
        130                 135                 140

Ile Asn Lys Cys Thr Leu Ile Ala Met Asp Leu Gly Glu Met Cys Glu
145                 150                 155                 160

Asp Thr Val Thr Tyr Lys Cys Pro Leu Leu Val Asn Thr Glu Pro Glu
                165                 170                 175

Asp Ile Asp Cys Trp Cys Asn Leu Thr Ser Thr Trp Val Met Tyr Gly
            180                 185                 190

Thr Cys Thr Gln Ser Gly Glu Arg Arg Arg Glu Lys Arg Ser Val Ala
        195                 200                 205

Leu Thr Pro His Ser Gly Met Gly Leu Glu Thr Arg Ala Glu Thr Trp
    210                 215                 220

Met Ser Ser Glu Gly Ala Trp Lys His Ala Gln Arg Val Glu Ser Trp
225                 230                 235                 240

Ile Leu Arg Asn Pro Gly Phe Ala Leu Leu Ala Gly Phe Met Ala Tyr
                245                 250                 255

Met Ile Gly Gln Thr Gly Ile Gln Arg Thr Val Phe Phe Val Leu Met
            260                 265                 270

Met Leu Val Ala Pro Ser Tyr Gly Met Arg Cys Val Gly Val Gly Asn
        275                 280                 285

Arg Asp Phe Val Glu Gly Val Ser Gly Gly Ala Trp Val Asp Leu Val
    290                 295                 300

Leu Glu His Gly Gly Cys Val Thr Thr Met Ala Gln Gly Lys Pro Thr
305                 310                 315                 320

Leu Asp Phe Glu Leu Thr Lys Thr Thr Ala Lys Glu Val Ala Leu Leu
                325                 330                 335

Arg Thr Tyr Cys Ile Glu Ala Ser Ile Ser Asn Ile Thr Thr Ala Thr
            340                 345                 350

Arg Cys Pro Thr Gln Gly Glu Pro Tyr Leu Lys Glu Glu Gln Asp Gln
        355                 360                 365

Gln Tyr Ile Cys Arg Arg Asp Val Val Asp Arg Gly Trp Gly Asn Gly
    370                 375                 380

Cys Gly Leu Phe Gly Lys Gly Val Val Thr Cys Ala Lys Phe Ser
385                 390                 395                 400

Cys Ser Gly Lys Ile Thr Gly Asn Leu Val Gln Ile Glu Asn Leu Glu
                405                 410                 415

Tyr Thr Val Val Val Thr Val His Asn Gly Asp Thr His Ala Val Gly
            420                 425                 430

Asn Asp Thr Ser Asn His Gly Val Thr Ala Thr Ile Thr Pro Arg Ser
        435                 440                 445

Pro Ser Val Glu Val Lys Leu Pro Asp Tyr Gly Glu Leu Thr Leu Asp
    450                 455                 460

Cys Glu Pro Arg Ser Gly Ile Asp Phe Asn Glu Met Ile Leu Met Lys
465                 470                 475                 480

Met Lys Lys Lys Thr Trp Leu Val His Lys Gln Trp Phe Leu Asp Leu
                485                 490                 495
```

Pro Leu Pro Trp Thr Ala Gly Ala Asp Thr Ser Glu Val His Trp Asn
            500                 505                 510

Tyr Lys Glu Arg Met Val Thr Phe Lys Val Pro His Ala Lys Arg Gln
            515                 520                 525

Asp Val Thr Val Leu Gly Ser Gln Glu Gly Ala Met His Ser Ala Leu
            530                 535                 540

Ala Gly Ala Thr Glu Val Asp Ser Gly Asp Gly Asn His Met Phe Ala
545                 550                 555                 560

Gly His Leu Lys Cys Lys Val Arg Met Glu Lys Leu Arg Ile Lys Gly
            565                 570                 575

Met Ser Tyr Thr Met Cys Ser Gly Lys Phe Ser Ile Asp Lys Glu Met
            580                 585                 590

Ala Glu Thr Gln His Gly Thr Thr Val Val Lys Val Lys Tyr Glu Gly
            595                 600                 605

Ala Gly Ala Pro Cys Lys Val Pro Ile Glu Ile Arg Asp Val Asn Lys
            610                 615                 620

Glu Lys Val Val Gly Arg Ile Ile Ser Ser Thr Pro Leu Ala Glu Asn
625                 630                 635                 640

Thr Asn Ser Val Thr Asn Ile Glu Leu Glu Pro Pro Phe Gly Asp Ser
            645                 650                 655

Tyr Ile Val Ile Gly Val Gly Asn Ser Ala Leu Thr Leu His Trp Phe
            660                 665                 670

Arg Lys Gly Ser Ser Ile Gly Lys Met Phe Glu Ser Thr Tyr Arg Gly
            675                 680                 685

Ala Lys Arg Met Ala Ile Leu Gly Lys Thr Ala Trp Asp Phe Gly Ser
            690                 695                 700

Val Gly Gly Leu Phe Thr Ser Leu Gly Lys Ala Val His Gln Val Phe
705                 710                 715                 720

Gly Ser Val Tyr Thr Thr Leu Phe Gly Gly Val Ser Trp Met Ile Arg
            725                 730                 735

Ile Leu Ile Gly Phe Leu Val Leu Trp Ile Gly Thr Asn Ser Arg Asn
            740                 745                 750

Thr Ser Met Ala Met Thr Cys Ile Ala Ala Gly Ile Val Thr Leu Tyr
            755                 760                 765

Leu Gly Val Met Val Gln Ala Asp Ser Gly Cys Val Val Ser Trp Lys
            770                 775                 780

Asn Lys Glu Leu Lys Cys Gly Ser Gly Ile Phe Ile Thr Asp Asn Val
785                 790                 795                 800

His Thr Trp Thr Glu Gln Tyr Lys Phe Gln Pro Glu Ser Pro Ser Lys
            805                 810                 815

Leu Ala Ser Ala Ile Gln Lys Ala His Glu Glu Asp Ile Cys Gly Ile
            820                 825                 830

Arg Ser Val Thr Arg Leu Glu Asn Leu Met Trp Lys Gln Ile Thr Pro
            835                 840                 845

Glu Leu Asn His Ile Leu Ser Glu Asn Glu Val Lys Leu Thr Ile Met
            850                 855                 860

Thr Gly Asp Ile Lys Gly Ile Met Gln Ala Gly Lys Arg Ser Leu Arg
865                 870                 875                 880

Pro Gln Pro Thr Glu Leu Lys Tyr Ser Trp Lys Thr Trp Gly Lys Ala
            885                 890                 895

Lys Met Leu Ser Thr Glu Ser His Asn Gln Thr Phe Leu Ile Asp Gly
            900                 905                 910

```
Pro Glu Thr Ala Glu Cys Pro Asn Thr Asn Arg Ala Trp Asn Ser Leu
        915                 920                 925

Glu Val Glu Asp Tyr Gly Phe Gly Val Phe Thr Thr Asn Ile Trp Leu
        930                 935                 940

Lys Leu Lys Glu Lys Gln Asp Val Phe Cys Asp Ser Lys Leu Met Ser
945                 950                 955                 960

Ala Ala Ile Lys Asp Asn Arg Ala Val His Ala Asp Met Gly Tyr Trp
                965                 970                 975

Ile Glu Ser Ala Leu Asn Asp Thr Trp Lys Ile Glu Lys Ala Ser Phe
        980                 985                 990

Ile Glu Val Lys Asn Cys His Trp Pro Lys Ser His Thr Leu Trp Ser
        995                1000                1005

Asn Gly Val Leu Glu Ser Glu Met Ile Ile Pro Lys Asn Leu Ala
   1010                1015                1020

Gly Pro Val Ser Gln His Asn Tyr Arg Pro Gly Tyr His Thr Gln
   1025                1030                1035

Ile Thr Gly Pro Trp His Leu Gly Lys Leu Glu Met Asp Phe Asp
   1040                1045                1050

Phe Cys Asp Gly Thr Thr Val Val Val Thr Glu Asp Cys Gly Asn
   1055                1060                1065

Arg Gly Pro Ser Leu Arg Thr Thr Thr Ala Ser Gly Lys Leu Ile
   1070                1075                1080

Thr Glu Trp Cys Cys Arg Ser Cys Thr Leu Pro Pro Leu Arg Tyr
   1085                1090                1095

Arg Gly Glu Asp Gly Cys Trp Tyr Gly Met Glu Ile Arg Pro Leu
   1100                1105                1110

Lys Glu Lys Glu Glu Asn Leu Val Asn Ser Leu Val Thr Ala Gly
   1115                1120                1125

His Gly Gln Val Asp Asn Phe Ser Leu Gly Val Leu Gly Met Ala
   1130                1135                1140

Leu Phe Leu Glu Glu Met Leu Arg Thr Arg Val Gly Thr Lys His
   1145                1150                1155

Ala Ile Leu Leu Val Ala Val Ser Phe Val Thr Leu Ile Thr Gly
   1160                1165                1170

Asn Met Ser Phe Arg Asp Leu Gly Arg Val Met Val Met Val Gly
   1175                1180                1185

Ala Thr Met Thr Asp Asp Ile Gly Met Gly Val Thr Tyr Leu Ala
   1190                1195                1200

Leu Leu Ala Ala Phe Lys Val Arg Pro Thr Phe Ala Ala Gly Leu
   1205                1210                1215

Leu Leu Arg Lys Leu Thr Ser Lys Glu Leu Met Met Thr Thr Ile
   1220                1225                1230

Gly Ile Val Leu Leu Ser Gln Ser Thr Ile Pro Glu Thr Ile Leu
   1235                1240                1245

Glu Leu Thr Asp Ala Leu Ala Leu Gly Met Met Val Leu Lys Met
   1250                1255                1260

Val Arg Asn Met Glu Lys Tyr Gln Leu Ala Val Thr Ile Met Ala
   1265                1270                1275

Ile Leu Cys Val Pro Asn Ala Val Ile Leu Gln Asn Ala Trp Lys
   1280                1285                1290

Val Ser Cys Thr Ile Leu Ala Val Val Ser Val Ser Pro Leu Phe
   1295                1300                1305

Leu Thr Ser Ser Gln Gln Lys Thr Asp Trp Ile Pro Leu Ala Leu
```

```
                   1310              1315              1320
Thr Ile Lys Gly Leu Asn Pro Thr Ala Ile Phe Leu Thr Thr Leu
        1325              1330              1335

Ser Arg Thr Ser Lys Lys Arg Ser Trp Pro Leu Asn Glu Ala Ile
        1340              1345              1350

Met Ala Val Gly Met Val Ser Ile Leu Ala Ser Ser Leu Leu Lys
        1355              1360              1365

Asn Asp Ile Pro Met Thr Gly Pro Leu Val Ala Gly Gly Leu Leu
        1370              1375              1380

Thr Val Cys Tyr Val Leu Thr Gly Arg Ser Ala Asp Leu Glu Leu
        1385              1390              1395

Glu Arg Ala Ala Asp Val Lys Trp Glu Asp Gln Ala Glu Ile Ser
        1400              1405              1410

Gly Ser Ser Pro Ile Leu Ser Ile Thr Ile Ser Glu Asp Gly Ser
        1415              1420              1425

Met Ser Ile Lys Asn Glu Glu Glu Glu Gln Thr Leu Thr Ile Leu
        1430              1435              1440

Ile Arg Thr Gly Leu Leu Val Ile Ser Gly Leu Phe Pro Val Ser
        1445              1450              1455

Ile Pro Ile Thr Ala Ala Ala Trp Tyr Leu Trp Glu Val Lys Lys
        1460              1465              1470

Gln Arg Ala Gly Val Leu Trp Asp Val Pro Ser Pro Pro Pro Met
        1475              1480              1485

Gly Lys Ala Glu Leu Glu Asp Gly Ala Tyr Arg Ile Lys Gln Lys
        1490              1495              1500

Gly Ile Leu Gly Tyr Ser Gln Ile Gly Ala Gly Val Tyr Lys Glu
        1505              1510              1515

Gly Thr Phe His Thr Met Trp His Val Thr Arg Gly Ala Val Leu
        1520              1525              1530

Met His Lys Gly Lys Arg Ile Glu Pro Ser Trp Ala Asp Val Lys
        1535              1540              1545

Lys Asp Leu Ile Ser Tyr Gly Gly Gly Trp Lys Leu Glu Gly Glu
        1550              1555              1560

Trp Lys Glu Gly Glu Glu Val Gln Val Leu Ala Leu Glu Pro Gly
        1565              1570              1575

Lys Asn Pro Arg Ala Val Gln Thr Lys Pro Gly Leu Phe Lys Thr
        1580              1585              1590

Asn Ala Gly Thr Ile Gly Ala Val Ser Leu Asp Phe Ser Pro Gly
        1595              1600              1605

Thr Ser Gly Ser Pro Ile Ile Asp Lys Lys Gly Lys Val Val Gly
        1610              1615              1620

Leu Tyr Gly Asn Gly Val Val Thr Arg Ser Gly Ala Tyr Val Ser
        1625              1630              1635

Ala Ile Ala Gln Thr Glu Lys Ser Ile Glu Asp Asn Pro Glu Ile
        1640              1645              1650

Glu Asp Asp Ile Phe Arg Lys Arg Arg Leu Thr Ile Met Asp Leu
        1655              1660              1665

His Pro Gly Ala Gly Lys Thr Lys Arg Tyr Leu Pro Ala Ile Val
        1670              1675              1680

Arg Glu Ala Ile Lys Arg Gly Leu Arg Thr Leu Ile Leu Ala Pro
        1685              1690              1695

Thr Arg Val Val Ala Ala Glu Met Glu Glu Ala Leu Arg Gly Leu
        1700              1705              1710
```

```
Pro Ile Arg Tyr Gln Thr Pro Ala Ile Arg Ala Val His Thr Gly
1715                1720                1725

Arg Glu Ile Val Asp Leu Met Cys His Ala Thr Phe Thr Met Arg
    1730                1735                1740

Leu Leu Ser Pro Val Arg Val Pro Asn Tyr Asn Leu Ile Ile Met
        1745                1750                1755

Asp Glu Ala His Phe Thr Asp Pro Ala Ser Ile Ala Ala Arg Gly
1760                1765                1770

Tyr Ile Ser Thr Arg Val Glu Met Gly Glu Ala Ala Gly Ile Phe
    1775                1780                1785

Met Thr Ala Thr Pro Pro Gly Ser Arg Asp Pro Phe Pro Gln Ser
        1790                1795                1800

Asn Ala Pro Ile Ile Asp Glu Glu Arg Glu Ile Pro Glu Arg Ser
1805                1810                1815

Trp Asn Ser Gly His Glu Trp Val Thr Asp Phe Lys Gly Lys Thr
    1820                1825                1830

Val Trp Phe Val Pro Ser Ile Lys Ala Gly Asn Asp Ile Ala Ala
        1835                1840                1845

Cys Leu Arg Lys Asn Gly Lys Lys Val Ile Gln Leu Ser Arg Lys
1850                1855                1860

Thr Phe Asp Ser Glu Tyr Val Lys Thr Arg Thr Asn Asp Trp Asp
    1865                1870                1875

Phe Val Val Thr Thr Asp Ile Ser Glu Met Gly Ala Asn Phe Lys
        1880                1885                1890

Ala Glu Arg Val Ile Asp Pro Arg Arg Cys Met Lys Pro Val Ile
1895                1900                1905

Leu Thr Asp Gly Glu Glu Arg Val Ile Leu Ala Gly Pro Met Pro
    1910                1915                1920

Val Thr His Ser Ser Ala Ala Gln Arg Arg Gly Arg Ile Gly Arg
        1925                1930                1935

Asn Pro Lys Asn Glu Asn Asp Gln Tyr Ile Tyr Met Gly Glu Pro
1940                1945                1950

Leu Glu Asn Asp Glu Asp Cys Ala His Trp Lys Glu Ala Lys Met
    1955                1960                1965

Leu Leu Asp Asn Ile Asn Thr Pro Glu Gly Ile Ile Pro Ser Met
        1970                1975                1980

Phe Glu Pro Glu Arg Glu Lys Val Asp Ala Ile Asp Gly Glu Tyr
1985                1990                1995

Arg Leu Arg Gly Glu Ala Arg Lys Thr Phe Val Asp Leu Met Arg
    2000                2005                2010

Arg Gly Asp Leu Pro Val Trp Leu Ala Tyr Arg Val Ala Ala Glu
        2015                2020                2025

Gly Ile Asn Tyr Ala Asp Arg Arg Trp Cys Phe Asp Gly Val Lys
2030                2035                2040

Asn Asn Gln Ile Leu Glu Glu Asn Val Glu Val Glu Ile Trp Thr
    2045                2050                2055

Lys Glu Gly Glu Arg Lys Lys Leu Lys Pro Arg Trp Leu Asp Ala
        2060                2065                2070

Arg Ile Tyr Ser Asp Pro Leu Ala Leu Lys Glu Phe Lys Glu Phe
2075                2080                2085

Ala Ala Gly Arg Lys Ser Leu Thr Leu Asn Leu Ile Thr Glu Met
    2090                2095                2100
```

```
Gly Arg Leu Pro Thr Phe Met Thr Gln Lys Ala Arg Asp Ala Leu
    2105                2110                2115
Asp Asn Leu Ala Val Leu His Thr Ala Glu Ala Gly Gly Arg Ala
    2120                2125                2130
Tyr Asn His Ala Leu Ser Glu Leu Pro Glu Thr Leu Glu Thr Leu
    2135                2140                2145
Leu Leu Leu Thr Leu Leu Ala Thr Val Thr Gly Gly Ile Phe Leu
    2150                2155                2160
Phe Leu Met Ser Ala Arg Gly Ile Gly Lys Met Thr Leu Gly Met
    2165                2170                2175
Cys Cys Ile Ile Thr Ala Ser Ile Leu Leu Trp Tyr Ala Gln Ile
    2180                2185                2190
Gln Pro His Trp Ile Ala Ala Ser Ile Ile Leu Glu Phe Phe Leu
    2195                2200                2205
Ile Val Leu Leu Ile Pro Glu Pro Glu Lys Gln Arg Thr Pro Gln
    2210                2215                2220
Asp Asn Gln Leu Thr Tyr Val Val Ile Ala Ile Leu Thr Val Val
    2225                2230                2235
Ala Ala Thr Met Ala Asn Glu Met Gly Phe Leu Glu Lys Thr Lys
    2240                2245                2250
Lys Asp Leu Gly Leu Gly Ser Ile Ala Thr Gln Gln Pro Glu Ser
    2255                2260                2265
Asn Ile Leu Asp Ile Asp Leu Arg Pro Ala Ser Ala Trp Thr Leu
    2270                2275                2280
Tyr Ala Val Ala Thr Thr Phe Val Thr Pro Met Leu Arg His Ser
    2285                2290                2295
Ile Glu Asn Ser Ser Val Asn Val Ser Leu Thr Ala Ile Ala Asn
    2300                2305                2310
Gln Ala Thr Val Leu Met Gly Leu Gly Lys Gly Trp Pro Leu Ser
    2315                2320                2325
Lys Met Asp Ile Gly Val Pro Leu Leu Ala Ile Gly Cys Tyr Ser
    2330                2335                2340
Gln Val Asn Pro Ile Thr Leu Thr Ala Ala Leu Phe Leu Leu Val
    2345                2350                2355
Ala His Tyr Ala Ile Ile Gly Pro Gly Leu Gln Ala Lys Ala Thr
    2360                2365                2370
Arg Glu Ala Gln Lys Arg Ala Ala Ala Gly Ile Met Lys Asn Pro
    2375                2380                2385
Thr Val Asp Gly Ile Thr Val Ile Asp Leu Asp Pro Ile Pro Tyr
    2390                2395                2400
Asp Pro Lys Phe Glu Lys Gln Leu Gly Gln Val Met Leu Leu Val
    2405                2410                2415
Leu Cys Val Thr Gln Val Leu Met Met Arg Thr Thr Trp Ala Leu
    2420                2425                2430
Cys Glu Ala Leu Thr Leu Ala Thr Gly Pro Ile Ser Thr Leu Trp
    2435                2440                2445
Glu Gly Asn Pro Gly Arg Phe Trp Asn Thr Thr Ile Ala Val Ser
    2450                2455                2460
Met Ala Asn Ile Phe Arg Gly Ser Tyr Leu Ala Gly Ala Gly Leu
    2465                2470                2475
Leu Phe Ser Ile Met Lys Asn Thr Thr Asn Thr Arg Arg Gly Thr
    2480                2485                2490
Gly Asn Ile Gly Glu Thr Leu Gly Glu Lys Trp Lys Ser Arg Leu
```

-continued

```
              2495                2500                2505
Asn Ala Leu Gly Lys Ser Glu Phe Gln Ile Tyr Lys Lys Ser Gly
        2510                2515                2520
Ile Gln Glu Val Asp Arg Thr Leu Ala Lys Glu Gly Ile Lys Arg
        2525                2530                2535
Gly Glu Thr Asp His His Ala Val Ser Arg Gly Ser Ala Lys Leu
        2540                2545                2550
Arg Trp Phe Val Glu Arg Asn Met Val Thr Pro Glu Gly Lys Val
        2555                2560                2565
Val Asp Leu Gly Cys Gly Arg Gly Gly Trp Ser Tyr Tyr Cys Gly
        2570                2575                2580
Gly Leu Lys Asn Val Arg Glu Val Lys Gly Leu Thr Lys Gly Gly
        2585                2590                2595
Pro Gly His Glu Glu Pro Ile Pro Met Ser Thr Tyr Gly Trp Asn
        2600                2605                2610
Leu Val Arg Leu Gln Ser Gly Val Asp Val Phe Phe Ile Pro Pro
        2615                2620                2625
Glu Lys Cys Asp Thr Leu Leu Cys Asp Ile Gly Glu Ser Ser Pro
        2630                2635                2640
Asn Pro Thr Val Glu Ala Gly Arg Thr Leu Arg Val Leu Asn Leu
        2645                2650                2655
Val Glu Asn Trp Leu Asn Asn Asn Thr Gln Phe Cys Ile Lys Val
        2660                2665                2670
Leu Asn Pro Tyr Met Pro Ser Val Ile Glu Lys Met Glu Ala Leu
        2675                2680                2685
Gln Arg Lys Tyr Gly Gly Ala Leu Val Arg Asn Pro Leu Ser Arg
        2690                2695                2700
Asn Ser Thr His Glu Met Tyr Trp Val Ser Asn Ala Ser Gly Asn
        2705                2710                2715
Ile Val Ser Ser Val Asn Met Ile Ser Arg Met Leu Ile Asn Arg
        2720                2725                2730
Phe Thr Met Arg Tyr Lys Lys Ala Thr Tyr Glu Pro Asp Val Asp
        2735                2740                2745
Leu Gly Ser Gly Thr Arg Asn Ile Gly Ile Glu Ser Glu Ile Pro
        2750                2755                2760
Asn Leu Asp Ile Ile Gly Lys Arg Ile Glu Lys Ile Lys Gln Glu
        2765                2770                2775
His Glu Thr Ser Trp His Tyr Asp Gln Asp His Pro Tyr Lys Thr
        2780                2785                2790
Trp Ala Tyr His Gly Ser Tyr Glu Thr Lys Gln Thr Gly Ser Ala
        2795                2800                2805
Ser Ser Met Val Asn Gly Val Val Arg Leu Leu Thr Lys Pro Trp
        2810                2815                2820
Asp Val Val Pro Met Val Thr Gln Met Ala Met Thr Asp Thr Thr
        2825                2830                2835
Pro Phe Gly Gln Gln Arg Val Phe Lys Glu Lys Val Asp Thr Arg
        2840                2845                2850
Thr Gln Glu Pro Lys Glu Gly Thr Lys Lys Leu Met Lys Ile Thr
        2855                2860                2865
Ala Glu Trp Leu Trp Lys Glu Leu Gly Lys Lys Lys Thr Pro Arg
        2870                2875                2880
Met Cys Thr Arg Glu Glu Phe Thr Arg Lys Val Arg Ser Asn Ala
        2885                2890                2895
```

Ala Leu Gly Ala Ile Phe Thr Asp Glu Asn Lys Trp Lys Ser Ala
2900                2905                2910

Arg Glu Ala Val Glu Asp Ser Arg Phe Trp Glu Leu Val Asp Lys
2915                2920                2925

Glu Arg Asn Leu His Leu Glu Gly Lys Cys Glu Thr Cys Val Tyr
2930                2935                2940

Asn Met Met Gly Lys Arg Glu Lys Lys Leu Gly Glu Phe Gly Lys
2945                2950                2955

Ala Lys Gly Ser Arg Ala Ile Trp Tyr Met Trp Leu Gly Ala Arg
2960                2965                2970

Phe Leu Glu Phe Glu Ala Leu Gly Phe Leu Asn Glu Asp His Trp
2975                2980                2985

Phe Ser Arg Glu Asn Ser Leu Ser Gly Val Glu Gly Glu Gly Leu
2990                2995                3000

His Lys Leu Gly Tyr Ile Leu Arg Asp Val Ser Lys Lys Glu Gly
3005                3010                3015

Gly Ala Met Tyr Ala Asp Asp Thr Ala Gly Trp Asp Thr Arg Ile
3020                3025                3030

Thr Leu Glu Asp Leu Lys Asn Glu Glu Met Val Thr Asn His Met
3035                3040                3045

Glu Gly Glu His Lys Lys Leu Ala Glu Ala Ile Phe Lys Leu Thr
3050                3055                3060

Tyr Gln Asn Lys Val Val Arg Val Gln Arg Pro Thr Pro Arg Gly
3065                3070                3075

Thr Val Met Asp Ile Ile Ser Arg Arg Asp Gln Arg Gly Ser Gly
3080                3085                3090

Gln Val Gly Thr Tyr Gly Leu Asn Thr Phe Thr Asn Met Glu Ala
3095                3100                3105

Gln Leu Ile Arg Gln Met Glu Gly Glu Gly Val Phe Lys Ser Ile
3110                3115                3120

Gln His Leu Thr Ile Thr Glu Glu Ile Ala Val Gln Asn Trp Leu
3125                3130                3135

Ala Arg Val Gly Arg Glu Arg Leu Ser Arg Met Ala Ile Ser Gly
3140                3145                3150

Asp Asp Cys Val Val Lys Pro Leu Asp Asp Arg Phe Ala Ser Ala
3155                3160                3165

Leu Thr Ala Leu Asn Asp Met Gly Lys Ile Arg Lys Asp Ile Gln
3170                3175                3180

Gln Trp Glu Pro Ser Arg Gly Trp Asn Asp Trp Thr Gln Val Pro
3185                3190                3195

Phe Cys Ser His His Phe His Glu Leu Ile Met Lys Asp Gly Arg
3200                3205                3210

Val Leu Val Val Pro Cys Arg Asn Gln Asp Glu Leu Ile Gly Arg
3215                3220                3225

Ala Arg Ile Ser Gln Gly Ala Gly Trp Ser Leu Arg Glu Thr Ala
3230                3235                3240

Cys Leu Gly Lys Ser Tyr Ala Gln Met Trp Ser Leu Met Tyr Phe
3245                3250                3255

His Arg Arg Asp Leu Arg Leu Ala Ala Asn Ala Ile Cys Ser Ala
3260                3265                3270

Val Pro Ser His Trp Val Pro Thr Ser Arg Thr Thr Trp Ser Ile
3275                3280                3285

```
His Ala Lys His Glu Trp Met Thr Thr Glu Asp Met     Leu Thr Val
    3290                3295                3300

Trp Asn Arg Val Trp Ile Gln Glu Asn Pro Trp Met     Glu Asp Lys
    3305                3310                3315

Thr Pro Val Glu Ser Trp Glu Glu Ile Pro Tyr Leu     Gly Lys Arg
    3320                3325                3330

Glu Asp Gln Trp Cys Gly Ser Leu Ile Gly Leu Thr     Ser Arg Ala
    3335                3340                3345

Thr Trp Ala Lys Asn Ile Gln Ala Ala Ile Asn Gln     Val Arg Ser
    3350                3355                3360

Leu Ile Gly Asn Glu Glu Tyr Thr Asp Tyr Met Pro     Ser Met Lys
    3365                3370                3375

Arg Phe Arg Arg Glu Glu Glu Glu Ala Gly Val Leu     Trp
    3380                3385                3390

<210> SEQ ID NO 26
<211> LENGTH: 5
<212> TYPE: PRT
<213> ORGANISM: Artificial Sequence
<220> FEATURE:
<223> OTHER INFORMATION: Derived from Dengue-2 virus

<400> SEQUENCE: 26

Gly Arg Ile Gly Arg
1               5

<210> SEQ ID NO 27
<211> LENGTH: 5
<212> TYPE: PRT
<213> ORGANISM: Artificial Sequence
<220> FEATURE:
<223> OTHER INFORMATION: Derived from Dengue-2 virus

<400> SEQUENCE: 27

Gly Ala Gly Lys Thr
1               5
```